(12) United States Patent
Nguyen et al.

(10) Patent No.: US 11,124,788 B2
(45) Date of Patent: Sep. 21, 2021

(54) ASX-SPECIFIC PROTEIN LIGASE

(71) Applicant: NANYANG TECHNOLOGICAL UNIVERSITY, Singapore (SG)

(72) Inventors: Kien Truc Giang Nguyen, Singapore (SG); James P. Tam, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 16/786,086

(22) Filed: Feb. 10, 2020

(65) Prior Publication Data

US 2020/0172893 A1  Jun. 4, 2020

Related U.S. Application Data

(62) Division of application No. 15/306,249, filed as application No. PCT/SG2015/050049 on Mar. 24, 2015, now Pat. No. 10,590,407.

(60) Provisional application No. 61/983,729, filed on Apr. 24, 2014.

(51) Int. Cl.
| | |
|---|---|
| *C12N 9/88* | (2006.01) |
| *C12N 9/00* | (2006.01) |
| *C12N 11/02* | (2006.01) |
| *C12N 11/06* | (2006.01) |
| *C12P 21/02* | (2006.01) |
| *C07K 1/10* | (2006.01) |
| *C07K 1/113* | (2006.01) |

(52) U.S. Cl.
CPC ............... *C12N 9/88* (2013.01); *C12N 9/93* (2013.01); *C12N 11/02* (2013.01); *C12N 11/06* (2013.01); *C12P 21/02* (2013.01); *C12Y 406/01* (2013.01); *C12Y 600/00* (2013.01); *C07K 1/10* (2013.01); *C07K 1/113* (2013.01)

(58) Field of Classification Search
None
See application file for complete search history.

(56) References Cited

U.S. PATENT DOCUMENTS

| | | | |
|---|---|---|---|
| 2010/0158924 | A1 | 6/2010 | Clerin et al. |
| 2013/0097737 | A1 | 4/2013 | Kovalic et al. |
| 2014/0259212 | A1 | 9/2014 | Plesch et al. |

OTHER PUBLICATIONS

Abe et al., "Asparaginyl Endopeptidase of Jack Bean Seeds—Purification, Characterization, and High Utility in Protein Sequence Analysis," *The Journal of Biological Chemistry*, 268(5):3525-3529, 1993.
Altschul et al., "Basic Local Alignment Search Tool," *J. Mol. Biol.* 215:403-410, 1990.
Altschul et al., "Gapped BLAST and PSI-BLAST: a new generation of protein database search programs," *Nucleic Acids Research* 25(17):3389-3402, 1997.
Arnison et al., "Ribosomally synthesized and post-translationally modified peptide natural products: overview and recommendations for a universal nomenclature," *Nat. Prod. Rep.* 30:108-160, 2013.
Barber et al., "The Two-step Biosynthesis of Cyclic Peptides from Linear Precursors in a Member of the Plant Family Caryophyllaceae Involves Cyclization by a Serine Protease-like Enzyme," *The Journal of Biological Chemistry* 288(18):12500-12510, 2013.
Becker et al., "Purification, cDNA cloning and characterization of proteinase B, an asparagine-specific endopeptidase from germinating vetch (*Vicia sativa* L.) seeds," *Eur. J. Biochem* 225:456-462, 1995.
Bolscher et al., "Sortase A as a tool for high-yield histatin Cyclization," *The FASEB Journal* 25(8):2650-2658, 2017.
Cascales et al., "Naturally occurring circular proteins: distribution, biosynthesis, and evolution," *Organic and Biomolecular Chemistry* 8:5035-5047, 2010.
Cole et al., "Retrocyclin: A primate peptide that protects cells from infection by T- and M-tropic strains of HIV-1," *PNAS* 99(4):1813-1818, 2002.
Conlan et al., "Insights into Processing and Cyclization Events Associated with Biosynthesis of the Cyclic Peptide Kalata B1," *The Journal of Biological Chemistry* 287(33):28037-28046, 2012.
Conlon et al., "Circular Micro-Proteins and Mechanisms of Cyclization," *Current Pharmaceutical Design* 17:4318-4328 (2011).
Craik et al., "Plant Cyclotides: a Unique Family of Cyclic and Knotted Proteins that Defines the Cyclic Cystine Knot Structural Motif," *J. Mol. Biol.* 294:1327-1336, 1999.
Craik, "Seamless Proteins Tie Up Their Loose Ends," *Science* 311:1563-1564, 2006.
Craik, "Host-Defense Activities of Cyclotides," *Toxins* 4:139-156, 2012.
Dall et al., "Mechanistic and structural studies on legumain explain its zymogenicity, distinct activation pathways, and regulation," *PNAS* 110(27):10940-10945, 2013.
Database Geneseq [Online] "Asparaginyl endopeptidase derived from clone 107," XP002772646, retrieved from EBI Accession No. AAR43039, Mar. 25, 2003.
Database Geneseq [Online] "G. max yield enhancing protein SEQ ID:164," XP002772647, retrieved from EBI Accession No. GSP: ARZ05348, Aug. 21, 2008.
Database Geneseq [Online] "Plant isolated polypeptide sequence, SEQ ID 19351," retrieved from EBI Accession No. GSP: AYF97933, Sep. 30, 2010.
Eisenbrandt et al., "Conjugative Pili of IncP Plasmids, and the Ti Plasmids T Pilus Are Composed of Cyclic Subunits," *The Journal of Biological Chemistry* 274(32):22548-22555, 1999.
Gharandaghi et al., "Mass spectrometric identification of proteins from silver-stained polyacrylamide gel: A method for the removal of silver ions to enhance sensitivity," *Electrophoresis* 20:601-605, 1999.
Gillon et al., "Biosynthesis of circular proteins in plants," *The Plant Journal* 53:505-515, 2008.
Gruber et al., "Distribution and Evolution of Circular Miniproteins in Flowering Plants," *The Plant Cell* 20:2471-2483, 2008.

(Continued)

*Primary Examiner* — Marsha Tsay
(74) *Attorney, Agent, or Firm* — Seed IP Law Group LLP

(57) ABSTRACT

The present invention is directed to enzymes having Asx-specific ligase and cyclase activity and to nucleic acids encoding those as well as methods of the manufacture of said enzymes. Further encompassed are methods and uses of these enzymes.

9 Claims, 30 Drawing Sheets

Specification includes a Sequence Listing.

(56) References Cited

OTHER PUBLICATIONS

Haase et al., "A Specific Protease Encoded by the Conjugative DNA Transfer Systems of IncP and Ti Plasmids Is Essential for Pilus Synthesis," *Journal of Bacteriology* 179(18):5728-5735, 1997.
Hackeng et al., "Protein synthesis by native chemical ligation: Expanded scope by using straightforward methodology," *PNAS* 96:10068-10073, 1999.
Ho et al., "Electrospray Ionisation Mass Spectrometry and Clinical Applications," *Clin Biochem Rev* 24:3-12, 2003.
Jack et al., "Bacteriocins of Gram-Positive Bacteria," *Microbial Reviews* 59(2):171-200, 1995.
Jia et al., "Semienzymatic Cyclization of Disulfide-rich Peptides Using Sortase A," *The Journal of Biological Chemistry* 289(10):6627-6638, 2014.
Kembhavi et al., "The Two Cysteine Endopeptidases of Legume Seeds: Purification and Characterization by Use of Specific Fluorometric Assays," *Archives of Biochemistry and Biophysics* 303(2):208-213, 1993.
Kleinkauf et al., "Nonribosomal Polypeptide Synthesis: The Biosynthesis of a Cyclic Peptide Antibiotic," *Cold Spring Harb Symp Quant Biol* 34:805-813, 1969.
Koehnke et al., "The mechanism of patellamide macrocyclization revealed by the characterization of the PatG macrocyclase domain," *Nat Struct Mol Biol.* 19(8):767-772, 2012. (17 pages).
Kohli et al., "Generality of Peptide Cyclization Catalyzed by Isolated Thioesterase Domains of Nonribosomal Peptide Synthetases," *Biochemistry* 40:7099-7108, 2001.
Lee et al., "Using Marine Natural Products to Discover a Protease that Catalyzes Peptide Macrocyclization of Diverse Substrates," *J Am Chem Soc.* 161(6):2122-2124, 2009. (9 pages).
Lee et al., "Development of Near-Infrared Fluorophore (NIRF)-Labeled Activity-Based Probes for in Vivo Imaging of Legumain," *ACS Chemical Biology* 5(2):233-243, 2010.
Luckett et al., "High-Resolution Structure of a Potent, Cyclic Proteinase Inhibitor from Sunflower Seeds," *J. Mol. Biol.* 290:525-533, 1999.
Mao et al., "Sortase-Mediated Protein Ligation: A New Method for Protein Engineering," *J. Am. Chem. Soc.* 126:2670-2671, 2004.
Min et al., "In vitro splicing of concanavalin A is catalyzed by asparaginyl endopeptidase," *Structural Biology* 1(8)502-504, 1994.
Motomayor et al., "Gamma vacuolar processing enzyme [Theobroma cacao]," NCBI Reference Sequence XP_007012236.1, run on Jul. 10, 2014, retrieved from http://www.ncbi.nlm.nih.gov/protein/590573851, 2 pages.
Myline et al., "Albumins and their processing machinery are hijacked for cyclic peptides in sunflower," *Nature Chemical Biology* 7:257-259, 2011.
Notification of Reasons for Rejection dated Mar. 5, 2019, for corresponding Japanese Patent Application No. 2016-563922.
Nguyen et al., "Discovery and Characterization of Novel Cyclotides Originated from Chimeric Precursors Consisting of Albumin-1 Chain a and Cyclotide Domains in the Fabaceae Family," *The Journal of Biological Chemistry* 286(27):24275-24287, 2011.
Nguyen et al., "Novel Cyclotides and Uncyclotides with Highly Shortened Precursors from *Chassalia chartacea* and Effects of Methionine Oxidation on Bioactivities," *The Journal of Biological Chemistry* 287(21):17598-17607, 2012.
Nguyen et al., "Butelase 1 is an Asx-specific ligase enabling peptide macrocyclization and synthesis," *Nature Chemical Biology* 10:732-738, 2014.
Nguyen et al., GenBank Accession No. KF918345.1, "Clitoria tenratea cte peptide ligase mRNA, complete cds," run on Jun. 8, 2014, retrieved from https://www.ncbi.nlm.nih.gov/nuccore/KF918345, 2 pages.
Office Action dated Jul. 29, 2019 for corresponding Chinese Application No. 201580022063.X (26 pages).
Pauletti et al., "Improvement of oral peptide bioavailability: Peptidomimetics and prodrug strategies," *Advanced Drug Delivery Reviews* 27:235-256, 1997.
Popp et al., "Making and Breaking Peptide Bonds: Protein Engineering Using Sortase," *Angew. Chem. Int. Ed.* 50:5024-5032, 2011.
Poth et al., "Discovery of Cyclotides in the Fabaceae Plant Family Provides New Insights in the Cyclization, Evolution, and Distribution of Circular Proteins," *ACS Chem. Biol.* 6:345-355, 2011.
Pritz et al., "Enzymatic ligation of peptides, peptide nucleic acids and proteins by means of sortase A," *Adv. Exp. Med. Biol.* 611:107-108, 2009.
Rotari et al., "Legumain Forms from Plants and Animals Differ in Their Specificity," *Biol. Chem.* 382:953-959, 2001.
Šali et al., "Comparative Protein Modelling by Satisfaction of Spatial Restraints," *J. Mol. Biol.* 234:779-815, 1993.
Saska et al., "An Asparaginyl Endopeptidase Mediates in Vivo Protein Backbone Cyclization," *The Journal of Biological Chemistry* 282(40):29721-29728, 2007.
Sieber et al., "Learning from Nature's Drug Factories: Nonribosomal Synthesis of Macrocyclic Peptides," *Journal of Bacteriology* 185(24):7036-7043, 2003.
Sivonen et al., "Cyanobactins—ribosomal cyclic peptides produced by cyanobacteria," *Appl Microbiol Biotechnol* 86:1213-1225, 2010.
Sojka et al., "IrAE—an asparaginyl endopeptidase (legumain) in the gut of the hard tick *Ixodes ricinus*," *Int J Parasitol* 37(7):713-724, 2007. (21 pages).
Strijbis et al., "Protein Ligation in Living Cells Using Sortase," *Traffic* 13:780-789, 2012.
Takeda et al., "Isolation and Analysis of cDNA Encoding a Precursor of *Canavalia ensiformis* Asparaginyl Endopeptidase (Legumain)," *J. Biochem* 116:541-546 (1994).
Tan et al., "Plant Cyclopeptides," *Chem. Rev.* 106:840-895, 2006.
Tang et al., "A Cyclic Antimicrobial Peptide Produced in Primate Leukocytes by the Ligation of Two Truncated α-Defensins," *Science* 286:498-502, 1999.
Ton-That et al., "Purification and characterization of sortase, the transpeptidase that cleaves surface proteins of *Staphylococcus aureus* at the LPXTG motif," *PNAS* 96(22):12424-12429, 1999.
Trauger et al., "Peptide cyclization catalyzed by the thioesterase domain of tyrocidine synthetase," *Nature* 407:215-218, 2000. (6 pages).
Webb et al., "About MODELLER," retrieved from https://salilab.org/modeler/, on Jan. 25, 2017, 2 pages.
Wong et al., "Orally Active Peptidic Bradykinin $B_1$ Receptor Antagonists Engineered from a Cyclotide Scaffold for Inflammatory Pain Treatment," *Angew. Chem. Int. Ed.* 51:5620-5624, 2012.
Wu et al., "Sortase A-Catalyzed Peptide Cyclization for the Synthesis of Macrocyclic Peptides and Glycopeptides," *Chem Commun (Camb).* 47(32):9218-9220, 2011. (10 pages).
Xu et al., "In Vitro Protein Splicing of Purified Precursor and the Identification of a Branched Intermediate," *Cell* 75:1371-1377, 1993.
Xu et al., "Intein-Mediated Ligation and Cyclization of Expressed Proteins," *Methods* 24:257-277, 2001.
Yang et al., "asparaginyl endopeptidase [Vigna radiata]," Data Base NCBI Protein, [online], Accession No. AAK15049, Mar. 2, 2001, retrieved on Feb. 21, 2019 via Internet <URL: http://www.ncbi.nlm.nih.gov/protein/AAK15049.1>.

SEQ ID Nos. 152-156
2314: TIVALIEDGTHVVQYGDVGLSK
1582: HQADVCHAYQLIK
 930: WAVLVAGSK
 771: GYVNYR
 763: HASGTYK
 842: trypsin autolysis fragment LP-1
Legumain probe-1 a b a a b c d e a)

b)

c)

(c) Kalata B1

ASX-SPECIFIC PROTEIN LIGASE

CROSS-REFERENCE TO RELATED APPLICATIONS

This application claims the benefit of priority of U.S. Provisional Patent Application No. 61/983,729 filed Apr. 24, 2014, the contents of which being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_508D1_SEQUENCE_LISTING.txt. The text file is 457 KB, was created on Feb. 6, 2020, and is being submitted electronically via EFS-Web.

FIELD OF THE INVENTION

The present invention lies in the technical field of enzyme technology and specifically relates to a novel enzyme having Asx-specific ligase and cyclase activity and to nucleic acids encoding those as well as methods of the manufacture of said enzymes. Further encompassed are methods and uses of these enzymes.

BACKGROUND OF THE INVENTION

Head-to-tail macrocyclization of peptides and proteins has been used as a strategy to constrain structures and enhance metabolic stability against proteolytic degradation. In addition, a constrained macrocyclic conformation may also improve pharmacological activity and oral bioavailability. Although most peptides and proteins are produced as linear chains, circular peptides ranging from 6 to 78 residues occur naturally in diverse organisms. These cyclic peptides usually display high resistance to heat denaturation and proteolysis and have inspired a new trend in protein engineering, as demonstrated by recent successes in the cyclization of cytokines, histatin, ubiquitin C-terminal hydrolase, conotoxin and bradykinin-grafted cyclotides. Furthermore, cyclic peptides have been used as therapeutics, including valinomycin, gramicidin S and cyclosporine.

To date chemical methods are typically used for the cyclization of peptides. One possible strategy is native chemical ligation. This method requires an N-terminal cysteine and a C-terminal thioester, requirements that limit its application for non-cysteine-containing peptides. Furthermore, chemical methods are not always feasible, especially for large peptides and proteins.

Although enzymatic methods employing a naturally-occurring cyclase would be ideal, currently only very few peptide cyclases are known and they are for various reasons not fully exploited. However, other enzymes such as sortase A and inteins of which the innate functions are not a cyclase have been applied successfully for cyclization of various peptides and proteins. Nonetheless, these enzymes have shortcomings. Sortase A, for example, is a transpeptidase that anchors surface proteins to bacterial cell wall. Its cyclization reaction usually requires an overnight incubation and 0.1 to 1 molar equivalents of enzyme. Furthermore, sortase A has a pentapeptide recognition sequence LPXTG (SEQ ID NO: 160) and leaves an unnecessary tag on the modified proteins. Inteins are autocatalytic splicing elements that have been used for expression of cyclotides, sunflower trypsin inhibitor, and q-defensin. The intein-mediated cyclization, however, requires genetic fusion of a target protein with the intein domain, a necessity that may affect the protein folding or solubility.

There is thus still need in the art for improved means to cyclize peptides and proteins that overcome the drawbacks of existing technologies and, ideally, are simple, fast and versatile.

SUMMARY OF THE INVENTION

The present invention meets this need by providing a novel Asx-specific protein ligase that meets the above requirements. The inventors have surprisingly found that this enzyme that has been isolated from the medicinal plant *Clitoria ternatea* is a naturally occurring cyclase that is used as a processing enzyme in the synthesis of cyclotides, a large family of plant cyclic peptides. It has been found that this enzyme is, by far, the fastest known ligase with catalytic activities as high as 542,000 $M^{-1}s^{-1}$. It recognizes a tripeptide motif, Asx-His-Val, at the C-terminus, and mediates peptide backbone cyclization by cleaving the sorting sequence His-Val and ligating Asx to the N-terminal residue to form a circular topology. It could be shown that the enzyme does not only efficiently cyclizes cyclotide precursors and various cysteine-rich peptides ranging in sizes from 14 to 58 residues, but also non-cysteine-containing peptides and green fluorescent protein (GFP). This makes it highly versatile and useful in a variety of applications where cyclization of a given peptide or protein is desired.

In a first aspect, the present invention thus relates to an isolated polypeptide comprising or consisting of the amino acid sequence as set forth in SEQ ID NO:1. The polypeptide consisting of the amino acid sequence set forth in SEQ ID NO:1 is also referred to as "butelase 1" herein.

In another aspect, the present invention also relates to nucleic acid molecules encoding the polypeptides described herein, as well as a vector containing such a nucleic acid, in particular a copying vector or an expression vector.

In a further aspect, the invention is also directed to a host cell, preferably a non-human host cell, containing a nucleic acid as contemplated herein or a vector as contemplated herein.

A still further aspect of the invention is a method for manufacturing a polypeptide as described herein, comprising culturing a host cell contemplated herein; and isolating the polypeptide from the culture medium or from the host cell.

In a still further aspect, the present invention relates to the use of polypeptides described herein for protein ligation, in particular for cyclizing one or more peptide(s).

Another aspect of the invention is directed to the use of polypeptides that comprise or consist of
  (i) any one of the amino acid sequences as set forth in SEQ ID Nos:3-109;
  (ii) an amino acid sequence that shares at least 60, preferably at least 70, more preferably at least 80, most preferably at least 90% sequence identity with any one of the amino acid sequences of (i) over its entire length;
  (iii) an amino acid sequence that shares at least 80, preferably at least 90, more preferably at least 95% sequence homology with any one of the amino acid sequences of (i) over its entire length; or
  (iv) a fragment of any one of (i)-(iii),
for ligating at least two peptides or cyclizing a peptide.

In still another aspect, the invention relates to a method for cyclizing a peptide, the method comprising incubating said peptide with the polypeptides described above in connection with the inventive uses under conditions that allow cyclization of said peptide.

In a still further aspect, the invention relates to a method for ligating at least two peptides, the method comprising incubating said peptides with the polypeptides described above in connection with the inventive uses under conditions that allow ligation of said peptides.

In another aspect, the invention relates to a solid support material onto which the isolated polypeptides of the invention are immobilized as well as the use thereof and methods that use such substrates.

In another aspect, the invention also encompasses a transgenic plant comprising a nucleic acid molecule encoding a polypeptide having protein ligase and/or cyclase activity as described herein. The polypeptide is preferably not naturally present in said plant. Accordingly, the present invention also features transgenic plants that express a heterologous polypeptide according to the invention.

(d) Jack bean legumain was used as a control. MS profile shows that jack beak legumain hydrolyzed the asparaginyl bond in kB1-NHV to give linear form of kB1. Peaks labeled with $K^+$ or $K_2^+$ are ion adducts corresponding to the binding of one or two potassium ions, respectively.

Figure 3:
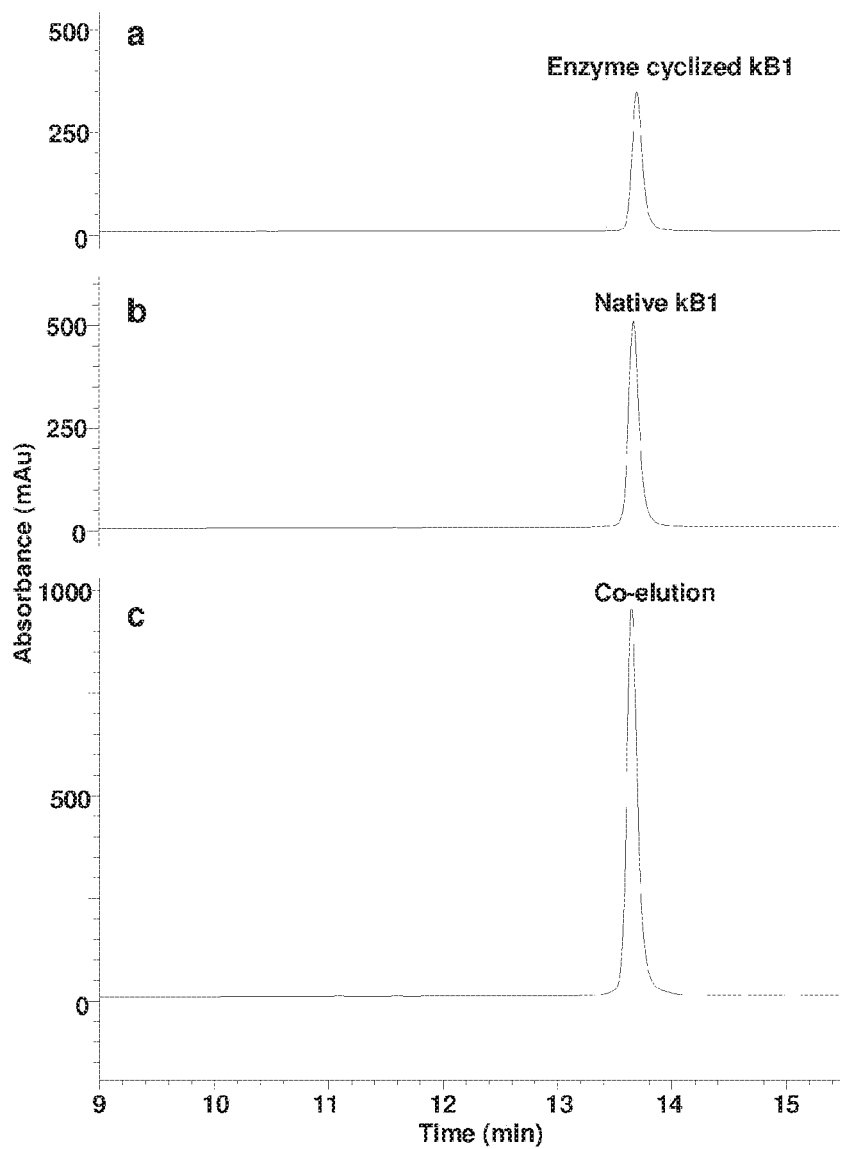

FIG. 3 shows the co-elution of enzyme-cyclized kB1 and native peptide. (a) HPLC profile of enzyme-cyclized kB1. (b) HPLC profile of native kB1 extracted from O. affinis. (c) Co-elution profile of enzyme-cyclized and native kB1.

Figure 4:
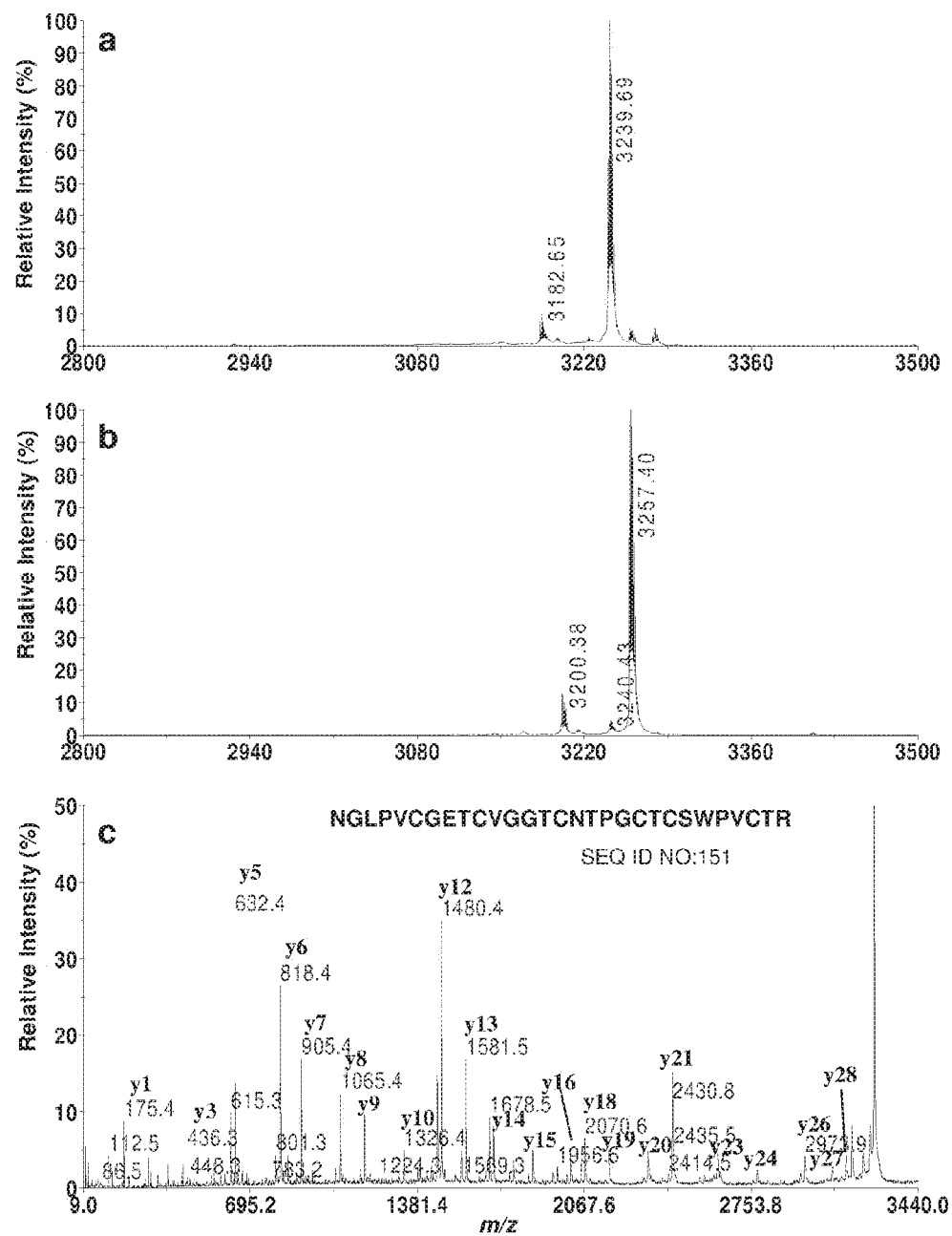

FIG. 4 shows MS evidence of a cyclic backbone in the enzyme-cyclized kB1 obtained from conversion of kB1-NHV by butelase 1. (a) MS profile of the cyclized kB1 after S-carbamido methylation. The cyclized kB1 has a m/z value of 2891, which became 3239 after S-alkylation. A minor peak at 3182 is observed due to incomplete alkylation where only 5 cysteines were modified. (b) MS profile of S-alkylated kB1 after tryptic digestion. A mass increase of 18 Da was observed, which indicated the addition of a water molecule and a cyclic backbone. (c) MS/MS profile of the 3257-Da tryptic fragment. The peptide sequence is shown at the top of the MS/MS spectrum. The y-ions are labeled at the top of corresponding peaks.

Figure 5:
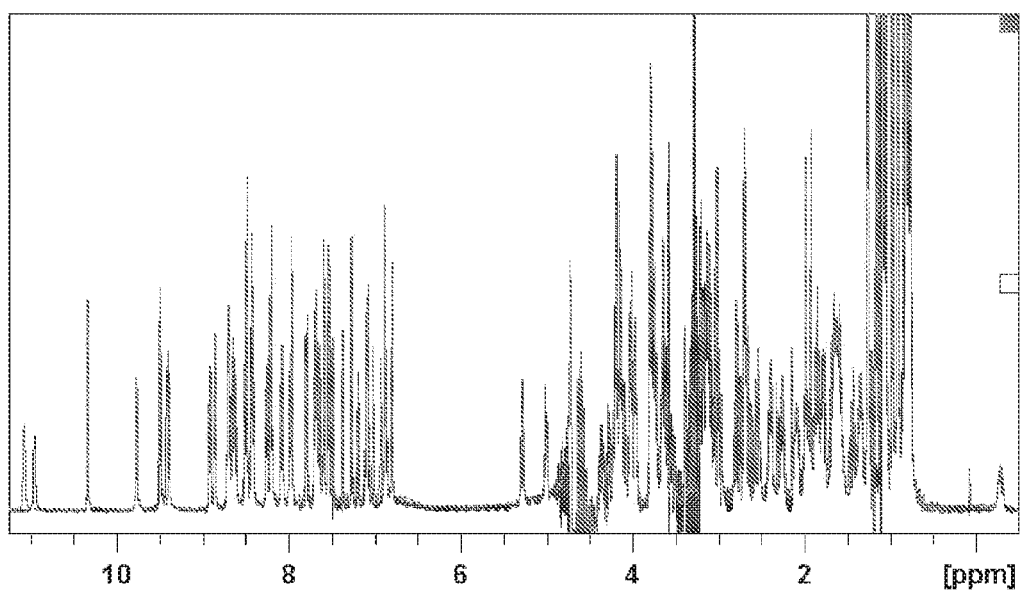

FIG. 5 shows 1D NMR spectra comparison of enzyme-cyclized kB1 (dark grey) and native kB1 (light grey). Peptides were dissolved in 95% $H_2O$/5% $D_2O$ at pH 4.3. The spectra were recorded at 298 K.

Figure 6:
Figure 6:
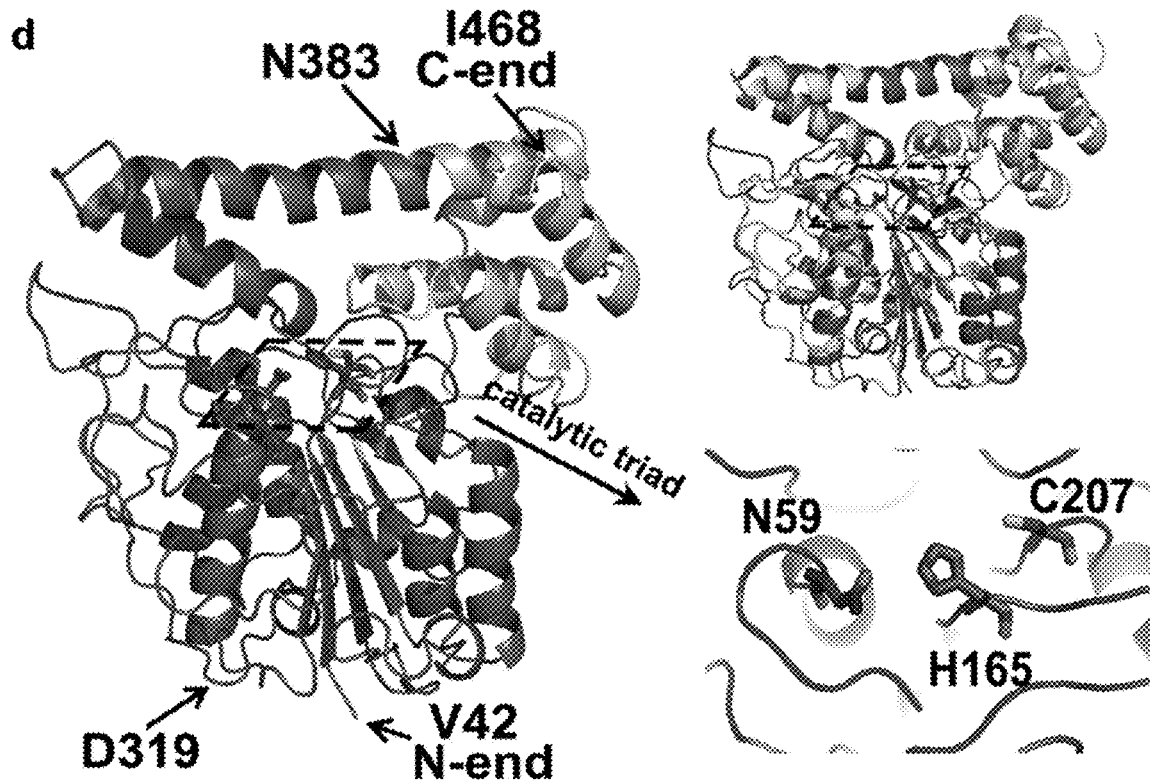

FIG. 6 shows isolation, characterization and homology modeling of butelase 1. (a) SDS-PAGE analysis of purified butelase 1. Proteins were visualized by silver staining. The left lane is purified butelase 1 and the right lane is a protein ladder with molecular weights (kDa) indicated. (b) Labeling of butelase 1 by the legumain-specific probe LP-1. Proteins were resolved by SDS-PAGE and visualized by a Typhoon scanner (GE Health Care) with a Cy5 filter. (c) Translated sequence of butelase 1 precursor (SEQ ID NO: 2) deduced from the EST sequences. The sequence is color-coded with the endoplasmic reticulum signal shown in black, N-terminal prodomain in orange, the AEP domain in blue, the active peptide region in magenta, and the LSAM domain in gray. The first and the last residues (V42 and N383) of the purified active enzyme are labeled. The conserved residues of the catalytic triad (Asn59, His165 and Cys207) are italic. Peptide sequences obtained from the in-gel tryptic digestion are underlined. (d)Modeling structure of zymogenic butelase 1 based on the structure of human legumain. The left panel shows the modeled zymogenic butelase 1 with the AEP domain shown in blue, active peptide region in magenta and LSAM domain in gray. The top-right panel shows the structure alignment of modeled butelase 1 and the template human legumain (PDB ID: 4FGU; yellow). The catalytic triad residues (Asn59, His165 and Cys207) are highlighted in red sticks within the black dashed box, and an enlarged view in the bottom-right panel.

Figure 7:
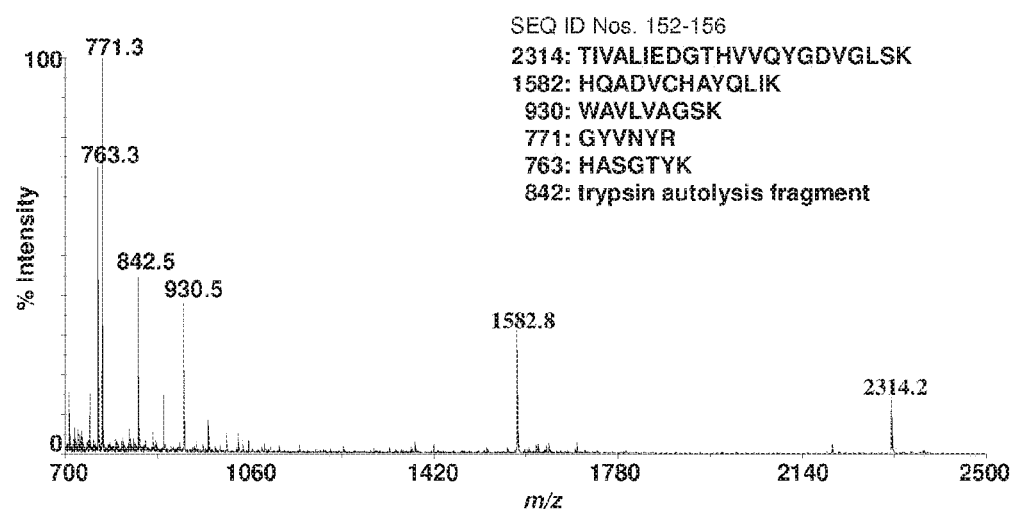

FIG. 7 shows the protein identification of butelase 1 by in-gel tryptic digestion. Five dominant tryptic fragments were sequenced by MS/MS and are shown at the top of the MS profile.

Figure 8:
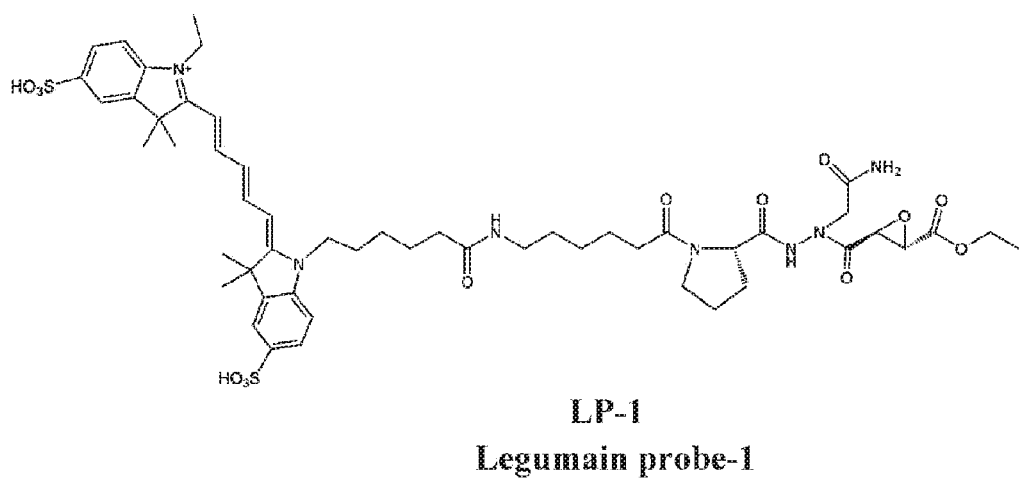

FIG. 8 shows the chemical structure of the leguman specific probe LP-1.

Figure 9:
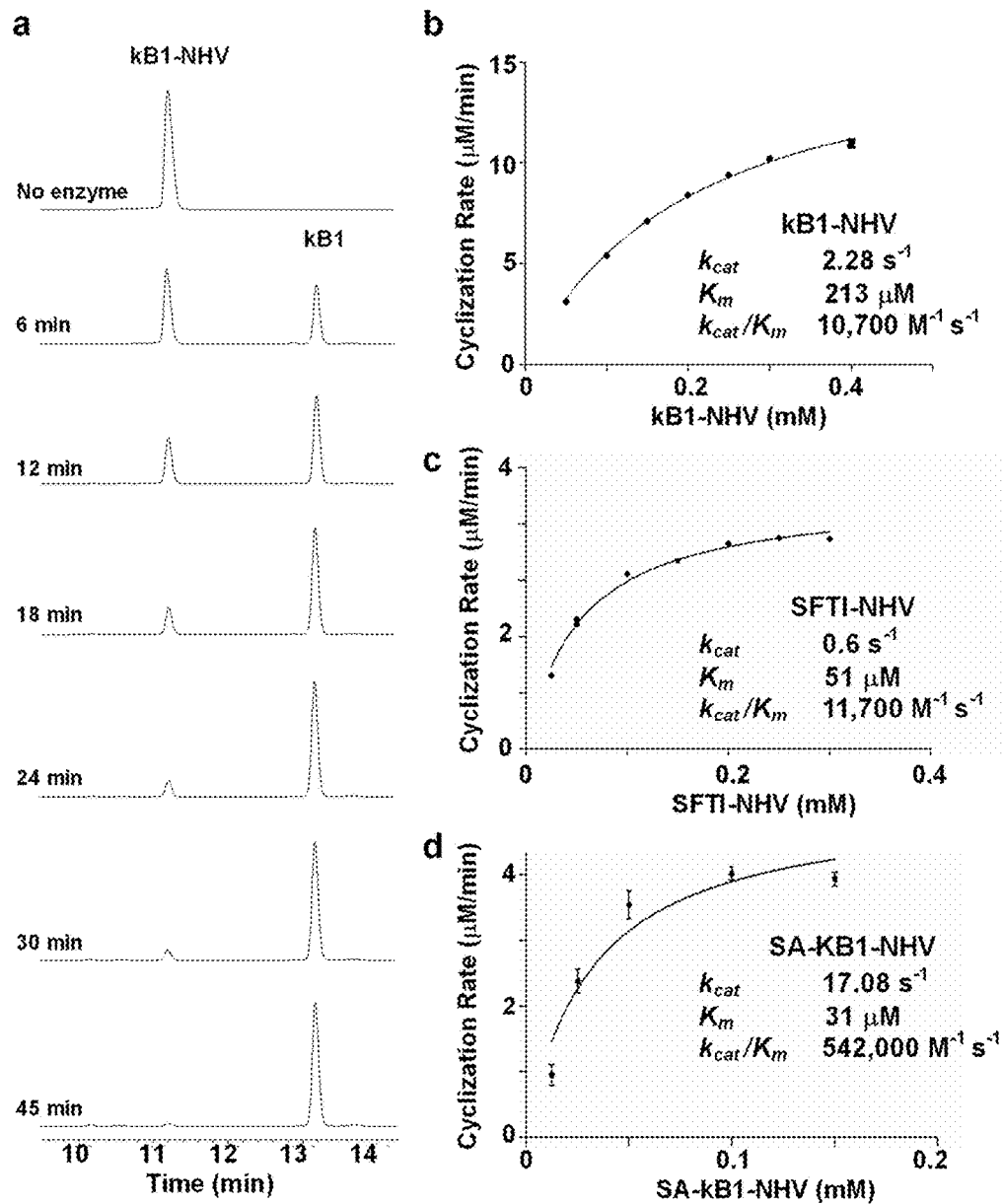

FIG. 9 shows the kinetic characterization of butelase 1 as a peptide cyclase. (a) RP-HPLC traces of the cyclization reaction over a time course of 45 min. The substrate kB1-NHV and the product kB1 are labeled. The assays were performed at 37° C. in the presence of 0.125 µM butelase 1 and 50 µM kB1-NHV. The absorbance was monitored at a wavelength of 220 nm. (b-d) Michaelis-Menten plots of butelase 1 kinetics for kB1-NHV (SEQ ID NO: 110), SFTI-NHV (SEQ ID NO: 135) and SA-kB1-NHV. The cyclization rates were calculated by converting the HPLC-peak areas of the products into concentrations. For the kinetic measurements of kB1-NHV (SEQ ID NO: 110) and SFTI-NHV (SEQ ID NO: 135), the assays were performed at 37° C. for 12 min in the presence of 0.125 µM butelase 1 and varying substrate concentrations. For SA-kB1-NHV, due to much faster cyclization rate, the enzyme concentration was used at 5 nM instead of 0.125 µM and the incubation time was reduced to 6 min.

Figure 10:
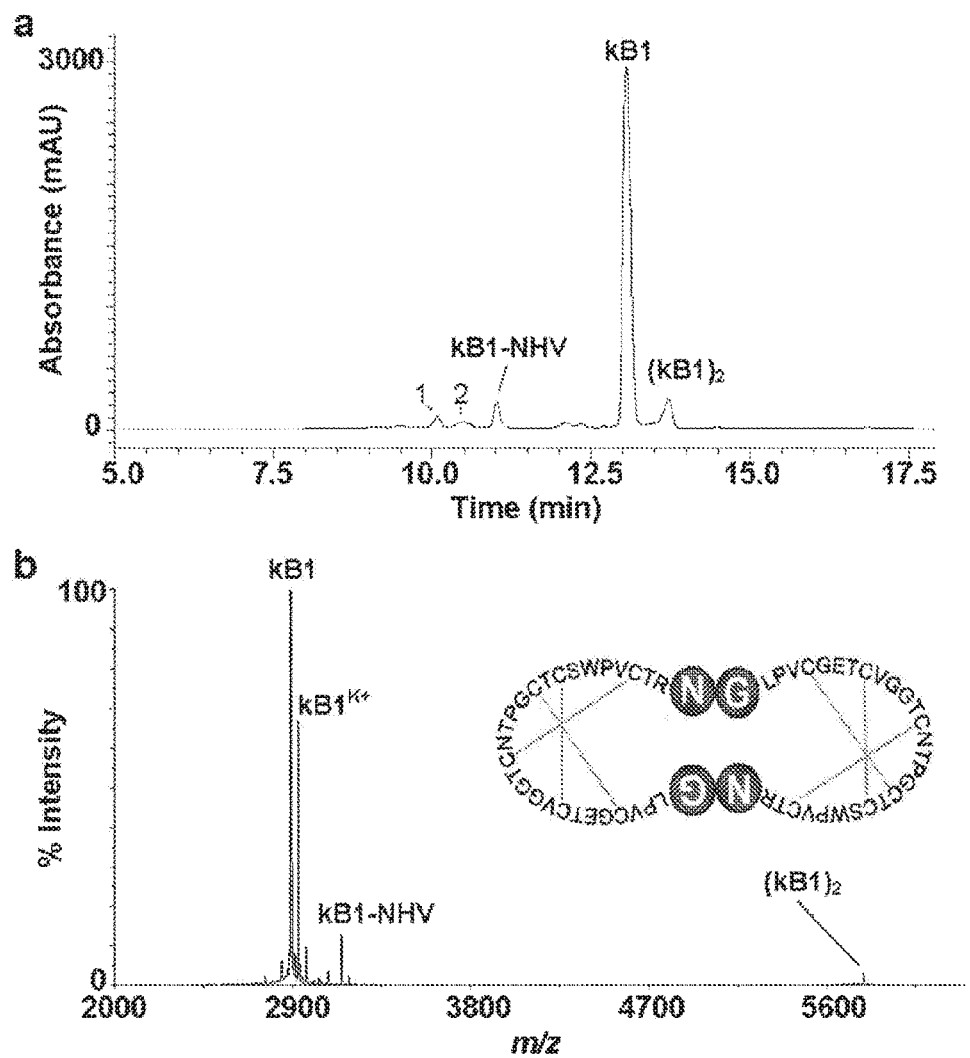

FIG. 10 shows cyclodimer formation of kB1. (a) RP-HPLC profile illustrates the cyclodimer formation of kB1. The reaction was performed at 37° C., for 4 h in the presence of 0.125 µvM butelase 1 and 500 µM kB1-NHV. Peak 1 is the isomer of kB1 with the same m/z value of 2891 as native cyclic kB1. Peak 2 has the m/z value of 2893, which indicates the reduction of one disulfide bond of kB1. The substrate kB1-NHV and the products, kB1 and $(kB1)_2$ are labeled at peak apex. (b) MS profile illustrates the cyclodimer formation of kB1 (SEQ ID NO: 139). Peak labeled with $K^+$ is the potassium adduct.

Figure 11:
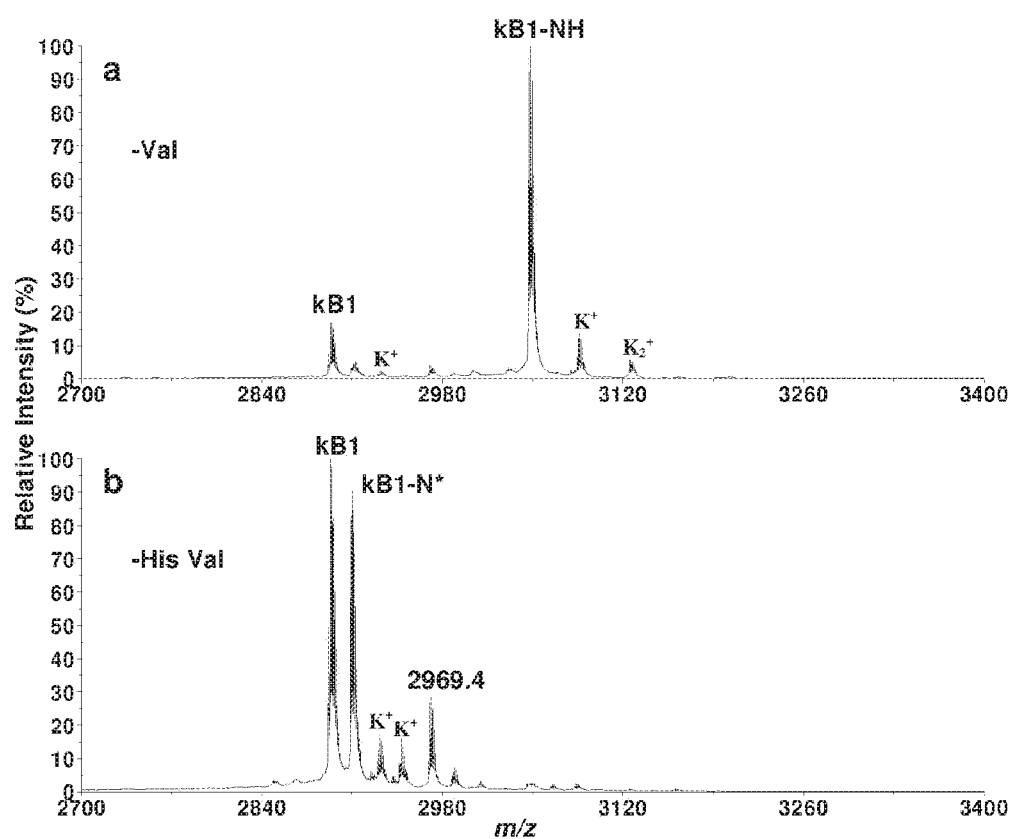

FIG. 11 shows MS profiles of kB1-NHV truncated analogs after treatment with butelase 1. Assays were performed at 37° C. for 30 h in the presence of 0.125 µM butelase 1 and 50 µM of each substrate. (a) MS profile of kB1-NH treated with butelase 1. (b) MS profile of kB1-N* treated with butelase 1. The kB1 product and truncated analogs, kB1-NH and kB1-N*, were labeled at the peak apex. The peak with an m/z value of 2969.4 represents a modified cyclic kB1 where one cysteine residue is S-alkylated with β-ME. Peaks labeled with $K^+$ and $K_2^+$ are ion adducts that correspond to the binding of one or two potassium ions, respectively.

Figure 12:
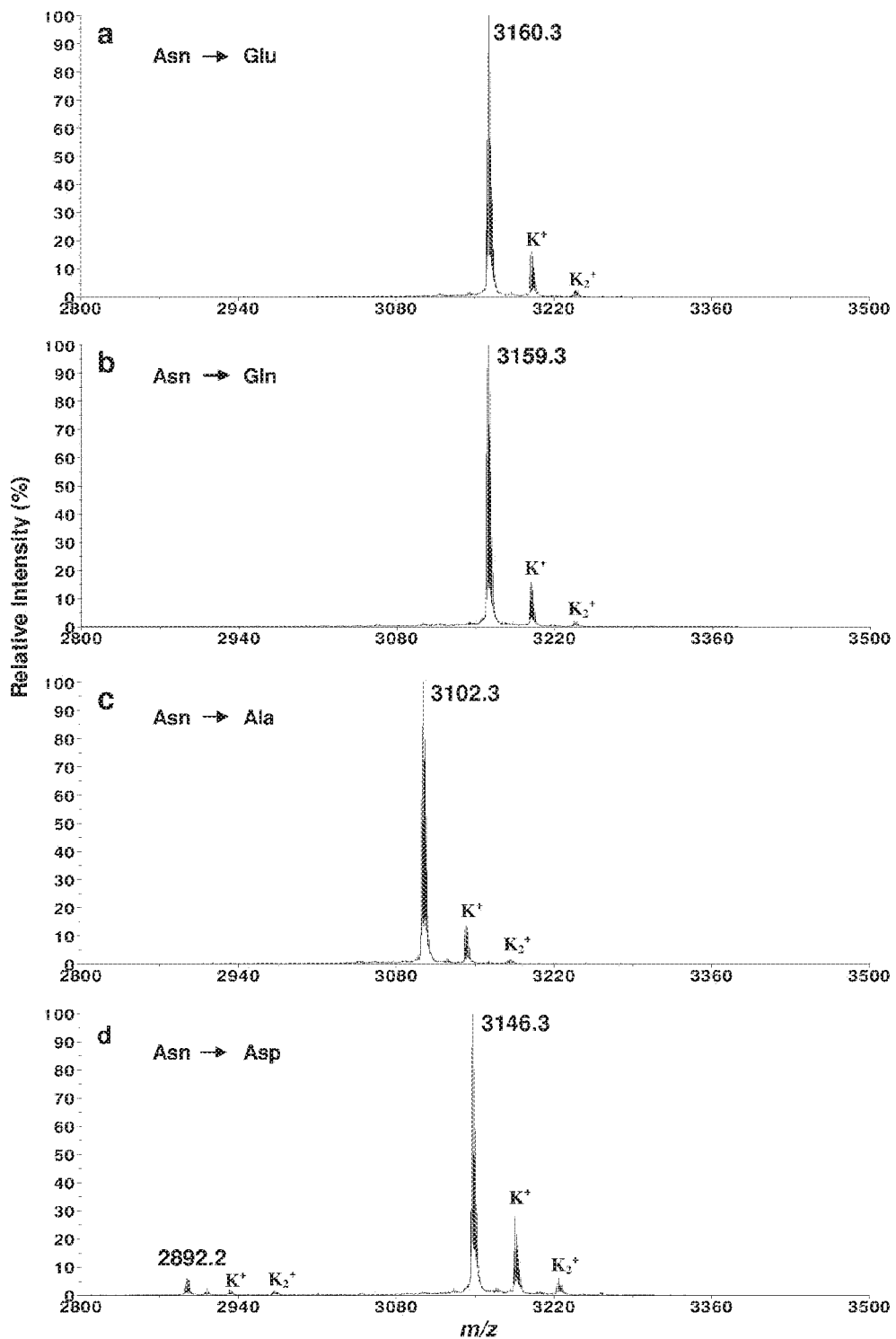

FIG. 12 shows MS profiles of the kB1-NHV analogs after treatment with butelase 1. (a-d) The conserved Asn at the P1 position was replaced by Glu, Gln, Ala or Asp residues in the kB1-NHV substrate. Assays were performed at 37° C. for 4 h in the presence of 0.125 pM butelase 1 and 50 μM of each substrate. The masses of the kB1-NHV analogs are labeled at the peak apex. In the case of kB1-DHV, a cyclized product was observed with an m/z value of 2892. Peaks labeled with $K^+$ and $K_2^+$ are ion adducts that correspond to the binding of one or two potassium ions, respectively.

Figure 13:
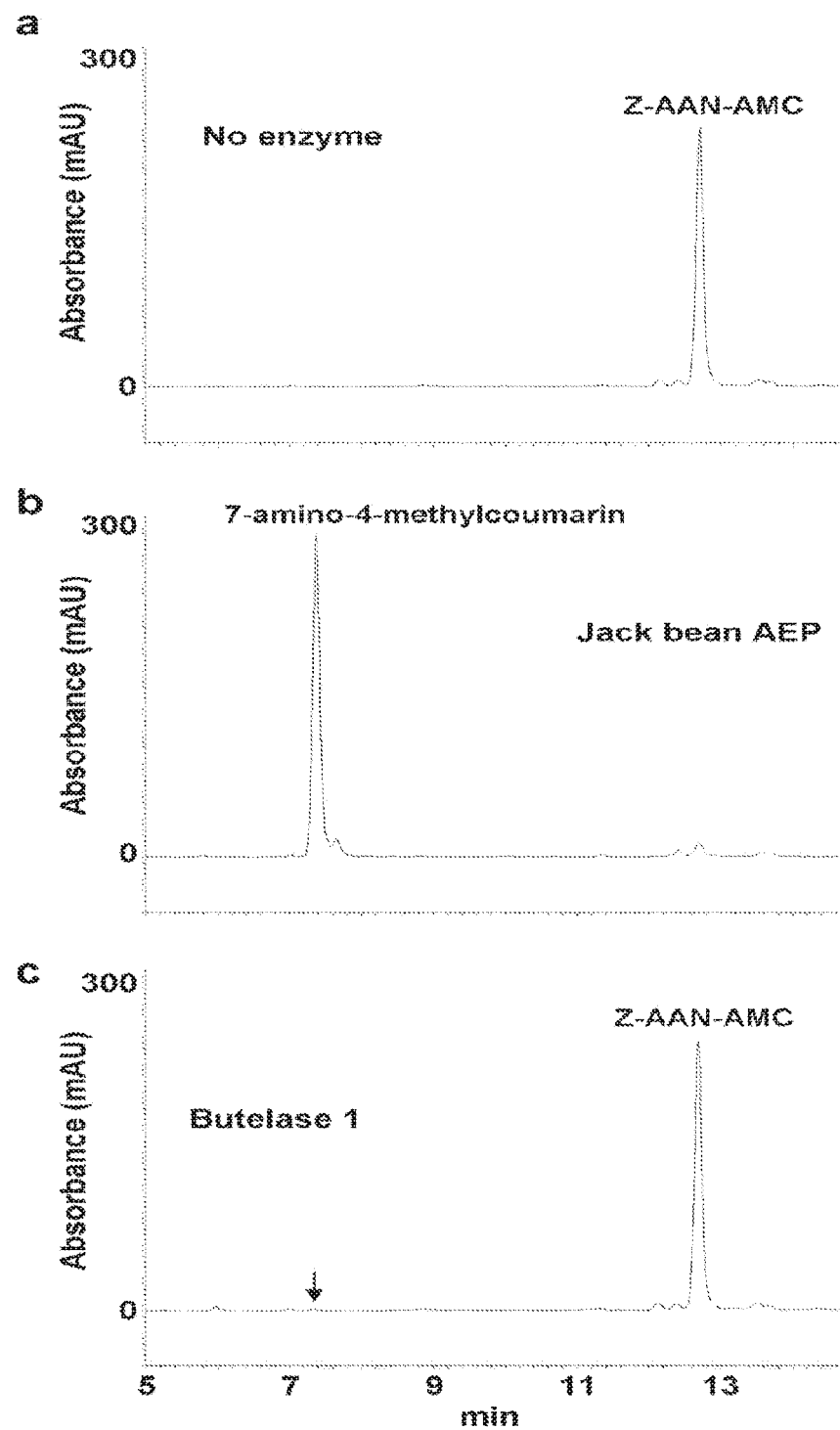

FIG. 13 shows HPLC profiles of Z-AAN-AMC treatment with jack bean legumain and butelase 1. (a) HPLC trace of Z-AAN-AMC as a control. (b) HPLC trace showing the hydrolyzed product 7-amino-4-methylcoumarin catalyzed by jack bean legumain. The assay was performed at 37° C. for 30 h in the presence of 8 μU jack bean legumain and 50 μM Z-AAN-AMC. (c) HPLC trace showing the effect of butelase 1 on Z-AAN-AMC. The assay was performed at 37° C. for 30 h in the presence of 0.125 μM butelase 1 and 50 μM Z-AAN-AMC. No significant hydrolyzed product (indicated by the arrow) was observed after 30 h incubation. The absorbance was monitored at a wavelength of 254 nm.

Figure 14:
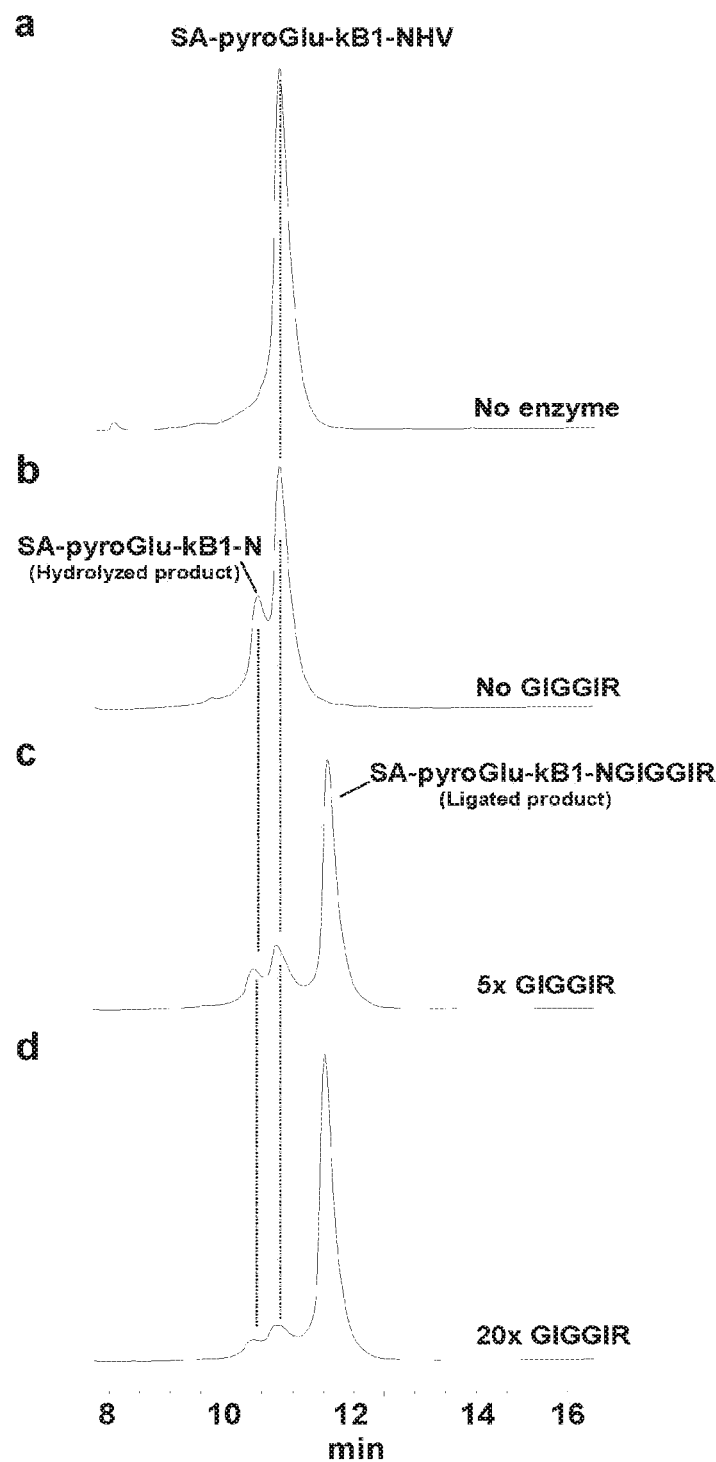

FIG. 14 shows HPLC profiles of SA-pyroGlu-kB1-NHV ligation with GIGGIR(SEQ ID NO:123). (a) HPLC trace of SA-pyroGlu-kB1-NHV as a control. (b) HPLC trace showing the hydrolyzed product SA-pyroGlu-kB1-N in the absence of butelase 1. (c) HPLC trace showing the ligation reaction in the presence of 5 time excess of GIGGIR (SEQ ID NO: 123) (250 pM). (d) HPLC trace showing the ligated reaction in the presence of 20 time excess of GIGGIR (SEQ ID NO: 123) (1 mM). The ligation reactions were performed at 37° C. for 20 min in the presence of 0.125 μM butelase 1 and 50 μM SA-pyroGlu-kB1-NHV and varying concentration of GIGGIR (SEQ ID NO: 123) (0-1 mM).

Figure 15:
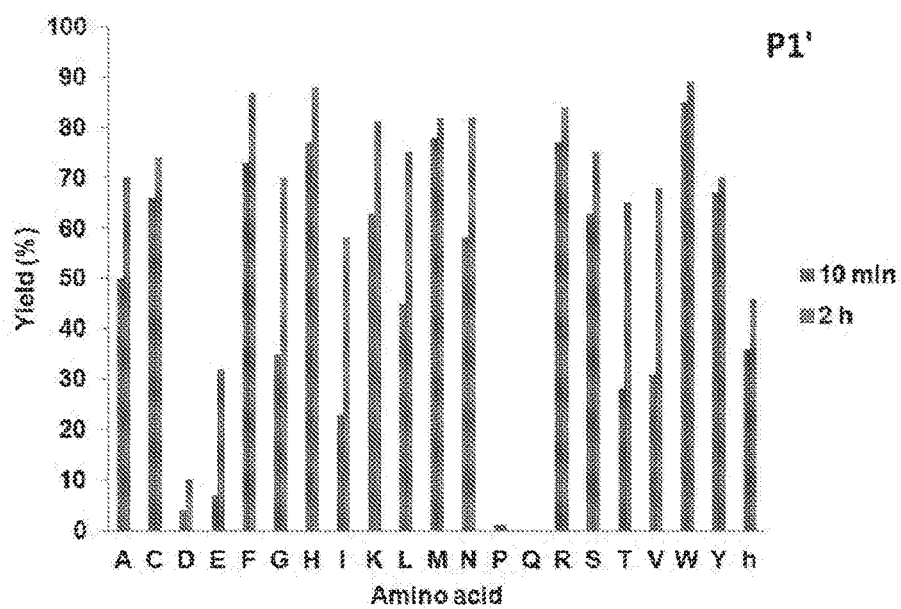
Figure 15:
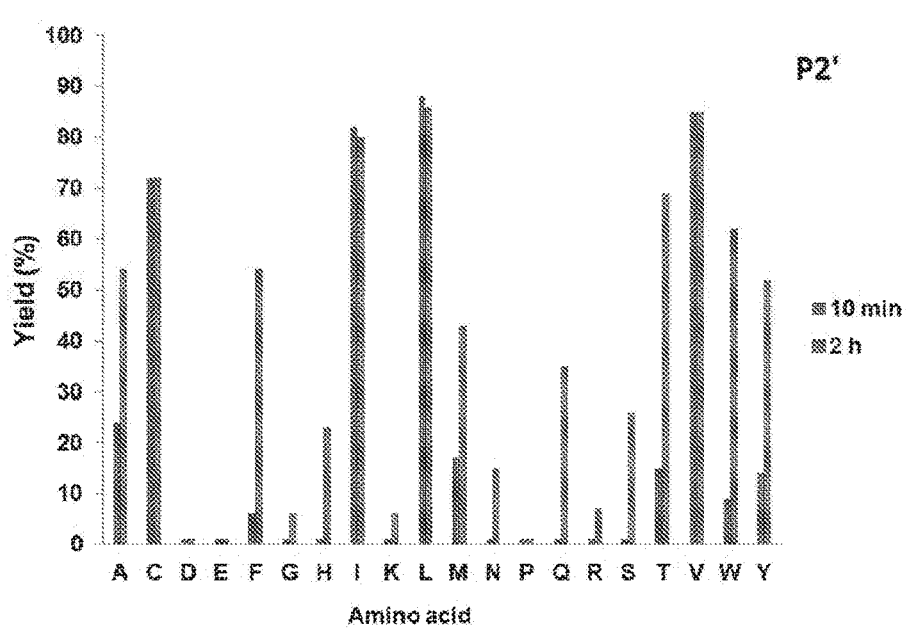

FIG. 15 shows the acceptor specificity of butelase-mediated peptide ligation. (a) Intermolecular ligation of KALVINHV (SEQ ID NO:122) and XIGGIR (SEQ ID NO:123) facilitated by butelase 1. The reactions were performed in the presence of 100 nM butelase 1, 100 μM KALVINHV (SEQ ID NO: 122) and 1 mM XIGGIR (SEQ ID NO: 123) and incubated for 10 min or 2 h. The ligation yields were calculated by converting the HPLC peak area into concentration. (b) Intermolecular ligation of KALVINHV (SEQ ID NO: 122) and LXGGIR (SEQ ID NO: 124) facilitated by butelase 1. The reactions were performed in the presence of 100 nM butelase 1, 100 μM KALVINHV (SEQ ID NO: 122) and 1 mM LXGGIR (SEQ ID NO: 124) and incubated for 10 min or 2 h. The ligation yields were calculated by converting the HPLC peak area into concentration.

Figure 16:
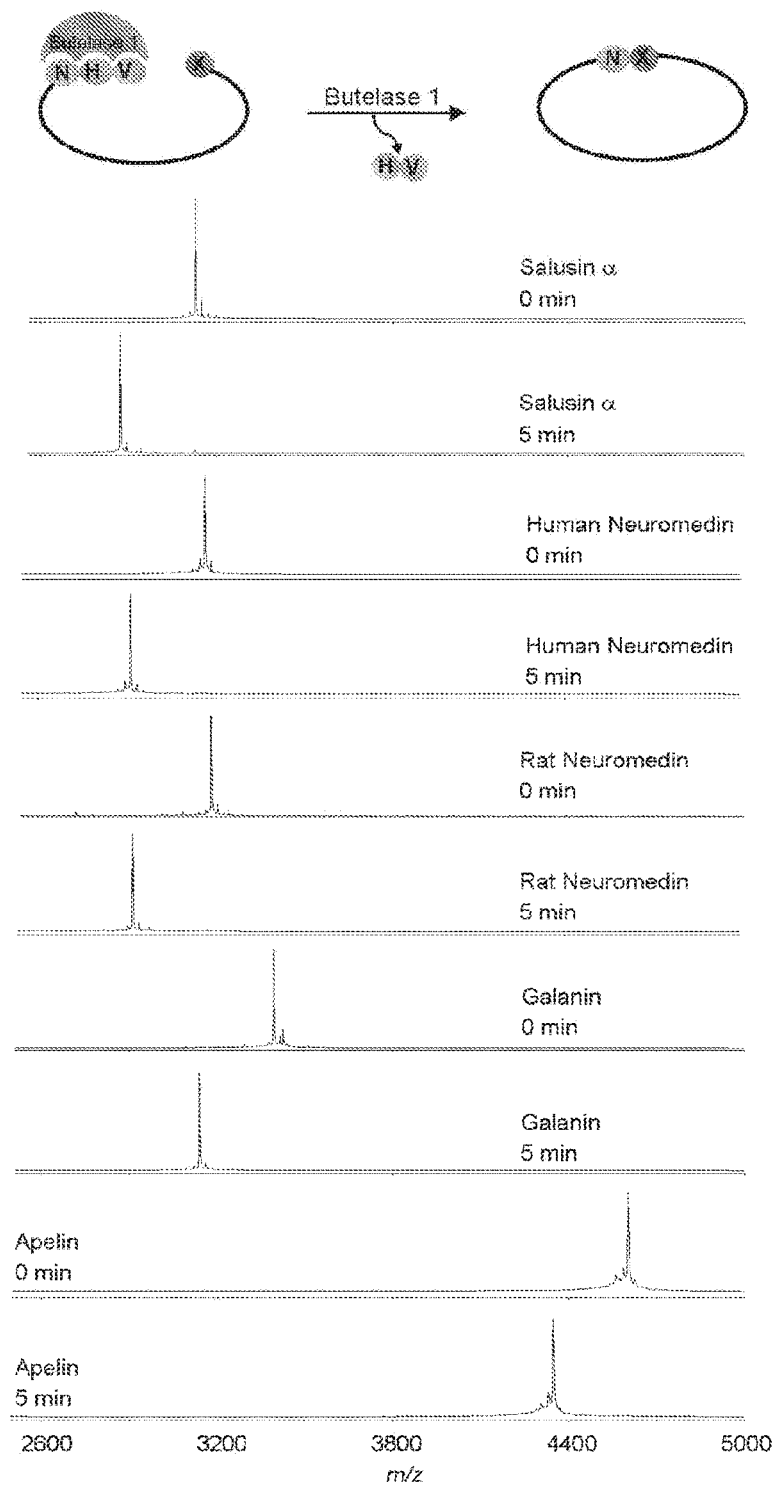

FIG. 16 shows the butelase mediated cyclization of human neuromedin U, salusin a, apelin and galanin and rat neuromedin U. The cyclization reactions were performed in 50 μl reaction mixtures containing 50 μM peptides and 0.1 μM butelase 1 (0.002 molar equivalent) at 37° C. and monitored by MS.

Figure 17:
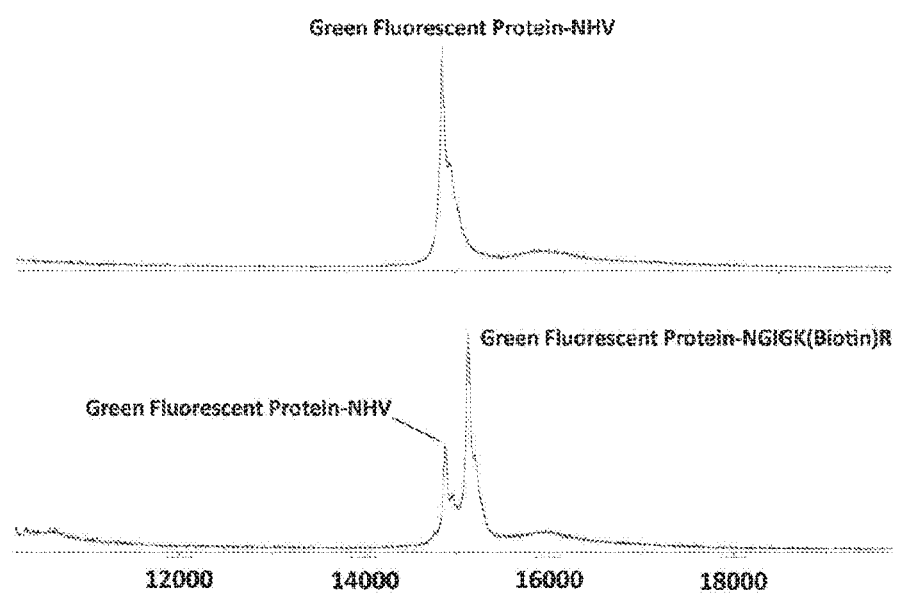

FIG. 17 shows the butelase mediated cyclization of a modified GFP ending with Asn-His-Val motif at the C-terminus and starting with Gly-Ile at the N-terminus. The cyclization reaction was carried in the presence of 25 μM GFP and 0.1 μM butelase 1 (0.004 molar equivalent). The cyclization reaction was monitored by high resolution ESI-MS.

Figure 18:
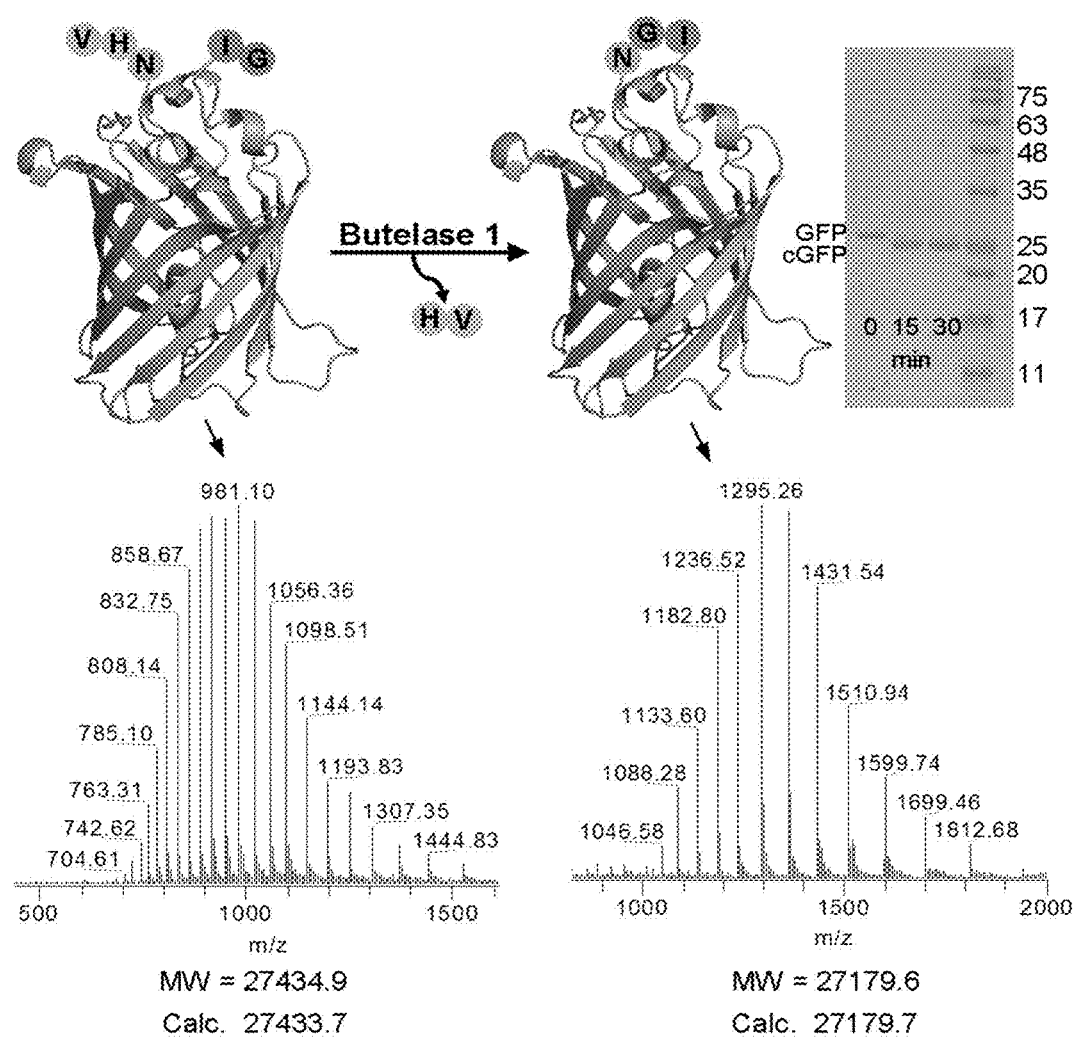

FIG. 18 shows the butelase mediated ligation of GFP with a short peptide GIGK(biotin)R (SEQ ID NO:134). The ligation reaction was performed at 37° C. for 30 minutes in the presence of 0.125 μM butelase 1, 50 μM GFP and 1mM of the peptide substrate and monitored by MS.

Figure 19:
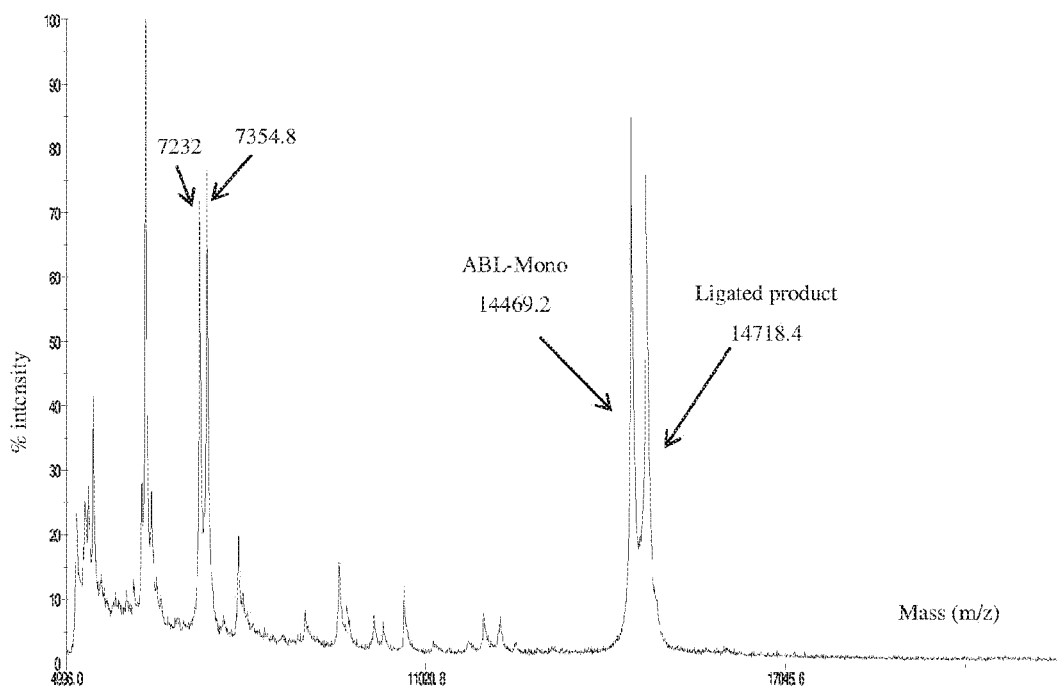
Figure 19:
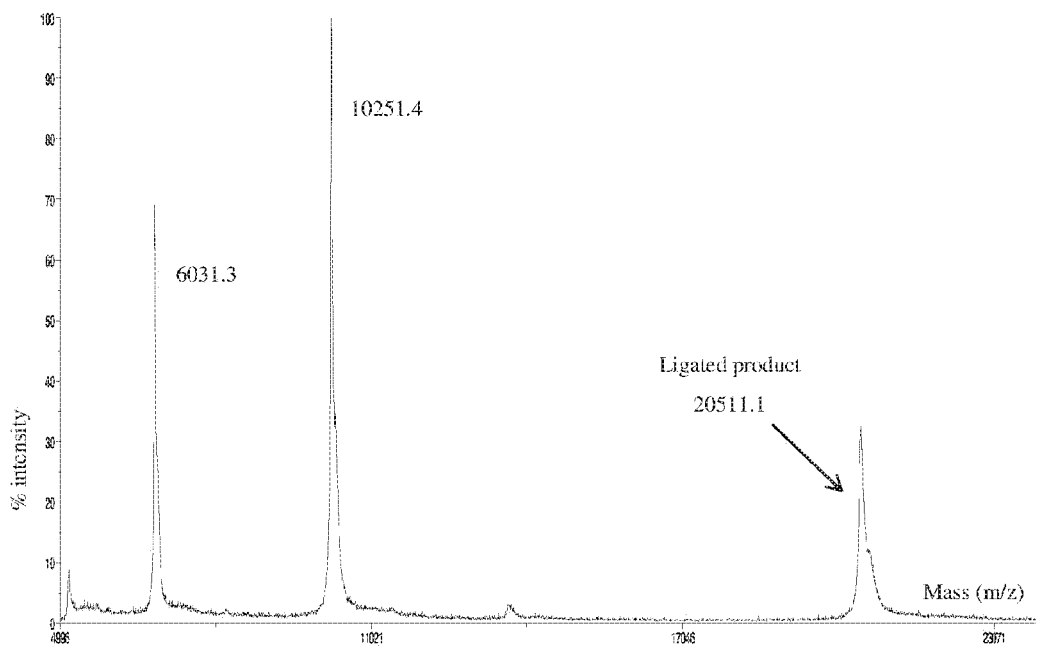

FIG. 19 shows the mass spectrometry profile of ligation between the fluorescently labelled peptide GIR-AMC (AMC=7-amino-4-methylcoumarin) and (a) ABL-Mono and (b) ERK-Darp for 20 minute incubation. 7232 and 7354.8 are the peaks of ABL-Mono and its ligated product protonated once. 10251.4 and 6031.3 are the peaks of ERK-Darp ligated product protonated once and twice.

Figure 20:
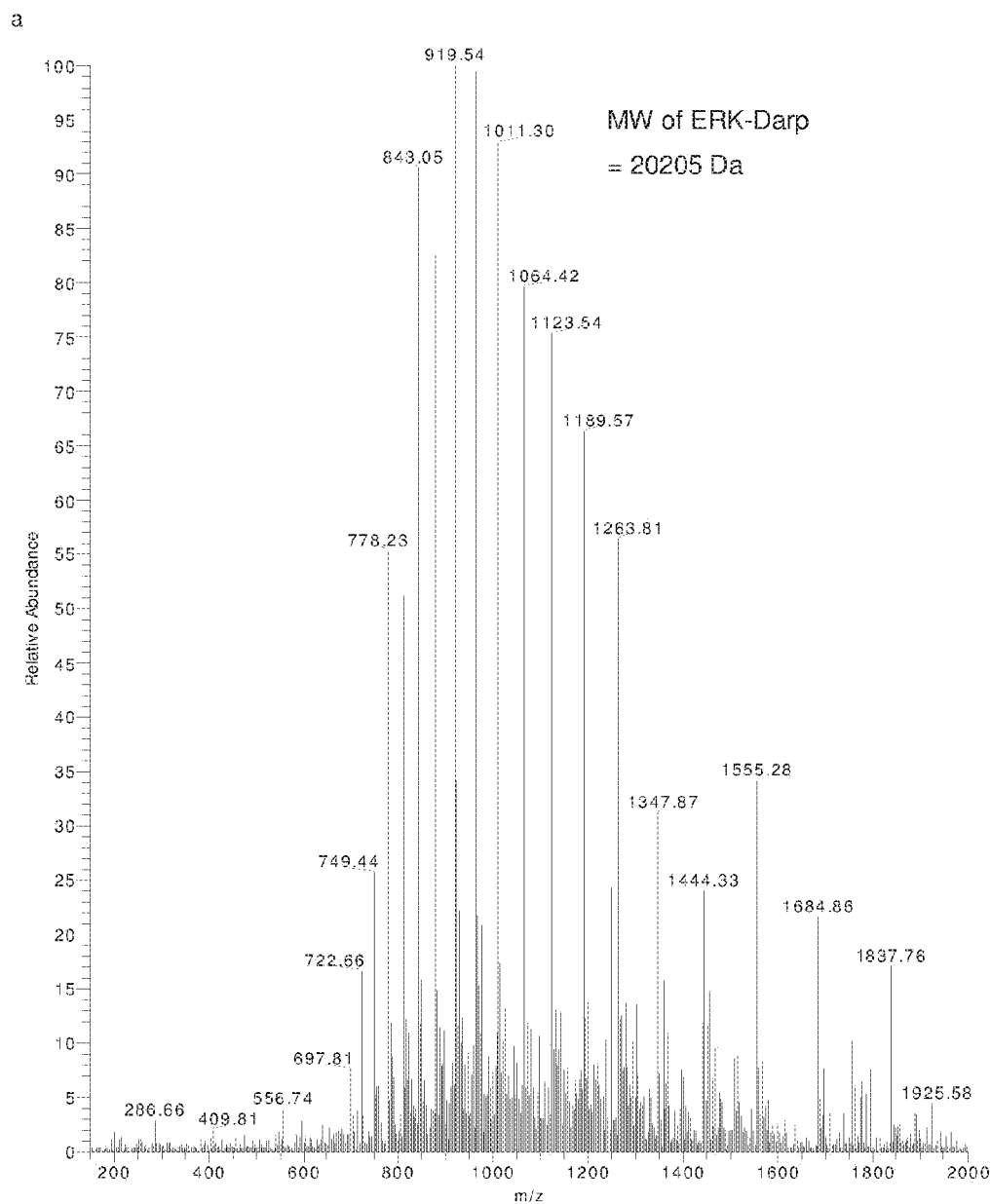
Figure 20:
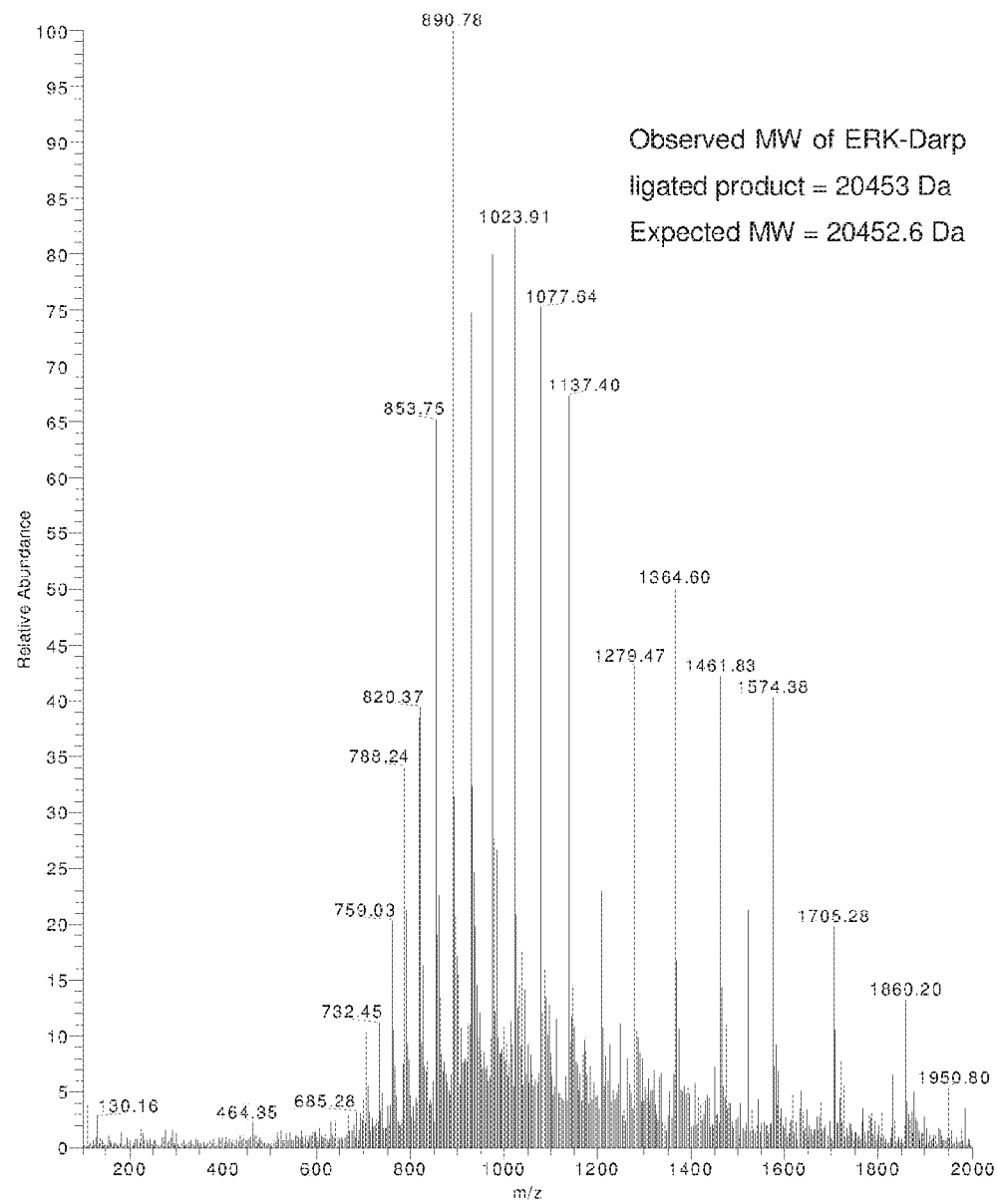
Figure 20:
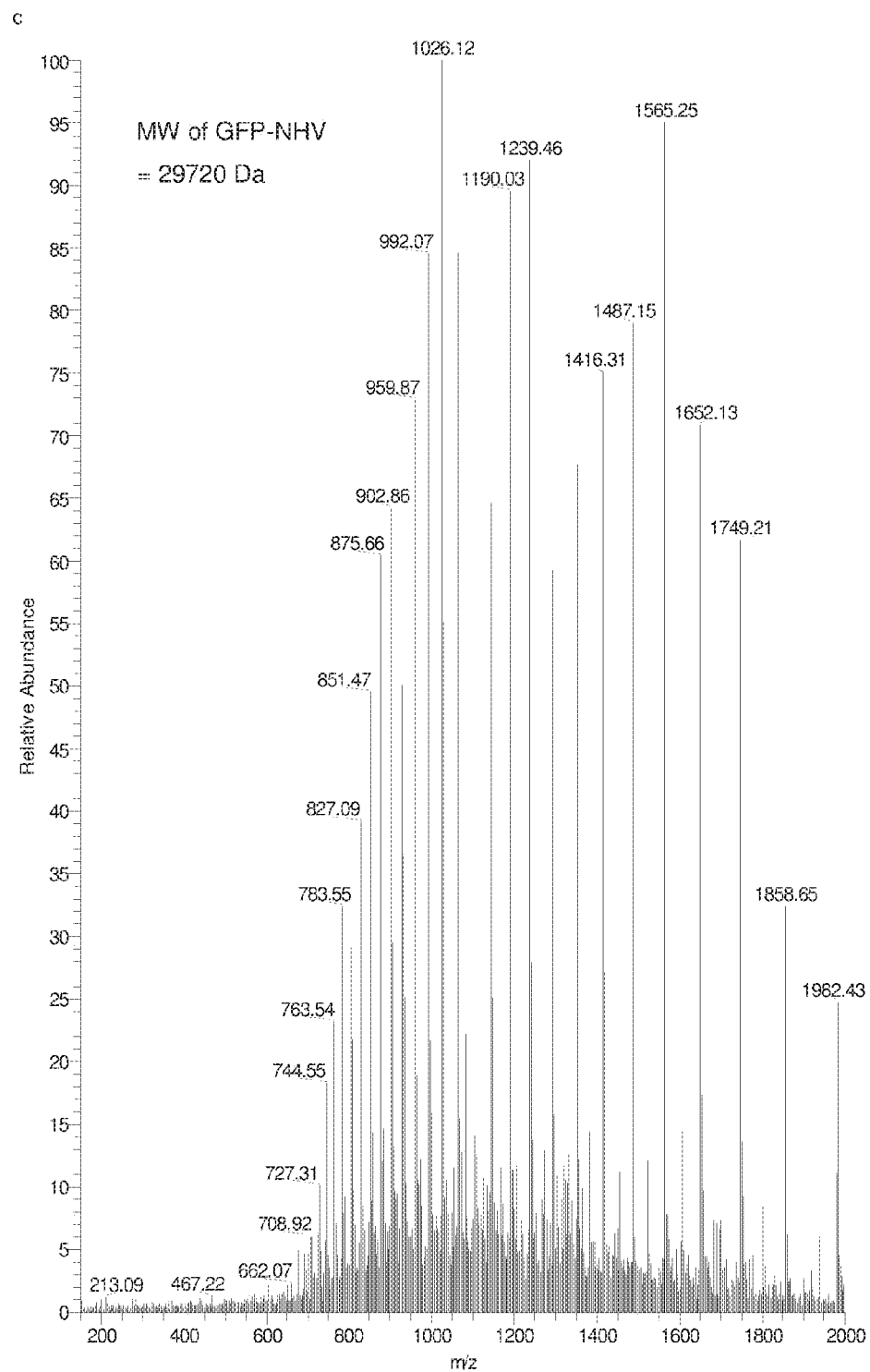
Figure 20:
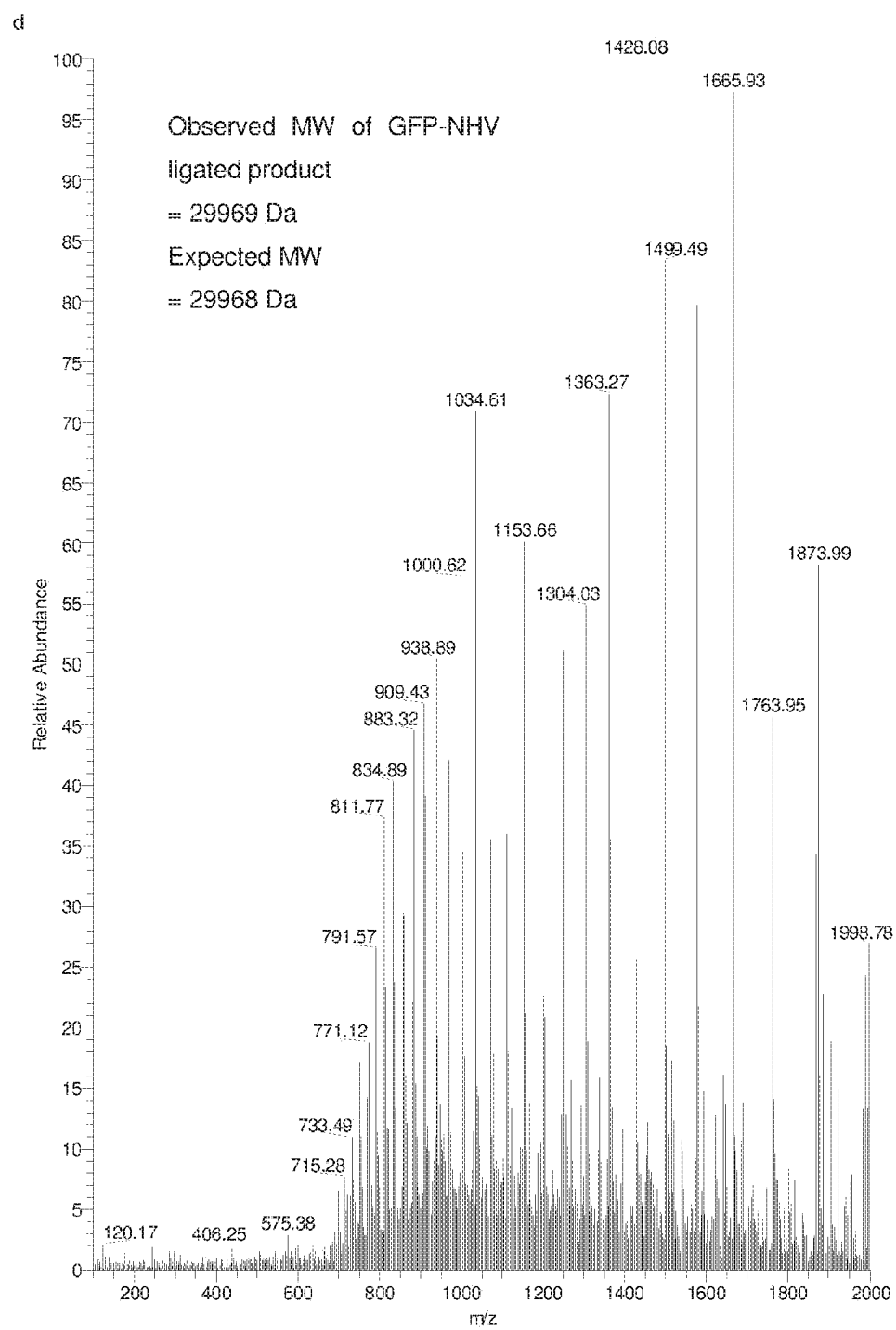

FIG. 20 shows the ESI-MS profiles of (a,c) ERK-Darp and GFP-NHV substrate as the negative controls, (b,d) 50 μM ERK-Darp and 50 μM GFP-NHV incubated with 1 mM FITC-GKNHV (SEQ ID NO: 150) and 50nM butelase 1 for 10 minute at 42° C.

Figure 21:
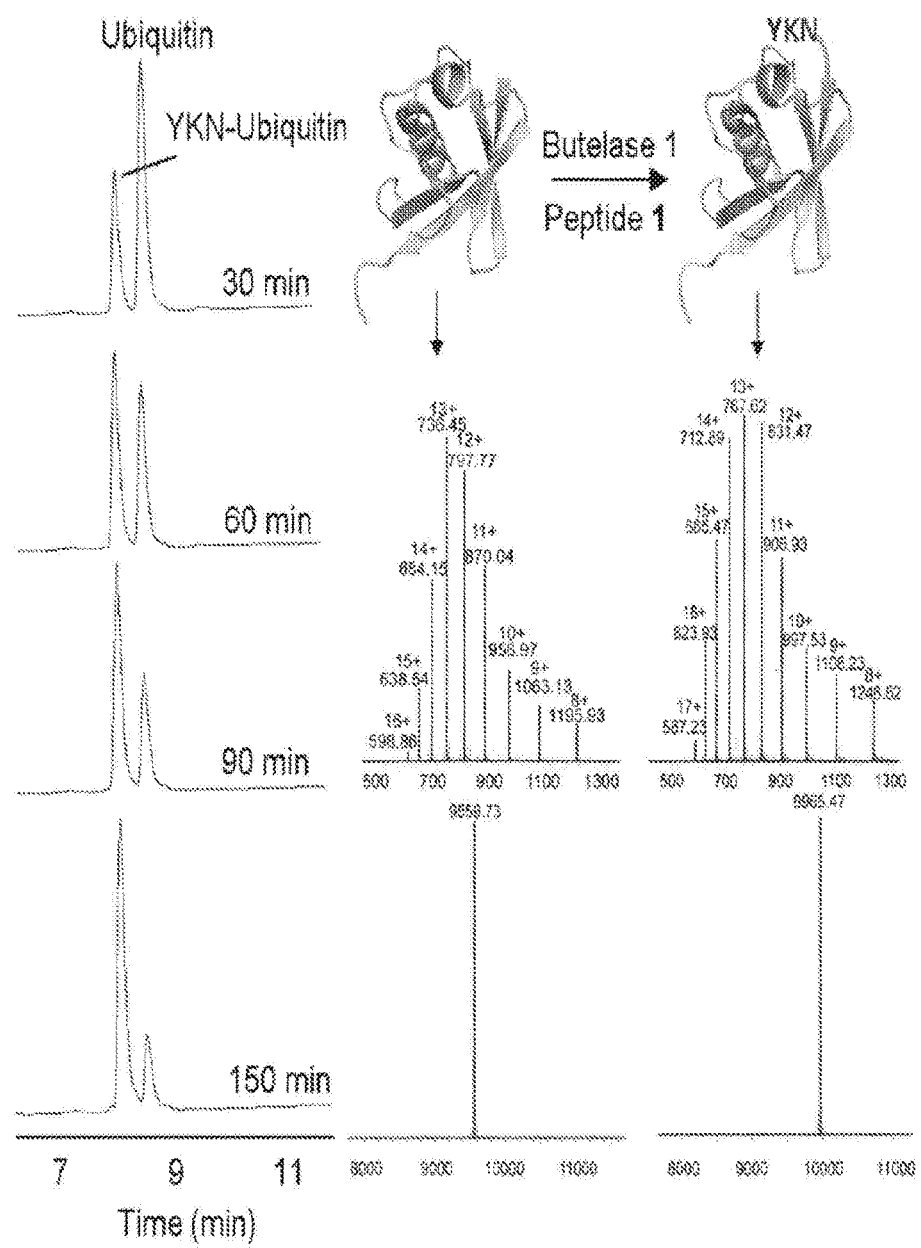

FIG. 21 shows the HPLC and MS profiles of ligation between an ubiquitin (SEQ ID NO:148) and the peptide YKN-thioglycolic acid-V.

Figure 22:
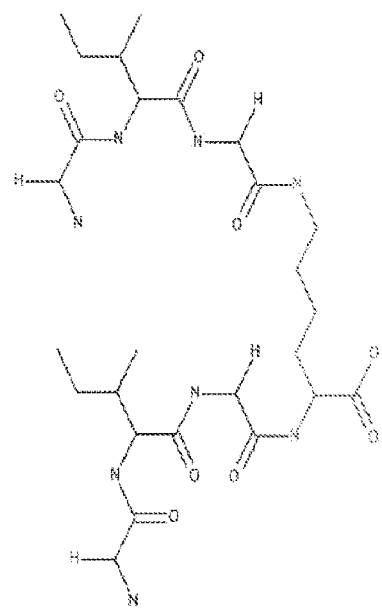
Figure 22:
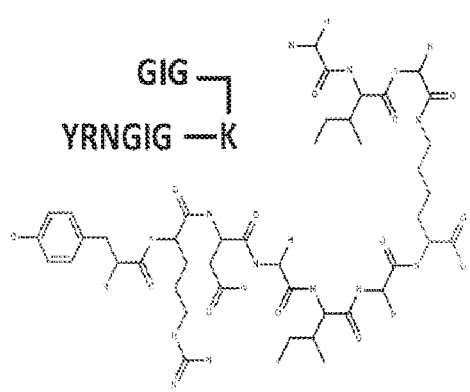
Figure 22:
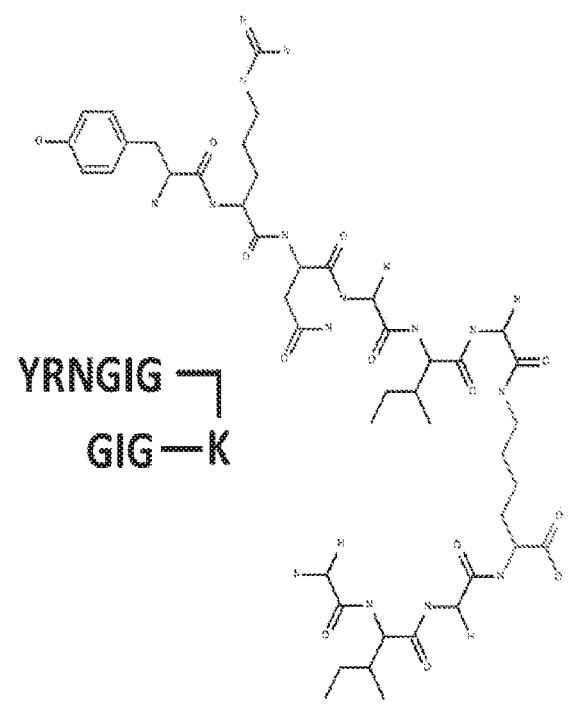
Figure 22:
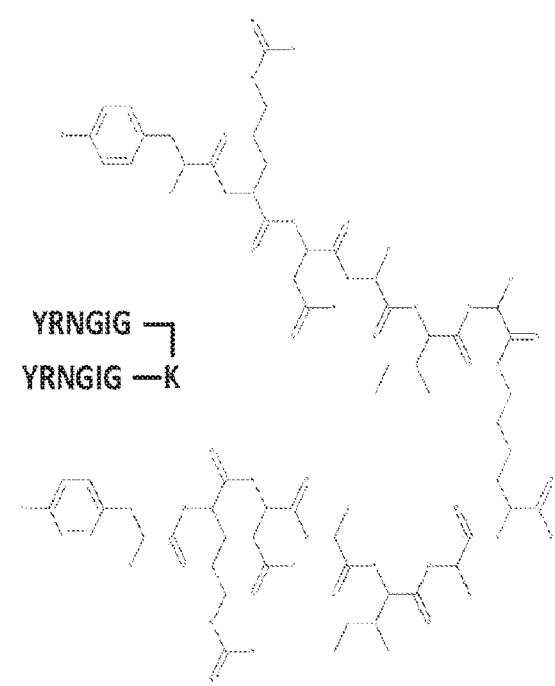
Figure 22:
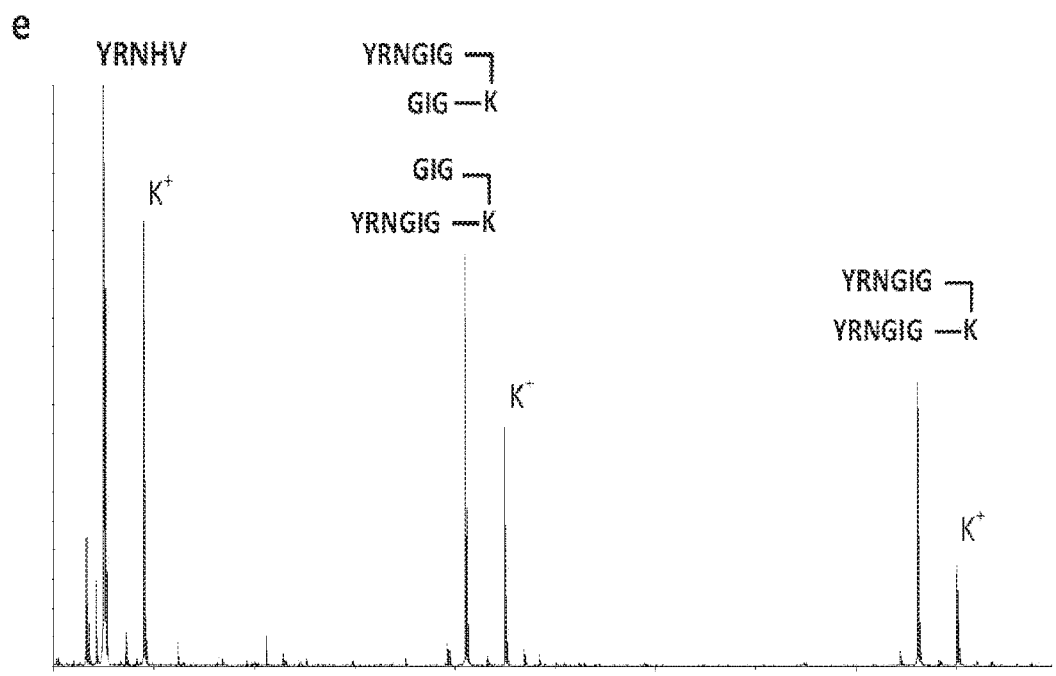

FIG. 22 shows the analysis of butelase 1-mediated dimerization. (a) Structure of G2K dimeric core peptide, (b) and (c) structures of the two different possible mono-ligated G2K peptide (SEQ ID NO: 162), (d) structure of the fully ligated dimer peptide (SEQ ID NO: 163). (e) Mass spectrometry analysis of the dimerization reaction shows the presences of both the mono-ligated and fully ligated dimer (SEQ ID NOS: 125, 162 and 163) respectively.

Figure 23:
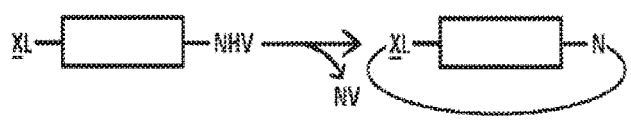
Figure 23:
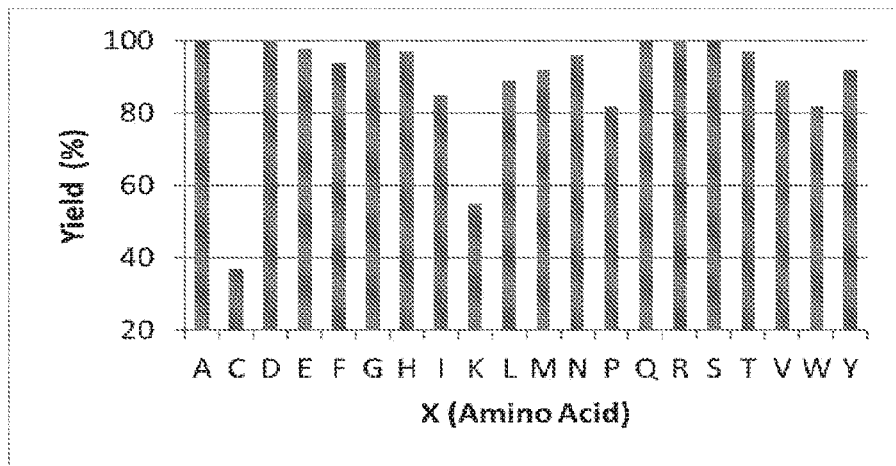
Figure 23:
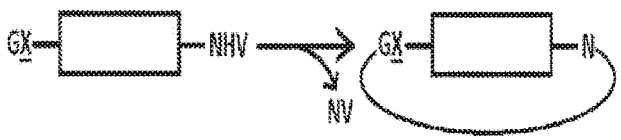
Figure 23:
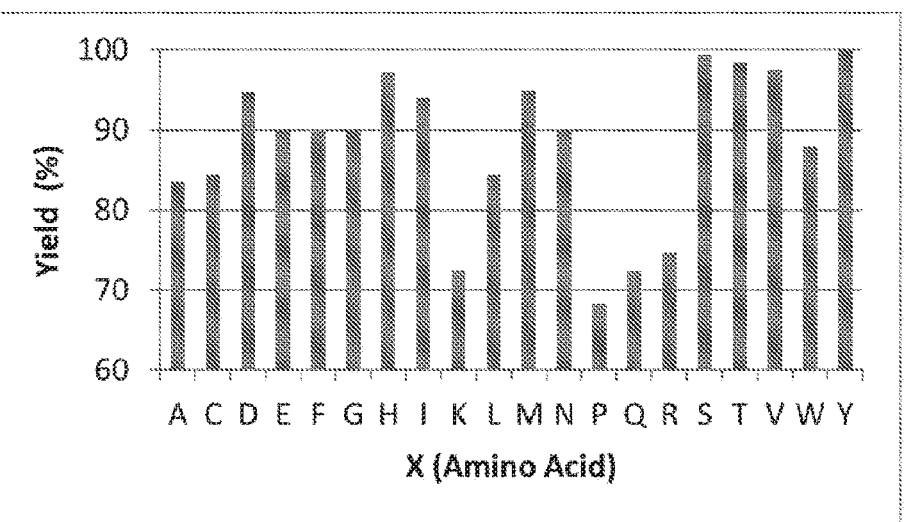
Figure 23:
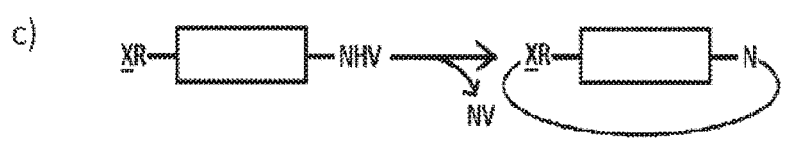
Figure 23:
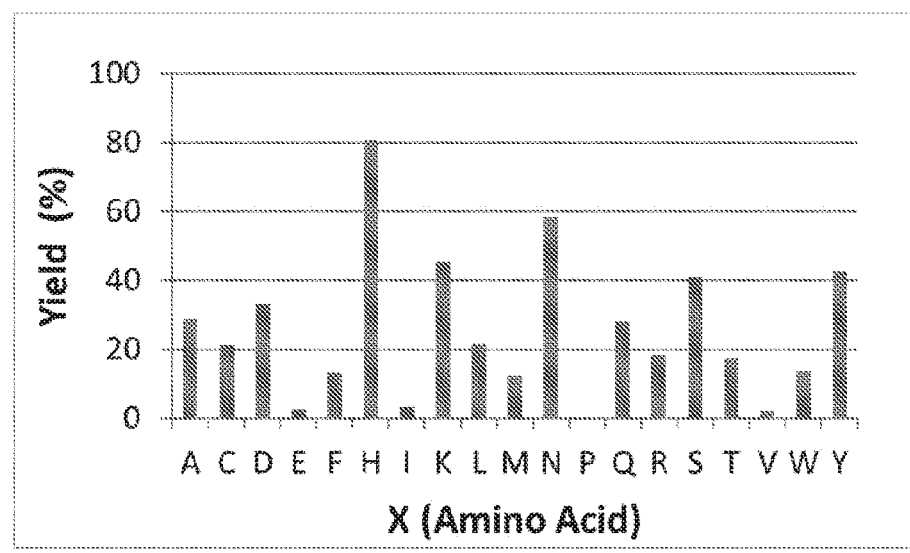

FIG. 23 shows the acceptor specificity of butelase-mediated peptide cyclization. The reactions were performed in the presence of 50 nM butelase 1, 50 μM peptide and incubated for 60 min at 42° C. The cyclization yields were calculated by converting the HPLC peak area into concentration. (a) Intramolecular cyclization of XLYRR-GRYLRRNHV (SEQ ID NO:157) facilitated by butelase 1. (b) Intramolecular ligation of XRLYRGRYLRRNHV (SEQ ID NO:158) facilitated by butelase 1. (c) Intramolecular ligation of GXLYRGRYLRRNHV (SEQ ID NO:159) facilitated by butelase 1.

Figure 24:
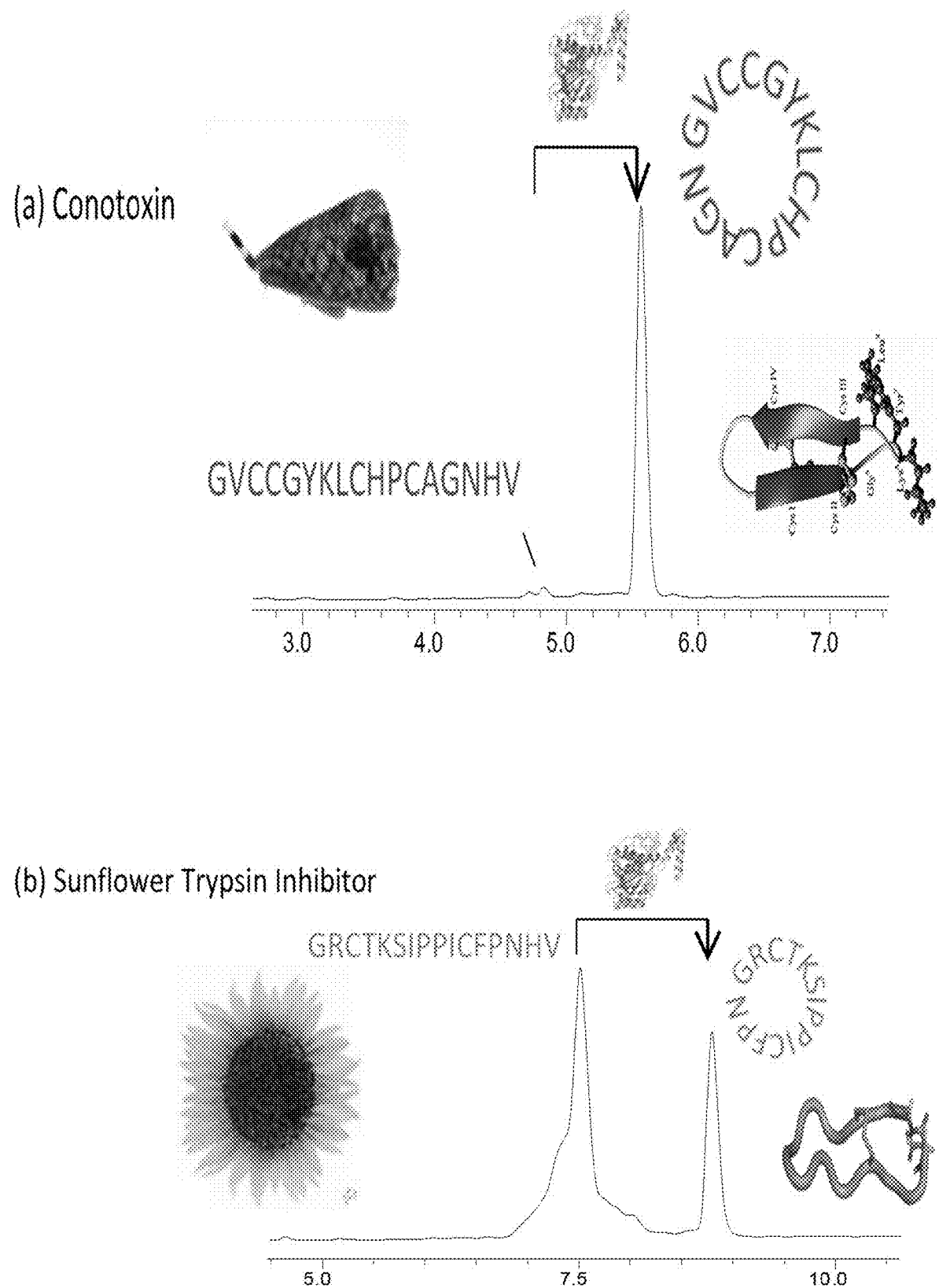
Figure 24:
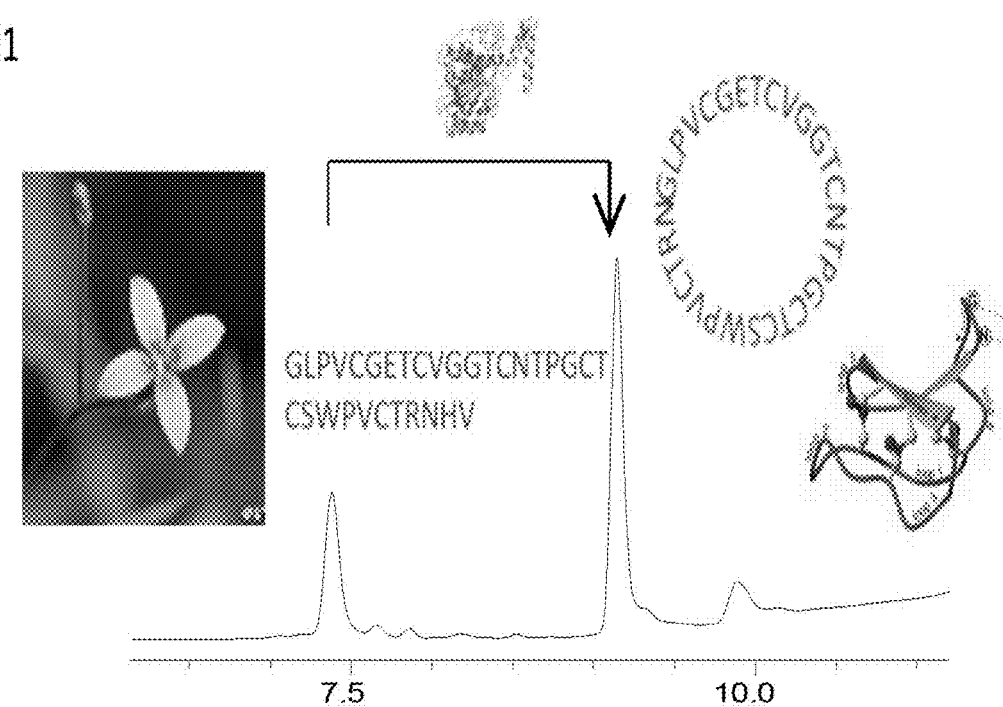

FIG. 24 shows cyclisation assays of peptide substrates (a) conotoxin GV-17 (SEQ ID NO: 111), (b) SFTI-NHV (SEQ ID NO: 135) and (c) kalata B1-NHV (SEQ ID NO: 110) by butelase 1 immobilized onto ProSwift ConA-1S affinity column.

DETAILED DESCRIPTION

The present invention is based on the inventors' identification of a peptide ligase/cyclase enzyme isolated from *Clitoria ternatea* that is capable of ligating/cyclizing peptides with very high catalytic activities. It recognizes a tripeptide motif, Asx-His-Val, at the C-terminus, and mediates peptide backbone cyclization by cleaving the sorting sequence His-Val and ligating Asx to the N-terminal residue to form a circular topology. Significantly, the enzyme can not only efficiently cyclizes cyclotide precursors and various cysteine-rich peptides ranging in sizes from 14 to 58 residues, but also non-cysteine-containing peptides and proteins, such as green fluorescent protein (GFP). This makes it highly versatile and useful in a variety of applications where cyclization of a given peptide or protein is desired.

The invention, in a first aspect, covers said enzyme in isolated form and, more specifically, is directed to an isolated polypeptide comprising, consisting essentially of or consisting of the amino acid sequence as set forth in SEQ ID NO:1. The polypeptide consisting of the amino acid sequence set forth in SEQ ID NO:1 is also referred to as "butelase 1" herein. "Isolated", as used herein, relates to the polypeptide in a form where it has been at least partially separated from other cellular components it may naturally occur or associate with. The polypeptide may be a recombinant polypeptide, i.e. polypeptide produced in a genetically engineered organism that does not naturally produce said polypeptide.

A polypeptide according to the present invention exhibits protein ligation activity, i.e. it is capable of forming a peptide bond between two amino acid residues, with these two amino acid residues being located on the same or different peptides or proteins, preferably on the same peptide or protein so that said ligation activity cyclizes said peptide or protein. Accordingly, in various embodiments, the polypeptide of the invention has cyclase activity. In various embodiments, this protein ligation or cyclase activity also includes an endopeptidase activity, i.e. the polypeptide form a peptide bond between two amino acid residues and at the same time cleaves an existing peptide bond. This means that cyclization need not to occur between the termini of a given peptide but can also occur between internal amino acid residues, with the amino acids C-terminal or N-terminal to the amino acid used for cyclization being cleaved off. In a preferred embodiment, the polypeptide forms a cyclized peptide by ligating the N-terminus to an internal amino acid and cleaving the remaining C-terminal amino acids.

The polypeptide as disclosed herein is "Asx-specific" in that the amino acid C-terminal to which ligation occurs, i.e. the C-terminal end of the peptide that is ligated, is either asparagine (Asn or N) or aspartic acid (Asp or D), preferably asparagine. In various embodiments, a polypeptide according to the present invention also has ligation activity for a peptide that has a C-terminal Asx (N or D) residue that is amidated, i.e. the C-terminal carboxy group is replaced by an amide group. This amide group is cleaved off in the course of the ligation reaction. Accordingly, such amidated peptide substrates, while still being ligated/cyclized, do not comprise the naturally occurring tripeptide motif NHV.

"Polypeptide", as used herein, relates to polymers made from amino acids connected by peptide bonds. The polypeptides, as defined herein, can comprise 50 or more amino acids, preferably 100 or more amino acids. "Peptides", as used herein, relates to polymers made from amino acids connected by peptide bonds. The peptides, as defined herein, can comprise 2 or more amino acids, preferably 5 or more amino acids, more preferably 10 or more amino acids, for example 10 to 50 amino acids.

In various embodiments, the polypeptide comprises or consists of an amino acid sequence that is at least 60%, 65%, 70%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical or homologous to the amino acid sequence set forth in SEQ ID NO:1 over its entire length. In some embodiments, it has an amino acid sequence that shares at least 60, preferably at least 70, more preferably at least 80, most preferably at least 90% sequence identity with the amino acid sequence set forth in SEQ ID NO:1 over its entire length or has an amino acid sequence that shares at least 80, preferably at least 90, more preferably at least 95% sequence homology with the amino acid sequence set forth in SEQ ID NO:1over its entire length.

In various embodiments, the polypeptide may be a precursor of the mature enzyme. In such embodiments, it may comprise or consist of the amino acid sequence set forth in SEQ ID NO:2. Also encompassed are polypeptides having an amino acid sequence that is at least 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical or homologous to the amino acid sequence set forth in SEQ ID NO:2 over its entire length.

The identity of nucleic acid sequences or amino acid sequences is generally determined by means of a sequence comparison. This sequence comparison is based on the BLAST algorithm that is established in the existing art and commonly used (cf. for example Altschul et al. (1990) "Basic local alignment search tool", J. Mol. Biol. 215:403-410, and Altschul et al. (1997): "Gapped BLAST and PSI-BLAST: a new generation of protein database search programs"; Nucleic Acids Res., 25, p. 3389-3402)and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

A comparison of this kind also allows a statement as to the similarity to one another of the sequences that are being compared. This is usually indicated as a percentage identity, i.e. the proportion of identical nucleotides or amino acid residues at the same positions or at positions corresponding to one another in an alignment. The more broadly construed term "homology", in the context of amino acid sequences, also incorporates consideration of the conserved amino acid exchanges, i.e. amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous and identical regions of various nucleic acid sequences or amino acid sequences are therefore defined by way of matches in the sequences. Such regions often exhibit identical functions. They can be small, and can encompass only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity and homology herein refer to the full length of the respectively indicated nucleic acid sequence or amino acid sequence.

In various embodiments, the polypeptide described herein comprises the amino acid residue N at the position corresponding to position 19 of SEQ ID NO:1; and/or the amino acid residue H at the position corresponding to position 124 of SEQ ID NO:1; and/or the amino acid residue C at the position corresponding to position 166 of SEQ ID NO:1. It has been found that these amino acid residues putatively play a role in the catalytic activity of the polypeptide. In preferred embodiments, the polypeptides thus comprise at least two, more preferably all three of the above indicated residues at the given or corresponding positions.

The isolated polypeptides of the present invention preferably have enzymatic activity, in particular protein ligase, preferably cyclase activity. In various embodiments, this means that they can ligate a given peptide with an efficiency of 80% or more, preferably 90% or more. The protein ligation, preferably cyclization, reaction is preferably comparably fast, i.e. said polypeptide can cyclize a given peptide with a $K_m$ of 500

M or less, preferably 250

M or less; and/or a $k_{cat}$ of at least 0.05 s$^{-1}$, preferably at least 0.5 s$^{-1}$, more preferably at least 1.0 s$^{-1}$, most preferably at least 1.5 s$^{-1}$. Preferred polypeptides satisfy both requirements, i.e. the $K_m$ and $k_{cat}$ requirement. Methods to determine such Michaelis-Menten kinetics are well known in the art and can be routinely applied by those skilled in the art. It is preferred that the polypeptides of the invention have at least 50%, more preferably at least 70, most preferably at least 90% of the protein ligase activity of the enzyme having the amino acid sequence of SEQ ID NO:1.

Polypeptides according to the embodiments described herein can comprise amino acid modifications, in particular amino acid substitutions, insertions, or deletions. Such polypeptides are, for example, further developed by targeted genetic modification, i.e. by way of mutagenesis methods, and optimized for specific purposes or with regard to special properties (for example, with regard to their catalytic activity, stability, etc.). In addition, nucleic acids contemplated herein can be introduced into recombination formulations and thereby used to generate entirely novel protein ligases, cyclases or other polypeptides.

In various embodiments, the polypeptides having ligase/cyclase activity may be posttranslationally modified, for example glycosylated. Such modification may be carried out by recombinant means, i.e. directly in the host cell upon production, or may be achieved chemically or enzymatically after synthesis of the polypeptide, for example in vitro.

The objective may be to introduce targeted mutations, such as substitutions, insertions, or deletions, into the known molecules in order, for example, to alter substrate specificity and/or improve the catalytic activity. For this purpose, in particular, the surface charges and/or isoelectric point of the molecules, and thereby their interactions with the substrate, can be modified. Alternatively or additionally, the stability of the polypeptide can be enhanced by way of one or more corresponding mutations, and its catalytic performance thereby improved. Advantageous properties of individual mutations, e.g. individual substitutions, can supplement one another.

In various embodiments, the polypeptide may be characterized in that it is obtainable from a polypeptide as described above as an initial molecule by single or multiple conservative amino acid substitution. The term "conservative amino acid substitution" means the exchange (substitution) of one amino acid residue for another amino acid residue, where such exchange does not lead to a change in the polarity or charge at the position of the exchanged amino acid, e.g. the exchange of a nonpolar amino acid residue for another nonpolar amino acid residue. Conservative amino acid substitutions in the context of the invention encompass, for example, G=A=S, I-V=L=M, D=E, N=Q, K=R, Y=F, S=T, G=A=I=V=L=M=Y=F=W=P=S=T.

Alternatively or additionally, the polypeptide may be characterized in that it is obtainable from a polypeptide contemplated herein as an initial molecule by fragmentation or by deletion, insertion, or substitution mutagenesis, and encompasses an amino acid sequence that matches the initial molecule over a length of at least 150, 160, 170, 180, 190, 200, 210, 220, 230, 240, 250, 260, 270, 280, 290, 300, 310, 320, 325, 330, 331, 332, 333, 334, 335, 336, 337, 338, 339, 340, 341, or 342 continuously connected amino acids. It is preferred that in such embodiments, the amino acids N19, H124 and C166 contained in the initial molecule are still present.

In various embodiments, the present invention thus also relates to fragments of the polypeptides described herein, with said fragments retaining enzymatic activity. It is preferred that they have at least 50%, more preferably at least 70, most preferably at least 90% of the protein ligase and/or cyclase activity of the initial molecule, preferably of the polypeptide having the amino acid sequence of SEQ ID NO:1. The fragments are preferably at least 150 amino acids in length, more preferably at least 200 or 250, most preferably at least 300. It is further preferred that these fragments comprise the amino acids N, H and C at positions corresponding to positions 19, 124 and 166 of SEQ ID NO:1. Preferred fragments therefore comprise amino acids 19-166, more preferably 10-200, most preferably 1-277 of the amino acid sequence set forth in SEQ ID NO:1.

The nucleic acid molecules encoding the polypeptides described herein, as well as a vector containing such a nucleic acid, in particular a copying vector or an expression vector also form part of the present invention.

These can be DNA molecules or RNA molecules. They can exist as an individual strand, as an individual strand complementary to said individual strand, or as a double strand. With DNA molecules in particular, the sequences of both complementary strands in all three possible reading frames are to be considered in each case. Also to be considered is the fact that different codons, i.e. base triplets, can code for the same amino acids, so that a specific amino acid sequence can be coded by multiple different nucleic acids. As a result of this degeneracy of the genetic code, all nucleic acid sequences that can encode one of the above-described polypeptides are included in this subject of the invention. The skilled artisan is capable of unequivocally determining these nucleic acid sequences, since despite the degeneracy of the genetic code, defined amino acids are to be associated with individual codons. The skilled artisan can therefore, proceeding from an amino acid sequence, readily ascertain nucleic acids coding for that amino acid sequence. In addition, in the context of nucleic acids according to the present invention one or more codons can be replaced by synonymous codons. This aspect refers in particular to heterologous expression of the enzymes contemplated herein. For example, every organism, e.g. a host cell of a production strain, possesses a specific codon usage. "Codon usage" is understood as the translation of the genetic code into amino acids by the respective organism. Bottlenecks in protein biosynthesis can occur if the codons located on the nucleic acid are confronted, in the organism, with a comparatively small number of loaded tRNA molecules. Also it codes for the same amino acid, the result is that a codon becomes translated in the organism less efficiently than a synonymous codon that codes for the same amino acid. Because of the presence of a larger number of tRNA molecules for the synonymous codon, the latter can be translated more efficiently in the organism.

By way of methods commonly known today such as, for example, chemical synthesis or the polymerase chain reaction (PCR) in combination with standard methods of molecular biology or protein chemistry, a skilled artisan has the ability to manufacture, on the basis of known DNA sequences and/or amino acid sequences, the corresponding nucleic acids all the way to complete genes. Such methods are known, for example, from Sambrook, J., Fritsch, E. F., and Maniatis, T, 2001, Molecular cloning: a laboratory manual, 3rd edition, Cold Spring Laboratory Press.

"Vectors" are understood for purposes herein as elements—made up of nucleic acids—that contain a nucleic acid contemplated herein as a characterizing nucleic acid region. They enable said nucleic acid to be established as a stable genetic element in a species or a cell line over multiple generations or cell divisions. In particular when used in bacteria, vectors are special plasmids, i.e. circular genetic elements. In the context herein, a nucleic acid as contemplated herein is cloned into a vector. Included among the vectors are, for example, those whose origins are bacterial plasmids, viruses, or bacteriophages, or predominantly synthetic vectors or plasmids having elements of widely differing derivations. Using the further genetic elements present in each case, vectors are capable of establishing themselves as stable units in the relevant host cells over multiple generations. They can be present extrachromosomally as separate units, or can be integrated into a chromosome resp. into chromosomal DNA.

Expression vectors encompass nucleic acid sequences which are capable of replicating in the host cells, by preference microorganisms, particularly preferably bacteria, that contain them, and expressing therein a contained nucleic acid. In various embodiments, the vectors described herein thus also contain regulatory elements that control expression of the nucleic acids encoding a polypeptide of the invention. Expression is influenced in particular by the promoter or promoters that regulate transcription. Expression can occur in principle by means of the natural promoter originally located in front of the nucleic acid to be expressed, but also by means of a host-cell promoter furnished on the expression vector or also by means of a modified, or entirely different, promoter of another organism or of another host cell. In the present case at least one promoter for expression of a nucleic acid as contemplated herein is made available and used for expression thereof. Expression vectors can furthermore be regulated, for example by way of a change in culture conditions or when the host cells containing them reach a specific cell density, or by the addition of specific substances, in particular activators of gene expression. One example of such a substance is the galactose derivative isopropyl-beta-D-thiogalactopyranoside (IPTG), which is used as an activator of the bacterial lactose operon (lac operon). In contrast to expression vectors, the contained nucleic acid is not expressed in cloning vectors.

In a further aspect, the invention is also directed to a host cell, preferably a non-human host cell, containing a nucleic acid as contemplated herein or a vector as contemplated herein. A nucleic acid as contemplated herein or a vector containing said nucleic acid is preferably transformed into a microorganism, which then represents a host cell according to an embodiment. Methods for the transformation of cells are established in the existing art and are sufficiently known to the skilled artisan. All cells are in principle suitable as host cells, i.e. prokaryotic or eukaryotic cells. Those host cells that can be manipulated in genetically advantageous fashion, e.g. as regards transformation using the nucleic acid or vector and stable establishment thereof, are preferred, for example single-celled fungi or bacteria. In addition, preferred host cells are notable for being readily manipulated in microbiological and biotechnological terms. This refers, for example, to easy culturability, high growth rates, low demands in terms of fermentation media, and good production and secretion rates for foreign proteins. The polypeptides can furthermore be modified, after their manufacture, by the cells producing them, for example by the addition of sugar molecules, formylation, amination, etc. Post-translation modifications of this kind can functionally influence the polypeptide.

Further embodiments are represented by those host cells whose activity can be regulated on the basis of genetic regulation elements that are made available, for example, on the vector, but can also be present a priori in those cells. They can be stimulated to expression, for example, by controlled addition of chemical compounds that serve as activators, by modifying the culture conditions, or when a specific cell density is reached. This makes possible economical production of the proteins contemplated herein. One example of such a compound is IPTG, as described earlier.

Preferred host cells are prokaryotic or bacterial cells. Bacteria are notable for short generation times and few demands in terms of culturing conditions. As a result, economical culturing methods resp. manufacturing methods can be established. In addition, the skilled artisan has ample experience in the context of bacteria in fermentation technology. Gram-negative or Gram-positive bacteria may be suitable for a specific production instance, for a wide variety of reasons to be ascertained experimentally in the individual case, such as nutrient sources, product formation rate, time requirement, etc.

Host cells contemplated herein can be modified in terms of their requirements for culture conditions, can comprise other or additional selection markers, or can also express other or additional proteins. They can, in particular, be those host cells that transgenically express multiple proteins or enzymes.

The host cell can, however, also be a eukaryotic cell, which is characterized in that it possesses a cell nucleus. A further embodiment is therefore represented by a host cell which is characterized in that it possesses a cell nucleus. In contrast to prokaryotic cells, eukaryotic cells are capable of post-translationally modifying the protein that is formed. Examples thereof are fungi such as Actinomycetes, or yeasts such as Saccharomyces or Kluyveromyces. This may be particularly advantageous, for example, when the proteins, in connection with their synthesis, are intended to experience specific modifications made possible by such systems. Among the modifications that eukaryotic systems carry out in particular in conjunction with protein synthesis are, for example, the bonding of low-molecular-weight compounds such as membrane anchors or oligosaccharides.

The host cells contemplated herein are cultured and fermented in a usual manner, for example in discontinuous or continuous systems. In the former case a suitable nutrient medium is inoculated with the host cells, and the product is harvested from the medium after a period of time to be ascertained experimentally. Continuous fermentations are notable for the achievement of a flow equilibrium in which, over a comparatively long period of time, cells die off in part but are also in part renewed, and the protein formed can simultaneously be removed from the medium.

Host cells contemplated herein are preferably used to manufacture the polypeptides described herein.

A further aspect of the invention is therefore a method for manufacturing a polypeptide as described herein, comprising culturing a host cell contemplated herein; and isolating the polypeptide from the culture medium or from the host cell. Culture conditions and mediums can be selected by those skilled in the art based on the host organism used by resorting to general knowledge and techniques known in the art.

In a still further aspect, the present invention relates to the use of polypeptides described above for protein ligation, in particular for cyclizing one or more peptide(s).

Also encompassed is the use of polypeptides that comprise, consist essentially of or consist of
(i) any one of the amino acid sequences as set forth in SEQ ID Nos:3-109;
(ii) an amino acid sequence that shares at least 60, preferably at least 70, more preferably at least 80, most preferably at least 90% sequence identity with any one of the amino acid sequences of (i) over its entire length;
(iii) an amino acid sequence that shares at least 80, preferably at least 90, more preferably at least 95% sequence homology with any one of the amino acid sequences of (i) over its entire length; or
(iv) a fragment of any one of (i)-(iii), wherein said fragment has ligase/cyclase activity, for ligating at least two peptides or proteins or cyclizing a peptide or protein.

In various embodiments of such uses, the polypeptides according to (i)-(iv) based on the amino acid sequences as set forth in SEQ ID Nos. 3-109 are polypeptides based on SEQ ID NO:1, such as those described above. This relates in particular to the conserved amino acid residues N, H and C at positions corresponding to positions 19, 124 and 166 of SEQ ID NO:1 and/or their activity and functionality.

It is understood that while the uses of the enzymes described herein are described in the following by reference to peptide substrates, they can similarly be used for the corresponding polypeptides or proteins. The invention thus also covers embodiments where polypeptides or proteins are used as substrates. These polypeptides or proteins can comprise the structural motifs as described below in the context of peptide substrates. Also encompassed are embodiments, where peptide fragments, such as fragments of human peptide hormones that retain functionality, or peptide derivatives, such as (backbone) modified peptides, including, for example, thiodepsipeptides, are utilized. Accordingly, the present invention also covers fragments and derivatives of the peptide substrates disclosed herein.

In various embodiments the peptide to be ligated or cyclized can be any peptide, typically at least 10 amino acids in length, as long as it contains a recognition and ligation sequence that is recognized, bound and ligated by the ligase/cyclase. This amino acid sequence of the peptide to be ligated or cyclized may comprise the amino acid residue N or D, preferably N. In various embodiments, the peptide to be cyclized comprises the amino acid sequence $(X)_o N/D(X)_p$, with X being any amino acid, o being an integer of 1 or more, preferably 2 or more, and p being an integer of 1 or more, preferably of 2 or more. In a preferred embodiment, $(X)_p$ is $H(X)_r$ or $HV(X)_r$, with r being 0 or an integer of 1 or more. In more preferred embodiments, the peptide comprises the amino acid sequence $(X)_o NH$ or $(X)_o NHV$. Said amino acid sequence is preferably located at or near the C-terminus of the peptide to be ligated or cyclized, as all amino acids C-terminal to the N will be cleaved off during ligation/cyclization. Accordingly, in all afore-mentioned embodiments, p or r are preferably integers of up to 20, preferably up to 5. Particularly preferred are embodiments, where p is 2, with $(X)_p$ preferably being HX or HV, or where r is 0.

In alternative embodiments, the peptide to be ligated or cyclized may comprise the amino acid sequence $(X)_o N^*/D^*$, wherein X is any amino acid, o is an integer of at least 2 and the C-terminal carboxy group (of the N or D residue) is replaced by a group of the formula —C(O)—N(R')$_2$, with R' being any residue, such as, for example, alkyl. In such embodiments, the terminal —C(O)OH group of the N or D residue, preferably the alpha-carboxy group in case of D, is modified to form the group —C(O)—N(R')$_2$. These C-terminally amidated D or N residues are indicated herein by D* and N*, respectively. It has been found that the enzymes disclosed herein can cleave the amide group and ligate said N or D residue to the N-terminus of another peptide of interest or the N-terminus of the same peptide that comprises the N or D residue.

The N-terminal part of the peptide to be ligated preferably comprises the amino acid sequence $X^1 X^2 (X)_q$, wherein X can be any amino acid; $X^1$ can be any amino acid with the exception of Pro; $X^2$ can be any amino acid, but preferably is a hydrophobic amino acid, such as Val, Ile or Leu, or Cys; and q is 0 or an integer of 1 or more. Preferred are in the $X^1$ position in the following order: G=H>M=W=F=R=A=I=K=L=N=S=Q=C>T=V=U>D=E. "=" indicates that the respective amino acids are similarly preferred, while ">" indicates a preference of the amino acids listed before the symbol over the ones listed after the symbol. Preferred in the $X^2$ position are in the following order: L>V>I>C>T>W>A=F>Y>M>Q>S. Less preferred in the $X^2$ position are P, D, E, G, K, R, N and H. Particularly preferred in the $X^1$ position are G and H and in the $X^2$ position L, V, I and C, such as the dipeptide sequences GL, GV, GI, GC, HL, HV, HI and HC.

In preferred embodiments, the peptide to be ligated or cyclized thus comprises in N- to C-terminal orientation, the amino acid sequence $X^1 X^2 (X)_q (X)_o N/D(X)_p$, wherein X, $X^1$, $X^2$, o, p, and q are defined as above, with o preferably being at least 7. In various embodiments, (1) q is 0 and o is an integer of at least 7; and/or (2) $X^1$ is G or H; and/or (3) $X^2$ is L, V, I or C; and/or (4) p is at least 2 but not more than 22, preferably 2-7, more preferably $H(X)_r$ or $HV(X)_r$, most preferably HX or HV. In various embodiments, (1) q is 0 and o is an integer of at least 7; and (2) $X^1$ is G or H; and (3) $X^2$ is L, V, I or C; and (4) p is at least 2 but not more than 22, preferably 2-7, more preferably $H(X)_r$ or $HV(X)_r$, most preferably HX or HV.

In various embodiments, the peptide to be cyclized is the linear precursor form of a cyclic cystine knot polypeptide, in particular a cyclotide. Cyclotides are a topologically unique family of plant proteins that are exceptionally stable. They comprise ~30 amino acids arranged in a head-to-tail cyclized peptide backbone that additionally is restrained by a cystine knot motif associated with six conserved cysteine residues. The cystine knot is built from two disulfide bonds and their connecting backbone segments forming an internal ring in the structure that is threaded by the third disulfide bond to form an interlocking and cross braced structure. Superimposed on this cystine knot core motif are a well-defined beta-sheet and a series of turns displaying short surface-exposed loops.

Cyclotides express a diversity of peptide sequences within their backbone loops and have a broad range of biological activities. They are thus of great interest for pharmaceutical applications. Some plants from which they are derived are used in indigenous medicines, including kalata-kalata, a tea from the plant *Oldenlandia affinis* that is used for accelerating childbirth in Africa that contains the prototypic cyclotide kalata B1 (kB1). Their exceptional stability means that they have attracted attention as potential templates in peptide-based drug design applications. In particular, the grafting of bioactive peptide sequences into a cyclotide framework offers the promise of a new approach to stabilize peptide-based therapeutics, thereby overcoming one of the major limitations on the use of peptides as drugs.

In various embodiments, the peptide to be cyclized is thus 10 or more amino acids in length, preferably up to 50 amino acids, in some embodiments about 25 to 35 amino acids in length. The peptide to be cyclized may comprise or consist of the amino acid of the precursor of cyclotide kalata B1 from *Oldenlandia affinis* as set forth in SEQ ID NO:110.

In various embodiments, the peptide to be cyclized comprises or consists of the amino acid sequence $(X)_nC(X)_nC(X)_nC(X)_nC(X)_nC(X)_nC(X)_nNHV(X)_n$ (SEQ ID NO: 161), wherein each n is an integer independently selected from 1 to 6 and X can be any amino acid. Such peptides are precursors of cyclic cystine knot polypeptides that form cystine bonds between the six cysteine residues, as described above, and which can be cyclized by the enzymes described herein by cleaving off the C-terminal $HV(X)_n$ sequence and ligating the (then C-terminal) N residue to the N-terminal residue.

The peptides to be cyclized may, in various embodiments, include the linear precursors disclosed in US2012/0244575. This document is for this purpose incorporated herein by reference in its entirety.

In various additional embodiments, the peptides to be cyclized include, but are not limited to linear precursors of peptide toxins and antimicrobial peptides, such as conotoxins, thanatins (insect antimicrobial peptides) and histatins (human saliva antimicrobial peptides). Other peptides that may be cyclized are precursors of cyclic human or animal peptide hormones, including, but not limited to neuromedin, salusin alpha, apelin and galanin. Exemplary peptides include or consist of any one of the amino acid sequences set forth in SEQ ID Nos. 111-116 and 128-132.

Further peptides that can be ligated or cyclized using the enzymes and methods disclosed herein include, without limitation, Adrenocorticotropic Hormone (ACTH), Adrenomedullin, Intermedin, Proadrenomedullin, Adropin, Agelenin, AGRP, Alarin, Insulin-Like Growth Factor-Binding Protein 5, Amylin, Amyloid b-Protein, Amphipathic Peptide Antibiotic, LAH4, Angiotensin I, Angiotensin II, A-Type (Atrial) Natriuretic Peptide (ANP), Apamin, Apelin, Bivalirudin, Bombesin, Lysyl-Bradykinin, B-Type (Brain) Natriuretic Peptide, C-Peptide (insulin precursor), Calcitonin, Cocaine-and Amphetamine-Regulated Transcript (CART), Calcitonin Gene Related Peptide (CGRP), Cholecystokinin (CCK)-33, Cytokine-Induced Neutrophil Chemoattractant-1/growth-related oncogene (CINC), Colivelin, Corticotropin-Releasing Factor (CRF), Cortistatin, C-Type Natriuretic Peptide (CNP), Decorsin, human neutrophil peptide-1 (HNP-1), HNP-2, HNP-3, HNP-4, human defensin HD5, HD6, human beta defensin-1 (hbd1), hbd2, hbd3, hbd4, Delta Sleep-Inducing Peptide (DSIP), Dermcidin-1L, Dynorphin A, Elafin, Endokinin C, Endokinin D, b-Lipotropin, g-Endorphin, Endothelin-1,Endothelin-2, Endothelin-3, Big-Endothelin-1, Big-Endothelin-2, Big-Endothelin-3, Enfuviritide, Exendin-4, MBP, Myelin Oligodendrocyte Protein (MOG), Glu-fibrinopeptide B, Galanin, Galanin-like Peptide, Big Gastrin (Human), Gastric Inhibitory Polypeptide (GIP), Gastrin Releasing Peptide, Ghrelin,Glucagon, Glucagon-like peptide-1 (GLP-1), GLP-2, Growth Hormone Releasing Factor (GRF, GHRF), Guanylin, Uroguanylin, Uroguanylin Isomer A, Uroguanylin Isomer B, Hepcidin, Liver-Expressed Antimicrobial Peptide (LEAP-2),Humanin, Joining Peptide (rJP), Kisspeptin-10, Kisspeptin-54, Liraglutide, LL-37 (Human Cathelicidine), Luteinizing Hormone Releasing Hormone (LHRH), Magainin 1, Mastoparan, a-Mating Factor, Mast Cell Degranulating (MCD) Peptide, Melanin-Concentrating Hormone (MCH), a-Melanocyte Stimulating Hormone (alpha-MSH), Midkine, Motilin, neuroendocrine regulatory peptide 1 (NERP1), NERP2,Neurokinin A, Neurokinin B, Neuromedin B, Neuromedin C, Neuromedin S, Neuromedin U8, Neuronostatin-13, Neuropeptide B-29, Neuropeptide S (NPS), Neuropeptide W-30, Neuropeptide Y (NPY), Neurotensin, Nociceptin, Nocistatin, Obestatin, Orexin-A, Osteocalcin, Oxytocin, Catestatin, Chromogranin A, Parathyroid Hormone (PTH), Peptide YY, Pituitary Adenylate Cyclase Activating Polypeptide 38 (PACAP-38), Platelet Factor-4, Plectasin, Pleiotrophin, Prolactin-Releasing Peptide, Pyroglutamylated RFamide Peptide (QRFP), RFamide-Related Peptide-1, Secretin, Serum Thymic Factor (FTS), Sodium Potassium ATPase Inhibitor-1 (SPAI-1), Somatostatin, Somatostatin-28, Stresscopin, Urocortin, Substance P, Echistatin, Enterotoxin STp, Guangxitoxin-1E, Urotensin II, Vasoactive intestinal peptide(VIP), and Vasopressin as well as fragments and derivatives thereof. The afore-mentioned peptides may be of human or animal, such as rat, mouse, pig, origin. All of them all well-known to those skilled in the art and their amino acid sequences are readily available.

In various other embodiments, polypeptides or proteins of more than 50 amino acids length are used as cyclization substrates. In such a reaction, the polypeptide/protein may be cyclized by ligating its C- to its N-terminus.

In various embodiments, two or more peptides are ligated by the enzymes of the invention. This may include formation of macrocycles consisting of two or more peptides, preferable are macrocyclic dimers. The peptides to be ligated can be any peptides, as long as at least one of them contains a recognition and ligation sequence that is recognized, bound and ligated by the ligase/cyclase. Suitable peptides have been described above in connection with the cyclization strategy. The same peptides can also be used for ligation to another peptide that may be the same or different. One of the peptides to be ligated may for example be a polypeptide that has enzymatic activity or another biological function. The peptides to be ligated may also include marker peptides or peptides that comprise a detectable marker, such as a fluorescent marker or biotin. According to such embodiments, a polypeptide that has bioactivity can be fused to a detectable marker. In various embodiments, at least one of the peptides to be ligated has a length of 25 amino acids or more, preferably 50 amino acids or more (and thus may be a "polypeptide", in the sense of the present invention).

The peptides to be ligated can comprise or consist of any of the amino acid sequences set forth in SEQ ID Nos. 117 to 127. Preferred peptides to be ligated to form (macrocyclic) dimers include the peptides having the amino acid sequence set forth in any one of SEQ ID Nos. 117-121. Preferred N-terminal peptides to be ligated (with one C-terminal peptide) to form a linear fusion peptide include the peptides having the amino acid sequence set forth in any one of SEQ ID Nos. 112, 115 and 117. Preferred C-terminal peptides to be ligated (with one N-terminal peptide) to form a linear fusion peptide include the peptides having the amino acid sequence set forth in any one of SEQ ID Nos. 113, 114 and 116.

The peptides to be ligated or cyclized can also be fusion peptides or polypeptides in which an Asx-containing tag has been C-terminally fused to the peptide of interest that is to be ligated or fused. The Asx-containing tag preferably has the amino acid sequence $N/D(X)_p$, with X being any amino acid and o and p both being independently from each other an integer of 1 or more, preferably 2 or more. In a preferred embodiment, the tag comprises or consists of the (C-terminal) amino acid sequence NH or NHV. Alternatively, an amidated N or D (N* or D* as defined above) may be fused to the C-terminal end of the peptide or polypeptide to be ligated or fused. The other peptide to which this fusion peptide or polypeptide is ligated can be as defined above. Alternatively, the fusion peptide or polypeptide may be cyclized by forming a bond between its C- and N-terminus. In one embodiment, the fusion peptide or polypeptide may be green fluorescent protein fused to the C-terminal tag of the amino acid sequence NHV (SEQ ID NO: 133) and the ligated peptide may be a biotinylated peptide of the amino acid sequence GIGK(biotinylated)R (SEQ ID NO: 134). Generally, polypeptides and proteins that may be ligated to peptides, such as peptides bearing signaling or detectable moieties, or cyclized using the methods and uses described herein, include, without limitation antibodies, antibody fragments, antibody-like molecules, antibody mimetics, peptide aptamers, hormones, various therapeutic proteins and the like.

In various embodiments, the ligase activity is used to fuse a peptide bearing a detectable moiety, such as a fluorescent group, including fluoresceins, such as fluorescein isothiocyanate (FITC), or coumarins, such as 7-Amino-4-methylcoumarin, to a polypeptide or protein, such as those mentioned above. In various embodiments, the protein can be an antibody fragment, such as a human anti-ABL scFv, for example with the amino acid sequence set forth in SEQ ID NO:146, or an antibody mimetic, such as a darpin (designed ankyrin repeat proteins), for example a darpin specific for human ERK, for example with the amino acid sequence set forth in SEQ ID NO:147.

In still another aspect, the invention relates to a method for cyclizing a peptide, polypeptide or protein, the method comprising incubating said peptide, polypeptide, or protein with the polypeptides having ligase/cyclase activity described above in connection with the inventive uses under conditions that allow cyclization of said peptide.

In a still further aspect, the invention relates to a method for ligating at least two peptides, polypeptides or proteins, the method comprising incubating said peptides, polypeptides or proteins with the polypeptides described above in connection with the inventive uses under conditions that allow ligation of said peptides.

The peptides, polypeptides and proteins to be cyclized or ligated according to these methods are, in various embodiments, similarly defined as the peptides, polypeptides and proteins to be cyclized or ligated according to the above-described uses.

In the methods and uses described herein, the enzyme and the substrate can be used in a molar ratio of 1:100 or higher, preferably 1:400 or higher, more preferably at least 1:1000.

The reaction is typically carried out in a suitable buffer system at a temperature that allows optimal enzyme activity, usually between ambient (20° C.) and 40° C.

In the above-described methods and uses, the polypeptides having ligase/cyclase activity may be immobilized on a suitable support material. Suitable support materials include various resins that are used in chromatography columns and the like. The support may have the form of beads or may be the surface of larger structure, such as a microtiter plate. Immobilization allows for a very easy and simple contacting with the substrate, as well as easy separation of enzyme and substrate after the synthesis. If the polypeptide with the enzymatic function is immobilized on a solid column material, the ligation/cyclization may be a continuous process and/or the substrate/product solution may be cycled over the column.

Accordingly, the present invention, in one aspect, also covers a solid support material comprising the isolated polypeptide according to the invention immobilized thereon. The solid support material may comprise a polymer resin, preferably in particulate form, such as those mentioned above. The isolated polypeptide can be immobilized on the solid support material by covalent or non-covalent interactions.

In exemplary embodiments, the polypeptides having ligase/cyclase activity are glycosylated and may be immobilized by means of concanavalin A (Con A), a lectin (carbohydrate-binding protein) that is isolated from Canavalia ensiformis (jack bean). It binds specifically to a-D-mannose and a-D-glucose containing biomolecules, including glycoproteins and glycolipids. Said ConA protein is used in immobilized form on affinity columns to immobilize glycoproteins and glycolipids. Accordingly, in various embodiments, the isolated polypeptide having ligase/cyclase activity is glycosylated and non-covalently bound to a carbohydrate-binding moiety, preferably concanavalin A, coupled to the solid support material surface.

The solid support materials described above can be used for the on-column cyclization and/or ligation of at least one substrate peptide or in a method for the cyclisation or ligation of at least one substrate peptide, comprising contacting a solution comprising the at least one substrate peptide with the solid support material described above under conditions that allow cyclization and/or ligation of the at least one substrate peptide. The substrate peptides are those described above and include also the above polypeptide substrate.

The invention also encompasses a transgenic plant comprising a nucleic acid molecule encoding a polypeptide having protein ligase and/or cyclase activity as described herein. The polypeptide is preferably not naturally present in said plant. Accordingly, the present invention also features transgenic plants that express a heterologous polypeptide according to the invention.

In various embodiments such transgenic plants may further comprise at least one nucleic acid molecule encoding one or more peptides to be cyclized or one or more peptides to be ligated. These may be peptides as defined above in connection with the uses and methods of the invention. In one embodiment, the peptide to be cyclized is a linear precursor form of a cyclic cystine knot polypeptide, for example like those defined above. These precursors of peptides or polypeptides to be cyclized may be naturally present in said plant but are preferably also artificially introduced, i.e. the nucleic acids encoding them are heterologous.

Such transgenic plants may, due to the co-expression of the enzyme and its substrate, therefore directly produce a cyclized peptide of interest.

All embodiments disclosed herein in relation to the polypeptides and nucleic acids are similarly applicable to the uses and methods described herein and vice versa.

The invention is further illustrated by the following non-limiting examples.

EXAMPLES

Materials. Z-AAN-AMC (N-carbobenzyloxy-Ala-Ala-Asn-7-amido-4-methylcoumarin) and peptide substrates were synthesized by GL Biochem (Shanghai). Oxidative folding of each peptide substrate was performed for 18 h at a peptide concentration of 30 mM in the buffer containing 50% acetonitrile, 100 mM ammonium bicarbonate, 3 mM reduced glutathione, pH 8.0. Jack bean legumain was purchased from Takara Bio (Japan). Native kB1 peptide was isolated from aerial parts of *O. affinis* and purified by using RP-HPLC. Legumain-specific LP-1 probe was provided by Matthew Bogyo (Stanford University).

Accession codes. The nucleotide sequence for butelase 1 has been deposited in the GenBank database under the accession number KF918345.

Example 1

In Vitro Screening of Asparaginyl Endopeptidase and Peptide Cyclase Activity

The asparaginyl endopeptidase (AEP) activity was determined by using the fluorogenic substrate Z-Ala-Ala-Asn-AMC (Z-AAN-AMC), a fluorogenic substrate selective for legumains (Kembhavi, A. A., Buttle, D. J., Knight, C. G. & Barrett, A. J. The two cysteine endopeptidases of legume seeds: purification and characterization by use of specific fluorometric assays. *Arch. Biochem. Biophys.* 303, 208-213 (1993); Sojka, D. et al. IrAE—An asparaginyl endopeptidase (legumain) in the gut of the hard tick Ixodes ricinus. *Int. J. Parasitol.* 37, 713-724 (2007), at a concentration of 100 mM in buffer A. Emitted fluorescence was measured with an excited wavelength of 380 nm and emission wavelength of 460 nm.

In a first experiment, the crude extract of *C. ternateawas* incubated with Z-AAN-AMC under the above-described conditions. A large increase in fluorescence intensity at 460 nm was observed indicating the presence of a putative legumain.

Then the cyclase activity was assayed. Generally, in vitro cyclization assays were performed in 50-ml reaction mixtures containing buffer A, 0.125 mM butelase 1 and varying peptide concentrations (0.5 to 400 mM). The enzyme concentration was estimated by UV absorbance at 280 nm. Each reaction was performed in triplicate at 37° C. and quenched by adding 5 ml of 1 M HCl solution. The peptides were separated by using a reversed-phase C18 analytical column (150×2.1 mm, Vydac) on a Nexera UHPLC system (Shimadzu). The cyclization velocities were calculated by converting the HPLC-peak areas of remained linear precursors or the cyclized products into concentrations. The identity of each HPLC peak was analyzed by MALDI-TOF MS and MS/MS (ABI 4800 MALDI TOF/TOF).

Figure 1:
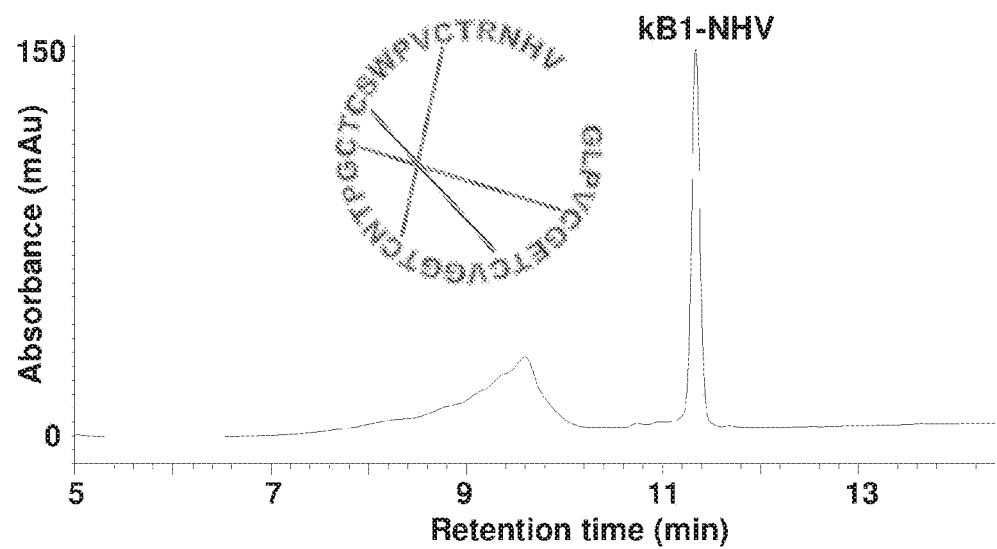
FIG. 1 shows the oxidative folding of kB1-NHV (SEQ ID NO: 110). The peptide was folded for 18 h at a 30 µM concentration in buffer containing 50% acetonitrile, 100 mM ammonium bicarbonate, 3 mM reduced glutathione, pH 8.0. The folded peptide eluted last in the RP-HPLC.
Figure 2:
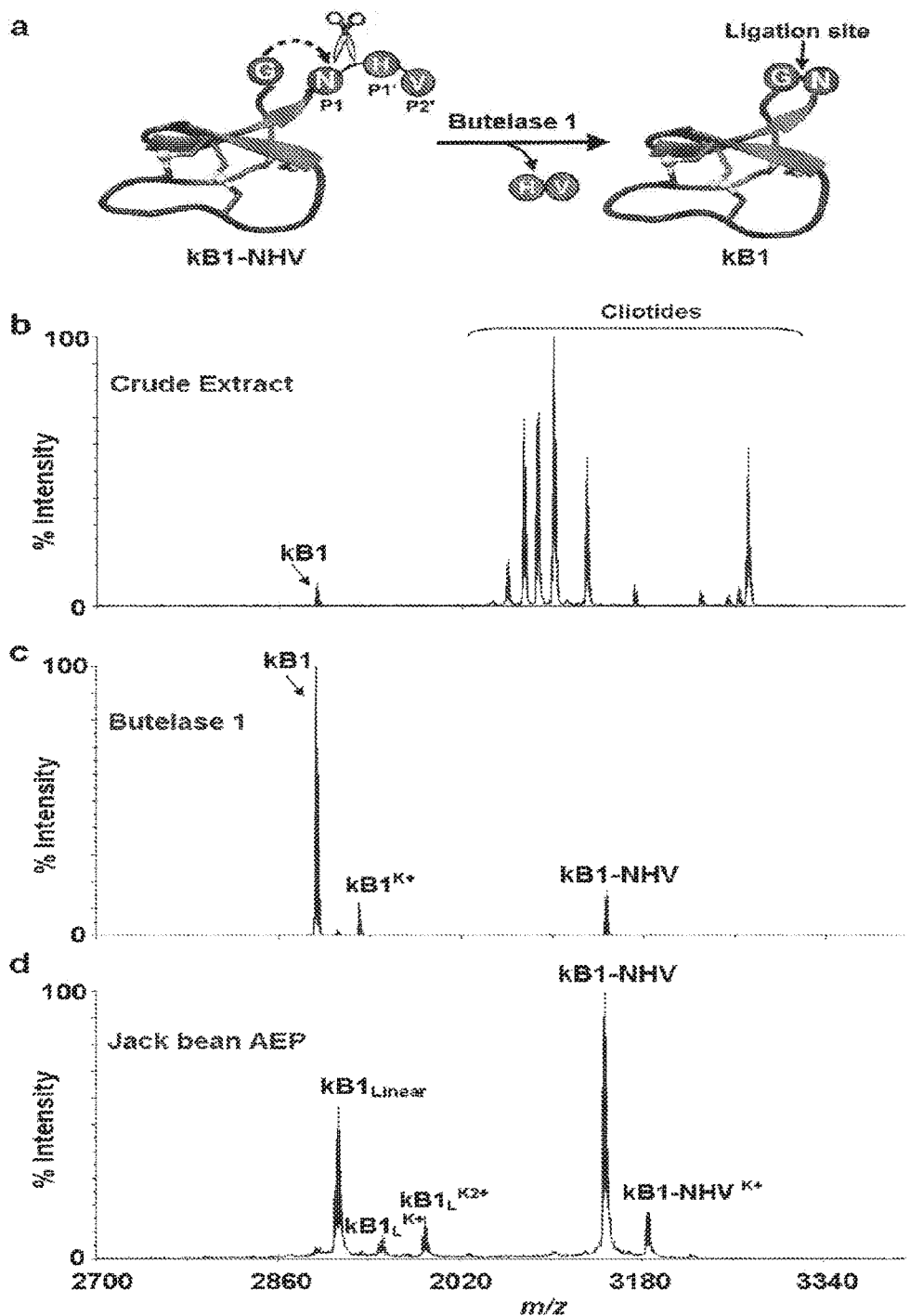
FIG. 2 shows the MS characterization of peptide cyclase activity. (a) Schematic illustration of kB1-NHV cyclization mediated by butelase 1. Residues at the recognition site of butelase 1 (P1, P1' and P2') are labeled. (b,c) MS profiles of kB1-NHV cyclization mediated by the crude extract of C. ternatea and purified butelase 1, respectively. Peptides in the bracket are cliotides, naturally occurring cyclotides in C. ternatea. The product, cyclic kB1, is indicated by the arrows.

The cyclase activity of the crude extract of *C. ternatea* was assayed using the peptide substrate kB1-NHV (SEQ ID NO:110), a 31-residue, linear and oxidatively folded form of the cyclotide kB1 with the His-Val sequence at the C-terminus as the propeptide (Table 1 and FIG. 1). Kalata B1(kB1), the prototypic cyclotide found in *Oldenlandia affinis* but not in *C. ternatea*, was selected as the substrate in our assays to distinguish it from native cyclotides produced by *C. ternatea*. The His-Val motif is conserved in the cyclotide precursors of *C. ternatea* and a C-terminal dipeptide has been shown to be sufficient for the biosynthesis of cyclotides (Nguyen, G. K., Lim, W. H., Nguyen, P. Q. & Tam, J. P. Novel Cyclotides and Uncyclotides with Highly Shortened Precursors from *Chassalia chartacea* and Effects of Methionine Oxidation on Bioactivities. *J. Biol. Chem.* 287, 17598-17607 (2012). Conlan, B. F. et al. Insights into Processing and Cyclization Events Associated with Biosynthesis of the Cyclic Peptide Kalata B1. *J. Biol. Chem.* 287, 28037-28046 (2012)). Treatment of kB1-NHV with the extract of *C. ternatea* yielded a new peptide which matched the calculated mass of native cyclic kB1 (FIG. 2a,b). This peptide product was further confirmed as cyclic kB1 by (1) co-elution with native cyclic kB1 in RP-HPLC (FIG. 3), (2) tryptic digestion which resulted in a mass increase of 18 Da suggesting a cyclic backbone, and MS/MS analysis confirming the kB1 sequence and Asn-Gly as the ligation site (FIGS. 4), and (3) 1D NMR which showed identical chemical shifts for the cyclized peptide and native cyclic kB1 (FIG. 5). For the 1D NMR spectra of kalata B1, native and butelase-cyclized kB1 peptides were prepared in 95% $H_2O$/5% $D_2O$ at 0.1 mM concentration, pH 4.3. 1D $^1H$ spectra of both peptides were recorded on a 600 MHz NMR spectrometer (Bruker) equipped with a cryo-probe. These results indicate the presence of a putative ligase capable of peptide macrocyclization in the crude extract of *C. ternatea*.

TABLE 1

Cyclization yields of peptide substrates mediated by butelase 1

| Peptide Substrate (SEQ ID NO:) | Sequence | Time (h) | Yield (%) |
|---|---|---|---|
| kB1-NHVIA (137) | GLPVCGETCVGGTCNTPGCTCSW PVCTR<u>N</u>HVIA | 3 | >95 |
| kB1-NHVI (136) | GLPVCGETCVGGTCNTPGCTCSW PVCTR<u>N</u>HVI | 2 | >95 |
| kB1-NHV (110) | GLPVCGETCVGGTCNTPGCTCSW PVCTR<u>N</u>HV | 0.8 | >95 |
| kB1-NH (138) | GLPVCGETCVGGTCNTPGCTCSW PVCTR<u>N</u>H | 4 | <5 |
| kB1-N* (139) | GLPVCGETCVGGTCNTPGCTCSW PVCTR<u>N</u>* | 4 | <10 |
| kB1-DHV (140) | GGLPVCGETCVGGTCNTPGCTCS WPVCTR<u>D</u>HV | 4 | <10 |
| kB1-AHV (141) | GLPVCGETCVGGTCNTPGCTCSW PVCTR<u>A</u>HV | 4 | <1 |
| kB1-QHV (142) | GLPVCGETCVGGTCNTPGCTCSW PVCTR<u>Q</u>HV | 4 | <1 |
| kB1-EHV (143) | GLPVCGETCVGGTCNTPGCTCSW PVCTR<u>E</u>HV | 4 | <1 |
| SA-kB1-NHV[a] (110) | GLPVCGETCVGGTCNTPGCTCSW PVCTR<u>N</u>HV | 0.2 | >95 |
| SFTI-NHV (135) | GRCTKSIPPICFP<u>N</u>HV | 0.8 | >95 |
| SFTI-DHV (144) | GRCTKSIPPICFP<u>D</u>HV | 4 | <10 |

Assays were performed at 37° C. and an enzyme-to-peptide ratio of 1:400 (0.125 μM butelase 1:50 μM peptide).
*indicates the amidated peptide at the C-terminus.
[a]S-carbamidomethylated kB1-NHV.

Example 2

Isolation, Purification, Identification and Characterization of Butelase 1

Attempts to isolate the peptide ligase guided by Z-AAN-AMC were unsuccessful. Fractions giving strong fluorescence intensity after HPLC separation of the crude extract were unable to cyclize kB1-NHV. Instead, a peptide corresponding to the linear form of kB1 with His-Val being hydrolyzed was observed. All HPLC-separated fractions were then directly screened using kB1-NHV as the substrate, and cyclase activity was found in fractions lacking fluorescence (FIG. 2c). This result demonstrates that the cyclase activity is separate from the AEP activity. As a control, commercial jack bean legumain was unable to cyclize kB1-NHV and generated only the linear form of kB1 (FIG. 2d).

The putative ligase was purified in several chromatographic steps to give a single protein band of 38 kDa on SDS-PAGE (FIG. 6a). For the isolation and purification 300 g pods of C. ternatea were homogenized with 500 ml of extraction buffer (20 mM sodium phosphate, 1 mM EDTA, 1 mM PMSF, 5 mM b-mercaptoethanol (b-ME), pH 6.0). The extraction was conducted at 4° C. to minimize protein degradation. The homogenate was centrifuged and filtered to remove plant debris. Ammonium sulfate was added to the supernatant to reach 20% saturation. The precipitated proteins were discarded and ammonium sulfate was continually added to the supernatant to reach 85% saturation. After centrifugation, the supernatant was discarded and the precipitated proteins were redissolved in 300 ml of extraction buffer. The dissolved sample was dialyzed overnight against 6 l of extraction buffer using a 10 kDa cut-off dialysis tubing. The dialyzed sample was centrifuged and filtered to give the crude extract of C. ternatea. This crude extract was applied to a flash column containing 100 ml slurry of Q-Sepharose Fast Flow anion-exchange resin (GE Healthcare). The column was wash with 800 ml of buffer A (20 mM phosphate buffer, 1 mM EDTA, 5 mM b-ME, pH 6.0) and eluted with 400 ml of buffer B (20 mM sodium phosphate, 1 mM EDTA, 5 mM b-ME, 200 mM KCl, pH 6.0). The eluent was concentrated to a final volume of 3 ml using 10 kDa cut-off centrifugal filter units (Amicon Ultra, Millipore). The concentrated sample was subjected to size exclusion chromatography using a BioSuite HPLC column (300×21.5 mm, Waters). Fractions with peptide cyclase activity were pulled and further purified by anion-exchange chromatography using an analytical PolyWAX HPLC column (200×4.6 mm, PolyLC). The enzyme purity was analyzed by SDS-PAGE and silver staining. Approximate 0.4 mg butelase 1 can be obtained from 300 g of plant materials.

Purified butelase 1 was analyzed by SDS-PAGE under denaturing condition. The gel was silver stained and the protein band was excised and subjected to in-gel tryptic digestion as described previously (Gharandaghi, F., Weinberg, C. R., Meagher, D. A., Imai, B. S. & Mische, S. M. Mass spectrometric identification of proteins from silver-stained polyacrylamide gel: A method for the removal of silver ions to enhance sensitivity. Electrophoresis 20, 601-605 (1999)). In-gel tryptic digestion gave five dominant peptide fragments that were then sequenced by MALDI-TOF MS/MS (FIG. 7). These fragments were BLAST searched against the transcriptome data of C. ternatea provided by the Beijing Genomics Institute, and were found to match a single sequence of a novel protein designated as butelase 1 (FIG. 6c). The enzyme remains stable with minimal loss of activity for 30 days at 4° C. It is relatively soluble in water of which a concentration of 10 mg/ml has been achieved.

Based on the EST sequences in the transcriptome of C. ternatea, butelase 1 was predicted to consist of 482 residues and have a mass of 53 kDa, whereas the purified active enzyme is approximately 38 kDa, suggesting that it is post-translationally modified by proteolytic processing (FIG. 6c). Incubating butelase 1 with PNGase F or glycopeptidase A produced no change in the molecular weight, indicating that butelase 1 is not N-glycosylated (data not shown). A BLASTp search against the NCBI non-redundant protein database showed that butelase 1 shares high sequence homology with several members of the legumain family. Butelase 1 has the highest homology with a legumain-like protein from Glycine max (NCBI reference sequence: XP_003525979) and VmPE-1 from Vigna mungo (GenBank: BAA76744.1) with 71% and 70% sequence identity, respectively. This result strongly suggests that butelase 1 is a novel member of the legumain family. The enzymological classification of butelase 1 was further supported by its labeling with the fluorescent probe LP-1, an aza-Asn epoxide probe specific for legumains (FIG. 6b and FIG. 8) (Lee, J. & Bogyo, M. Development of Near-Infrared Fluorophore (NIRF)-Labeled Activity-Based Probes for in Vivo Imaging of Legumain. ACS Chem. Biol. 5, 233-243 (2010)).

Legumains are produced as inactive zymogens that undergo autoproteolytic activation to release the N- and C-terminal prodomains. Edman sequencing revealed VEGTR as the N-terminal sequence of butelase 1. The C-terminal processing site was predicted to occur between Asn383 and Ser384, which is based on the apparent molecular weight of 38 kDa, and the auto-cleavage site of other legumains such as proteinase B from Vicia sativa and jack bean legumain (FIG. 6c) (Becker, C. et al. Purification, Cdna Cloning and Characterization of Proteinase-B, an Asparagine-Specific Endopeptidase from Germinating Vetch (Vicia-Sativa L) Seeds. Eur. J. Biochem. 228, 456-462 (1995); Abe, Y. et al. Asparaginyl Endopeptidase of Jack Bean-Seeds—Purification, Characterization, and High Utility in Protein-Sequence Analysis. J. Biol. Chem. 268, 3525-3529 (1993)).

MODELLER was used to construct a homology model of butelase 1 based on the zymogen of human legumain, the only member of the legumain family with a known crystal structure (Safi, A. & Blundell, T. L. Comparative protein modelling by satisfaction of spatial restraints. J. Mol. Biol. 234, 779-815 (1993); Dall, E. & Brandstetter, H. Mechanistic and structural studies on legumain explain its zymogenicity, distinct activation pathways, and regulation. Proc. Natl. Acad. Sci. U. S. A. 110, 10940-10945 (2013)). The zymogen of butelase 1 (V42-1468) shares 37.8% sequence identity with human legumain. The constructed model of butelase 1 agrees well with the template structure of human legumain with a RMSD of 0.352Å for the backbone $C_a$ (FIG. 6d).

Previous study defined the zymogen of human legumain into three structural parts: the AEP active domain, the active peptide region, and the legumain stabilization and activity modulation (LSAM) domain. The latter two domains are auto-cleaved during enzyme activation in human legumain. Similarly, the modeled structure of butelase 1 can also be divided into three parts: the putative AEP active domain (marine blue, V42-T318), the active peptide region (magenta, D319-N383) and the LSAM domain (gray, S385-1468, which is excluded in the final active form of butelase 1). Overall, the AEP active domain of butelase 1 retains 49.8% sequence identity (V42-T318) and displays a good structural alignment of the catalytic triad (Asn59, His165 and Cys207) with that of human legumain (FIG. 6d).

The kinetics of butelase 1 as a peptide cyclase were determined by HPLC and MS analysis using two non-native linear peptide substrates derived from different plant families, the 31-residue kB1-NHV and the 16-residue SFTI-NHV(SEQ ID NO:135). Despite being non-native substrates with different lengths and sequences, butelase 1 efficiently cyclized these peptides in excellent yields (Table 1).

RP-HPLC traces of the cyclization reaction revealed that butelase 1 converted about 40% of kB1-NHV into cyclic kB1 within 6 min, and reached >95% conversion within 45 min, at an enzyme-to-peptide ratio of 1:400 (FIG. 9a). The apparent kinetic parameters of butelase 1 for kB1-NHV calculated from Michaelis-Menten plot using GraphPad Prismare 2.28±0.05 s$^{-1}$ for k$_{cat}$, 213±10 mM for K$_m$ and 10,700 M$^{-1}$ s$^{-1}$ for catalytic efficiency (k$_{cat}$/K$_m$) (FIG. 9b). In addition, a 58-residue, cyclodimer of kB1 (<10%) was observed at high substrate concentrations (>400 mM), suggesting that butelase 1 is able to perform intermolecular ligation and cyclization of long peptide (FIG. 10).

With SFT1-NHV, butelase 1 also showed >95% conversion yield with the k$_{cat}$ of 0.6±0.02 s$^{-1}$, K$_m$ of 51±4 mM, and catalytic efficiency of 11,700 M$^{-1}$ s$^{-1}$ (FIG. 9c). These data suggest that butelase 1 could cyclize a wide range of peptide substrates.

Since both SFTI and kB1 exist in nature as cyclic peptides stabilized by disulfide bonds, it was then determined whether conformational assistance by disulfide bonds is required for the cyclization reaction by butelase 1. S-alkylation of the reduced kB1-NHV with iodoacetamide gave SA-kB1-NHV. Treatment of 50 mM S-alkylated peptide (SA-kB1-NHV) with 0.125 mM butelase 1 resulted in >95% conversion to its cyclic form within 12 min (Table 1). Kinetic analysis showed a 50-fold improvement in the catalytic efficiency of SA-kB1-NHV compared to kB1-NHV (FIG. 9d). This result demonstrates that disulfide bonds are not required for peptide cyclization by butelase 1.

To investigate the requirement of the P1' and P2' positions of the C-terminal propeptide, four analogs of kB1-NHV were synthesized (Table 1). Analogs with the longer propeptides than kB1-NHV displayed a small decrease in the cyclization rates, with catalytic efficiencies of 4032 and 2971 M$^{-1}$ s$^{-1}$ for kB1-NHVI(SEQ ID NO:136) and kB1-NHVIA (SEQ ID NO:137), respectively (Table 1 and Table 2). In contrast, butelase 1 was significantly less efficient in cyclizing two truncated analogs lacking either Val or His-Val (SEQ ID NO:138; SEQ ID NO:139) with <10% cyclic kB1 yield after 4 h, and an incomplete reaction after 30 h (FIG. 11). This result indicates that a C-terminal HV dipeptide is necessary for an efficient cyclization reaction by butelase 1.

TABLE 2

Kinetic parameters of butelase 1 for various peptide substrates

| Peptide Substrate | k$_{cat}$ (s$^{-1}$) | K$_m$ (μM) | k$_{cat}$/K$_m$ (M$^{-1}$ s$^{-1}$) |
|---|---|---|---|
| SA-kB1-NHV | 17.08 ± 5 | 31.5 ± 8 | 542,000 |
| kB1-NHV | 2.28 ± 0.05 | 213 ± 10 | 10,700 |
| kB1-NHVIA | 0.38 ± 0.01 | 129 ± 9 | 2971 |
| kB1-NHVI | 0.25 ± 0.01 | 62 ± 5 | 4032 |
| SFTI-NHV | 0.6 ± 0.02 | 51 ± 4 | 10,700 |
| MrIA conotoxin | 2.2 ± 0.2 | 7.9 ± 2 | 278,000 |

To determine the substrate specificity of butelase 1 at the P1 position, analog substrates of kB1-NHV were prepared by individually replacing the conserved Asn residue with Ala or closely related residues such as Asp, Glu and Gln (Table 1; SEQ ID Nos. 140, 141, 142, 143). No cyclization of kB1-AHV, kB1-QHV or kB1-EHV was observed after incubating with butelase 1 for 4 h (FIG. 12). Butelase 1 was able to cyclize kB1-DHV, but at about a hundred-fold slower than kB1-NHV and with less than 10% cyclized product after 4 h. Similarly, we compared the activity of butelase 1 on SFT1-NHV and SFT1-DHV (SEQ ID NO:144). Butelase 1 cyclized both peptide substrates, but was significantly more efficient with SFTI-NHV than SFTI-DHV. These results demonstrate that a C-terminal NHV tripeptide tag is necessary and sufficient for cyclization by butelase 1.

To provide the evidence of generality, it was examined whether butelase 1 can cyclize non-plant-derived proteins using substrates derived from conotoxin (MrIA; SEQ ID NO:111), a thanatin analog (insect antimicrobial peptide; SEQ ID NO:112), and histatin-1a, histatin-1b, histatin-3a, and histatin-3b (human saliva antimicrobial proteins; SEQ ID Nos. 113-116) (Table 3). Butelase 1 efficiently cyclized all tested peptides.

TABLE 3

Ligation yields of peptides tested for cyclization

| Peptides | Sequence | Yield (%) |
|---|---|---|
| MrIA = Conotoxin | GVCCGYKLCHPCAGNHV (SEQ ID NO: 111) | 95 |
| Thanatin analog | GISKKPVPIIYCNRRTGKCQRMNHV (SEQ ID NO: 112) | 95 |
| Histatin-1a | SADSHEKRHHGYRRKFHEKHHSHRE FPFYGDYGSNYLYDNHV (SEQ ID NO: 113) | 90 |
| Histatin-1b | GLPDSHEKRHHGYRRKFHEKHHSHR EFPFYGDYGSNYLYDNHV (SEQ ID NO: 114) | 90 |
| Histatin-3a | GADSHAKRHHGYKRKFHEKHHSHRG YRSNYLYDNHV (SEQ ID NO: 115) | 90 |
| Histatin-3b | GLDSHAKRHHGYKRKFHEKHHSHRG YRSNYLYDNHV (SEQ ID NO: 116) | 90 |

To determine why Z-AAN-AMC was not useful in assaying for butelase 1, 0.125 mM purified enzyme was incubated with 50 mM Z-AAN-AMC. No apparent increase in the fluorescence intensity was observed after incubating for 30 h, indicating that butelase 1 did not hydrolyze Z-AAN-AMC. RP-HPLC analysis showed that <3% hydrolyzed product was formed (FIG. 13). As a positive control, jack bean legumain completely hydrolyzed Z-AAN-AMC under the same experimental conditions. This result suggests that butelase 1 has evolved to function as a ligase rather than a protease.

The cyclodimerization of kB1 suggests that butelase 1 is able to mediate intermolecular peptide ligation. It is worthwhile to point out that the high sequence diversity of >24 native cyclotides isolated from *C. ternatea* also provides tantalizing hints that butelase 1 is a promiscuous enzyme with broad substrate specificity. To define the N-terminal specificity of an acceptor nucleophile, KALVINHV (SEQ ID NO:122) was used as a model peptide and evaluated its ligation efficiency with XIGGIR(X=any one of the 20 naturally occurring amino acids (G,A,V,L,I,F,Y,W,H,R,K,S,T,D,E,N,Q,P,C,M); SEQ ID NO:123). The reactions were performed in the presence of 0.1 mM butelase 1, 50 mM KALVINHV (SEQ ID NO: 122) and 1 mM XIGGIR (SEQ ID NO: 123). Butelase 1 efficiently mediated the intermolecular peptide ligation with broad specificity, accepting most natural amino acids at the P1" position except for Pro and acidic amino acids such as Asp and Glu (FIG. 15a). The ligation yields reached 60-80% within 10 min of incubation for most peptides with <5% hydrolysis of the asparaginyl bond observed.

To define the specificity at the P2" position, a second peptide library was synthesized: LXGGIR (SEQ ID NO:124) (X=any one of the 20 naturally occurring amino acids). Butelase 1 exhibits a more stringent requirement at the P2" as compared to the P1" position and displays a high preference for hydrophobic amino acids, particularly Ile, Leu and Val (FIG. 15b). This result also explains the high catalytic efficiency of butelase 1 for conotoxin and histatin-3.

In addition ligation activity was also tested for the peptides YRNHV (SEQ ID NO:125)+GLPVR (SEQ ID NO:126) and TRNHV (SEQ ID NO:127) +GLPVR (SEQ ID NO:126).The ligation yields reached 60 within 10 min of incubation.

To demonstrate the generality of butelase 1, five non-cysteine-containing peptide hormones with sizes ranging from 26 to 40 residues were selected. Four sequences were derived from human peptides (neuromedin U (SEQ ID NO:128), salusin a (SEQ ID NO:129), apelin (SEQ ID NO:131), and galanin (SEQ ID NO:132)) and one from rat (neuromedin U; SEQ ID NO:130) (Table 4). Human galanin and neuromedin U contain an intrinsic Asn residue, thus enabling "traceless" ligation without leaving any additional sorting sequences in the final cyclized products. For other peptides, an additional Asn-His-Val sequence was added at the C-terminus and a Gly or Gly-Ile was added at the N-terminus as the linker sequence. The cyclization reactions were performed in 50 µl reaction mixtures containing 50 µM peptides and 0.1 µM butelase 1 (0.002 molar equivalent) at 37° C. HPLC and mass spectrometry were used to monitor the reactions. Remarkably, butelase 1 achieved >95% cyclization yields within 5 min for all peptides tested (FIG. 16). The fact that these peptides were randomly selected and share no sequence homology suggests the promiscuity and mimimal substrate requirement of butelase 1.

TABLE 4

| Peptide | Sequence | Origin |
|---|---|---|
| Neuromedin U | RVDEEFQSPFASQSRGYFLF RPRNHV (SEQ ID NO: 128) | H. sapiens |
| Salusin | GISGALPPAPAAPRPALRAQ RAGPAGPGAKNHV (SEQ ID NO: 129) | H. sapiens |
| Neuromedin U | GIKYKVNEYQGPVAPSGGFF LFRPRNHV (SEQ ID NO: 130) | R. norvegicus |
| Galanin | GLTSGWTLNSAGYLLGPHAV GNHRSFSDKNHV (SEQ ID NO: 132) | H. sapiens |
| Apelin | GLVQPRGSRNGPGPWQGGRR KFRRQRPRLSHKGPMPFNHV (SEQ ID NO: 131) | H. sapiens |

Next the kinetics of cyclization of these peptide substrates were examined. The apparent kinetic parameters of butelase 1 were calculated from Michaelis-Menten plot using GraphPad Prism (Table 5). The catalytic efficiencies fall in the range of $1 \times 10^5$ to $1.3 \times 10^6$ $M^{-1}$ $s^{-1}$ which is consistent with our previous study on cysteine-rich peptides. This result confirmed that disulfides, and in turn a folded structure maintained by multiple disulfides, are not required for the cyclization by butelase 1.

TABLE 5

| Peptide | $k_{cat}$ ($s^{-1}$) | $K_m$ (uM) | $k_{cat}/K_m$ ($M^{-1}$ $S^{-1}$) |
|---|---|---|---|
| Galanin | 3.54 ± 0.31 | 34.2 ± 6.5 | 103,000 |
| Apelin | 5.78 ± 0.25 | 6.7 ± 1.4 | 859,000 |
| Neuromedin U | 5.78 ± 0.36 | 8.7 ± 2.1 | 664,000 |
| Rat neuromedin U | 26.55 ± 2.48 | 20.2 ± 5.9 | 1,314,000 |

In addition, a trial ligation of green fluorescent protein with a C-terminal NHV-tag (SEQ ID NO:133) with a short peptide GIGK(biotin)R (SEQ ID NO:134) was performed to demonstrate the application of butelase 1 for protein labeling. For the reaction, 50 µM GFP with NHV tag, 0.125 µM butelase 1 and 1 mM GIGK(biotin)R (SEQ ID NO: 134) were incubated for 30 minutes at 37° C. The results are shown in FIG. 17.

To demonstrate that butelase 1 can cyclize proteins, a modified GFP ending with Asn-His-Val motif at the C-terminus and starting with Gly-Ile at the N-terminus was constructed (SEQ ID NO:145). The cyclization reaction was carried in the presence of 25 µM GFP and 0.1 µM butelase 1 (0.004 molar equivalent). The cyclization reaction completed within 15 min with >90% yield as monitored by SDS page and high resolution ESI-MS (FIG. 18). For comparison, sortase-mediated cyclization of GFP required an incubation of 24 hours and 1 molar equivalent of sortase A. The catalytic rate of butelase 1 is thus nearly 10,000 faster than sortase A using GFP as a model protein. This result demonstrated that butelase 1 is a powerful ligase with promising potential and can provide an alternative method for cyclization of peptide and proteins.

To investigate the ability of butelase 1 for introducing a functional group, such as biotin and fluorophores to proteins, C-terminal and N-terminal ligation was performed and the results analyzed by different techniques. For C-terminal ligation, the substrates tested are ABL-Mono (synthetic human scFv fragment against ABL protein; SEQ ID NO:146), and ERK-Darp (synthetic human antibody mimetic (darpin) specific for ERK; SEQ ID NO:147) (Table 6). For N-terminal ligation, the substrates tested were an ubiquitin protein (SEQ ID NO:148), and peptide 1 (YKNHV, SEQ ID NO: 149) or a thioglycolic acid variant (thiodepsipeptide) thereof (YKN-thioglycolic acid-V).

TABLE 6

| Peptide | Sequence | Vector |
|---|---|---|
| GFP-NHV (SEQ ID NO: 133) | MHHHHHHSSGVDLGTENLYFQSMSKGEE LFTGVVPILVELDGDVNGHKFSVSGEGE GDATYGKLTLKFICTTGKLPVPWPTLVT TLTYGVQCFSRYPDHMKQHDFFKSAMPE GYVQERTIFFKDDGNYKTRAEVKFEGDT LVNRIELKGIDFKEDGNILGHKLEYNYN SHNVYIMADKQKNGIKVNFKIRHNIEDG SVQLADHYQQNTPIGDGPVLLPDNHYLS TQSALSKDPNEKRDHMVLLEFVTAAGIT LGMDELYK<u>NHV</u> | pNIC28-Bsa4 |
| ABL-Mono (SEQ ID NO: 146) | MHHHHHHSSGVDLGTENLYFQSMGGSGS SVSSVPTKLEVVDATPTSLKISWDAYYS SWQNVKYYRITYGETGGDSPVQEFTVPG YYSTATISGLKPGVDYTITVYAYDTFFP GYEPNSPISINYRT<u>NHV</u> | — |

TABLE 6-continued

| Peptide | Sequence | Vector |
|---|---|---|
| ERK-Darp (SEQ ID NO: 147) | MHHHHHHSSGVDLGTENLYFQSMGSDLG KKLLEAARAGQDDEVRILMANGADVNAH DDQGSTPLHLAAWIGHPEIVEVLLKHGA DVNARDTDGWTPLHLAADNGHLEIVEVL LKYGADVNAQDAYGLTPLHLAADRGHLE IVEVLLKHGADVNAQDKFGKTAFDISID NGNEDLAEILQKL<u>NHV</u> | – |
| Ubiquitin analog (SEQ ID NO: 148) | <u>MGI</u>MQIFVKTLTGKTITLEVEPSDTIEN VKAKIQDKEGIPPDQQRLIFAGKQLEDG RTLSDYNIQKESTLHLVLRLRGGHHHHH H | pET3a |

To investigate the capability of butelase 1 for C-terminal ligation, ABL-Mono with 14469.2 Da MW and ERK-Darp with 20270.2 Da MW were incubated with a fluorescent containing peptide GIR-AMC (AMC =7-Amino-4-methyl-coumarin) in the presence of butelase 1. The reactions were monitored by MS (FIG. 19). Peaks detected at 14718.4 Da and 20511.1 Da are the ligated products of ABL-Mono and ERK-Darp with the addition of GIR-AMC and removal of His, Val and water molecule. ERK-Darp reaches nearly 90% conversion yield after 20 minute incubation.

Due to the large MW of ERK-Darp, GFP-NHV and their ligated products with the FITC-labelled peptide FITC-GKNHV (SEQ ID NO:150), analysis by MS was not accurate enough. ESI-MS, with specialty in ionizing macromolecules (Ho et al., Clin Biochem. Rev. (2003) 24(1), 3-12), was used to examine the large ligated products. For the ligatino reaction, 50 µM ERK-Darp and 50 µM GFP-NHV were incubated with 1 mM FITC-GKNHV (SEQ ID NO: 150) and 50 nM butelase 1 for 10 minute at 42° C. The product samples for ESI-MS were first isolated by UPLC to reduce the salt concentration. The result of ESI-MS was analyzed by ESI prot 1.0 program. The MW of ERK-Darp obtained by ESI-MS is 20205±1.5 Da, with only 239 Da difference to the theoretical MW. The MW of putative ligated product is 20453±1.6 Da and this proves the successful protein ligation. The MW of GFP-NHV and the putative ligated product are 29720.0±0.7 Da and 29969.3±0.7 Da respectively (FIG. 20).

For the N-terminal ligation, the reaction conditions were: 100 µM ubiquitin, 0.1 µM butelase 1, 500 µM peptide 1, incubated at 42° C. The reaction yield was 82% after 150 minutes. The reaction was monitored by HPLC and MS (FIG. 21).

Peptide dendrimers have been shown to have increased activity due to increased binding affinity. To test the possibility of using butelase 1 as a ligase to generate dendrimeric peptides, ligation of model peptide YRNHV (SEQ ID NO:125) to dimeric peptide G2K (two GIG sequences linked by a K residue) was carried out (FIG. 22). 50 µM G2K, 20 nM butelase 1 and 250 µM YRNHV (SEQ ID NO: 125) peptide were incubated at 37° C. for 1 h. Mass spectrometry was used to monitor the reaction at the end of the incubation (FIG. 22). The result provides a proof-of-concept that butelase 1 is able to act as a ligase for the dimerization of peptides.

The dimerization capabilities were also tested with peptides GV-10, SV-10, HV-10, EV-10 and RV-10 (SEQ ID Nos. 117-121). The results are shown in Table 7.

TABLE 7

Dimerization and cyclization of small peptides

| Peptides | Sequence | Yield (%) |
|---|---|---|
| GV-10 (SEQ ID NO: 117) | GLPPPIFNHV → Cyclo(GLPPPIFN)$_2$ | 50 |
| SV-10 (SEQ ID NO: 118) | SLPPPIFNHV → Cyclo(SLPPPIFN)$_2$ | 50 |
| HV-10 (SEQ ID NO: 119) | HLPPPIFNHV → Cyclo(HLPPPIFN)$_2$ | 50 |
| EV-9 (SEQ ID NO: 120) | EINSTEINHV → Cyclo(EINSTEIN), EINSTEINEINSTEINHV | 20 |
| RV-10 (SEQ ID NO: 121) | RVTRPVNHV → Cyclo(RVTRPVN), Cyclo(RVTRPVN)$_2$ | 20 |

Example 3

N-terminal Cyclization Specificity

To further study the N-terminal specificity of butelase 1 with respect to its cyclase activity, three peptide libraries were synthesized and tested for cyclization:

Peptide library 1:
(SEQ ID NO: 157)
XLYRRGRYLRRNHV

Peptide library 2:
(SEQ ID NO: 158)
XRLYRGRYLRRNHV

Peptide library 3:
(SEQ ID NO: 159)
GXLYRGRYLRRNHV

In the afore-mentioned peptide libraries X designates any one of the 20 natural amino acids, as defined above. The cyclized peptides have the same sequence as given above, with the exception that the C-terminal residues HV have been cleaved off and the C-terminal N covalently linked to the N-terminal amino acid of the respective peptide. The reaction was performed in the presence of 50 nM butelase 1, 50 µM peptide, 42° C. for 60 min. The results of this cyclization activity test are shown as cyclization yields of the three peptide libraries in FIG. 23 a)-c).

From this experiment, it can be concluded that when the P2" residue (the residue at position 2 as calculated from N- to C-terminus)is any one of Leu/Val/Ile/Cys, then the P1" residue (i.e. the N-terminal residue at position 1) is not important, which is similar to the result we obtained from the intermolecular ligation of KALVINHV (SEQ ID NO: 122) with XIGGIR (SEQ ID NO: 123) (Example 2). Further, when the P1" residue is Gly, then P2" can be any residue and still allow efficient cyclization.

Example 4

Reversible Immobilization of Butelase 1 on Concanavalin A Resin for On-Column Peptide Cyclization Concanavalin A (Con A) is a lectin (carbohydrate-binding protein) that is isolated from *Canavalia ensiformis* (jack bean). It binds specifically to α-D-mannose and α-D-glucose containing biomolecules, including glycoproteins and glycolipids. Butelase 1 was recombinantly expressed and isolated in glycosylated form as a protein of about 37 kDa (data not shown). It was immobilized onto ProSwift® ConA-1S affinity column (Thermo Scientific) through its carbohydrate moieties. The immobilized butelase 1 was fully functional and was able to catalyze the on-column cyclization of SFTI-1, kB1 (kalata B1) and conotoxin. The reaction was performed in the presence of 50 µg immobilized butelase 1 and 50 µM of peptide substrates. UPLC profile illustrating the cyclisation of (a) Conotoxin GV-17 (SEQ ID NO:111) (b) SFTI-NHV (SEQ ID NO:135) (c) kB1 (SEQ ID NO:110) is shown in FIG. 24.

---

The invention claimed is:

1. A solid support material comprising immobilized thereon an isolated polypeptide having protein ligase or cyclase activity comprising or consisting of
   (i) the amino acid sequence as set forth in SEQ ID NO: 1;
   (ii) an amino acid sequence that shares at least 95% sequence identity with the amino acid sequence set forth in SEQ ID NO: 1 over its entire length and comprising:
      1) the amino acid residue N at the position corresponding to position 18 of SEQ ID NO: 1;
      2) the amino acid residue H at the position corresponding to position 124 of SEQ ID NO: 1; and
      3) the amino acid residue C at the position corresponding to position 166 of SEQ ID NO: 1; or
   (iii) a fragment of any one of (i)-(ii) comprising amino acids 10-200 of the amino acid sequence set forth in SEQ ID NO: 1;
wherein the solid support material comprises a particulate polymer resin material;
wherein the isolated polypeptide is immobilized on the solid support material by covalent or non-covalent interactions, wherein, if the isolated polypeptide is non-covalently immobilized on the solid support material, the isolated polypeptide is glycosylated and non-covalently bound to a carbohydrate- binding moiety coupled to the solid support material surface; and
wherein immobilization of the isolated polypeptide allows for contacting with a substrate and ligation or cyclization reaction of the substrate by the isolated polypeptide.

2. The solid support material of claim 1, wherein the isolated polypeptide comprises or consists of the amino acid sequence set forth in SEQ ID NO: 2.

3. The solid support material of claim 1, wherein said isolated polypeptide can cyclize a given peptide with a yield efficiency of 80% or more.

4. The solid support material of claim 3, wherein the yield efficiency is 90% or more.

5. The solid support material of claim 1, wherein said isolated polypeptide can cyclize a given peptide with
   (i) a $K_m$ of 500 μM or less;
   (ii) a $k_{cat}$ of at least 0.05 s$^{-1}$; or
   (iii) both (i) and (ii).

6. The solid support material of claim 1, wherein the isolated polypeptide is glycosylated.

7. The solid support material of claim 5, wherein the isolated polypeptide is non-covalently bound to a carbohydrate-binding moiety coupled to the solid support material surface.

8. The solid support material of claim 7, wherein the carbohydrate-binding moiety is concanavalin A.

9. The solid support material of claim 1, wherein the solid support material is a particulate resin material for chromatography columns.

* * * * *

SEQUENCE LISTING

```
<160> NUMBER OF SEQ ID NOS: 163

<210> SEQ ID NO 1
<211> LENGTH: 342
<212> TYPE: PRT
<213> ORGANISM: Clitoria ternatea

<400> SEQUENCE: 1

Val Glu Gly Thr Arg Trp Ala Val Leu Val Ala Gly Ser Lys Gly Tyr
1               5                   10                  15

Val Asn Tyr Arg His Gln Ala Asp Val Cys His Ala Tyr Gln Ile Leu
            20                  25                  30

Lys Lys Gly Gly Leu Lys Asp Glu Asn Ile Ile Val Phe Met Tyr Asp
        35                  40                  45

Asp Ile Ala Tyr Asn Glu Ser Asn Pro His Pro Gly Val Ile Ile Asn
    50                  55                  60

His Pro Tyr Gly Ser Asp Val Tyr Lys Gly Val Pro Lys Asp Tyr Val
65                  70                  75                  80

Gly Glu Asp Ile Asn Pro Pro Asn Phe Tyr Ala Val Leu Leu Ala Asn
                85                  90                  95

Lys Ser Ala Leu Thr Gly Thr Gly Ser Gly Lys Val Leu Asp Ser Gly
            100                 105                 110

Pro Asn Asp His Val Phe Ile Tyr Tyr Thr Asp His Gly Gly Ala Gly
        115                 120                 125

Val Leu Gly Met Pro Ser Lys Pro Tyr Ile Ala Ala Ser Asp Leu Asn
    130                 135                 140

Asp Val Leu Lys Lys His Ala Ser Gly Thr Tyr Lys Ser Ile Val
145                 150                 155                 160

Phe Tyr Val Glu Ser Cys Glu Ser Gly Ser Met Phe Asp Gly Leu Leu
                165                 170                 175

Pro Glu Asp His Asn Ile Tyr Val Met Gly Ala Ser Asp Thr Gly Glu
            180                 185                 190

Ser Ser Trp Val Thr Tyr Cys Pro Leu Gln His Pro Ser Pro Pro Pro
        195                 200                 205

Glu Tyr Asp Val Cys Val Gly Asp Leu Phe Ser Val Ala Trp Leu Glu
    210                 215                 220

Asp Cys Asp Val His Asn Leu Gln Thr Glu Thr Phe Gln Gln Gln Tyr
225                 230                 235                 240

Glu Val Val Lys Asn Lys Thr Ile Val Ala Leu Ile Glu Asp Gly Thr
                245                 250                 255

His Val Val Gln Tyr Gly Asp Val Gly Leu Ser Lys Gln Thr Leu Phe
            260                 265                 270

Val Tyr Met Gly Thr Asp Pro Ala Asn Asp Asn Asn Thr Phe Thr Asp
        275                 280                 285
```

```
Lys Asn Ser Leu Gly Thr Pro Arg Lys Ala Val Ser Gln Arg Asp Ala
    290                 295                 300
Asp Leu Ile His Tyr Trp Glu Lys Tyr Arg Arg Ala Pro Glu Gly Ser
305                 310                 315                 320
Ser Arg Lys Ala Glu Ala Lys Lys Gln Leu Arg Glu Val Met Ala His
                325                 330                 335
Arg Met His Ile Asp Asn
            340
```

<210> SEQ ID NO 2
<211> LENGTH: 482
<212> TYPE: PRT
<213> ORGANISM: Clitoria ternatea

<400> SEQUENCE: 2

```
Met Lys Asn Pro Leu Ala Ile Leu Phe Leu Ile Ala Thr Val Val Ala
1               5                   10                  15
Val Val Ser Gly Ile Arg Asp Asp Phe Leu Arg Leu Pro Ser Gln Ala
                20                  25                  30
Ser Lys Phe Phe Gln Ala Asp Asp Asn Val Glu Gly Thr Arg Trp Ala
            35                  40                  45
Val Leu Val Ala Gly Ser Lys Gly Tyr Val Asn Tyr Arg His Gln Ala
        50                  55                  60
Asp Val Cys His Ala Tyr Gln Ile Leu Lys Lys Gly Leu Lys Asp
65                  70                  75                  80
Glu Asn Ile Ile Val Phe Met Tyr Asp Asp Ile Ala Tyr Asn Glu Ser
                85                  90                  95
Asn Pro His Pro Gly Val Ile Ile Asn His Pro Tyr Gly Ser Asp Val
            100                 105                 110
Tyr Lys Gly Val Pro Lys Asp Tyr Val Gly Glu Asp Ile Asn Pro Pro
        115                 120                 125
Asn Phe Tyr Ala Val Leu Leu Ala Asn Lys Ser Ala Leu Thr Gly Thr
130                 135                 140
Gly Ser Gly Lys Val Leu Asp Ser Gly Pro Asn Asp His Val Phe Ile
145                 150                 155                 160
Tyr Tyr Thr Asp His Gly Gly Ala Gly Val Leu Gly Met Pro Ser Lys
                165                 170                 175
Pro Tyr Ile Ala Ala Ser Asp Leu Asn Asp Val Leu Lys Lys Lys His
            180                 185                 190
Ala Ser Gly Thr Tyr Lys Ser Ile Val Phe Tyr Val Glu Ser Cys Glu
        195                 200                 205
Ser Gly Ser Met Phe Asp Gly Leu Leu Pro Glu Asp His Asn Ile Tyr
210                 215                 220
Val Met Gly Ala Ser Asp Thr Gly Glu Ser Ser Trp Val Thr Tyr Cys
225                 230                 235                 240
Pro Leu Gln His Pro Ser Pro Pro Glu Tyr Asp Val Cys Val Gly
                245                 250                 255
Asp Leu Phe Ser Val Ala Trp Leu Glu Asp Cys Asp Val His Asn Leu
            260                 265                 270
Gln Thr Glu Thr Phe Gln Gln Tyr Glu Val Lys Asn Lys Thr
        275                 280                 285
Ile Val Ala Leu Ile Glu Asp Gly Thr His Val Gln Tyr Gly Asp
290                 295                 300
Val Gly Leu Ser Lys Gln Thr Leu Phe Val Tyr Met Gly Thr Asp Pro
305                 310                 315                 320
```

```
Ala Asn Asp Asn Asn Thr Phe Thr Asp Lys Asn Ser Leu Gly Thr Pro
                325                 330                 335

Arg Lys Ala Val Ser Gln Arg Asp Ala Asp Leu Ile His Tyr Trp Glu
            340                 345                 350

Lys Tyr Arg Arg Ala Pro Glu Gly Ser Ser Arg Lys Ala Glu Ala Lys
            355                 360                 365

Lys Gln Leu Arg Glu Val Met Ala His Arg Met His Ile Asp Asn Ser
        370                 375                 380

Val Lys His Ile Gly Lys Leu Leu Phe Gly Ile Glu Lys Gly His Lys
385                 390                 395                 400

Met Leu Asn Asn Val Arg Pro Ala Gly Leu Pro Val Val Asp Asp Trp
                405                 410                 415

Asp Cys Phe Lys Thr Leu Ile Arg Thr Phe Glu Thr His Cys Gly Ser
            420                 425                 430

Leu Ser Glu Tyr Gly Met Lys His Met Arg Ser Phe Ala Asn Leu Cys
        435                 440                 445

Asn Ala Gly Ile Arg Lys Glu Gln Met Ala Glu Ala Ser Ala Gln Ala
    450                 455                 460

Cys Val Ser Ile Pro Asp Asn Pro Trp Ser Ser Leu His Ala Gly Phe
465                 470                 475                 480

Ser Val

<210> SEQ ID NO 3
<211> LENGTH: 488
<212> TYPE: PRT
<213> ORGANISM: Clitoria ternatea

<400> SEQUENCE: 3

Met Ala Val Asp His Cys Phe Leu Lys Lys Thr Cys Tyr Tyr Gly
1               5                   10                  15

Phe Val Leu Trp Ser Trp Met Leu Met Met Ser Leu His Ser Lys Ala
                20                  25                  30

Ala Arg Leu Asn Pro Gln Lys Glu Trp Asp Ser Val Ile Arg Leu Pro
            35                  40                  45

Thr Glu Pro Val Asp Ala Asp Thr Asp Glu Val Gly Thr Arg Trp Ala
        50                  55                  60

Val Leu Val Ala Gly Ser Asn Gly Tyr Glu Asn Tyr Arg His Gln Ala
65                  70                  75                  80

Asp Val Cys His Ala Tyr Gln Leu Leu Ile Lys Gly Gly Leu Lys Glu
                85                  90                  95

Glu Asn Ile Val Val Phe Met Tyr Asp Asp Ile Ala Trp His Glu Leu
            100                 105                 110

Asn Pro Arg Pro Gly Val Ile Asn Asn Pro Arg Gly Glu Asp Val
        115                 120                 125

Tyr Ala Gly Val Pro Lys Asp Tyr Thr Gly Glu Asp Val Thr Ala Glu
    130                 135                 140

Asn Leu Phe Ala Val Ile Leu Gly Asp Arg Ser Lys Val Lys Gly Gly
145                 150                 155                 160

Ser Gly Lys Val Ile Asn Ser Lys Pro Glu Asp Arg Ile Phe Ile Phe
                165                 170                 175

Tyr Ser Asp His Gly Gly Pro Gly Val Leu Gly Met Pro Asn Glu Gln
            180                 185                 190

Ile Leu Tyr Ala Met Asp Phe Ile Asp Val Leu Lys Lys Lys His Ala
        195                 200                 205
```

Ser Gly Gly Tyr Arg Glu Met Val Ile Tyr Val Glu Ala Cys Glu Ser
            210                 215                 220

Gly Ser Leu Phe Glu Gly Ile Met Pro Lys Asp Leu Asn Val Phe Val
225                 230                 235                 240

Thr Thr Ala Ser Asn Ala Gln Glu Asn Ser Trp Gly Thr Tyr Cys Pro
                245                 250                 255

Gly Thr Glu Pro Ser Pro Pro Glu Tyr Thr Thr Cys Leu Gly Asp
            260                 265                 270

Leu Tyr Ser Val Ala Trp Met Glu Asp Ser Glu Ser His Asn Leu Arg
            275                 280                 285

Arg Glu Thr Val Asn Gln Gln Tyr Arg Ser Val Lys Glu Arg Thr Ser
290                 295                 300

Asn Phe Lys Asp Tyr Ala Met Gly Ser His Val Met Gln Tyr Gly Asp
305                 310                 315                 320

Thr Asn Ile Thr Ala Glu Lys Leu Tyr Leu Phe Gln Gly Phe Asp Pro
                325                 330                 335

Ala Thr Val Asn Leu Pro Pro His Asn Gly Arg Ile Glu Ala Lys Met
            340                 345                 350

Glu Val Val His Gln Arg Asp Ala Glu Leu Leu Phe Met Trp Gln Met
            355                 360                 365

Tyr Gln Arg Ser Asn His Leu Leu Gly Lys Lys Thr His Ile Leu Lys
370                 375                 380

Gln Ile Ala Glu Thr Val Lys His Arg Asn His Leu Asp Gly Ser Val
385                 390                 395                 400

Glu Leu Ile Gly Val Leu Leu Tyr Gly Pro Gly Lys Gly Ser Pro Val
                405                 410                 415

Leu Gln Ser Val Arg Asp Pro Gly Leu Pro Leu Val Asp Asn Trp Ala
            420                 425                 430

Cys Leu Lys Ser Met Val Arg Val Phe Glu Ser His Cys Gly Ser Leu
            435                 440                 445

Thr Gln Tyr Gly Met Lys His Met Arg Ala Phe Ala Asn Ile Cys Asn
            450                 455                 460

Ser Gly Val Ser Glu Ser Ser Met Glu Glu Ala Cys Met Val Ala Cys
465                 470                 475                 480

Gly Gly His Asp Ala Gly His Leu
                485

<210> SEQ ID NO 4
<211> LENGTH: 359
<212> TYPE: PRT
<213> ORGANISM: Clitoria ternatea

<400> SEQUENCE: 4

Glu Asp Val Asn Ala His Asn Phe Phe Ala Val Leu Leu Gly Asn Lys
1               5                   10                  15

Ser Ala Leu Thr Gly Gly Ser Gly Lys Val Val Asp Ser Gly Pro Asp
            20                  25                  30

Asp His Ile Phe Ile Phe Tyr Ser Asp His Gly Gly Pro Gly Val Leu
        35                  40                  45

Gly Met Pro Thr His Pro Tyr Leu Tyr Ala Asp Asp Leu Asn Glu Val
    50                  55                  60

Leu Lys Lys Lys His Ala Ser Gly Thr Tyr Lys Arg Leu Val Phe Tyr
65                  70                  75                  80

Ile Glu Ala Cys Glu Ser Gly Ser Ile Phe Glu Gly Leu Leu Pro Glu

```
            85                  90                  95
Asp Ile Asp Ile Tyr Ala Thr Thr Ala Ser Asn Ala Thr Glu Ser Ser
            100                 105                 110

Ser Pro Thr Tyr Cys Pro Arg Pro Ala Glu His Ala Pro Phe Pro
        115                 120                 125

Glu Tyr Thr Thr Cys Leu Gly Asp Leu Tyr Ser Ile Thr Trp Met Glu
    130                 135                 140

Asp Ser Asp Ile His Asn Leu Arg Thr Glu Thr Leu His Gln Gln Tyr
145                 150                 155                 160

Glu Leu Val Lys Gly Ile Thr Phe Ala Asp Ser Glu Gly Ser His Val
                165                 170                 175

Met Gln Tyr Gly Asp Ile Asp Leu Ser Ser Asp Val Leu Phe Gln Tyr
            180                 185                 190

Leu Gly Thr Asn Pro Ala Asn Asp Asn Phe Thr Phe Val Asp Glu Asn
        195                 200                 205

Tyr Leu Arg Ser Ser Ser Lys Pro Val Asn Gln His Asp Ala Asp Leu
    210                 215                 220

Ile His Phe Trp Asp Lys Phe Arg Lys Ala Pro Gly Asp Ser Ala Lys
225                 230                 235                 240

Lys Asn Thr Ala Gln Lys Gln Leu Leu Glu Val Met Ser His Arg Met
                245                 250                 255

His Ile Asp Asn Thr Val Gln Leu Ile Gly Lys Leu Leu Phe Gly Ile
            260                 265                 270

Glu Lys Gly Pro Glu Ile Leu Asn Asn Val Arg Pro Val Gly Ser Val
        275                 280                 285

Leu Val Asp Asp Trp Ala Cys Met Lys Ala Met Val Arg Thr Phe Glu
    290                 295                 300

Thr His Cys Gly Ser Leu Ser Gln Tyr Gly Met Lys His Met Arg Ser
305                 310                 315                 320

Phe Ala Asn Ile Cys Asn Ala Gly Ile Lys Asn Glu Gln Met Ala Glu
                325                 330                 335

Ala Ser Gly Gln Ala Cys Val Ser Ile Pro Ala Asn Pro Trp Ser Ser
            340                 345                 350

Leu Gln Arg Gly Phe Ser Ala
        355

<210> SEQ ID NO 5
<211> LENGTH: 193
<212> TYPE: PRT
<213> ORGANISM: Clitoria ternatea

<400> SEQUENCE: 5

Met Asp Thr Phe Pro Pro Leu Leu Leu Cys Leu Phe Val Leu Ala Ala
1               5                   10                  15

Val Val Ser Ala Arg Arg Gly Leu Ala Gly Glu Phe Arg Arg Leu Ala
            20                  25                  30

Ser Glu Pro Asp Ile Asp His Asn Phe Arg Gly Thr Lys Trp Ala Val
        35                  40                  45

Leu Leu Ala Gly Ser Arg Gly Phe Phe Asp Tyr Arg His Gln Ala Asp
    50                  55                  60

Val Cys His Ala Tyr Gln Leu Leu Arg Lys Gly Gly Leu Lys Glu Glu
65                  70                  75                  80

Asn Ile Ile Val Phe Met Tyr Asp Asp Ile Ala Asn Asn Glu Glu Asn
                85                  90                  95
```

-continued

```
Pro Arg Pro Gly Val Ile Ile Asn Ser Pro His Gly Asp Asn Val Tyr
            100                 105                 110

Lys Gly Val Pro Lys Asp Tyr Val Gly Glu Asp Val Asn Ala Asp Asn
        115                 120                 125

Phe Phe Ala Ala Ile Leu Gly Asn Lys Ser Ala Leu Thr Gly Gly Ser
130                 135                 140

Gly Lys Val Val Asp Ser Gly Pro Asn Asp His Ile Phe Ile Tyr Tyr
145                 150                 155                 160

Ser Asp His Gly Gly Pro Gly Val Leu Gly Met Pro Thr Ser Ser Tyr
                165                 170                 175

Val Phe Ala Ser Asp Leu Ile Glu Val Leu Lys Lys His Ala Ser
            180                 185                 190

Gly

<210> SEQ ID NO 6
<211> LENGTH: 150
<212> TYPE: PRT
<213> ORGANISM: Clitoria ternatea

<400> SEQUENCE: 6

Met Asp Thr Phe Pro Leu Leu Leu Cys Leu Phe Val Leu Ala Ala
1               5                   10                  15

Val Val Ser Ala Arg Arg Gly Leu Ala Gly Glu Phe Arg Arg Leu Ala
            20                  25                  30

Ser Glu Pro Asp Ile Asp His Asn Phe Arg Gly Thr Lys Trp Ala Val
        35                  40                  45

Leu Leu Ala Gly Ser Arg Gly Phe Phe Asp Tyr Arg His Gln Ala Asp
50                  55                  60

Val Cys His Ala Tyr Gln Leu Leu Arg Lys Gly Gly Leu Lys Glu Glu
65                  70                  75                  80

Asn Ile Ile Val Phe Met Tyr Asp Asp Ile Ala Phe Asn Lys Lys Asn
                85                  90                  95

Pro Arg Pro Gly Val Ile Ile Asn Lys Pro Asp Gly Gly Asp Val Tyr
            100                 105                 110

Lys Gly Val Pro Lys Asp Tyr Thr Gly Glu Asn Val Asn Val Asn Asn
        115                 120                 125

Phe Leu Ala Val Leu Leu Gly Asn Lys Ser Ala Leu Thr Gly Gly Ser
130                 135                 140

Gly Lys Val Leu Asn Ser
145                 150

<210> SEQ ID NO 7
<211> LENGTH: 86
<212> TYPE: PRT
<213> ORGANISM: Clitoria ternatea

<400> SEQUENCE: 7

Ala Asp Leu Ile His Phe Trp Glu Lys Phe Arg Arg Ala Thr Lys Gly
1               5                   10                  15

Ser Pro Arg Lys Ala Glu Ala Glu Lys Gln Leu Arg Glu Val Thr Ser
            20                  25                  30

His Arg Met His Ile Asp His Ser Val Lys His Ile Gly Lys Leu Leu
        35                  40                  45

Phe Gly Ile Glu Lys Gly Ser Lys Met Leu Asn Ser Val Arg Pro Ala
50                  55                  60

Gly Leu Pro Ile Val Asp Asp Trp Asp Cys Leu Lys Thr Met Val Arg
```

Thr Phe Glu Thr His Cys
                85

<210> SEQ ID NO 8
<211> LENGTH: 473
<212> TYPE: PRT
<213> ORGANISM: Oldenlandia affinis

<400> SEQUENCE: 8

Met Val Arg Tyr Leu Ala Gly Ala Val Leu Leu Val Val Leu Ser
1               5                   10                  15

Val Ala Ala Val Ser Gly Ala Arg Asp Gly Asp Tyr Leu His Leu
                20                  25                  30

Pro Ser Glu Val Ser Arg Phe Phe Arg Pro Gln Glu Thr Asn Asp His
            35                  40                  45

Gly Glu Asp Ser Val Gly Thr Arg Trp Ala Val Leu Ile Ala Gly Ser
        50                  55                  60

Lys Gly Tyr Ala Asn Tyr Arg His Gln Ala Gly Val Cys His Ala Tyr
65                  70                  75                  80

Gln Ile Leu Lys Arg Gly Gly Leu Lys Asp Glu Asn Ile Val Val Phe
                85                  90                  95

Met Tyr Asp Asp Ile Ala Tyr Asn Glu Ser Asn Pro Arg Pro Gly Val
                100                 105                 110

Ile Ile Asn Ser Pro His Gly Ser Asp Val Tyr Ala Gly Val Pro Lys
            115                 120                 125

Asp Tyr Thr Gly Glu Glu Val Asn Ala Lys Asn Phe Leu Ala Ala Ile
        130                 135                 140

Leu Gly Asn Lys Ser Ala Ile Thr Gly Gly Ser Gly Lys Val Val Asp
145                 150                 155                 160

Ser Gly Pro Asn Asp His Ile Phe Ile Tyr Tyr Thr Asp His Gly Ala
                165                 170                 175

Ala Gly Val Ile Gly Met Pro Ser Lys Pro Tyr Leu Tyr Ala Asp Glu
                180                 185                 190

Leu Asn Asp Ala Leu Lys Lys Lys His Ala Ser Gly Thr Tyr Lys Ser
            195                 200                 205

Leu Val Phe Tyr Leu Glu Ala Cys Glu Ser Gly Ser Met Phe Glu Gly
        210                 215                 220

Ile Leu Pro Glu Asp Leu Asn Ile Tyr Ala Leu Thr Ser Thr Asn Thr
225                 230                 235                 240

Thr Glu Ser Ser Trp Cys Tyr Tyr Cys Pro Ala Gln Glu Asn Pro Pro
                245                 250                 255

Pro Pro Glu Tyr Asn Val Cys Leu Gly Asp Leu Phe Ser Val Ala Trp
            260                 265                 270

Leu Glu Asp Ser Asp Val Gln Asn Ser Trp Tyr Glu Thr Leu Asn Gln
        275                 280                 285

Gln Tyr His His Val Asp Lys Arg Ile Ser His Ala Ser His Ala Thr
            290                 295                 300

Gln Tyr Gly Asn Leu Lys Leu Gly Glu Glu Gly Leu Phe Val Tyr Met
305                 310                 315                 320

Gly Ser Asn Pro Ala Asn Asp Asn Tyr Thr Ser Leu Asp Gly Asn Ala
                325                 330                 335

Leu Thr Pro Ser Ser Ile Val Asn Gln Arg Asp Ala Asp Leu Leu
            340                 345                 350

His Leu Trp Glu Lys Phe Arg Lys Ala Pro Glu Gly Ser Ala Arg Lys
            355                 360                 365

Glu Glu Ala Gln Thr Gln Ile Phe Lys Ala Met Ser His Arg Val His
370                 375                 380

Ile Asp Ser Ser Ile Lys Leu Ile Gly Lys Leu Leu Phe Gly Ile Glu
385                 390                 395                 400

Lys Cys Thr Glu Ile Leu Asn Ala Val Arg Pro Ala Gly Gln Pro Leu
                405                 410                 415

Val Asp Asp Trp Ala Cys Leu Arg Ser Leu Val Gly Thr Phe Glu Thr
            420                 425                 430

His Cys Gly Ser Leu Ser Glu Tyr Gly Met Arg His Thr Arg Thr Ile
            435                 440                 445

Ala Asn Ile Cys Asn Ala Gly Ile Ser Glu Glu Gln Met Ala Glu Ala
        450                 455                 460

Ala Ser Gln Ala Cys Ala Ser Ile Pro
465                 470

<210> SEQ ID NO 9
<211> LENGTH: 486
<212> TYPE: PRT
<213> ORGANISM: Hedyotis biflora

<400> SEQUENCE: 9

Met Val Arg Tyr Pro Ala Gly Val Val Leu Leu Val Thr Ile Thr
1               5                   10                  15

Ile Ser Val Val Ala Glu Ala Arg Asp Gly Tyr Leu Lys Leu Pro Ser
                20                  25                  30

Glu Phe Ser Ala Phe Leu Arg Pro Asn Glu Thr Asn Asp Asn Ser Val
            35                  40                  45

Ser Thr Arg Trp Ala Val Leu Ile Ala Gly Ser Lys Asp Tyr Trp Asn
        50                  55                  60

Tyr Arg His Gln Ala Asp Val Cys His Ala Tyr Gln Ile Leu Lys Arg
65                  70                  75                  80

Gly Gly Leu Lys Asp Glu Asn Ile Val Val Phe Met Tyr Asp Asp Ile
                85                  90                  95

Ala Tyr Asn Glu Glu Asn Pro Arg Pro Gly Val Ile Ile Asn Ser Pro
            100                 105                 110

His Gly Ser Asp Val Tyr Ala Gly Val Pro Lys Asp Tyr Thr Gly Asp
        115                 120                 125

Glu Val Asn Ala Lys Asn Phe Leu Ala Ala Ile Leu Gly Asp Lys Ser
130                 135                 140

Ala Ile Thr Gly Gly Ser Gly Lys Val Val Asp Ser Gly Pro Asn Asp
145                 150                 155                 160

His Ile Phe Ile Tyr Tyr Ser Asp His Gly Gly Pro Gly Val Leu Gly
                165                 170                 175

Met Pro Ser Gly Pro Tyr Leu Tyr Ala Asp Glu Leu Asn Asp Ala Leu
            180                 185                 190

Lys Lys Lys His Ala Ser Gly Thr Tyr Lys Ser Leu Val Phe Tyr Leu
        195                 200                 205

Glu Ala Cys Glu Ser Gly Ser Ile Phe Glu Gly Leu Leu Pro Glu Gly
    210                 215                 220

Leu Asn Ile Tyr Ala Thr Thr Ala Ser Asn Ala Glu Glu Ser Ser Trp
225                 230                 235                 240

Gly Thr Tyr Cys Pro Gly Glu Tyr Pro Ser Pro Ser Glu Tyr Glu
                245                 250                 255

```
Thr Cys Leu Gly Asp Leu Tyr Ser Val Ala Trp Met Glu Asp Ser Glu
            260                 265                 270

Val His Asn Leu Arg Ser Glu Thr Leu Lys Gln Gln Tyr His Leu Val
            275                 280                 285

Lys Thr Arg Thr Ser Asn Gly Asn Ser Ala Tyr Gly Ser His Val Met
290                 295                 300

Gln Tyr Gly Asp Leu Lys Leu Ser Val Asp Asn Leu Phe Leu Tyr Met
305                 310                 315                 320

Gly Thr Asn Pro Ala Asn Asp Asn Tyr Thr Phe Val Asp Asp Asn Ala
                325                 330                 335

Leu Arg Pro Ser Ser Lys Ala Ile Asn Gln Arg Asp Ala Asp Leu Val
            340                 345                 350

His Phe Trp Asp Lys Phe Arg Lys Ala Pro Glu Gly Ser Leu Arg Lys
            355                 360                 365

Glu Glu Ala Ala Lys Gln Val Phe Glu Ala Met Ser His Arg Met His
370                 375                 380

Ile Asp Ser Ser Ile Lys Leu Val Gly Lys Leu Leu Phe Gly Ile Glu
385                 390                 395                 400

Arg Gly Ser Glu Ile Leu Asn Ala Val Arg Pro Ala Gly Gln Pro Leu
                405                 410                 415

Ala Asp Asp Trp Ala Cys Leu Lys Ser Leu Val Arg Thr Phe Glu Thr
            420                 425                 430

His Cys Gly Ser Leu Ser Gln Tyr Gly Met Lys His Met Arg Thr Val
            435                 440                 445

Ala Asn Ile Cys Asn Ala Gly Ile Thr Lys Glu Gln Met Ala Glu Ala
            450                 455                 460

Ala Ala Gln Ala Cys Val Ser Val Pro Ser Asn Pro Trp Ser Ser Leu
465                 470                 475                 480

Ser Gly Gly Phe Ser Ala
                485

<210> SEQ ID NO 10
<211> LENGTH: 483
<212> TYPE: PRT
<213> ORGANISM: Phaseolus vulgaris

<400> SEQUENCE: 10

Met Asp Gly Phe Pro Ile Leu Phe Leu Leu Ala Thr Leu Ile Thr Leu
1               5                   10                  15

Val Ser Gly Gly Arg Asp Glu Ile Leu Arg Leu Pro Ser Glu Ala Ser
            20                  25                  30

Arg Phe Phe Gln Ala Pro Ala Ala Asp Gln Asn Gln Glu Gly Thr Arg
        35                  40                  45

Trp Ala Leu Leu Ile Ala Gly Ser Asn Gly Tyr Trp Asn Tyr Arg His
    50                  55                  60

Gln Ser Asp Val Cys His Ala Tyr Gln Leu Leu Arg Lys Gly Gly Leu
65                  70                  75                  80

Lys Glu Glu Asn Ile Val Val Phe Met Tyr Asp Asp Ile Ala Phe Asn
                85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Val Gly Glu Asp Val Thr
        115                 120                 125

Val Asn Asn Phe Phe Ala Ala Ile Leu Gly Asn Lys Ser Ala Leu Thr
```

```
                130               135               140
Gly Gly Ser Gly Lys Val Ile Asp Ser Gly Pro Asn Asp His Ile Phe
145                 150                 155                 160

Ile Tyr Tyr Ser Asp His Gly Pro Gly Val Leu Gly Met Pro Thr
                165                 170                 175

Ser Pro Tyr Met Tyr Ala Ser Asp Leu Ile Glu Val Leu Lys Lys
                180                 185                 190

His Ala Ser Glu Thr Tyr Lys Ser Leu Val Phe Tyr Leu Glu Ala Cys
                195                 200                 205

Glu Ser Gly Ser Ile Phe Glu Gly Leu Leu Pro Glu Gly Met Asn Ile
                210                 215                 220

Tyr Ala Thr Thr Ala Ala Asn Ala Glu Glu Ser Ser Trp Gly Thr Tyr
225                 230                 235                 240

Cys Pro Gly Glu Tyr Pro Ser Pro Pro Glu Tyr Glu Thr Cys Leu
                245                 250                 255

Gly Asp Leu Tyr Ser Val Ala Trp Met Glu Asp Ser Asp Ile His Asn
                260                 265                 270

Leu Gln Thr Glu Thr Leu His Gln Gln Phe Glu Leu Val Lys Gln Arg
                275                 280                 285

Thr Ile Asn Gly Asn Ser Ala Tyr Gly Ser His Val Met Gln Tyr Gly
290                 295                 300

Asp Ile Gly Leu Ser Lys Asn Asn Leu Ser Leu Tyr Leu Gly Thr Asn
305                 310                 315                 320

Pro Ala Asn Asp Asn Phe Ala Phe Arg Glu Lys Asn Ser Leu Val Pro
                325                 330                 335

Pro Ser Lys Ala Val Asn Gln Arg Asp Ala Asp Leu Val His Leu Trp
                340                 345                 350

Asp Lys Tyr Arg Lys Ala Pro Val Gly Ser Ser Arg Lys Ser Val Ala
                355                 360                 365

Gln Lys Gln Ile Leu Glu Ala Met Ser His Arg Met His Ile Asp Asp
                370                 375                 380

Ser Met Lys Leu Ile Gly Lys Leu Leu Phe Gly Ile Glu Glu Gly Pro
385                 390                 395                 400

Lys Leu Leu Asn Ser Val Arg Pro Ala Gly Gln Pro Leu Val Asp Asp
                405                 410                 415

Trp Asp Cys Leu Lys Thr Leu Val Arg Thr Phe Glu Thr His Cys Gly
                420                 425                 430

Ser Leu Ser Gln Tyr Gly Met Lys His Met Arg Ser Phe Ala Asn Phe
                435                 440                 445

Cys Asn Ala Gly Ile Gly Lys Glu Gln Met Ala Glu Ala Ser Ala Gln
                450                 455                 460

Ala Cys Val Ser Ile Pro Ala Thr Pro Trp Ser Ser Leu Arg Ser Gly
465                 470                 475                 480

Phe Ser Ala

<210> SEQ ID NO 11
<211> LENGTH: 484
<212> TYPE: PRT
<213> ORGANISM: Glycine max

<400> SEQUENCE: 11

Met Asp Arg Phe Pro Ile Leu Phe Leu Val Ala Thr Leu Ile Thr Leu
1               5                   10                  15

Ala Ser Gly Ala Arg His Asp Ile Leu Arg Leu Pro Ser Glu Ala Ser
```

-continued

```
                 20                  25                  30
Arg Phe Phe Lys Ala Pro Ala Asn Ala Asp Gln Asn Asp Glu Gly Thr
             35                  40                  45
Arg Trp Ala Val Leu Val Ala Gly Ser Asn Gly Tyr Trp Asn Tyr Arg
 50                  55                  60
His Gln Ser Asp Val Cys His Ala Tyr Gln Leu Leu Arg Lys Gly Gly
 65                  70                  75                  80
Val Lys Glu Glu Asn Ile Val Val Phe Met Tyr Asp Asp Ile Ala Phe
                 85                  90                  95
Asn Glu Glu Asn Pro Arg Pro Gly Val Ile Ile Asn Ser Pro His Gly
                100                 105                 110
Asn Asp Val Tyr Lys Gly Val Pro Lys Asp Tyr Val Gly Glu Asp Val
            115                 120                 125
Thr Val Asp Asn Phe Phe Ala Ala Ile Leu Gly Asn Lys Ser Ala Leu
            130                 135                 140
Thr Gly Gly Ser Gly Lys Val Val Asp Ser Gly Pro Asn Asp His Ile
145                 150                 155                 160
Phe Ile Tyr Tyr Ser Asp His Gly Gly Pro Gly Val Leu Gly Met Pro
                165                 170                 175
Thr Asn Pro Tyr Met Tyr Ala Ser Asp Leu Ile Glu Val Leu Lys Lys
            180                 185                 190
Lys His Ala Ser Gly Thr Tyr Lys Ser Leu Val Phe Tyr Leu Glu Ala
        195                 200                 205
Cys Glu Ser Gly Ser Ile Phe Glu Gly Leu Leu Pro Glu Gly Leu Asn
    210                 215                 220
Ile Tyr Ala Thr Thr Ala Ser Asn Ala Glu Glu Ser Ser Trp Gly Thr
225                 230                 235                 240
Tyr Cys Pro Gly Glu Tyr Pro Ser Pro Pro Glu Tyr Glu Thr Cys
                245                 250                 255
Leu Gly Asp Leu Tyr Ser Val Ala Trp Met Glu Asp Ser Asp Ile His
            260                 265                 270
Asn Leu Arg Thr Glu Thr Leu His Gln Gln Tyr Asp Leu Val Lys Glu
        275                 280                 285
Arg Thr Met Asn Gly Asn Ser Ile Tyr Gly Ser His Val Met Gln Tyr
    290                 295                 300
Gly Asp Ile Gly Leu Ser Lys Asn Asn Leu Val Leu Tyr Leu Gly Thr
305                 310                 315                 320
Asn Pro Ala Asn Asp Asn Phe Thr Phe Val His Lys Asn Ser Leu Val
                325                 330                 335
Pro Pro Ser Lys Ala Val Asn Gln Arg Asp Ala Asp Leu Ile His Phe
            340                 345                 350
Trp Asp Lys Phe Arg Lys Ala Pro Val Gly Ser Ser Arg Lys Ala Ala
        355                 360                 365
Ala Glu Lys Glu Ile Leu Glu Ala Met Ser His Arg Met His Ile Asp
    370                 375                 380
Asp Asn Met Lys Leu Ile Gly Lys Leu Leu Phe Gly Ile Glu Lys Gly
385                 390                 395                 400
Pro Glu Leu Leu Ser Ser Val Arg Pro Ala Gly Gln Pro Leu Val Asp
                405                 410                 415
Asp Trp Asp Cys Leu Lys Thr Leu Val Arg Thr Phe Glu Thr His Cys
            420                 425                 430
Gly Ser Leu Ser Gln Tyr Gly Met Lys His Met Arg Ser Phe Ala Asn
        435                 440                 445
```

```
Phe Cys Asn Ala Gly Ile Arg Lys Glu Gln Met Ala Glu Ala Ser Ala
    450                 455                 460
Gln Ala Cys Val Ser Ile Pro Ala Ser Ser Trp Ser Ser Leu His Arg
465                 470                 475                 480
Gly Phe Ser Ala
```

<210> SEQ ID NO 12
<211> LENGTH: 483
<212> TYPE: PRT
<213> ORGANISM: Homo sapiens

<400> SEQUENCE: 12

```
Met Asp Arg Phe Pro Ile Leu Phe Leu Leu Ala Thr Leu Ile Thr Leu
1               5                   10                  15
Ala Ser Gly Ala Arg His Asp Ile Leu Arg Leu Pro Ser Glu Ala Ser
                20                  25                  30
Thr Phe Phe Lys Ala Pro Gly Gly Asp Gln Asn Asp Glu Gly Thr Arg
            35                  40                  45
Trp Ala Val Leu Ile Ala Gly Ser Asn Gly Tyr Trp Asn Tyr Arg His
        50                  55                  60
Gln Ser Asp Val Cys His Ala Tyr Gln Leu Leu Arg Lys Gly Gly Leu
65                  70                  75                  80
Lys Glu Glu Asn Ile Val Val Phe Met Tyr Asp Asp Ile Ala Phe Asn
                85                  90                  95
Glu Glu Asn Pro Arg Pro Gly Val Ile Ile Asn Ser Pro His Gly Asn
            100                 105                 110
Asp Val Tyr Lys Gly Val Pro Lys Asp Tyr Ile Gly Glu Asp Val Thr
        115                 120                 125
Val Gly Asn Phe Phe Ala Ala Ile Leu Gly Asn Lys Ser Ala Leu Thr
130                 135                 140
Gly Gly Ser Gly Lys Val Val Asp Ser Gly Pro Asn Asp His Ile Phe
145                 150                 155                 160
Ile Tyr Tyr Ser Asp His Gly Gly Pro Gly Val Leu Gly Met Pro Thr
                165                 170                 175
Asn Pro Tyr Val Tyr Ala Ser Asp Leu Ile Glu Val Leu Lys Lys Lys
            180                 185                 190
His Ala Ser Gly Ser Tyr Lys Ser Leu Val Phe Tyr Leu Glu Ala Cys
        195                 200                 205
Glu Ser Gly Ser Ile Phe Glu Gly Leu Leu Pro Glu Gly Leu Asn Ile
210                 215                 220
Tyr Ala Thr Thr Ala Ser Asn Ala Glu Glu Ser Ser Trp Gly Thr Tyr
225                 230                 235                 240
Cys Pro Gly Glu Tyr Pro Ser Pro Pro Ser Glu Tyr Glu Thr Cys Leu
                245                 250                 255
Gly Asp Leu Tyr Ser Val Ala Trp Met Glu Asp Ser Asp Ile His Asn
            260                 265                 270
Leu Gln Thr Glu Thr Leu His Gln Gln Tyr Glu Leu Val Lys Gln Arg
        275                 280                 285
Thr Met Asn Gly Asn Ser Ile Tyr Gly Ser His Val Met Gln Tyr Gly
290                 295                 300
Asp Ile Gly Leu Ser Glu Asn Asn Leu Val Leu Tyr Leu Gly Thr Asn
305                 310                 315                 320
Pro Ala Asn Asp Asn Phe Thr Phe Val Leu Lys Asn Ser Leu Val Pro
                325                 330                 335
```

```
Pro Ser Lys Ala Val Asn Gln Arg Asp Ala Asp Leu Ile His Phe Trp
            340                 345                 350

Asp Lys Phe Arg Lys Ala Pro Val Gly Ser Ser Arg Lys Ala Ala Ala
            355                 360                 365

Glu Lys Gln Ile Leu Glu Ala Met Ser His Arg Met His Ile Asp Asp
            370                 375                 380

Ser Met Lys Arg Ile Gly Lys Leu Phe Phe Gly Ile Glu Lys Gly Pro
385                 390                 395                 400

Glu Leu Leu Ser Ser Val Arg Pro Ala Gly Gln Pro Leu Val Asp Asp
            405                 410                 415

Trp Asp Cys Leu Lys Thr Leu Val Arg Thr Phe Glu Thr His Cys Gly
            420                 425                 430

Ser Leu Ser Gln Tyr Gly Met Lys His Met Arg Ser Phe Ala Asn Phe
            435                 440                 445

Cys Asn Ala Gly Ile Arg Lys Glu Gln Met Ala Glu Ala Ser Ala Gln
            450                 455                 460

Ala Cys Val Asn Ile Pro Ala Ser Ser Trp Ser Ser Met His Arg Gly
465                 470                 475                 480

Phe Ser Ala

<210> SEQ ID NO 13
<211> LENGTH: 483
<212> TYPE: PRT
<213> ORGANISM: Vigna mungo

<400> SEQUENCE: 13

Met Asn Arg Phe Pro Ile Ile Phe Val Val Ala Asn Leu Ile Thr Leu
1               5                   10                  15

Val Ser Gly Gly Arg Asp Glu Ile Leu Arg Met Pro Ser Glu Ala Ser
            20                  25                  30

Arg Phe Phe Gln Ala Pro Ala Thr Asp Glu Asn Asp Glu Gly Thr Arg
            35                  40                  45

Trp Ala Val Leu Ile Ala Gly Ser Asn Gly Tyr Trp Asn Tyr Arg His
        50                  55                  60

Gln Ser Asp Val Cys His Ala Tyr Gln Leu Leu Thr Lys Gly Gly Leu
65                  70                  75                  80

Lys Glu Glu Asn Ile Val Val Phe Met Tyr Asp Asp Ile Ala Phe Asn
                85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Val Gly Glu Asp Val Thr
            115                 120                 125

Val Asn Asn Phe Phe Ala Ala Ile Leu Gly Asn Lys Ser Ala Leu Thr
130                 135                 140

Gly Gly Ser Gly Lys Val Val Asn Ser Gly Pro Asn Asp His Ile Phe
145                 150                 155                 160

Ile Tyr Tyr Ser Asp His Gly Gly Pro Gly Val Leu Gly Met Pro Thr
                165                 170                 175

Ser Pro Tyr Met Tyr Ala Ser Asp Leu Ile Glu Val Leu Lys Lys Lys
            180                 185                 190

His Ala Ser Gly Thr Tyr Lys Ser Leu Ala Phe Tyr Leu Glu Gly Cys
            195                 200                 205

Glu Ser Gly Ser Ile Phe Gly Gly Leu Leu Pro Glu Gly Leu Asn Ile
210                 215                 220
```

```
Tyr Ala Thr Thr Ala Ala Asn Ala Glu Glu Ser Ser Trp Gly Thr Tyr
225                 230                 235                 240

Cys Pro Gly Asp Asn Pro Ser Pro Pro Glu Tyr Glu Thr Cys Leu
            245                 250                 255

Gly Asp Leu Tyr Ser Val Ala Trp Met Glu Asp Ser Asp Ile His Asn
                260                 265                 270

Leu Arg Thr Glu Thr Leu His Gln Gln Phe Glu Leu Val Lys Gln Arg
            275                 280                 285

Thr Met Asn Gly Asn Ser Ala Tyr Gly Ser His Val Met Gln Tyr Gly
290                 295                 300

Asp Val Gly Leu Ser Lys Asn Val Ser Leu Tyr Leu Gly Thr Asn
305                 310                 315                 320

Pro Ala Asn Asp Asn Phe Pro Phe Arg Glu Lys Asn Ser Leu Val Pro
            325                 330                 335

Pro Ser Lys Ala Val Asn Gln Arg Asp Ala Asp Leu Val His Phe Trp
            340                 345                 350

Asp Lys Phe Pro Lys Ala Pro Leu Gly Ser Ser Arg Lys Ser Val Ala
            355                 360                 365

Gln Lys Gln Ile Leu Glu Ala Met Ser His Arg Met His Ile Asp Asp
370                 375                 380

Ser Val Thr Leu Ile Gly Lys Leu Leu Phe Gly Ile Glu Gly Pro
385                 390                 395                 400

Glu Leu Leu Ser Ser Val Arg Pro Ala Gly Gln Pro Leu Val Asp Asp
                405                 410                 415

Trp Asp Cys Leu Lys Thr Leu Val Arg Thr Phe Glu Thr His Cys Gly
            420                 425                 430

Ser Leu Ser Gln Tyr Gly Met Lys His Met Arg Ser Phe Ala Asn Leu
            435                 440                 445

Cys Asn Ala Gly Ile Arg Lys Glu Gln Met Ala Glu Ala Ser Ala Gln
450                 455                 460

Ala Cys Val Ser Ile Pro Ala Thr Pro Trp Ser Ser Leu Ser Ser Gly
465                 470                 475                 480

Phe Ser Ala

<210> SEQ ID NO 14
<211> LENGTH: 488
<212> TYPE: PRT
<213> ORGANISM: Cicer arietinum

<400> SEQUENCE: 14

Met Tyr Arg Phe Pro Thr Pro Thr Leu Leu Phe Leu Ile Val Thr Leu
1               5                   10                  15

Ile Ala Leu Val Ser Ser Asn Pro Glu Asp Phe Leu Arg Leu Pro Ser
                20                  25                  30

Glu Ser Ser Arg Phe Phe His Ser Pro Ser Ala Asp Asp Lys Glu Asn
            35                  40                  45

Asn Glu Gly Thr Arg Trp Ala Ile Leu Ile Ala Gly Ser Asn Gly Tyr
        50                  55                  60

Trp Asn Tyr Arg His Gln Ser Asp Val Cys His Ala Tyr Gln Val Leu
65                  70                  75                  80

Arg Lys Gly Gly Leu Lys Glu Glu Asn Ile Val Val Phe Met Tyr Asp
                85                  90                  95

Asp Ile Ala Phe Asn Glu Glu Asn Pro Arg Pro Gly Val Ile Ile Asn
                100                 105                 110
```

Ser Pro His Gly Asp Asp Val Tyr Lys Gly Val Pro Lys Asp Tyr Thr
            115                 120                 125

Gly Glu Asp Val Asn Val Asp Asn Phe Phe Ala Ala Leu Leu Gly Asn
        130                 135                 140

Lys Ser Ala Leu Thr Gly Gly Ser Gly Lys Val Val Asp Ser Gly Pro
145                 150                 155                 160

Asn Asp His Ile Phe Ile Tyr Tyr Ser Asp His Gly Gly Pro Gly Val
                165                 170                 175

Leu Gly Met Pro Thr Ser Pro Tyr Met Tyr Ala Ser Asp Leu Ile Glu
            180                 185                 190

Val Leu Lys Lys Lys His Ala Ser Gly Thr Tyr Lys Ser Leu Val Phe
        195                 200                 205

Tyr Leu Glu Ala Cys Glu Ser Gly Ser Ile Phe Glu Gly Leu Leu Pro
            210                 215                 220

Glu Gly Leu Asn Ile Tyr Ala Thr Thr Ala Ala Asn Ala Asp Glu Ser
225                 230                 235                 240

Ser Trp Gly Thr Tyr Cys Pro Gly Glu Phe Pro Ser Pro Pro Glu
                245                 250                 255

Tyr Glu Thr Cys Leu Gly Asp Leu Tyr Ser Val Ala Trp Met Glu Asp
            260                 265                 270

Ser Asp Met His Asn Leu Gln Ser Glu Thr Leu His Gln Gln Tyr Glu
            275                 280                 285

Leu Val Lys Glu Arg Thr Lys Asn Gly Asn Thr Leu Tyr Gly Ser His
        290                 295                 300

Val Met Gln Tyr Gly Asp Ile Gly Leu Ser Glu Asn Ser Leu Phe Leu
305                 310                 315                 320

Tyr Leu Gly Thr Asn Pro Ala Asn Glu Asn Phe Thr Phe Val Gly Arg
                325                 330                 335

Asn Ser Leu Val Pro Pro Ser Lys Ala Val Asn Gln Arg Asp Ala Asp
            340                 345                 350

Leu Val His Phe Trp Asp Lys Phe Arg Lys Ala Pro Gln Gly Ser Pro
            355                 360                 365

Arg Lys Ala Ala Ala Glu Lys Gln Val Leu Glu Ala Met Ser His Arg
    370                 375                 380

Met His Ile Asp Asp Ser Ile Lys Leu Val Gly Lys Leu Leu Phe Gly
385                 390                 395                 400

Met Glu Lys Gly Pro Glu Val Leu Thr Ser Val Arg Pro Ala Gly Gln
                405                 410                 415

Pro Leu Ala Asp Asp Trp Asn Cys Leu Lys Thr Leu Val Arg Thr Phe
            420                 425                 430

Glu Thr Tyr Cys Gly Ser Leu Ser Gln Tyr Gly Met Lys His Met Arg
        435                 440                 445

Ser Phe Ala Asn Phe Cys Asn Ala Gly Ile His Lys Glu Gln Met Ala
    450                 455                 460

Glu Ala Ser Ala Gln Ala Cys Val Asn Val Pro Ala Asn Pro Trp Ser
465                 470                 475                 480

Ser Leu Arg Ser Gly Phe Ser Ala
                485

<210> SEQ ID NO 15
<211> LENGTH: 492
<212> TYPE: PRT
<213> ORGANISM: Ricinus communis

<400> SEQUENCE: 15

```
Met Thr Ile Arg Leu Ser Thr Gly Ile Ile Leu Ile Leu Thr Leu
1               5                   10                  15

Cys Gly Val Val Ser Ser Arg Asp Ile Val Gly Asp Val Ile Arg
            20                  25                  30

Leu Pro Ser Glu Ala Ser Arg Phe Arg Pro Ala Asp Gly Lys Asn
        35                  40                  45

Gly Asp Asp Ser Ala Gly Thr Arg Trp Ala Ile Leu Ile Ala Gly
    50                  55                  60

Ser Asn Gly Tyr Trp Asn Tyr Arg His Gln Ala Asp Val Cys His Ala
65                  70                  75                  80

Tyr Gln Leu Leu Arg Lys Gly Gly Leu Lys Glu Asn Ile Ile Val
                85                  90                  95

Phe Met Tyr Asp Asp Ile Ala Tyr Asn Glu Glu Asn Pro Arg Gln Gly
                100                 105                 110

Ile Ile Ile Asn Asn Pro His Gly Glu Asp Val Tyr Lys Gly Val Pro
                115                 120                 125

Lys Asp Tyr Thr Gly Glu Asn Val Thr Val Gly Asn Phe Phe Ala Ala
    130                 135                 140

Ile Leu Gly Asn Arg Thr Ala Leu Thr Gly Gly Arg Gly Lys Val Val
145                 150                 155                 160

Asp Ser Gly Pro Asn Asp His Ile Phe Val Tyr Tyr Thr Asp His Gly
                165                 170                 175

Gly Pro Gly Val Leu Gly Met Pro Thr Asn Pro Tyr Leu Tyr Ala Asn
                180                 185                 190

Asp Leu Ile Asp Val Leu Lys Lys Lys His Ala Ser Gly Thr Tyr Lys
                195                 200                 205

Ser Leu Val Phe Tyr Leu Glu Ala Cys Glu Ser Gly Ser Ile Phe Glu
    210                 215                 220

Gly Leu Leu Pro Glu Gly Leu Asn Ile Tyr Ala Thr Thr Ala Ser Asn
225                 230                 235                 240

Ala Glu Glu Ser Ser Trp Gly Thr Tyr Cys Pro Gly Glu Tyr Pro Ser
                245                 250                 255

Pro Pro Pro Glu Tyr Glu Thr Cys Leu Gly Asp Leu Tyr Ser Ile Ala
                260                 265                 270

Trp Met Glu Asp Ser Asp Val His Asn Leu Gln Thr Glu Thr Leu His
                275                 280                 285

Gln Gln Tyr Glu Leu Val Lys Arg Arg Thr Ser Asn Gly Asn Ser Ala
    290                 295                 300

Tyr Gly Ser His Val Met Gln Tyr Gly Asp Val Gly Leu Ser Arg Glu
305                 310                 315                 320

Asn Leu Phe Leu Tyr Met Gly Thr Asn Pro Ala Asn Asp Asn Tyr Thr
                325                 330                 335

Phe Val Asp Glu Asn Ser Leu Thr Pro Pro Ser Lys Ala Val Asn Gln
                340                 345                 350

Arg Asp Ala Asp Leu Val His Phe Trp Asp Lys Tyr Arg Lys Ala Pro
    355                 360                 365

Asp Gly Ser Ala Arg Lys Asp Gln Ala Gln Lys Gln Phe Val Glu Ala
    370                 375                 380

Met Ser His Arg Met His Ile Asp His Ser Val Lys Leu Ile Gly Lys
385                 390                 395                 400

Leu Leu Phe Gly Leu Glu Lys Ala Ser Glu Val Leu Ser Thr Val Arg
                405                 410                 415
```

```
Pro Ala Gly Gln Pro Leu Val Asp Asp Trp Asp Cys Leu Lys Lys Leu
                420                 425                 430

Val Arg Thr Phe Glu Thr His Cys Gly Ser Ile Ser Gln Tyr Gly Met
            435                 440                 445

Lys His Met Arg Ser Leu Ala Asn Leu Cys Asn Ala Gly Ile Arg Glu
450                 455                 460

Glu Gln Met Ala Glu Ala Ser Ala Gln Ala Cys Ile Thr Phe Pro Ser
465                 470                 475                 480

Gly Pro Trp Ser Ser Leu His Lys Gly Phe Ser Ala
                485                 490

<210> SEQ ID NO 16
<211> LENGTH: 487
<212> TYPE: PRT
<213> ORGANISM: Theobroma cacao

<400> SEQUENCE: 16

Met Thr Arg Leu Val Ser Gly Val Ile Leu Leu Leu Ser Leu Thr
1                5                  10                  15

Gly Ile Val Ser Ala Gly Arg Asp Ile Thr Gly Asp Val Leu Arg Leu
                20                  25                  30

Pro Ser Glu Ala Ser Lys Phe Phe Arg Gly Ser Asn Asp Asp Glu Val
            35                  40                  45

Glu Gly Thr Arg Trp Ala Val Leu Ile Ala Gly Ser Asn Gly Tyr Trp
50                  55                  60

Asn Tyr Arg His Gln Ala Asp Val Cys His Ala Tyr Gln Leu Leu Lys
65                  70                  75                  80

Lys Gly Gly Leu Lys Asp Glu Asn Ile Ile Val Phe Met Tyr Asp Asp
                85                  90                  95

Ile Ala Phe Asn Glu Glu Asn Pro Arg Pro Gly Ile Ile Ile Asn Ser
                100                 105                 110

Pro His Gly Asp Asp Val Tyr Glu Gly Val Pro Lys Asp Tyr Thr Gly
            115                 120                 125

Glu Asp Val Thr Val Asn Asn Leu Leu Ala Ala Ile Leu Gly Asn Lys
130                 135                 140

Thr Ala Leu Thr Gly Gly Ser Gly Lys Val Val Asp Ser Gly Pro Asn
145                 150                 155                 160

Asp His Ile Phe Ile Tyr Tyr Thr Asp His Gly Gly Pro Gly Val Leu
                165                 170                 175

Gly Met Pro Thr Phe Pro Tyr Leu Tyr Ala Asp Asp Leu Ile Glu Val
            180                 185                 190

Leu Lys Lys Lys His Ala Ser Gly Thr Tyr Lys Ser Leu Val Phe Tyr
195                 200                 205

Leu Glu Ala Cys Glu Ser Gly Ser Ile Phe Glu Gly Leu Leu Pro Glu
210                 215                 220

Gly Leu Asn Ile Tyr Ala Thr Thr Ala Ser Asn Ala Glu Glu Ser Ser
225                 230                 235                 240

Trp Gly Thr Tyr Cys Pro Gly Glu Tyr Pro Ser Pro Pro Glu Tyr
            245                 250                 255

Glu Thr Cys Leu Gly Asp Leu Tyr Ser Val Ala Trp Met Glu Asp Ser
            260                 265                 270

Asp Ile His Asn Leu Gln Thr Glu Thr Leu His Gln Gln Tyr Glu Leu
            275                 280                 285

Val Lys Arg Arg Thr Ile Asn Gly Asn Ser Ala Tyr Gly Ser His Val
```

```
            290                 295                 300
Met Gln Tyr Gly Asp Ile Gly Leu Ser Lys Asp Ile Val Phe Val Tyr
305                 310                 315                 320

Leu Gly Thr Asn Pro Ala Asn Asp Asn Phe Thr Phe Val Asp Glu Asn
                325                 330                 335

Ser Leu Gln Pro Pro Thr Lys Ala Val Asn Gln Arg Asp Ala Asp Leu
            340                 345                 350

Val His Phe Trp Asp Lys Tyr Arg Lys Ala Pro Asp Gly Ser Val Arg
        355                 360                 365

Lys Leu Glu Ala Gln Lys Gln Phe Val Glu Ala Met Ser His Arg Met
370                 375                 380

His Ile Asp Asn Ser Met Lys Leu Ile Gly Lys Leu Leu Phe Gly Ile
385                 390                 395                 400

Glu Lys Gly Pro Glu Val Met Lys Thr Val Arg Pro Ala Gly Gln Pro
                405                 410                 415

Leu Val Asp Asp Trp Lys Cys Leu Lys Lys Met Val Arg Thr Phe Glu
            420                 425                 430

Thr His Cys Gly Ser Leu Ala Gln Tyr Gly Met Lys His Met Arg Ser
        435                 440                 445

Leu Ala Asn Ile Cys Asn Ala Gly Ile Gln Thr Glu Gln Met Ala Glu
    450                 455                 460

Ala Ser Ala Gln Ala Cys Val Ser Ile Pro Ser Gly His Trp Ser Ser
465                 470                 475                 480

Val Gln Lys Gly Phe Ser Ala
                485

<210> SEQ ID NO 17
<211> LENGTH: 484
<212> TYPE: PRT
<213> ORGANISM: Medicago truncatula

<400> SEQUENCE: 17

Met Ala Arg Phe Leu Phe Leu Ile Ile Ala Thr Leu Ile Pro Ile Phe
1               5                   10                  15

Ser Ala Ala Thr Ala Thr Ala Gly Asp Asp Phe Leu Arg Leu Pro Ser
            20                  25                  30

Gln Ala Ser Arg Phe Phe Gln Ser Asp Asp Asn Asn Glu Gly Thr
        35                  40                  45

Lys Trp Ala Ile Leu Ile Ala Gly Ser Asn Gly Tyr Trp Asn Tyr Arg
50                  55                  60

His Gln Ser Asp Val Cys His Ala Tyr Gln Val Leu Arg Lys Gly Gly
65                  70                  75                  80

Leu Lys Glu Glu Asn Ile Ile Val Phe Met Tyr Asp Asp Ile Ala Asp
                85                  90                  95

Asn Gln Glu Asn Pro Arg Pro Gly Val Ile Ile Asn Ser Pro His Gly
            100                 105                 110

Asp Asp Val Tyr Lys Gly Val Pro Lys Asp Tyr Thr Gly Asp Asp Val
        115                 120                 125

Asn Val Asn Asn Phe Phe Ala Ala Leu Leu Gly Asn Lys Ser Ala Leu
    130                 135                 140

Thr Gly Gly Ser Gly Lys Val Val Asp Ser Gly Pro Asn Asp His Ile
145                 150                 155                 160

Phe Ile Tyr Tyr Ser Asp His Gly Gly Pro Gly Val Leu Gly Met Pro
                165                 170                 175
```

```
Thr Gly Pro Phe Met Tyr Ala Thr Asp Leu Ile Glu Val Leu Lys Lys
            180                 185                 190

Lys His Ala Ser Glu Thr Tyr Lys Ser Leu Val Phe Tyr Leu Glu Ala
        195                 200                 205

Cys Glu Ser Gly Ser Ile Phe Glu Gly Leu Leu Pro Glu Gly Leu Asn
    210                 215                 220

Ile Tyr Ala Thr Thr Ala Ala Asn Ala Glu Glu Ser Ser Trp Gly Thr
225                 230                 235                 240

Tyr Cys Pro Gly Glu Asn Pro Ser Pro Pro Glu Tyr Glu Thr Cys
                245                 250                 255

Leu Gly Asp Leu Tyr Ser Val Ala Trp Met Glu Asp Ser Asp Ile His
            260                 265                 270

Asn Leu Gln Thr Glu Thr Leu His Gln Gln Tyr Glu Leu Val Lys Glu
        275                 280                 285

Arg Thr Ser Asn Gly Asn Ser Ile Tyr Gly Ser His Val Met Gln Phe
    290                 295                 300

Gly Asp Ile Gly Leu Ser Arg Asp Ser Leu Phe Leu Tyr Leu Gly Ser
305                 310                 315                 320

Asn Pro Ala Asn Glu Asn Phe Thr Phe Met Gly Arg Asn Ser Leu Val
                325                 330                 335

Pro Pro Ser Lys Thr Val Asn Gln Arg Asp Ala Asp Leu Ile His Phe
            340                 345                 350

Trp Asp Lys Phe Arg Lys Ala Pro Gln Gly Ser Pro Arg Lys Val Ala
        355                 360                 365

Ala Gln Lys Gln Val Leu Glu Ala Met Ser His Arg Met His Ile Asp
    370                 375                 380

Glu Ser Ile Lys Leu Val Gly Lys Leu Leu Phe Gly Met Lys Lys Gly
385                 390                 395                 400

Pro Glu Val Leu Ala Ser Val Arg Pro Ala Gly Gln Pro Val Val Asp
                405                 410                 415

Asp Trp Asp Cys Leu Lys Ser Leu Val Arg Thr Phe Glu Thr Tyr Cys
            420                 425                 430

Gly Ser Leu Ser Gln Tyr Gly Met Lys His Met Arg Ser Phe Ala Asn
        435                 440                 445

Phe Cys Asn Ala Gly Ile His Ser Glu Gln Met Ala Glu Ala Ser Ala
    450                 455                 460

Gln Ala Cys Ile Asn Ile Pro Ala Asn Pro Trp Ser Ser Leu His Gly
465                 470                 475                 480

Gly Phe Ser Ala

<210> SEQ ID NO 18
<211> LENGTH: 493
<212> TYPE: PRT
<213> ORGANISM: Populus tomentosa

<400> SEQUENCE: 18

Met Thr Arg Leu Ile Ala Gly Val Ile Phe Leu Leu Ile Ala Phe Cys
1               5                   10                  15

Gly Ile Ala Val Gly Val Arg Asp Ile Val Gly Asp Val Leu Arg Leu
            20                  25                  30

Pro Ser Glu Ala Ser Arg Phe Phe Arg Ser Gly Lys Phe Asn Asp Asp
        35                  40                  45

Asn Ser Asp Asp Asp Ser Ser Gly Thr Arg Trp Ala Ile Leu Leu Ala
50                  55                  60
```

```
Gly Ser Asn Gly Tyr Trp Asn Tyr Arg His Gln Ala Asp Val Cys His
 65                  70                  75                  80

Ala Tyr Gln Leu Leu Arg Lys Gly Gly Leu Lys Glu Glu Asn Ile Ile
                 85                  90                  95

Val Phe Met Tyr Asp Asp Ile Ala Asp Asn Pro Glu Asn Pro Arg Pro
            100                 105                 110

Gly Val Ile Ile Asn Asn Pro Gln Gly Glu Asp Val Tyr Glu Gly Val
        115                 120                 125

Pro Lys Asp Tyr Thr Gly Gln Asp Val Thr Val Gly Asn Phe Phe Ala
130                 135                 140

Ala Ile Leu Gly Asn Lys Thr Ala Leu Thr Gly Gly Ser Gly Lys Val
145                 150                 155                 160

Val Asp Ser Gly Pro Asn Asp His Ile Phe Ile Tyr Tyr Thr Asp His
                165                 170                 175

Gly Gly Pro Gly Val Leu Gly Met Pro Thr Asn Pro Tyr Leu Tyr Ala
            180                 185                 190

Asp Asp Leu Ile Asp Val Leu Lys Lys Lys His Ala Ser Gly Thr Tyr
        195                 200                 205

Lys Ser Leu Val Phe Tyr Leu Glu Ala Cys Glu Ser Gly Ser Ile Phe
210                 215                 220

Glu Gly Leu Leu Pro Gln Gly Leu Asn Ile Tyr Ala Thr Thr Ala Ser
225                 230                 235                 240

Asn Ala Glu Glu Ser Ser Trp Gly Thr Tyr Cys Pro Gly Glu Tyr Pro
                245                 250                 255

Ser Pro Pro Pro Glu Tyr Glu Thr Cys Leu Gly Asp Leu Tyr Ser Val
            260                 265                 270

Ala Trp Met Glu Asp Ser Asp Ile His Asn Leu Arg Thr Glu Thr Leu
        275                 280                 285

His Gln Gln Tyr Glu Leu Val Lys Arg Arg Thr Ser Asp Glu Asn Ser
290                 295                 300

Ala Tyr Gly Ser His Val Met Gln Tyr Gly Asp Val Gly Leu Ser Lys
305                 310                 315                 320

Glu Asp Leu Phe Gln Tyr Met Gly Thr Asn Pro Ala Asn Asp Asn Phe
                325                 330                 335

Thr Phe Leu Glu Asp Asn Ser Leu Arg Pro Pro Ser Lys Ala Val Asn
            340                 345                 350

Gln Arg Asp Ala Asp Leu Val His Phe Trp Ala Lys Tyr Arg Lys Ala
        355                 360                 365

Pro Glu Gly Ser Ser Arg Lys Val Glu Ala Gln Lys Gln Phe Val Glu
370                 375                 380

Ala Met Ser His Arg Met His Ile Asp His Ser Ile Lys Leu Ile Gly
385                 390                 395                 400

Lys Leu Leu Phe Gly Ile Glu Lys Ala Ser Glu Val Leu Asn Asn Val
                405                 410                 415

Arg Pro Ala Gly Gln Pro Leu Val Asp Asp Trp Val Cys Leu Lys Thr
            420                 425                 430

Leu Val Arg Thr Phe Glu Thr His Cys Gly Ser Ile Ser Gln Tyr Gly
        435                 440                 445

Met Lys His Met Arg Ser Leu Ala Asn Leu Cys Asn Ala Gly Ile Val
450                 455                 460

Lys Glu Gln Met Ala Glu Ala Ser Ala Gln Ala Cys Val Ser Ile Pro
465                 470                 475                 480

Ser Gly Ser Trp Ser Ser Leu His Lys Gly Phe Ser Ala
```

<210> SEQ ID NO 19
<211> LENGTH: 489
<212> TYPE: PRT
<213> ORGANISM: Populus trichocarpa

<400> SEQUENCE: 19

```
Met Thr Gly Leu Ala Thr Gly Ala Ile Phe Leu Leu Ile Ser Leu Cys
1               5                   10                  15

Gly Ile Ala Ala Ala Gly Arg Asp Thr Val Gly Asp Val Leu Arg Leu
            20                  25                  30

Pro Ser Glu Ala Ser Arg Phe Phe His Asn Asp Asn Ser Asp Asp
        35                  40                  45

Asp Ser Thr Gly Thr Arg Trp Ala Ile Leu Leu Ala Gly Ser Asn Gly
    50                  55                  60

Tyr Trp Asn Tyr Arg His Gln Ala Asp Val Cys His Ala Tyr Gln Leu
65                  70                  75                  80

Leu Arg Lys Gly Gly Leu Lys Glu Glu Asn Ile Ile Val Phe Met Tyr
                85                  90                  95

Asp Asp Ile Ala Tyr Asn Ser Glu Asn Pro Arg Arg Gly Val Ile Ile
            100                 105                 110

Asn Ser Pro Gln Gly Glu Asp Val Tyr Lys Gly Val Pro Lys Asp Tyr
        115                 120                 125

Thr Gly Glu Asp Val Thr Val Gly Asn Phe Phe Ala Ala Ile Leu Gly
    130                 135                 140

Asn Lys Thr Ala Leu Thr Gly Gly Ser Gly Lys Val Val Asp Ser Gly
145                 150                 155                 160

Pro Asn Asp His Ile Phe Ile Tyr Tyr Thr Asp His Gly Gly Pro Gly
                165                 170                 175

Val Leu Gly Met Pro Thr Asn Pro Tyr Leu Tyr Ala Asp Asp Leu Ile
            180                 185                 190

Asp Val Leu Lys Lys Lys His Ala Ser Gly Thr Tyr Lys Ser Leu Val
        195                 200                 205

Phe Tyr Leu Glu Ala Cys Glu Ser Gly Ser Ile Phe Glu Gly Leu Leu
    210                 215                 220

Pro Gln Gly Leu Asn Ile Tyr Ala Thr Thr Ala Ser Asn Ala Glu Glu
225                 230                 235                 240

Ser Ser Trp Gly Thr Tyr Cys Pro Gly Glu Asn Pro Ser Pro Pro Pro
                245                 250                 255

Glu Tyr Glu Thr Cys Leu Gly Asp Leu Tyr Ser Val Ala Trp Met Glu
            260                 265                 270

Asp Ser Asp Ile His Asn Leu Gln Thr Glu Thr Leu His Gln Gln Tyr
        275                 280                 285

Glu Leu Val Lys Arg Arg Thr Ser Asn Asp Asn Ser Pro Tyr Gly Ser
    290                 295                 300

His Val Met Gln Tyr Gly Asp Val Gly Leu Ser Lys Asp Asn Ile Phe
305                 310                 315                 320

Leu Tyr Met Gly Thr Asn Pro Ala Asn Asp Asn Phe Thr Phe Met Asp
                325                 330                 335

Glu Asn Leu Leu Arg Pro Arg Ser Lys Ala Val Asn Gln Arg Asp Ala
            340                 345                 350

Asp Leu Val His Phe Trp Asp Lys Tyr Arg Lys Ala Pro Glu Gly Ser
        355                 360                 365
```

```
Ser Arg Lys Val Glu Ala Gln Lys Gln Phe Val Glu Ala Met Ser His
    370                 375                 380

Arg Met His Ile Asp His Ser Ile Lys Leu Ile Gly Lys Leu Leu Phe
385                 390                 395                 400

Gly Ile Glu Lys Ala Ser Glu Val Leu Asn Ala Ile Arg Pro Ala Gly
                405                 410                 415

Gln Pro Leu Val Asp Asp Trp Asp Cys Leu Lys Thr Leu Val Arg Thr
            420                 425                 430

Phe Glu Thr His Cys Gly Ser Val Ser Gln Tyr Gly Met Lys His Met
                435                 440                 445

Arg Ser Leu Ala Asn Leu Cys Asn Ala Gly Ile Gly Lys Glu Gln Met
450                 455                 460

Ala Glu Ala Ser Ala Gln Ala Cys Val Ser Phe Pro Ser Gly Pro Trp
465                 470                 475                 480

Ser Thr Leu His Lys Gly Phe Ser Ala
                485

<210> SEQ ID NO 20
<211> LENGTH: 494
<212> TYPE: PRT
<213> ORGANISM: Malus hupehensis var. mengshanensis
<220> FEATURE:
<221> NAME/KEY: misc_feature
<222> LOCATION: (264)..(264)
<223> OTHER INFORMATION: Xaa can be any naturally occurring amino acid

<400> SEQUENCE: 20

Met Thr Arg Leu Ala Ser Ala Val Val Leu Leu Phe Leu Ala Ser Val
1               5                   10                  15

Leu Ala Ser Ala Ala Gly Ser Arg Asp Leu Ile Gly Asp Val Leu Arg
                20                  25                  30

Leu Pro Ser Glu Ala Ser Arg Phe Phe Gly Arg Gly Asp Asp Ala Pro
            35                  40                  45

Asp Gln Gln Asp Asp Gly Thr Val Gly Thr Arg Trp Ala Val Leu Ile
50                  55                  60

Ala Gly Ser Asn Gly Tyr Trp Asn Tyr Arg His Gln Ala Asp Ile Cys
65                  70                  75                  80

His Ala Tyr Gln Leu Leu Lys Lys Gly Gly Leu Lys Asp Glu Asn Ile
                85                  90                  95

Val Val Phe Met Tyr Asp Asp Ile Ala Tyr Asn Glu Glu Asn Pro Arg
                100                 105                 110

Gln Gly Val Ile Ile Asn Ser Pro His Gly Ser Asp Val Tyr Glu Gly
            115                 120                 125

Val Pro Lys Asp Tyr Thr Gly Glu Asp Val Thr Val Asn Asn Phe Phe
130                 135                 140

Ala Ala Ile Leu Gly Asn Lys Thr Ala Leu Thr Gly Gly Ser Gly Lys
145                 150                 155                 160

Val Val Asp Ser Gly Pro Asn Asp His Ile Phe Ile Tyr Tyr Thr Asp
                165                 170                 175

His Gly Gly Pro Gly Ile Leu Gly Met Pro Thr Ser Pro Tyr Ile Tyr
            180                 185                 190

Ala Asn Asp Leu Ile Glu Val Leu Lys Lys His Ala Ala Gly Thr
                195                 200                 205

Tyr Lys Ser Leu Val Phe Tyr Leu Glu Ala Cys Glu Ser Gly Ser Ile
210                 215                 220

Phe Glu Gly Leu Leu Pro Glu Gly Leu Asn Ile Phe Ala Thr Thr Ala
```

```
                225                 230                 235                 240
Ser Asn Ala Glu Glu Ser Ser Trp Gly Thr Tyr Cys Pro Gly Glu Tyr
                    245                 250                 255

Pro Ser Pro Pro Glu Tyr Xaa Thr Cys Leu Gly Asp Leu Tyr Ser
                260                 265                 270

Val Val Trp Met Glu Asp Ser Asp Val His Asn Leu Arg Ser Glu Thr
                275                 280                 285

Leu His Gln Gln Tyr Glu Leu Val Lys Met Arg Thr Ala Asn Asp Asn
            290                 295                 300

Ser Gly Phe Gly Ser His Val Met Gln Tyr Gly Asp Val Gly Leu Ser
305                 310                 315                 320

Lys Asn Asn Leu Phe Val Tyr Met Gly Thr Asn Pro Ala Asn Asp Asn
                325                 330                 335

Tyr Thr Phe Leu Gly Glu Asn Ser Leu Arg Pro Ser Ser Lys Ala Val
                340                 345                 350

Asn Gln Arg Asp Ala Asp Leu Leu Arg Phe Trp His Lys Tyr Arg Lys
            355                 360                 365

Ala Pro Glu Gly Ser Ala Arg Lys Ile Gln Ala Gln Lys Asp Phe Val
        370                 375                 380

Glu Ala Met Ser His Arg Met His Ile Asp Gln Thr Met Lys Leu Ile
385                 390                 395                 400

Gly Lys Leu Leu Phe Gly Ile Glu Lys Gly Pro Gln Val Leu Asn Ala
                405                 410                 415

Val Arg Pro Ala Gly Gln Pro Leu Val Asp Asp Trp Asp Cys Leu Lys
                420                 425                 430

Thr Met Val Arg Ser Phe Glu Thr His Cys Gly Ser Leu Ser Gln Tyr
            435                 440                 445

Gly Met Lys His Met Arg Ser Leu Ala Asn Ile Cys Asn Ala Gly Met
        450                 455                 460

Thr Gln Glu Gln Met Ala Glu Ala Ser Ala Gln Ala Cys Val Ser Ala
465                 470                 475                 480

Pro Ser Gly Arg Trp Ser Ser Leu His Arg Gly Phe Ser Ala
                485                 490

<210> SEQ ID NO 21
<211> LENGTH: 480
<212> TYPE: PRT
<213> ORGANISM: Glycine max

<400> SEQUENCE: 21

Met Pro Thr Phe Phe Leu Pro Thr Leu Leu Leu Leu Ile Ala Phe
1               5                   10                  15

Ala Thr Ser Val Ser Gly Arg Arg Asp Leu Val Gly Asp Phe Leu Arg
                20                  25                  30

Leu Pro Ser Glu Thr Asp Asn Asp Asn Phe Lys Gly Thr Arg Trp
            35                  40                  45

Ala Val Leu Leu Ala Gly Ser Asn Gly Tyr Trp Asn Tyr Arg His Gln
        50                  55                  60

Ala Asp Val Cys His Ala Tyr Gln Ile Leu Arg Lys Gly Gly Leu Lys
65                  70                  75                  80

Glu Glu Asn Ile Ile Val Phe Met Tyr Asp Asp Ile Ala Phe Asn Gly
                85                  90                  95

Glu Asn Pro Arg Pro Gly Val Ile Ile Asn Lys Pro Asp Gly Gly Asp
                100                 105                 110
```

```
Val Tyr Lys Gly Val Pro Lys Asp Tyr Thr Gly Glu Asp Val Thr Val
            115                 120                 125

Asp Asn Phe Phe Ala Ala Leu Leu Gly Asn Lys Ser Ala Leu Thr Gly
130                 135                 140

Gly Ser Gly Lys Val Val Asp Ser Gly Pro Asp Asp His Ile Phe Val
145                 150                 155                 160

Tyr Tyr Thr Asp His Gly Gly Pro Val Leu Gly Met Pro Ala Gly
            165                 170                 175

Pro Tyr Leu Tyr Ala Asp Asp Leu Ile Glu Val Leu Lys Lys His
            180                 185                 190

Ala Ser Gly Thr Tyr Lys Asn Leu Val Phe Tyr Leu Glu Ala Cys Glu
            195                 200                 205

Ser Gly Ser Ile Phe Glu Gly Leu Leu Pro Glu Asp Ile Asn Ile Tyr
    210                 215                 220

Ala Thr Thr Ala Ser Asn Ala Glu Glu Ser Ser Trp Gly Thr Tyr Cys
225                 230                 235                 240

Pro Gly Glu Tyr Pro Ser Pro Pro Glu Tyr Thr Thr Cys Leu Gly
            245                 250                 255

Asp Leu Tyr Ser Val Ala Trp Met Glu Asp Ser Asp Arg His Asn Leu
            260                 265                 270

Arg Thr Glu Thr Leu His Gln Gln Tyr Lys Leu Val Lys Glu Arg Thr
            275                 280                 285

Ile Ser Gly Asp Ser Tyr Tyr Gly Ser His Val Met Gln Tyr Gly Asp
            290                 295                 300

Val Gly Leu Ser Arg Asp Val Leu Phe His Tyr Leu Gly Thr Asp Pro
305                 310                 315                 320

Ala Asn Asp Asn Phe Thr Phe Val Asp Glu Asn Ser Leu Trp Ser Pro
                325                 330                 335

Ser Lys Pro Val Asn Gln Arg Asp Ala Asp Leu Ile His Phe Trp Asp
            340                 345                 350

Lys Phe Arg Lys Ala Pro Glu Gly Ser Leu Arg Lys Asn Thr Ala Gln
            355                 360                 365

Lys Gln Val Leu Glu Ala Met Ser His Arg Met His Val Asp Asn Ser
370                 375                 380

Val Lys Leu Ile Gly Lys Leu Phe Gly Ile Glu Lys Gly Pro Glu
385                 390                 395                 400

Val Leu Asn Ala Val Arg Pro Ala Gly Ser Ala Leu Val Asp Asp Trp
                405                 410                 415

His Cys Leu Lys Thr Met Val Arg Thr Phe Glu Thr His Cys Gly Ser
            420                 425                 430

Leu Ser Gln Tyr Gly Met Lys His Met Arg Ser Phe Ala Asn Ile Cys
            435                 440                 445

Asn Val Gly Ile Lys Asn Glu Gln Met Ala Glu Ala Ser Ala Gln Ala
            450                 455                 460

Cys Val Ser Ile Pro Ser Asn Pro Trp Ser Ser Leu Gln Arg Gly Phe
465                 470                 475                 480

<210> SEQ ID NO 22
<211> LENGTH: 481
<212> TYPE: PRT
<213> ORGANISM: Glycine max

<400> SEQUENCE: 22

Met Ala Thr Leu Leu Leu Pro Thr Leu Leu Leu Leu Ile Pro Phe Ala
1               5                   10                  15
```

```
Thr Leu Val Ser Ala Arg Pro His Leu Ala Gly Asp Phe Leu Arg Leu
            20                  25                  30

Pro Ser Glu Thr Asp Asn Asp Asn Val Gln Gly Thr Arg Trp Ala
        35                  40                  45

Val Leu Leu Ala Gly Ser Asn Gly Tyr Trp Asn Tyr Arg His Gln Ala
 50                  55                  60

Asp Val Cys His Ala Tyr Gln Ile Leu Arg Lys Gly Gly Leu Lys Glu
 65                  70                  75                  80

Glu Asn Ile Ile Val Phe Met Tyr Asp Asp Ile Ala Phe Asn Gly Glu
                85                  90                  95

Asn Pro Arg Pro Gly Val Ile Ile Asn Lys Pro Asp Gly Gly Asp Val
            100                 105                 110

Tyr Glu Gly Val Pro Lys Asp Tyr Thr Gly Glu Asp Val Thr Val Gly
            115                 120                 125

Asn Phe Phe Ala Ala Leu Leu Gly Asn Lys Ser Ala Leu Thr Gly Gly
 130                 135                 140

Ser Gly Lys Val Val Asp Ser Gly Pro Asp Asp His Ile Phe Val Tyr
145                 150                 155                 160

Tyr Thr Asp His Gly Gly Pro Gly Val Leu Gly Met Pro Ala Gly Pro
                165                 170                 175

Tyr Leu Tyr Ala Asp Asp Leu Ile Glu Val Leu Lys Lys Lys His Ala
            180                 185                 190

Ser Gly Thr Tyr Lys Asn Leu Val Phe Tyr Leu Glu Ala Cys Glu Ser
            195                 200                 205

Gly Ser Ile Phe Glu Gly Leu Leu Pro Glu Asp Ile Asn Ile Tyr Ala
            210                 215                 220

Thr Thr Ala Ser Asn Ala Glu Glu Ser Ser Trp Gly Thr Tyr Cys Pro
225                 230                 235                 240

Gly Glu Tyr Pro Ser Pro Pro Glu Tyr Ser Thr Cys Leu Gly Asp
                245                 250                 255

Leu Tyr Ser Val Ala Trp Met Glu Asp Ser Asp Arg His Asn Leu Arg
            260                 265                 270

Thr Glu Thr Leu His Gln Gln Tyr Lys Leu Val Lys Glu Arg Thr Ile
            275                 280                 285

Ser Gly Asp Ser Tyr Tyr Gly Ser His Val Met Gln Tyr Gly Asp Val
            290                 295                 300

Arg Leu Ser Ser Asp Val Leu Phe His Tyr Leu Gly Thr Asp Pro Ala
305                 310                 315                 320

Asn Asp Asn Phe Thr Phe Val Asp Glu Asn Ser Leu Trp Ser Pro Ser
                325                 330                 335

Lys Pro Val Asn Gln Arg Asp Ala Asp Leu Ile His Phe Trp Asp Lys
            340                 345                 350

Phe Arg Lys Ala Pro Glu Gly Ser Leu Arg Lys Asn Ala Ala Gln Lys
            355                 360                 365

Gln Val Leu Glu Ala Met Ser His Arg Met His Val Asp Asn Ser Val
            370                 375                 380

Lys Leu Ile Gly Lys Leu Leu Phe Gly Ile Glu Lys Gly Pro Glu Val
385                 390                 395                 400

Leu Asn Ala Val Arg Pro Ala Gly Ser Ala Leu Val Asp Asp Trp His
                405                 410                 415

Cys Leu Lys Thr Met Val Arg Thr Phe Glu Thr His Cys Gly Ser Leu
            420                 425                 430
```

-continued

```
Ser Gln Tyr Gly Met Lys His Met Arg Ser Phe Ala Asn Ile Cys Asn
            435                 440                 445
Val Gly Ile Lys Asn Glu Gln Met Ala Glu Ala Ser Ala Gln Ala Cys
450                 455                 460
Val Ser Ile Pro Ser Asn Pro Trp Ser Ser Leu Gln Arg Gly Phe Ser
465                 470                 475                 480
Ala

<210> SEQ ID NO 23
<211> LENGTH: 494
<212> TYPE: PRT
<213> ORGANISM: Prunus persica

<400> SEQUENCE: 23

Met Thr Arg Leu Ala Ser Ala Val Val Leu Phe Leu Val Ser Leu
1               5                   10                  15
Ser Ser Phe Ala Ala Gly Ser Arg Asp Leu Ile Gly Asp Val Leu Arg
                20                  25                  30
Leu Pro Ser Glu Ala Ser Arg Phe Gly Arg Gly Asp Asp Gly Pro
            35                  40                  45
Asp Glu Gln Asp Asp Gly Thr Val Gly Thr Arg Trp Ala Val Leu Ile
50                  55                  60
Ala Gly Ser Asn Gly Tyr Trp Asn Tyr Arg His Gln Ala Asp Ile Cys
65                  70                  75                  80
His Ala Tyr Gln Leu Leu Lys Lys Gly Gly Leu Lys Asp Glu Asn Ile
                85                  90                  95
Val Val Phe Met Tyr Asp Asp Ile Ala Tyr Asn Glu Glu Asn Pro Arg
            100                 105                 110
Pro Gly Val Ile Ile Asn Ser Pro His Gly Asp Asp Val Tyr Lys Gly
        115                 120                 125
Val Pro Lys Asp Tyr Thr Gly Asp Asp Val Thr Val Asn Asn Phe Phe
130                 135                 140
Ala Ala Ile Leu Gly Asn Lys Thr Ala Leu Thr Gly Gly Thr Gly Lys
145                 150                 155                 160
Val Val Asp Ser Gly Pro Asn Asp His Ile Phe Ile Tyr Tyr Ser Asp
                165                 170                 175
His Gly Gly Pro Gly Val Leu Gly Met Pro Thr Ser Pro Tyr Ile Tyr
            180                 185                 190
Ala Asn Asp Leu Ile Glu Val Leu Lys Lys His Ala Ala Gly Thr
        195                 200                 205
Tyr Lys Ser Leu Val Phe Tyr Leu Glu Ala Cys Glu Ser Gly Ser Ile
210                 215                 220
Phe Glu Gly Leu Leu Pro Glu Gly Leu Asn Ile Phe Ala Thr Thr Ala
225                 230                 235                 240
Ser Asn Ala Glu Glu Ser Ser Trp Gly Thr Tyr Cys Pro Gly Glu Tyr
                245                 250                 255
Pro Ser Pro Pro Pro Glu Tyr Glu Thr Cys Leu Gly Asp Leu Tyr Ser
            260                 265                 270
Val Ala Trp Met Glu Asp Ser Asp Ile His Asn Leu Arg Ser Glu Thr
        275                 280                 285
Leu His Gln Gln Tyr Glu Leu Val Lys Thr Arg Thr Ala Asn Asp Asn
    290                 295                 300
Ser Gly Phe Gly Ser His Val Met Gln Tyr Gly Asp Val Gly Leu Ser
305                 310                 315                 320
```

```
Lys Glu Asn Leu Phe Val Tyr Met Gly Thr Asn Pro Ala Asn Asp Asn
                325                 330                 335

Tyr Thr Phe Leu Gly Glu Asn Ser Leu Arg Pro Ser Thr Lys Ala Val
            340                 345                 350

Asn Gln Arg Asp Ala Asp Leu Val His Phe Trp His Lys Tyr Arg Lys
        355                 360                 365

Ala Pro Glu Gly Ser Pro Arg Lys Ile Gln Ala Gln Lys Asp Phe Val
    370                 375                 380

Glu Ala Met Ser His Arg Met His Met Asp Gln Thr Met Lys Leu Ile
385                 390                 395                 400

Gly Lys Leu Leu Phe Gly Ile Lys Lys Gly Pro Glu Val Leu Asn Thr
                405                 410                 415

Val Arg Pro Ala Gly Gln Pro Leu Val Asp Asp Trp Asp Cys Leu Lys
            420                 425                 430

Thr Met Val Arg Ser Phe Glu Thr Tyr Cys Gly Ser Leu Ser Gln Tyr
        435                 440                 445

Gly Met Lys His Met Arg Ser Leu Ala Asn Ile Cys Asn Ala Gly Met
    450                 455                 460

Thr Lys Glu Gln Met Thr Glu Ala Ser Ala Gln Ala Cys Thr Ser Val
465                 470                 475                 480

Pro Ser Ser Arg Trp Ser Ser Leu His Arg Gly Phe Ser Ala
                485                 490

<210> SEQ ID NO 24
<211> LENGTH: 487
<212> TYPE: PRT
<213> ORGANISM: Arachis diogoi

<400> SEQUENCE: 24

Met Glu Ser Leu Leu Arg Ile Thr Leu Leu Phe Phe Ala Phe Thr Thr
1               5                   10                  15

Phe Val Ala Ser Ala Ser Gly Arg Arg Asp Ile Val Gly Gly Thr Leu
            20                  25                  30

Arg Leu Pro Ser Glu Ala Ile Ser Arg Phe Phe His Glu Pro Glu Asn
        35                  40                  45

Glu Gly Thr Lys Trp Ala Val Leu Leu Ala Gly Ser Asn Gly Tyr Trp
    50                  55                  60

Asn Tyr Arg His Gln Ala Asp Ile Cys His Ala Tyr Gln Leu Leu Arg
65                  70                  75                  80

Ser Gly Gly Val Lys Glu Glu Asn Ile Ile Val Phe Met Phe Asp Asp
                85                  90                  95

Ile Ala Tyr Ser Glu Glu Asn Pro Arg Pro Gly Val Ile Ile Asn Lys
            100                 105                 110

Pro Asp Gly Gly Asp Val Tyr Lys Gly Val Pro Lys Asp Tyr Thr Gly
        115                 120                 125

Lys Asp Val Asn Val Asn Asn Phe Phe Ala Ala Leu Leu Gly Asn Lys
    130                 135                 140

Ser Ala Leu Thr Gly Gly Ser Gly Lys Val Val Asp Ser Gly Pro Asn
145                 150                 155                 160

Asp His Ile Phe Val Phe Tyr Ser Asp His Gly Gly Pro Gly Ile Leu
                165                 170                 175

Gly Met Pro Val Gly Pro Tyr Leu Tyr Ala Asn Asp Leu Asn Glu Val
            180                 185                 190

Leu Lys Lys Lys His Ala Ser Gly Gly Tyr Lys Ser Leu Val Phe Tyr
        195                 200                 205
```

-continued

Leu Glu Ala Cys Glu Ser Gly Ser Ile Phe Glu Gly Leu Leu Pro Glu
            210                 215                 220

Asp Ile Asn Ile Tyr Ala Thr Thr Ala Ser Asn Ala Val Glu Ser Ser
225                 230                 235                 240

Trp Gly Thr Tyr Cys Pro Gly Glu Asp Pro Ser Pro Pro Pro Glu Tyr
                245                 250                 255

Ser Thr Cys Leu Gly Asp Leu Tyr Ser Ile Ser Trp Met Glu Asp Ser
            260                 265                 270

Asp Thr His Asn Leu Arg Thr Glu Thr Leu His Gln Gln Tyr Lys Leu
        275                 280                 285

Val Lys Asp Arg Thr Leu Asn Gly Asn Ala Tyr Tyr Gly Ser His Ala
290                 295                 300

Met Gln Tyr Gly Asp Val Gly Ile Ser Glu Asn Leu Leu Phe Gln Tyr
305                 310                 315                 320

Leu Gly Thr Asn Pro Ala Asn Asp Asn Tyr Thr Phe Val Asp Glu Asn
                325                 330                 335

Ser Leu Arg Thr Pro Ser Lys Ala Val Asn Gln Arg Asp Ala Asp Leu
            340                 345                 350

Ile His Phe Trp Glu Lys Phe Arg Lys Ala Pro Glu Gly Ser Ser Ser
        355                 360                 365

Lys Ile Thr Ala Gln Lys Gln Val Glu Val Met Ser His Arg Met
370                 375                 380

His Ile Asp Asn Ser Val Lys Leu Ile Gly Asn Leu Leu Phe Gly Thr
385                 390                 395                 400

Glu Lys Gly Pro Glu Leu Leu Ser Ala Val Arg Pro Ala Gly Lys Pro
                405                 410                 415

Leu Val Asp Asp Trp Asp Cys Leu Lys Asn Met Val Arg Thr Phe Glu
            420                 425                 430

Thr His Cys Gly Ser Leu Ser Gln Tyr Gly Met Lys His Met Arg Thr
        435                 440                 445

Phe Ala Asn Ile Cys Asn Ala Gly Ile His Lys Asp Gln Met Asp Glu
450                 455                 460

Ala Thr Ala Gln Ala Cys Val Ser Ile Pro Ser Asn Pro Trp Ser Ser
465                 470                 475                 480

Leu Glu Arg Gly Phe Ser Ala
                485

<210> SEQ ID NO 25
<211> LENGTH: 493
<212> TYPE: PRT
<213> ORGANISM: Populus trichocarpa

<400> SEQUENCE: 25

Met Thr Arg Leu Ile Ala Gly Val Ile Phe Leu Leu Ile Ser Phe Cys
1               5                   10                  15

Gly Ile Ala Val Gly Val Arg Asp Ile Val Gly Asp Val Leu Arg Leu
            20                  25                  30

Pro Ser Glu Ala Ser Arg Phe Phe Arg Pro Gly Lys Phe Asn Asp Asp
        35                  40                  45

Asn Ser Asp Asp Asp Ser Ser Gly Thr Arg Trp Ala Ile Leu Leu Ala
    50                  55                  60

Gly Ser Asn Gly Tyr Trp Asn Tyr Arg His Gln Ala Asp Val Cys His
65                  70                  75                  80

Ala Tyr Gln Leu Leu Arg Gln Gly Gly Leu Lys Glu Glu Asn Ile Ile

```
            85                  90                  95
Val Phe Met Tyr Asp Asp Ile Ala Asp Asn Pro Glu Asn Pro Arg Pro
                100                 105                 110

Gly Val Ile Ile Asn Asn Pro Gln Gly Glu Asp Val Tyr Lys Gly Val
            115                 120                 125

Pro Lys Asp Tyr Thr Gly Pro Asp Val Thr Val Gly Asn Phe Phe Ala
    130                 135                 140

Ala Ile Leu Gly Asn Lys Thr Ala Leu Thr Gly Gly Ser Gly Lys Val
145                 150                 155                 160

Ile Asp Ser Gly Pro Asn Asp His Ile Phe Ile Tyr Tyr Thr Asp His
                165                 170                 175

Gly Gly Pro Gly Val Leu Gly Met Pro Thr Asn Pro Tyr Leu Tyr Ala
                180                 185                 190

Asp Asp Leu Ile Asp Val Leu Lys Lys His Ala Ser Gly Thr Tyr
            195                 200                 205

Lys Ser Leu Val Phe Tyr Leu Glu Ala Cys Glu Ser Gly Ser Ile Phe
    210                 215                 220

Glu Gly Leu Leu Pro Gln Gly Leu Asn Ile Tyr Ala Thr Thr Ala Ser
225                 230                 235                 240

Asn Ala Glu Glu Ser Ser Trp Gly Thr Tyr Cys Pro Gly Glu Tyr Pro
                245                 250                 255

Ser Pro Pro Glu Tyr Glu Thr Cys Leu Gly Asp Leu Tyr Ser Val
        260                 265                 270

Ala Trp Met Glu Asp Ser Asp Ile His Asn Leu Arg Thr Glu Thr Leu
        275                 280                 285

His Gln Gln Tyr Glu Leu Val Lys Arg Arg Thr Ser Tyr Asp Asn Ser
        290                 295                 300

Pro Tyr Gly Ser His Val Met Gln Tyr Gly Asp Val Gly Leu Ser Lys
305                 310                 315                 320

Asp Asp Leu Phe Gln Tyr Met Gly Thr Asn Pro Ala Asn Asp Asn Tyr
                325                 330                 335

Thr Phe Val Glu Glu Asn Ser Leu Arg Pro His Ser Lys Val Val Asn
                340                 345                 350

Gln Arg Asp Ala Asp Leu Val His Phe Trp Thr Lys Tyr Arg Lys Ala
        355                 360                 365

Pro Glu Gly Ser Ser Arg Lys Val Glu Ala Gln Lys Gln Phe Val Glu
        370                 375                 380

Ala Met Ser His Arg Met His Ile Asp His Ser Ile Lys Leu Ile Gly
385                 390                 395                 400

Lys Leu Leu Phe Gly Ile Glu Lys Ala Ser Glu Ala Leu Asn Thr Val
                405                 410                 415

Arg Pro Ala Gly Gln Pro Leu Val Asp Asp Trp Val Cys Leu Lys Thr
        420                 425                 430

Leu Val Arg Thr Phe Glu Thr His Cys Gly Ser Ile Ser Gln Tyr Gly
        435                 440                 445

Met Lys His Met Arg Ser Leu Ala Asn Leu Cys Asn Ala Gly Ile Val
        450                 455                 460

Lys Glu Gln Met Ala Glu Ala Ser Ala Gln Ala Cys Val Ser Phe Pro
465                 470                 475                 480

Ser Gly Ser Trp Ser Ser Leu His Lys Gly Phe Ser Ala
                485                 490

<210> SEQ ID NO 26
```

<211> LENGTH: 492
<212> TYPE: PRT
<213> ORGANISM: Cicer arietinum

<400> SEQUENCE: 26

```
Met Asp Arg Ser Lys Ile Ser Thr Leu Leu Phe Leu Ile Val Ala Leu
1               5                   10                  15

Thr Phe Leu Ala Ala Val Ser Ala Val Arg Asp Leu Pro Gly Asp Tyr
            20                  25                  30

Leu Arg Leu Pro Ser Asp Ala Ser Arg Phe His Glu Pro Glu Asn
        35                  40                  45

Asp Asp Asn Val Gln Gly Thr Arg Trp Ala Ile Leu Leu Ala Gly Ser
    50                  55                  60

Asn Gly Tyr Trp Asn Tyr Arg His Gln Ala Asp Val Cys His Ala Tyr
65                  70                  75                  80

Gln Ile Leu Arg Lys Gly Gly Leu Lys Glu Glu Asn Ile Ile Val Phe
                85                  90                  95

Met Tyr Asp Asp Ile Ala Phe Asp Ile Glu Asn Pro Arg Pro Gly Val
            100                 105                 110

Ile Ile Asn Lys Pro Asp Gly Gly Asp Val Tyr Ala Gly Val Pro Lys
        115                 120                 125

Asp Tyr Thr Gly Asp Asp Val Asn Val Asp Asn Phe Tyr Ala Ala Leu
    130                 135                 140

Leu Gly Asn Lys Ser Ala Leu Thr Gly Gly Ser Gly Lys Val Val Asp
145                 150                 155                 160

Ser Gly Pro Asn Asp His Ile Phe Val Tyr Tyr Thr Asp His Gly Gly
                165                 170                 175

Pro Gly Val Leu Gly Met Pro Val Gly Pro Tyr Leu Tyr Ala Ser Asp
            180                 185                 190

Leu Asn Glu Val Leu Lys Lys His Ala Ser Gly Ser Tyr Lys Ser
    195                 200                 205

Leu Val Phe Tyr Leu Glu Ala Cys Glu Ser Gly Ser Ile Phe Glu Gly
        210                 215                 220

Leu Leu Pro Glu Asn Ile Asn Ile Tyr Ala Thr Thr Ala Ser Asn Ala
225                 230                 235                 240

Asp Glu Ser Ser Trp Gly Thr Tyr Cys Pro Gly Glu Tyr Pro Pro Pro
                245                 250                 255

Pro Pro Glu Tyr Ser Thr Cys Leu Gly Asp Leu Tyr Ser Val Ala Trp
            260                 265                 270

Met Glu Asp Ser Asp Ile His Asn Leu Arg Thr Glu Ser Leu His Gln
        275                 280                 285

Gln Tyr Lys Val Val Lys Asp Arg Thr Ile Asn Gly Val Tyr Tyr Gly
    290                 295                 300

Ser His Val Met Glu Tyr Gly Asp Val Gly Leu Ser Asn Asn His Leu
305                 310                 315                 320

Phe Ile Tyr Leu Gly Thr Asn Pro Ala Asn Asp Asn Ile Ser Phe Val
                325                 330                 335

Asp Glu Ser Ser Leu Thr Leu Arg Ser Pro Ser Ala Ala Val Asn Gln
            340                 345                 350

Arg Asp Ala Asp Leu Ile His Phe Trp Asp Lys Phe Arg Lys Ala Pro
        355                 360                 365

Glu Gly Ser Ala Arg Lys Asn Glu Ala Glu Lys Gln Val Leu Glu Ala
    370                 375                 380

Met Ser His Arg Lys His Val Asp Asn Ser Val Glu Leu Ile Gly Lys
```

```
                385                 390                 395                 400
Leu Leu Phe Gly Ile Glu Lys Gly Pro Glu Leu Phe Asn Thr Val Arg
                    405                 410                 415

Pro Ala Gly Leu Pro Leu Val Asp Asn Trp Asp Cys Leu Lys Thr Met
                    420                 425                 430

Val Arg Thr Phe Glu Thr His Cys Gly Ser Leu Ser Gln Tyr Gly Met
                    435                 440                 445

Lys His Met Arg Ser Phe Ala Asn Ile Cys Asn Ala Gly Ile Gln Asn
            450                 455                 460

Glu Gln Met Ala Glu Ala Ser Ala Gln Ala Cys Ser Asn Ile Pro Ala
465                 470                 475                 480

Asn Pro Trp Ser Ser Leu His Arg Gly Phe Ser Ala
                485                 490

<210> SEQ ID NO 27
<211> LENGTH: 493
<212> TYPE: PRT
<213> ORGANISM: Vitis vinifera

<400> SEQUENCE: 27

Met Thr Ile Phe Pro Ala Val Ala Ala Phe Leu Ala Leu Ser Thr
1               5                   10                  15

Leu Val Ala Gly Gly Arg His Phe Ala Gly Asp Asn Gly Leu Leu Leu
                    20                  25                  30

Pro Ser Glu Ala Ser Arg Phe Phe Arg Pro Gly Gly Ala Ala Asp Asp
                35                  40                  45

Asp Thr Gly Ala Glu Ser Ala Gly Thr Arg Trp Ala Val Leu Ile Ala
    50                  55                  60

Gly Ser Asn Gly Tyr Trp Asn Tyr Arg His Gln Ala Asp Ile Cys His
65                  70                  75                  80

Ala Tyr Gln Leu Leu Lys Lys Gly Gly Leu Lys Asp Glu Asn Ile Ile
                85                  90                  95

Val Phe Met Tyr Asp Asp Ile Ser Phe Asn Glu Glu Asn Pro Arg Pro
                100                 105                 110

Gly Ile Ile Ile Asn Ser Pro His Gly Glu Asp Val Tyr Glu Gly Val
                115                 120                 125

Pro Lys Asp Tyr Thr Gly Glu Asp Val Thr Val Asp Asn Phe Phe Ala
            130                 135                 140

Val Ile Leu Gly Asn Lys Thr Ala Leu Ser Gly Gly Ser Gly Lys Val
145                 150                 155                 160

Leu Asp Ser Gly Pro Asn Asp His Ile Phe Ile Tyr Tyr Ser Asp His
                165                 170                 175

Gly Gly Pro Gly Val Leu Gly Met Pro Thr Ser Pro Tyr Leu Tyr Ala
                180                 185                 190

Asn Asp Leu Ile Glu Val Leu Lys Lys Lys His Ala Ser Gly Thr Tyr
            195                 200                 205

Asn Ser Leu Val Phe Tyr Leu Glu Ala Cys Glu Ser Gly Ser Ile Phe
            210                 215                 220

Glu Gly Leu Leu Pro Glu Gly Leu Asn Ile Tyr Ala Thr Thr Ala Ala
225                 230                 235                 240

Asn Ala Glu Glu Ser Ser Trp Gly Thr Tyr Cys Pro Gly Glu Asp Pro
                245                 250                 255

Ser Pro Pro Pro Glu Tyr Glu Thr Cys Leu Gly Asp Leu Tyr Ser Val
                260                 265                 270
```

```
Ala Trp Met Glu Asp Ser Asp Val His Asn Leu Arg Thr Glu Thr Leu
            275                 280                 285

Arg Gln Gln Tyr Glu Leu Val Lys Lys Arg Thr Ala Asn Asp Asn Ser
        290                 295                 300

Val Tyr Gly Ser His Val Met Gln Tyr Gly Asp Leu Gly Leu Asn Lys
305                 310                 315                 320

Glu Asp Leu Val Leu Tyr Met Gly Thr Asn Pro Ala Asn Asp Asn Tyr
                325                 330                 335

Thr Phe Val Asp Asn Asn Ser Leu Arg Leu Pro Ser Lys Ala Val Asn
            340                 345                 350

Gln Arg Asp Ala Asp Leu Val His Phe Trp Asp Lys Phe Arg Lys Ala
        355                 360                 365

Pro Glu Gly Ser Pro Arg Lys Ala Glu Ala Gln Lys Gln Phe Leu Glu
370                 375                 380

Ala Met Ser His Arg Thr His Ile Asp His Ala Ile Lys Leu Val Gly
385                 390                 395                 400

Arg Leu Leu Phe Gly Met Lys Lys Gly Ser Glu Val Leu Lys Thr Val
                405                 410                 415

Arg Pro Ala Gly Gln Pro Leu Val Asp Asp Trp His Cys Leu Lys Thr
            420                 425                 430

Leu Val Arg Thr Phe Glu Ala His Cys Gly Ser Leu Ser Gln Tyr Gly
        435                 440                 445

Met Lys His Met Arg Ser Ile Ala Asn Ile Cys Asn Ala Gly Ile Glu
450                 455                 460

Lys Glu Gln Met Ala Glu Ala Ser Ala Gln Ala Cys Val Thr Ile Pro
465                 470                 475                 480

Pro Gly Pro Trp Ser Ser Leu Asp Lys Gly Phe Ser Ala
                485                 490

<210> SEQ ID NO 28
<211> LENGTH: 484
<212> TYPE: PRT
<213> ORGANISM: Phaseolus vulgaris

<400> SEQUENCE: 28

Met Ala Thr Thr Thr Ala Thr Thr Ser Leu Leu Ala Leu Leu Leu Leu
1               5                   10                  15

Phe Leu Val Ala Leu Val Ser Ala Gly Arg Asp Leu Val Gly Asp Phe
                20                  25                  30

Leu Arg Leu Pro Ser Asp Ser Gly Asn Gly Asp Asn Val His Gly Thr
            35                  40                  45

Arg Trp Ala Ile Leu Phe Ala Gly Ser Ser Gly Tyr Trp Asn Tyr Arg
        50                  55                  60

His Gln Ala Asp Ile Cys His Ala Tyr Gln Leu Arg Lys Gly Gly
65                  70                  75                  80

Leu Lys Asp Glu Asn Ile Ile Val Phe Met Tyr Asp Asp Ile Ala Phe
                85                  90                  95

Asn Ser Glu Asn Pro Arg Arg Gly Val Ile Ile Asn Ser Pro Asn Gly
                100                 105                 110

Asp Asp Val Tyr Lys Gly Val Pro Lys Asp Tyr Thr Gly Glu Asp Val
            115                 120                 125

Thr Ala His Asn Phe Tyr Ala Ala Leu Leu Gly Asp Lys Ser Lys Leu
        130                 135                 140

Thr Gly Gly Ser Gly Lys Val Val Asn Ser Gly Pro Asn Asp His Ile
145                 150                 155                 160
```

Phe Ile Phe Tyr Ser Asp His Gly Gly Pro Gly Val Leu Gly Ser Pro
                165                 170                 175

Ala Gly Pro Tyr Ile Tyr Ala Ser Asp Leu Asn Glu Val Leu Lys Lys
            180                 185                 190

Lys His Ala Ser Gly Thr Tyr Lys Asn Leu Val Phe Tyr Leu Glu Ala
        195                 200                 205

Cys Glu Ser Gly Ser Ile Phe Glu Gly Leu Leu Pro Glu Asp Ile Asn
    210                 215                 220

Val Tyr Ala Thr Thr Ala Ser Asn Ala Asp Glu Ser Ser Trp Gly Thr
225                 230                 235                 240

Tyr Cys Pro Gly Glu Asp Pro Ser Pro Pro Glu Tyr Ser Thr Cys
                245                 250                 255

Leu Gly Asp Leu Tyr Ser Val Ala Trp Met Glu Asp Ser Asp Arg His
            260                 265                 270

Asn Leu Arg Thr Glu Thr Leu His Gln Gln Tyr Lys Leu Val Lys Glu
        275                 280                 285

Arg Thr Ile Ser Gly Gly Leu Tyr Tyr Gly Ser His Val Met Gln Tyr
    290                 295                 300

Gly Asp Val Gly Leu Ser Lys Asp Ile Leu Phe His Tyr Leu Gly Thr
305                 310                 315                 320

Asp Pro Ala Asn Glu Asn Leu Thr Phe Val Asp Glu Asn Ser Leu Trp
                325                 330                 335

Ser Ser Ser Lys Ala Val Asn Gln Arg Asp Ala Asp Leu Val His Phe
            340                 345                 350

Trp Asp Lys Phe Arg Lys Ala Pro Glu Gly Ser Pro Lys Lys Asn Glu
        355                 360                 365

Ala Arg Lys Gln Val Leu Glu Val Met Ser His Arg Met His Ile Asp
    370                 375                 380

Asp Ser Val Glu Leu Val Gly Lys Leu Leu Phe Gly Ile Glu Lys Ala
385                 390                 395                 400

Pro Glu Leu Leu Asn Ala Val Arg Pro Ala Gly Ser Ala Leu Val Asp
                405                 410                 415

Asp Trp Asp Cys Leu Lys Thr Met Val Arg Thr Phe Glu Thr His Cys
            420                 425                 430

Gly Ser Leu Ser Gln Tyr Gly Met Lys His Met Arg Ser Phe Ala Asn
        435                 440                 445

Met Cys Asn Val Gly Ile Lys Lys Glu Gln Met Arg Glu Ala Ser Ala
    450                 455                 460

Gln Ala Cys Val Thr Ile Pro Ala Asn Pro Trp Ser Ser Leu Gln Arg
465                 470                 475                 480

Gly Phe Ser Ala

<210> SEQ ID NO 29
<211> LENGTH: 484
<212> TYPE: PRT
<213> ORGANISM: Phaseolus vulgaris

<400> SEQUENCE: 29

Met Ala Thr Thr Thr Ala Thr Ser Leu Leu Ala Leu Leu Leu Leu
1               5                   10                  15

Phe Leu Val Ala Leu Val Ser Ala Gly Arg Asp Leu Val Gly Asp Phe
            20                  25                  30

Leu Arg Leu Pro Ser Asp Ser Gly Asn Gly Asp Asn Val His Gly Thr
        35                  40                  45

```
Arg Trp Ala Ile Leu Phe Ala Gly Ser Ser Gly Tyr Trp Asn Tyr Arg
 50                  55                  60
His Gln Ala Asp Ile Cys His Ala Tyr Gln Leu Leu Arg Lys Gly Gly
 65                      70                  75                  80
Leu Lys Asp Glu Asn Ile Ile Val Phe Met Tyr Asp Asp Ile Ala Phe
                     85                  90                  95
Asn Ser Glu Asn Pro Arg Arg Gly Val Ile Ile Asn Ser Pro Asn Gly
                100                 105                 110
Asp Glu Val Tyr Lys Gly Val Pro Lys Asp Tyr Thr Gly Glu Asp Val
                115                 120                 125
Thr Ala His Asn Phe Tyr Ala Ala Leu Leu Gly Asp Lys Ser Lys Leu
130                 135                 140
Thr Gly Ser Gly Lys Val Val Asn Ser Gly Pro Asn Asp His Ile
145                 150                 155                 160
Phe Ile Phe Tyr Ser Asp His Gly Gly Pro Gly Val Leu Gly Ser Pro
                165                 170                 175
Ala Gly Pro Tyr Ile Tyr Ala Ser Asp Leu Asn Glu Val Leu Lys Lys
                180                 185                 190
Lys His Ala Ser Gly Thr Tyr Lys Asn Leu Val Phe Tyr Leu Glu Ala
                195                 200                 205
Cys Glu Ser Gly Ser Ile Phe Glu Gly Leu Leu Pro Glu Asp Ile Asn
210                 215                 220
Val Tyr Ala Thr Thr Ala Ser Asn Ala Asp Glu Ser Ser Trp Gly Thr
225                 230                 235                 240
Tyr Cys Pro Gly Glu Asp Pro Ser Pro Pro Glu Tyr Ser Thr Cys
                245                 250                 255
Leu Gly Asp Leu Tyr Ser Val Ala Trp Met Glu Asp Ser Asp Arg His
                260                 265                 270
Asn Leu Arg Thr Glu Thr Leu His Gln Gln Tyr Lys Leu Val Lys Glu
                275                 280                 285
Arg Thr Ile Ser Gly Gly Leu Tyr Tyr Gly Ser His Val Met Gln Tyr
290                 295                 300
Gly Asp Val Gly Leu Ser Lys Asp Ile Leu Phe His Tyr Leu Gly Thr
305                 310                 315                 320
Asp Pro Ala Asn Glu Asn Leu Thr Phe Val Asp Glu Asn Ser Leu Trp
                325                 330                 335
Ser Ser Ser Lys Ala Val Asn Gln Arg Asp Ala Asp Leu Val His Phe
                340                 345                 350
Trp Asp Lys Phe Arg Lys Ala Pro Glu Gly Ser Pro Lys Lys Asn Glu
                355                 360                 365
Ala Arg Lys Gln Val Leu Glu Val Met Ser His Arg Met His Ile Asp
370                 375                 380
Asp Ser Val Glu Leu Val Gly Lys Leu Leu Phe Gly Ile Glu Lys Ala
385                 390                 395                 400
Pro Glu Leu Leu Asn Ala Val Arg Pro Ala Gly Ser Ala Leu Val Asp
                405                 410                 415
Asp Trp Asp Cys Leu Lys Thr Met Val Arg Thr Phe Glu Thr His Cys
                420                 425                 430
Gly Ser Leu Ser Gln Tyr Gly Met Lys His Met Arg Ser Phe Ala Asn
                435                 440                 445
Met Cys Asn Val Gly Ile Lys Lys Glu Gln Met Arg Glu Ala Ser Ala
450                 455                 460
```

-continued

```
Gln Ala Cys Val Thr Ile Pro Ala Asn Pro Trp Ser Ser Leu Gln Arg
465                 470                 475                 480

Gly Phe Ser Ala
```

<210> SEQ ID NO 30
<211> LENGTH: 493
<212> TYPE: PRT
<213> ORGANISM: Vitis vinifera

<400> SEQUENCE: 30

```
Met Thr Ile Phe Pro Ala Ala Val Ala Ala Leu Leu Ala Leu Ser Thr
1               5                   10                  15

Leu Val Ala Gly Gly Arg His Phe Ala Gly Asp Asn Gly Leu Leu Leu
            20                  25                  30

Pro Ser Glu Ala Ser Arg Phe Phe Arg Pro Gly Gly Ala Ala Asp Asp
        35                  40                  45

Asp Thr Gly Gly Glu Ser Ala Gly Thr Arg Trp Ala Val Leu Ile Ala
50                  55                  60

Gly Ser Asn Gly Tyr Trp Asn Tyr Arg His Gln Ala Asp Ile Cys His
65                  70                  75                  80

Ala Tyr Gln Leu Leu Lys Lys Gly Gly Leu Lys Asp Glu Asn Ile Ile
            85                  90                  95

Val Phe Met Tyr Asp Asp Ile Ser Phe Asn Glu Glu Asn Pro Arg Pro
        100                 105                 110

Gly Ile Ile Ile Asn Ser Pro His Gly Glu Asp Val Tyr Glu Gly Val
    115                 120                 125

Pro Lys Asp Tyr Thr Gly Glu Asp Val Thr Val Asp Asn Phe Phe Ala
130                 135                 140

Val Ile Leu Gly Asn Lys Thr Ala Leu Ser Gly Gly Ser Gly Lys Val
145                 150                 155                 160

Leu Asp Ser Gly Pro Asn Asp His Ile Phe Ile Tyr Tyr Ser Asp His
            165                 170                 175

Gly Gly Pro Gly Val Leu Gly Met Pro Thr Ser Pro Tyr Leu Tyr Ala
        180                 185                 190

Asn Asp Leu Ile Glu Val Leu Lys Lys Lys His Ala Ser Gly Thr Tyr
    195                 200                 205

Asn Ser Leu Val Phe Tyr Leu Glu Ala Cys Glu Ser Gly Ser Ile Phe
210                 215                 220

Glu Gly Leu Leu Pro Glu Gly Leu Asn Ile Tyr Ala Thr Thr Ala Ala
225                 230                 235                 240

Asn Ala Glu Glu Ser Ser Trp Gly Thr Tyr Cys Pro Gly Glu Asp Pro
            245                 250                 255

Ser Pro Pro Glu Tyr Glu Thr Cys Leu Gly Asp Leu Tyr Ser Val
        260                 265                 270

Ala Trp Met Glu Asp Ser Asp Val His Asn Leu Arg Thr Glu Thr Leu
    275                 280                 285

Arg Gln Gln Tyr Glu Leu Val Lys Lys Arg Thr Ala Asn Asp Asn Ser
290                 295                 300

Val Tyr Gly Ser His Val Met Gln Tyr Gly Asp Leu Gly Leu Asn Lys
305                 310                 315                 320

Glu Asp Leu Val Leu Tyr Met Gly Thr Asn Pro Ala Asn Asp Asn Tyr
            325                 330                 335

Thr Phe Val Asp Asn Asn Ser Leu Arg Leu Pro Ser Lys Ala Val Asn
        340                 345                 350
```

Gln Arg Asp Ala Asp Leu Val His Phe Trp Asp Lys Phe Arg Lys Ala
        355                 360                 365

Pro Glu Gly Ser Pro Arg Lys Ala Glu Ala Gln Lys Gln Phe Leu Glu
    370                 375                 380

Ala Met Ser His Arg Thr His Ile Asp His Ala Ile Lys Leu Val Gly
385                 390                 395                 400

Arg Leu Leu Phe Gly Met Lys Lys Gly Ser Glu Val Leu Lys Thr Val
                405                 410                 415

Arg Pro Ala Gly Gln Pro Leu Val Asp Asp Trp His Cys Leu Lys Thr
            420                 425                 430

Leu Val Arg Thr Phe Glu Ala His Cys Gly Ser Leu Ser Gln Tyr Gly
        435                 440                 445

Met Lys His Met Arg Ser Ile Ala Asn Ile Cys Asn Ala Gly Ile Glu
    450                 455                 460

Lys Glu Gln Met Ala Glu Ala Ser Ala Gln Ala Cys Val Thr Ile Pro
465                 470                 475                 480

Pro Gly Pro Trp Ser Ser Leu Asp Lys Gly Phe Ser Ala
                485                 490

<210> SEQ ID NO 31
<211> LENGTH: 493
<212> TYPE: PRT
<213> ORGANISM: Cucumis sativus

<400> SEQUENCE: 31

Met Ala Arg Ile Pro Thr Gly Val Leu Leu Ser Leu Leu Phe Leu Ala
1               5                   10                  15

Val Ile Gly Leu Pro Ala Gly Ala Arg Asp Leu Pro Gly Asp Phe Leu
            20                  25                  30

Arg Leu Pro Ser Glu Ala Leu Lys Phe Phe Arg Gly Gly Ala Ser Asp
        35                  40                  45

Ala Ser Asp Glu Asp Ser Val Gly Thr Arg Trp Ala Val Leu Ile Ala
    50                  55                  60

Gly Ser Asn Gly Tyr Trp Asn Tyr Arg His Gln Ala Asp Ile Cys His
65                  70                  75                  80

Ala Tyr Gln Leu Leu Arg Lys Asn Gly Leu Lys Asp Glu Asn Ile Ile
                85                  90                  95

Val Phe Met Tyr Asp Asp Ile Ala Phe Asn Pro Glu Asn Pro Arg Pro
            100                 105                 110

Gly Val Ile Ile Asn His Pro Lys Gly Ser Asp Val Tyr His Gly Val
        115                 120                 125

Pro Lys Asp Tyr Thr Gly Glu Asp Val Thr Val Asn Asn Phe Phe Ala
    130                 135                 140

Ala Ile Leu Gly Asn Lys Thr Ala Leu Thr Gly Gly Ser Gly Lys Val
145                 150                 155                 160

Val Asp Ser Gly Pro Asn Asp His Ile Phe Ile Tyr Tyr Ser Asp His
                165                 170                 175

Gly Gly Pro Gly Val Leu Gly Met Pro Thr Tyr Pro Tyr Met Tyr Ala
            180                 185                 190

Asp Asp Leu Asn Lys Val Leu Lys Lys His Ala Ala Gly Ser Tyr
        195                 200                 205

Lys Ser Leu Val Phe Tyr Leu Glu Ala Cys Glu Ser Gly Ser Ile Phe
    210                 215                 220

Glu Gly Leu Leu Pro Glu Gly Leu Asn Ile Tyr Thr Thr Thr Ala Ser
225                 230                 235                 240

```
Asn Ala Tyr Glu Ser Ser Trp Gly Thr Tyr Cys Pro Gly Asp Tyr Pro
                245                 250                 255

Ser Pro Pro Glu Tyr Asp Thr Cys Leu Gly Asp Leu Tyr Ser Val
        260                 265                 270

Ala Trp Leu Glu Asp Ser Asp Asn His Asn Leu Lys Thr Glu Ser Leu
            275                 280                 285

Arg Gln Gln Tyr Glu Leu Val Lys Lys Arg Thr Ile Ser Gly Gln Tyr
        290                 295                 300

Ala Tyr Gly Ser His Val Met Gln Tyr Gly Asp Leu Met Leu Asn Lys
305                 310                 315                 320

Asn Ala Leu Phe Ser Tyr Leu Gly Thr Asp Pro Ala Asn Glu Asn Asn
                325                 330                 335

Thr Phe Val Glu Glu Asn Ser Leu Arg Pro Ala Thr Lys Phe Thr Asn
            340                 345                 350

Gln Arg Asp Ala Asp Leu Val His Phe Trp Glu Lys Phe Arg Lys Ala
        355                 360                 365

Pro Glu Gly Ser Leu Thr Lys Val Glu Ala Gln Lys Lys Phe Val Glu
    370                 375                 380

Ala Met Ser His Arg Ala His Ile Asp Asn Ser Val Lys Leu Val Gly
385                 390                 395                 400

Lys Leu Leu Phe Gly Ile Lys Glu Gly Pro Glu Val Leu Glu Ala Ile
                405                 410                 415

Arg Pro Ala Gly Arg Pro Leu Val Asp Asp Trp Asn Cys Leu Arg Asn
            420                 425                 430

Met Val Arg Ser Phe Glu Ala Arg Cys Gly Ser Leu Ser Gln Tyr Gly
        435                 440                 445

Met Lys His Met Arg Ser Phe Ala Asn Leu Cys Asn Ala Gly Ile Ser
    450                 455                 460

Lys Glu Gln Met Ala Glu Ala Ser Ala Gln Ala Cys Met Ser Val Pro
465                 470                 475                 480

Pro Gly Pro Trp Ser Ser Leu Leu Lys Gly Phe Thr Ala
                485                 490

<210> SEQ ID NO 32
<211> LENGTH: 493
<212> TYPE: PRT
<213> ORGANISM: Cucumis sativus

<400> SEQUENCE: 32

Met Ala Arg Ile Pro Thr Gly Val Leu Leu Ser Leu Leu Phe Leu Ala
1               5                   10                  15

Val Ile Gly Leu Pro Ala Gly Ala Arg Asp Leu Pro Gly Asp Phe Leu
            20                  25                  30

Arg Leu Pro Ser Glu Ala Leu Lys Phe Phe Arg Gly Gly Ala Ser Asp
        35                  40                  45

Ala Ser Asp Glu Asp Ser Val Gly Thr Arg Trp Ala Val Leu Ile Ala
    50                  55                  60

Gly Ser Asn Gly Tyr Trp Asn Tyr Arg His Gln Ala Asp Ile Cys His
65                  70                  75                  80

Ala Tyr Gln Leu Leu Arg Lys Asn Gly Leu Lys Asp Glu Asn Ile Ile
                85                  90                  95

Val Phe Met Tyr Asp Asp Ile Ala Phe Asn Pro Glu Asn Pro Arg Pro
            100                 105                 110

Gly Val Ile Ile Asn His Pro Lys Gly Ser Asp Val Tyr His Gly Val
```

```
                    115                 120                 125
Pro Lys Asp Tyr Thr Gly Glu Asp Val Thr Val Asn Phe Phe Ala
            130                 135                 140
Ala Ile Leu Gly Asn Lys Thr Ala Leu Thr Gly Gly Ser Gly Lys Val
145                 150                 155                 160
Val Asp Ser Gly Pro Asn Asp His Ile Phe Ile Tyr Tyr Ser Asp His
                165                 170                 175
Gly Gly Pro Gly Val Leu Gly Met Pro Thr Tyr Pro Tyr Met Tyr Ala
            180                 185                 190
Asp Asp Leu Asn Lys Val Leu Lys Lys His Ala Ala Gly Ser Tyr
            195                 200                 205
Lys Ser Leu Val Phe Tyr Leu Glu Ala Cys Glu Ser Gly Ser Ile Phe
210                 215                 220
Glu Gly Leu Leu Pro Glu Gly Leu Asn Ile Tyr Thr Thr Thr Ala Ser
225                 230                 235                 240
Asn Ala Tyr Glu Ser Ser Trp Gly Thr Tyr Cys Pro Gly Asp Tyr Pro
                245                 250                 255
Ser Pro Pro Glu Tyr Asp Thr Cys Leu Gly Asp Leu Tyr Ser Val
                260                 265                 270
Ala Trp Leu Glu Asp Ser Asp Asn His Asn Leu Lys Thr Glu Ser Leu
            275                 280                 285
Arg Gln Gln Tyr Glu Leu Val Lys Lys Arg Thr Leu Ser Gly Gln Tyr
            290                 295                 300
Ala Tyr Gly Ser His Val Met Gln Tyr Gly Asp Leu Met Leu Asn Lys
305                 310                 315                 320
Asn Ala Leu Phe Ser Tyr Leu Gly Thr Asp Pro Ala Asn Glu Asn Asn
                325                 330                 335
Thr Phe Val Glu Glu Asn Ser Leu Arg Pro Ala Thr Lys Phe Thr Asn
                340                 345                 350
Gln Arg Asp Ala Asp Leu Val His Phe Trp Glu Lys Phe Arg Lys Ala
            355                 360                 365
Pro Glu Gly Ser Leu Thr Lys Val Glu Ala Gln Lys Lys Phe Val Glu
            370                 375                 380
Ala Met Ser His Arg Ala His Ile Asp Asn Ser Val Lys Leu Val Gly
385                 390                 395                 400
Lys Leu Leu Phe Gly Ile Lys Glu Gly Pro Glu Val Leu Glu Ala Ile
                405                 410                 415
Arg Pro Ala Gly Arg Pro Leu Val Asp Asp Trp Asn Cys Leu Arg Asn
            420                 425                 430
Met Val Arg Ser Phe Glu Ala Arg Cys Gly Ser Leu Ser Gln Tyr Gly
            435                 440                 445
Met Lys His Met Arg Ser Phe Ala Asn Leu Cys Asn Ala Gly Ile Ser
            450                 455                 460
Lys Glu Gln Met Ala Glu Ala Ser Ala Gln Ala Cys Met Ser Val Pro
465                 470                 475                 480
Pro Gly Pro Trp Ser Ser Leu Leu Lys Gly Phe Thr Ala
                485                 490
```

<210> SEQ ID NO 33
<211> LENGTH: 493
<212> TYPE: PRT
<213> ORGANISM: Vicia sativa

<400> SEQUENCE: 33

```
Met Gly Ser Ser Gln Leu Ser Thr Leu Leu Phe Phe Thr Ile Val Val
1               5                   10                  15

Thr Phe Leu Thr Val Val Ser Ser Gly Arg Asp Leu Pro Gly Asp Tyr
            20                  25                  30

Leu Arg Leu Pro Ser Glu Thr Ser Arg Phe Phe Arg Glu Pro Lys Asn
        35                  40                  45

Asp Asp Asp Phe Glu Gly Thr Arg Trp Ala Ile Leu Leu Ala Gly Ser
50                  55                  60

Asn Gly Tyr Trp Asn Tyr Arg His Gln Ser Asp Val Cys His Ala Tyr
65                  70                  75                  80

Gln Leu Leu Arg Lys Gly Gly Ser Lys Glu Glu Asn Ile Ile Val Phe
                85                  90                  95

Met Tyr Asp Asp Ile Ala Ser Asn Glu Glu Asn Pro Arg Pro Gly Val
                100                 105                 110

Ile Ile Asn Lys Pro Asp Gly Asp Val Tyr Ala Gly Val Pro Lys
                115                 120                 125

Asp Tyr Thr Gly Ala Glu Val His Ala Asp Asn Phe Tyr Ala Ala Leu
        130                 135                 140

Leu Gly Asn Lys Ser Ala Leu Thr Gly Gly Ser Gly Lys Val Val Asp
145                 150                 155                 160

Ser Gly Pro Asn Asp His Ile Phe Val Tyr Tyr Thr Asp His Gly Gly
                165                 170                 175

Pro Gly Val Leu Gly Met Pro Val Gly Pro Tyr Leu Tyr Ala Ser Asp
                180                 185                 190

Leu Asn Glu Val Leu Lys Lys Lys His Ala Ser Gly Thr Tyr Lys Ser
            195                 200                 205

Leu Val Phe Tyr Leu Glu Ala Cys Glu Ser Gly Ser Ile Phe Glu Gly
        210                 215                 220

Leu Leu Pro Asp Asp Leu Asn Ile Tyr Ala Thr Thr Ala Ser Asn Ala
225                 230                 235                 240

Glu Glu Ser Ser Trp Gly Tyr Tyr Cys Pro Gly Asp Lys Pro Pro Pro
                245                 250                 255

Pro Pro Glu Tyr Ser Thr Cys Leu Gly Asp Leu Tyr Ser Ile Ala Trp
                260                 265                 270

Met Glu Asp Ser Glu Val His Asn Leu Gln Thr Glu Ser Leu Gln Gln
                275                 280                 285

Gln Tyr Lys Leu Val Lys Asn Arg Thr Ile Ser Glu Pro Tyr Gly Ser
        290                 295                 300

His Val Met Glu Tyr Gly Asp Ile Gly Leu Ser Lys Asn Asp Leu Tyr
305                 310                 315                 320

Gln Tyr Leu Gly Thr Asn Pro Ala Asn Asp Asn Ser Phe Val Asp
                325                 330                 335

Glu Thr Glu Asn Ser Leu Lys Leu Arg Thr Pro Ser Ala Ala Val Asn
                340                 345                 350

Gln Arg Asp Ala Asp Leu Ile His Phe Trp Glu Lys Phe Arg Lys Ala
            355                 360                 365

Pro Glu Gly Ser Ser Gln Lys Asn Glu Ala Glu Lys Gln Val Leu Glu
        370                 375                 380

Ala Met Ser His Arg Lys His Ile Asp Asn Ser Val Lys Leu Ile Gly
385                 390                 395                 400

Gln Leu Leu Phe Gly Ile Glu Lys Gly Thr Glu Leu Leu Asp Val Val
                405                 410                 415

Arg Pro Ala Gly Ser Pro Leu Val Asp Asn Trp Asp Cys Leu Lys Thr
```

```
                    420                 425                 430
Met Val Lys Thr Phe Glu Thr His Cys Gly Ser Leu Ser Gln Tyr Gly
                435                 440                 445

Met Lys His Met Arg Ser Phe Ala Asn Ile Cys Asn Ala Gly Ile Pro
            450                 455                 460

Asn Glu Pro Met Ala Glu Ala Ser Ala Gln Ala Cys Ala Ser Ile Pro
465                 470                 475                 480

Ala Asn Pro Trp Ser Ser Leu Gln Gly Gly Phe Ser Ala
                485                 490

<210> SEQ ID NO 34
<211> LENGTH: 493
<212> TYPE: PRT
<213> ORGANISM: Medicago truncatula

<400> SEQUENCE: 34

Met Asp Phe Ser Gln Phe Ser Thr Ile Leu Phe Leu Thr Val Ile Leu
1               5                   10                  15

Thr Ile Phe Ala Ala Val Ser Gly Ser Arg Asp Leu Pro Gly Asp Tyr
                20                  25                  30

Ile Arg Leu Pro Ser Gln Ser Gln Ala Ser Arg Phe Phe His Glu Pro
            35                  40                  45

Glu Asn Asp Asp Asn Asp Gln Gly Thr Arg Trp Ala Ile Leu Leu Ala
50                  55                  60

Gly Ser Asn Gly Tyr Trp Asn Tyr Arg His Gln Ala Asp Val Cys His
65                  70                  75                  80

Ala Tyr Gln Leu Leu Arg Lys Gly Gly Leu Lys Glu Glu Asn Ile Ile
                85                  90                  95

Val Phe Met Tyr Asp Asp Ile Ala Ser Asn Val Glu Asn Pro Arg Pro
            100                 105                 110

Gly Val Ile Ile Asn Lys Pro Asp Gly Gly Asp Val Tyr Glu Gly Val
        115                 120                 125

Pro Lys Asp Tyr Thr Gly Ala Glu Val His Ala Asp Asn Phe Tyr Ala
130                 135                 140

Ala Leu Leu Gly Asn Lys Ser Ala Leu Thr Gly Gly Ser Gly Lys Val
145                 150                 155                 160

Val Asp Ser Gly Pro Asn Asp His Ile Phe Val Tyr Tyr Thr Asp His
                165                 170                 175

Gly Gly Pro Gly Val Leu Gly Met Pro Val Gly Pro Tyr Leu Tyr Ala
            180                 185                 190

Ser Asp Leu Asn Glu Val Leu Lys Lys His Ala Ser Gly Ser Tyr
        195                 200                 205

Lys Ser Leu Val Phe Tyr Leu Glu Ala Cys Glu Ser Gly Ser Ile Phe
210                 215                 220

Glu Gly Leu Leu Pro Glu Asp Ile Asn Ile Tyr Ala Thr Thr Ala Ser
225                 230                 235                 240

Asn Ala Val Glu Ser Ser Trp Gly Thr Tyr Cys Pro Gly Glu Tyr Pro
                245                 250                 255

Pro Pro Pro Pro Glu Tyr Ser Thr Cys Leu Gly Asp Leu Tyr Ser Ile
            260                 265                 270

Ala Trp Met Glu Asp Ser Asp Ile His Asn Leu Arg Thr Glu Ser Leu
        275                 280                 285

His Gln Gln Tyr Lys Leu Val Lys Asp Arg Thr Ile Asn Gly Tyr Tyr
    290                 295                 300
```

```
Gly Ser His Val Met Glu Tyr Gly Asp Val Gly Leu Ser Asn Asn His
305                 310                 315                 320

Leu Phe Leu Tyr Leu Gly Thr Asn Pro Ala Asn Asp Asn Ile Ser Phe
                325                 330                 335

Val Asp Glu Ser Ser Leu Lys Leu Arg Ser Pro Ser Thr Ala Val Asn
            340                 345                 350

Gln Arg Asp Ala Asp Leu Ile His Phe Trp Asp Lys Phe Arg Lys Ala
        355                 360                 365

Pro Glu Gly Ser Leu Arg Lys Asn Glu Ala Gln Lys Glu Val Leu Glu
    370                 375                 380

Ala Met Ser His Arg Met His Val Asp Asn Ser Ala Lys Leu Ile Gly
385                 390                 395                 400

Lys Leu Leu Phe Gly Ile Glu Lys Gly Thr Glu Leu Leu Gly Asn Val
                405                 410                 415

Arg Pro Ala Gly Ser Pro Leu Val Asp Asn Trp Asp Cys Leu Lys Thr
            420                 425                 430

Met Val Lys Thr Phe Glu Thr His Cys Gly Ser Leu Ser Gln Tyr Gly
        435                 440                 445

Met Lys His Met Arg Ser Phe Ala Asn Ile Cys Asn Ala Gly Ile Gln
    450                 455                 460

Thr Glu Gln Met Ala Glu Ala Ser Ala Gln Ala Cys Ala Ser Ile Pro
465                 470                 475                 480

Ala Asn Pro Trp Ser Ser Leu Gln Arg Gly Phe Ser Ala
                485                 490

<210> SEQ ID NO 35
<211> LENGTH: 494
<212> TYPE: PRT
<213> ORGANISM: Fragaria vesca subsp. vesca

<400> SEQUENCE: 35

Met Thr Arg Leu Ala Ala Val Val Ala Val Leu Phe Phe Leu Val
1               5                   10                  15

Ser Leu Phe Ser Ser Ser Thr Ser Ala Arg Asp Leu Pro Gly Asp Val
                20                  25                  30

Leu Arg Leu Pro Ser Glu Thr Ser Arg Phe Phe Arg Ala Gly Asp Asp
            35                  40                  45

Gln Gln Asp Asp Gly Thr Val Gly Thr Arg Trp Ala Val Leu Ile Ala
    50                  55                  60

Gly Ser Asn Gly Tyr Trp Asn Tyr Arg His Gln Ala Asp Ile Cys His
65                  70                  75                  80

Ala Tyr Gln Leu Leu Lys Lys Gly Gly Leu Lys Asp Glu Asn Ile Val
                85                  90                  95

Val Phe Met Tyr Asp Asp Ile Ala Tyr Asn Glu Glu Asn Pro Arg Gln
                100                 105                 110

Gly Val Ile Ile Asn Ser Pro His Gly Asp Asp Val Tyr Lys Gly Val
            115                 120                 125

Pro Lys Asp Tyr Thr Gly Glu Asp Val Thr Val Gly Asn Phe Phe Ala
    130                 135                 140

Ala Ile Leu Gly Asn Lys Thr Ala Ile Ser Gly Gly Ser Gly Lys Val
145                 150                 155                 160

Val Asp Ser Gly Pro Asn Asp His Ile Phe Ile Tyr Tyr Ser Asp His
                165                 170                 175

Gly Gly Pro Gly Val Leu Gly Met Pro Thr Ser Pro Tyr Ile Tyr Ala
            180                 185                 190
```

```
Asp Arg Leu Ile Glu Val Leu Lys Lys His Ala Ala Gly Thr Tyr
        195                 200                 205

Glu Ser Leu Val Phe Tyr Leu Glu Ala Cys Glu Ser Gly Ser Ile Phe
210                 215                 220

Glu Gly Leu Leu Pro Glu Gly Leu Asn Ile Phe Ala Thr Thr Ala Ser
225                 230                 235                 240

Asn Ala Glu Glu Ser Ser Trp Gly Thr Tyr Cys Pro Gly Glu Tyr Pro
                245                 250                 255

Ser Pro Pro Pro Glu Tyr Glu Thr Cys Leu Gly Asp Leu Tyr Ser Val
                260                 265                 270

Ala Trp Met Glu Asp Ser Asp Ile His Asn Leu Arg Ser Glu Thr Leu
        275                 280                 285

His Gln Gln Tyr Glu Leu Val Lys Ser Arg Thr Ala Ser Asp Asn Ser
        290                 295                 300

Pro Tyr Gly Ser His Val Met Gln Tyr Gly Asp Ile Pro Leu Ser Lys
305                 310                 315                 320

Asn Asn Leu Phe Met Tyr Met Gly Thr Asn Pro Ala Asn Asp Asn Tyr
                325                 330                 335

Thr Phe Met Pro Gln Asn Phe Leu Arg Pro Ser Ser Ser Lys Ala Val
            340                 345                 350

Asn Gln Arg Asp Ala Asp Leu Val His Phe Trp His Lys Tyr Arg Lys
        355                 360                 365

Ala Pro Glu Gly Ser Ala Arg Lys Ala Gln Ala Gln Lys Glu Phe Leu
    370                 375                 380

Glu Ala Met Ser His Arg Met His Ile Asp Glu Ser Val Lys Leu Ile
385                 390                 395                 400

Gly Lys Leu Leu Phe Gly Ile Lys Lys Gly Pro Glu Val Leu Ser Ala
                405                 410                 415

Val Arg Pro Ala Gly Gln Pro Leu Val Asp Asp Trp Asp Cys Leu Lys
            420                 425                 430

Thr Met Val Arg Ser Phe Glu Thr Tyr Cys Gly Ser Leu Ser Gln Tyr
        435                 440                 445

Gly Met Lys His Met Arg Ser Leu Ala Asn Ile Cys Asn Ala Gly Met
    450                 455                 460

Thr Lys Glu Gln Met Ala Glu Ala Ser Gln Ala Cys Val Asn Val
465                 470                 475                 480

Pro Ser Gly Arg Trp Ser Ser Leu His Arg Gly Phe Ser Ala
            485                 490

<210> SEQ ID NO 36
<211> LENGTH: 482
<212> TYPE: PRT
<213> ORGANISM: Solanum tuberosum

<400> SEQUENCE: 36

Met Asn Arg Ser Ile Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
                20                  25                  30

Gly Ser Arg Phe Phe Asp Ala Asp Glu Asn Asp Ser Val Gly Thr Arg
            35                  40                  45

Trp Ala Ile Leu Leu Ala Gly Ser Asn Gly Tyr Trp Asn Tyr Arg His
    50                  55                  60

Gln Ala Asp Ile Cys His Ala Tyr Gln Leu Leu Lys Lys Gly Gly Leu
```

```
            65                  70                  75                  80
Lys Asp Glu Asn Ile Val Val Phe Met Tyr Asp Asp Ile Ala Asn Asn
                85                  90                  95
Glu Glu Asn Pro Arg Gln Gly Val Ile Ile Asn Ser Pro His Gly Glu
            100                 105                 110
Asp Val Tyr Lys Gly Val Pro Lys Asp Tyr Thr Gly Asp Val Thr
            115                 120                 125
Val Asn Asn Phe Leu Ala Ala Leu Leu Gly Asn Lys Thr Ala Ile Thr
        130                 135                 140
Gly Gly Ser Gly Lys Val Val Asp Ser Gly Pro Asn Asp His Ile Phe
145                 150                 155                 160
Ile Phe Tyr Ser Asp His Gly Gly Ala Gly Val Ile Gly Met Pro Thr
                165                 170                 175
Asp Pro Tyr Leu Tyr Ala Asn Asp Leu Ile Asp Ala Leu Lys Lys Lys
            180                 185                 190
His Ala Ser Gly Thr Tyr Lys Ser Leu Val Phe Tyr Leu Glu Ala Cys
            195                 200                 205
Glu Ser Gly Ser Met Phe Glu Gly Leu Leu Pro Glu Gly Leu Asn Ile
        210                 215                 220
Tyr Ala Thr Thr Ala Ser Asn Ala Asp Glu Ser Ser Trp Gly Thr Tyr
225                 230                 235                 240
Cys Pro Gly Glu Phe Pro Ser Pro Ile Glu Tyr Gly Thr Cys Leu
                245                 250                 255
Gly Asp Leu Tyr Ser Ile Ser Trp Met Glu Asp Ser Glu Arg His Asn
            260                 265                 270
Leu Arg Thr Glu Thr Leu Lys Gln Gln Tyr His Leu Val Lys Glu Arg
        275                 280                 285
Thr Ala Ser Gly Asn Pro Ala Tyr Gly Ser His Val Met Gln Tyr Gly
        290                 295                 300
Asp Val His Leu Ser Lys Asp Val Leu Phe Leu Tyr Met Gly Thr Asp
305                 310                 315                 320
Pro Ala Asn Asp Asn Ser Thr Phe Met Asp Asp Asn Ser Met Arg Val
                325                 330                 335
Ser Lys Ala Val Asn Gln Arg Asp Ala Asp Leu Val His Phe Trp Tyr
            340                 345                 350
Lys Phe His Lys Ala Pro Glu Gly Ser Val Arg Lys Thr Glu Ala Gln
            355                 360                 365
Lys Gln Leu Asn Glu Ala Ile Ser His Arg Met His Leu Asp Asn Ser
        370                 375                 380
Ile Ala Leu Val Gly Lys Leu Leu Phe Gly Ile Lys Lys Gly Pro Glu
385                 390                 395                 400
Val Leu Thr Ser Val Arg Pro Ala Gly Gln Pro Leu Val Asp Asp Trp
                405                 410                 415
Asp Cys Leu Lys Ser Tyr Val Arg Thr Phe Glu Thr His Cys Gly Ser
            420                 425                 430
Leu Ser Gln Tyr Gly Met Lys His Met Arg Ser Val Ala Asn Ile Cys
        435                 440                 445
Asn Ala Gly Ile Lys Met Glu Gln Met Val Glu Ala Ser Ala Gln Ala
        450                 455                 460
Cys Pro Ser Val Pro Ser Asn Thr Trp Ser Ser Leu Gln Arg Gly Phe
465                 470                 475                 480
Ser Ala
```

<210> SEQ ID NO 37
<211> LENGTH: 482
<212> TYPE: PRT
<213> ORGANISM: Solanum tuberosum

<400> SEQUENCE: 37

```
Met Asn Arg Ser Ile Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
            20                  25                  30

Gly Ser Arg Phe Phe Asp Ala Asp Glu Asn Asp Ser Val Gly Thr Arg
        35                  40                  45

Trp Ala Ile Leu Leu Ala Gly Ser Asn Gly Tyr Trp Asn Tyr Arg His
    50                  55                  60

Gln Ala Asp Ile Cys His Ala Tyr Gln Leu Leu Lys Lys Gly Gly Leu
65                  70                  75                  80

Lys Asp Glu Asn Ile Val Val Phe Met Tyr Asp Asp Ile Ala Asn Asn
                85                  90                  95

Glu Glu Asn Pro Arg Gln Gly Val Ile Ile Asn Ser Pro His Gly Glu
            100                 105                 110

Asp Val Tyr Lys Gly Val Pro Lys Asp Tyr Thr Gly Asp Asp Val Thr
        115                 120                 125

Val Asn Asn Phe Leu Ala Ala Leu Leu Gly Asn Lys Thr Ala Ile Thr
130                 135                 140

Gly Gly Ser Gly Lys Val Val Asp Ser Gly Pro Asn Asp His Ile Phe
145                 150                 155                 160

Ile Phe Tyr Ser Asp His Gly Gly Ala Gly Val Ile Gly Met Pro Thr
                165                 170                 175

Asp Pro Tyr Leu Tyr Ala Asn Asp Leu Ile Asp Ala Leu Lys Lys Lys
            180                 185                 190

His Ala Ser Gly Thr Tyr Lys Ser Leu Val Phe Tyr Leu Glu Ala Cys
        195                 200                 205

Glu Ser Gly Ser Met Phe Glu Gly Leu Leu Pro Glu Gly Leu Asn Ile
    210                 215                 220

Tyr Ala Thr Thr Ala Ser Asn Ala Asp Glu Ser Ser Trp Gly Thr Tyr
225                 230                 235                 240

Cys Pro Gly Glu Phe Pro Ser Pro Ile Glu Tyr Gly Thr Cys Leu
                245                 250                 255

Gly Asp Leu Tyr Ser Ile Ser Trp Met Glu Asp Ser Gly Arg His Asn
            260                 265                 270

Leu Arg Thr Glu Thr Leu Lys Gln Gln Tyr His Leu Val Lys Glu Arg
        275                 280                 285

Thr Ala Ser Gly Asn Pro Ala Tyr Gly Ser His Val Met Gln Tyr Gly
    290                 295                 300

Asp Val His Leu Ser Lys Asp Val Leu Phe Leu Tyr Met Gly Thr Asp
305                 310                 315                 320

Pro Ala Asn Asp Asn Ser Thr Phe Met Asp Asp Asn Ser Met Arg Val
                325                 330                 335

Ser Lys Ala Val Asn Gln Arg Asp Ala Asp Leu Val His Phe Trp Tyr
            340                 345                 350

Lys Phe His Lys Ala Pro Glu Gly Ser Val Arg Lys Thr Glu Ala Gln
        355                 360                 365

Lys Gln Leu Asn Glu Ala Ile Ser His Arg Met His Leu Asp Asn Ser
    370                 375                 380
```

-continued

```
Ile Ala Leu Val Gly Lys Leu Leu Phe Gly Ile Lys Lys Gly Pro Glu
385                 390                 395                 400

Val Leu Thr Ser Val Arg Pro Ala Gly Gln Pro Leu Val Asp Asp Trp
            405                 410                 415

Asp Cys Leu Lys Ser Tyr Val Arg Thr Phe Glu Thr His Cys Gly Ser
        420                 425                 430

Leu Ser Gln Tyr Gly Met Lys His Met Arg Ser Val Ala Asn Ile Cys
    435                 440                 445

Asn Ala Gly Ile Lys Met Glu Gln Met Val Glu Ala Ser Ala Gln Ala
450                 455                 460

Cys Pro Ser Val Pro Ser Asn Thr Trp Ser Ser Leu Gln Arg Gly Phe
465                 470                 475                 480

Ser Ala

<210> SEQ ID NO 38
<211> LENGTH: 454
<212> TYPE: PRT
<213> ORGANISM: Glycine max

<400> SEQUENCE: 38

Met Asp Arg Phe Pro Ile Leu Phe Leu Leu Ala Thr Leu Ile Thr Leu
1               5                   10                  15

Ala Ser Gly Ala Arg His Asp Ile Leu Arg Leu Pro Ser Glu Ala Ser
            20                  25                  30

Thr Phe Phe Lys Ala Pro Gly Gly Asp Gln Asn Asp Glu Gly Thr Arg
        35                  40                  45

Trp Ala Val Leu Ile Ala Gly Ser Asn Gly Tyr Trp Asn Tyr Arg His
    50                  55                  60

Gln Ser Asp Val Cys His Ala Tyr Gln Leu Leu Arg Lys Gly Gly Leu
65                  70                  75                  80

Lys Glu Glu Asn Ile Val Val Phe Met Tyr Asp Asp Ile Ala Phe Asn
                85                  90                  95

Glu Glu Asn Pro Arg Pro Gly Val Ile Ile Asn Ser Pro His Gly Asn
            100                 105                 110

Asp Val Tyr Lys Gly Val Pro Lys Asp Tyr Ile Gly Glu Asp Val Thr
        115                 120                 125

Val Gly Asn Phe Phe Ala Ala Ile Leu Gly Asn Lys Ser Ala Leu Thr
    130                 135                 140

Gly Gly Ser Gly Lys Val Val Asp Ser Gly Pro Asn Asp His Ile Phe
145                 150                 155                 160

Ile Tyr Tyr Ser Asp His Gly Gly Pro Gly Val Leu Gly Met Pro Thr
                165                 170                 175

Asn Pro Tyr Met Tyr Ala Ser Asp Leu Ile Glu Val Leu Lys Lys Lys
            180                 185                 190

His Ala Ser Gly Ser Tyr Lys Ser Leu Val Phe Tyr Leu Glu Ala Cys
        195                 200                 205

Glu Ser Gly Ser Ile Phe Glu Gly Leu Leu Pro Glu Gly Leu Asn Ile
    210                 215                 220

Tyr Ala Thr Thr Ala Ser Asn Ala Glu Glu Ser Ser Trp Gly Thr Tyr
225                 230                 235                 240

Cys Pro Gly Glu Tyr Pro Ser Pro Ser Glu Tyr Glu Thr Cys Leu
                245                 250                 255

Gly Asp Leu Tyr Ser Val Ala Trp Met Glu Asp Ser Asp Ile His Asn
            260                 265                 270
```

-continued

Leu Gln Thr Glu Thr Leu His Gln Gln Tyr Glu Leu Val Lys Gln Arg
         275                 280                 285

Thr Met Asn Gly Asn Ser Ile Tyr Gly Ser His Val Met Gln Tyr Gly
    290                 295                 300

Asp Ile Gly Leu Ser Glu Asn Asn Leu Val Leu Tyr Leu Asp Leu Ile
305                 310                 315                 320

His Phe Trp Asp Lys Phe Arg Lys Ala Pro Val Gly Ser Ser Arg Lys
                325                 330                 335

Ala Ala Ala Glu Lys Gln Ile Leu Glu Ala Met Ser His Arg Met His
            340                 345                 350

Ile Asp Asp Ser Met Lys Arg Ile Gly Lys Leu Phe Phe Gly Ile Glu
        355                 360                 365

Lys Gly Pro Glu Leu Leu Ser Ser Val Arg Pro Ala Gly Gln Pro Leu
    370                 375                 380

Val Asp Asp Trp Asp Cys Leu Lys Thr Leu Val Arg Thr Phe Glu Thr
385                 390                 395                 400

His Cys Gly Ser Leu Ser Gln Tyr Gly Met Lys His Met Arg Ser Phe
                405                 410                 415

Ala Asn Phe Cys Asn Ala Gly Ile Arg Lys Glu Gln Met Ala Glu Ala
            420                 425                 430

Ser Ala Gln Ala Cys Val Asn Ile Pro Ala Ser Ser Trp Ser Ser Met
        435                 440                 445

His Arg Gly Phe Ser Ala
    450

<210> SEQ ID NO 39
<211> LENGTH: 490
<212> TYPE: PRT
<213> ORGANISM: Papaver rhoeas

<400> SEQUENCE: 39

Met Val Lys Phe Leu Phe Ser Val Ile Ile Leu Phe Phe Leu Leu Ser
1               5                   10                  15

Ala Val Gly Ser Ser Ala Arg Asn Ile Glu Glu Asp Gly Val Ile Arg
            20                  25                  30

Leu Pro Ser Glu Val Lys Asp Phe Ile Asn Gly Lys Asn Ile Asp Asp
        35                  40                  45

Asp Ser Val Gly Gly Thr Arg Trp Ala Val Leu Ile Ala Gly Ser Ser
    50                  55                  60

Gly Tyr Trp Asn Tyr Arg His Gln Ala Asp Val Cys His Ala Tyr Gln
65                  70                  75                  80

Val Leu Lys Arg Gly Gly Val Lys Asp Glu Asn Ile Val Val Phe Met
                85                  90                  95

Tyr Asp Asp Ile Ala Leu Asn Glu Glu Asn Pro Arg Pro Gly Val Ile
            100                 105                 110

Ile Asn His Pro Lys Gly Glu Asp Val Tyr Ala Gly Val Pro Lys Asp
        115                 120                 125

Tyr Thr Gly Arg Asp Val Thr Ala His Asn Phe Tyr Ser Val Leu Leu
    130                 135                 140

Gly Asn Lys Thr Ala Val Lys Gly Gly Ser Gly Lys Val Ile Asp Ser
145                 150                 155                 160

Gly Pro Asn Asp His Ile Phe Ile Tyr Tyr Ser Asp His Gly Gly Pro
                165                 170                 175

Gly Val Leu Gly Met Pro Thr Tyr Pro Tyr Leu Tyr Ala Asp Asp Leu

```
                180             185                 190
    Val Asn Val Leu Lys Gln Lys His Ala Leu Gly Ala Tyr Lys Ser Leu
                    195                 200             205
    Val Phe Tyr Leu Glu Ala Cys Glu Ser Gly Ser Ile Phe Glu Gly Ile
                210                 215                 220
    Leu Pro Lys Gly Leu Asn Ile Tyr Ala Thr Thr Ala Ser Asn Ala Glu
    225                 230                 235                 240
    Glu Ser Ser Trp Gly Thr Tyr Cys Pro Gly Glu Phe Pro Ser Pro Pro
                    245                 250                 255
    Ser Glu Tyr Glu Thr Cys Leu Gly Asp Leu Tyr Ser Val Ala Trp Met
                260                 265                 270
    Glu Asp Ser Asp Val His Asn Leu Arg Ser Glu Thr Leu Lys Gln Gln
                275                 280                 285
    Tyr His Leu Val Lys Glu Arg Thr Gln Asn Ala Asn Ser Ala Tyr Gly
                290                 295                 300
    Ser His Val Met Gln Tyr Gly Asp Leu Glu Val Ser Lys Glu Asp Leu
    305                 310                 315                 320
    Phe Leu Tyr Met Gly Thr Asn Pro Ala Asn Asp Asn Lys Phe Ile
                    325                 330                 335
    Glu Gln Asn Ser Leu Pro Ser Leu Ser Gly Ser Val Asn Gln Arg Glu
                340                 345                 350
    Ala Asp Leu Ile His Phe Trp Gln Lys Tyr Arg Lys Ala Pro Glu Gly
                355                 360                 365
    Ser Gln Arg Lys Ala Asp Ala Gln Lys Gln Phe Val Glu Val Met Ala
                370                 375                 380
    His Arg Met His Val Asp His Ser Ile Lys Leu Ile Gly Lys Leu Leu
    385                 390                 395                 400
    Phe Gly Phe Glu Lys Gly Pro Gln Val Leu Glu Ala Val Arg Pro Ala
                    405                 410                 415
    Gly Gln Pro Leu Val Asp Asp Trp Asp Cys Leu Lys Thr Met Val Arg
                420                 425                 430
    Thr Phe Glu Ala Gln Cys Gly Ser Leu Ser Gln Tyr Gly Met Lys His
                435                 440                 445
    Met Arg Ser Val Ala Asn Ile Cys Asn Ala Gly Ile Lys Lys Glu Gln
                450                 455                 460
    Met Ala Glu Ala Ala Ser Gln Ala Cys Val Thr Ile Pro Asn Gly Ser
    465                 470                 475                 480
    Trp Ser Ser Thr His Gln Gly Phe Ser Ala
                    485                 490

<210> SEQ ID NO 40
<211> LENGTH: 483
<212> TYPE: PRT
<213> ORGANISM: Vigna radiata

<400> SEQUENCE: 40

Met Ala Thr Thr Thr Thr Ser Leu Ser Thr Leu Phe Leu Leu Phe Leu
    1               5                   10                  15
    Ala Thr Val Ala Leu Val Ala Ala Gly Arg Asp Leu Val Gly Asp Phe
                    20                  25                  30
    Leu Arg Leu Pro Ser Asp Ser Gly Asn Asp Asp Asn Val Lys Gly Thr
                35                  40                  45
    Arg Trp Ala Ile Leu Phe Ala Gly Ser Asn Gly Tyr Trp Asn Tyr Arg
                50                  55                  60
```

```
His Gln Ala Asp Ile Cys His Ala Tyr Gln Ile Leu Arg Lys Gly Gly
 65                  70                  75                  80

Leu Lys Glu Glu Asn Ile Ile Val Phe Met Tyr Asp Asp Ile Ala Phe
                 85                  90                  95

Asn Trp Asp Asn Pro Arg Pro Gly Val Ile Ile Asn Lys Pro Asp Gly
            100                 105                 110

Asp Asp Val Tyr Glu Gly Val Pro Lys Asp Tyr Thr Gly Glu Asp Ala
        115                 120                 125

Thr Ala His Asn Phe Tyr Ser Ala Leu Leu Gly Asp Lys Ser Ala Leu
    130                 135                 140

Thr Gly Ser Gly Lys Val Val Asn Ser Gly Pro Asp Asp Arg Ile
145                 150                 155                 160

Phe Ile Phe Tyr Ser Asp His Gly Gly Pro Gly Val Leu Gly Thr Pro
                165                 170                 175

Ala Gly Pro Tyr Ile Tyr Ala Ser Asp Leu Val Glu Val Leu Lys Lys
            180                 185                 190

Lys His Ala Ser Gly Thr Tyr Lys Asn Leu Val Phe Tyr Leu Glu Ala
        195                 200                 205

Cys Glu Ala Gly Ser Ile Phe Glu Gly Leu Leu Pro Glu Asp Ile Asn
    210                 215                 220

Ile Tyr Ala Thr Thr Ala Ser Asn Ala Glu Glu Ser Ser Trp Gly Thr
225                 230                 235                 240

Tyr Cys Pro Gly Glu Tyr Pro Ser Pro Pro Glu Tyr Ser Thr Cys
                245                 250                 255

Leu Gly Asp Leu Tyr Ser Val Ala Trp Met Glu Asp Ser Asp Arg His
            260                 265                 270

Asn Leu Arg Thr Glu Ser Leu His Gln Gln Tyr Lys Val Val Lys Asp
        275                 280                 285

Arg Thr Leu Ser Gly Gly Trp Tyr Gly Ser His Val Met Gln Tyr Gly
    290                 295                 300

Asp Val Glu Phe Ser Lys Asp Thr Leu Phe Leu Tyr Leu Gly Thr Asp
305                 310                 315                 320

Pro Ala Asn Asp Asn Leu Thr Phe Val Asp Glu Asn Ser Leu Trp Ser
                325                 330                 335

Ser Ser Thr Ala Val Asn Gln Arg Asp Ala Asp Leu Val His Phe Trp
            340                 345                 350

His Lys Phe Arg Lys Ala Pro Glu Gly Ser Pro Lys Lys Asn Glu Ala
        355                 360                 365

Arg Lys Gln Val Leu Glu Val Met Ser His Arg Met His Ile Asp Asp
    370                 375                 380

Ser Val Lys Leu Val Gly Lys Leu Leu Phe Gly Phe Glu Lys Ala Pro
385                 390                 395                 400

Glu Val Leu Asn Ala Val Arg Pro Ala Gly Ser Ala Leu Val Asp Asp
                405                 410                 415

Trp Ala Cys Leu Lys Thr Met Val Arg Thr Phe Glu Thr His Cys Gly
            420                 425                 430

Ser Leu Ser Gln Tyr Gly Met Lys His Met Arg Ser Phe Ala Asn Ile
        435                 440                 445

Cys Asn Val Gly Ile Lys Lys Glu Gln Met Ala Glu Ala Ser Ala Gln
    450                 455                 460

Ala Cys Val Thr Val Pro Ala Ser Ser Trp Ser Ser Leu Gln Arg Gly
465                 470                 475                 480

Phe Ser Ala
```

<210> SEQ ID NO 41
<211> LENGTH: 489
<212> TYPE: PRT
<213> ORGANISM: Nicotiana tabacum

<400> SEQUENCE: 41

```
Met Ile Arg Tyr Val Ala Gly Thr Leu Phe Leu Ile Gly Leu Ala Leu
1               5                   10                  15

Asn Val Ala Val Ser Glu Ser Arg Asn Val Leu Lys Leu Pro Ser Glu
            20                  25                  30

Val Ser Arg Phe Phe Gly Ala Asp Glu Ser Asn Ala Gly Asp His Asp
        35                  40                  45

Asp Asp Ser Val Gly Thr Arg Trp Ala Ile Leu Leu Ala Gly Ser Asn
50                  55                  60

Gly Tyr Trp Asn Tyr Arg His Gln Ala Asp Ile Cys His Ala Tyr Gln
65                  70                  75                  80

Leu Leu Lys Lys Gly Gly Leu Lys Asp Glu Asn Ile Val Val Phe Met
                85                  90                  95

Tyr Asp Asp Ile Ala Asn Asn Glu Glu Asn Pro Arg Arg Gly Val Ile
            100                 105                 110

Ile Asn Ser Pro His Gly Glu Asp Val Tyr Lys Gly Val Pro Lys Asp
        115                 120                 125

Tyr Thr Gly Asp Asp Val Thr Val Asp Asn Phe Phe Ala Val Ile Leu
130                 135                 140

Gly Asn Lys Thr Ala Leu Ser Gly Gly Ser Gly Lys Val Val Asn Ser
145                 150                 155                 160

Gly Pro Asn Asp His Ile Phe Ile Phe Tyr Ser Asp His Gly Gly Pro
                165                 170                 175

Gly Val Leu Gly Met Pro Thr Asp Pro Tyr Leu Tyr Ala Asn Asp Leu
            180                 185                 190

Ile Asp Val Leu Lys Lys His Ala Ser Gly Thr Tyr Lys Ser Leu
        195                 200                 205

Val Phe Tyr Leu Glu Ala Cys Glu Ser Gly Ser Ile Phe Glu Gly Leu
210                 215                 220

Leu Pro Glu Gly Leu Asn Ile Tyr Ala Thr Thr Ala Ser Asn Ala Glu
225                 230                 235                 240

Glu Ser Ser Trp Gly Thr Tyr Cys Pro Gly Glu Tyr Pro Ser Pro Pro
                245                 250                 255

Ile Glu Tyr Met Thr Cys Leu Gly Asp Leu Tyr Ser Ile Ser Trp Met
            260                 265                 270

Glu Asp Ser Glu Leu His Asn Leu Arg Thr Glu Ser Leu Lys Gln Gln
        275                 280                 285

Tyr His Leu Val Lys Glu Arg Thr Ala Thr Gly Asn Pro Val Tyr Gly
290                 295                 300

Ser His Val Met Gln Tyr Gly Asp Leu His Leu Ser Lys Asp Ala Leu
305                 310                 315                 320

Tyr Leu Tyr Met Gly Thr Asn Pro Ala Asn Asp Asn Tyr Thr Phe Met
                325                 330                 335

Asp Asp Asn Ser Leu Arg Val Ser Lys Ala Val Asn Gln Arg Asp Ala
            340                 345                 350

Asp Leu Leu His Phe Trp His Lys Phe Arg Thr Ala Pro Glu Gly Ser
        355                 360                 365

Val Arg Lys Ile Glu Ala Gln Lys Gln Leu Asn Glu Ala Ile Ser His
```

```
                    370                 375                 380
Arg Val His Leu Asp Asn Ser Val Ala Leu Val Gly Lys Leu Leu Phe
385                 390                 395                 400

Gly Ile Glu Lys Gly Pro Glu Val Leu Ser Gly Val Arg Pro Ala Gly
                405                 410                 415

Gln Pro Leu Val Asp Asp Trp Asp Cys Leu Lys Ser Phe Val Arg Thr
                420                 425                 430

Phe Glu Thr His Cys Gly Ser Leu Ser Gln Tyr Gly Met Lys His Met
                435                 440                 445

Arg Ser Ile Ala Asn Ile Cys Asn Ala Gly Ile Lys Lys Glu Gln Met
                450                 455                 460

Val Glu Ala Ser Ala Gln Ala Cys Pro Ser Val Pro Ser Asn Thr Trp
465                 470                 475                 480

Ser Ser Leu His Arg Gly Phe Ser Ala
                485

<210> SEQ ID NO 42
<211> LENGTH: 482
<212> TYPE: PRT
<213> ORGANISM: Solanum lycopersicum

<400> SEQUENCE: 42

Met Asn Arg Ser Val Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
                20                  25                  30

Gly Ser Arg Phe Phe Asp Ala Asp Glu Ile Asp Ser Val Gly Thr Arg
            35                  40                  45

Trp Ala Ile Leu Leu Ala Gly Ser Asn Gly Tyr Trp Asn Tyr Arg His
        50                  55                  60

Gln Ala Asp Ile Cys His Ala Tyr Gln Leu Leu Lys Lys Gly Gly Leu
65                  70                  75                  80

Lys Asp Glu Asn Ile Val Val Phe Met Tyr Asp Asp Ile Ala Asn Asn
                85                  90                  95

Glu Glu Asn Pro Arg Gln Gly Val Ile Ile Asn Ser Pro His Gly Glu
            100                 105                 110

Asp Val Tyr Asn Gly Val Pro Lys Asp Tyr Thr Gly Asp Asp Val Thr
        115                 120                 125

Val Asp Asn Phe Leu Ala Ala Leu Leu Gly Asn Lys Thr Ala Leu Thr
130                 135                 140

Gly Gly Ser Gly Lys Val Val Asp Ser Gly Pro Asn Asp His Ile Phe
145                 150                 155                 160

Ile Phe Tyr Ser Asp His Gly Gly Ala Gly Val Leu Gly Met Pro Thr
                165                 170                 175

Asn Pro Tyr Leu Tyr Ala Asn Asp Leu Ile Asp Ala Leu Lys Met Lys
            180                 185                 190

His Ala Ser Gly Thr Tyr Lys Ser Leu Val Phe Tyr Leu Glu Ala Cys
        195                 200                 205

Glu Ser Gly Ser Met Phe Glu Gly Leu Leu Pro Glu Gly Leu Asn Ile
    210                 215                 220

Tyr Ala Thr Thr Ala Ser Asn Ala Asp Glu Ser Ser Trp Gly Thr Tyr
225                 230                 235                 240

Cys Pro Gly Glu Tyr Pro Ser Pro Pro Ile Glu Tyr Asp Thr Cys Leu
                245                 250                 255
```

```
Gly Asp Leu Tyr Ser Ile Ser Trp Met Glu Asp Ser Glu Arg His Asn
            260                 265                 270

Leu Arg Thr Glu Ser Leu Lys Gln Gln Tyr His Leu Val Lys Glu Arg
            275                 280                 285

Thr Ala Ser Gly Asn Pro Ala Tyr Gly Ser His Val Met Gln Tyr Gly
            290                 295                 300

Asp Val His Leu Ser Lys Asp Ala Val Phe Leu Tyr Met Gly Thr Asp
305                 310                 315                 320

Pro Ala Asn Asp Asn Ser Thr Phe Met Asp Asp Asn Ser Leu Arg Val
                325                 330                 335

Ser Lys Ala Val Asn Gln Arg Asp Ala Asp Leu Val His Phe Trp Tyr
            340                 345                 350

Lys Phe His Lys Ala Pro Glu Gly Ser Val Ser Lys Thr Glu Ala Gln
            355                 360                 365

Lys Arg Leu Asn Glu Ala Ile Ser His Arg Met His Leu Asp Asn Ser
            370                 375                 380

Ile Ala Leu Val Gly Lys Leu Leu Phe Gly Ile Lys Lys Gly Pro Glu
385                 390                 395                 400

Val Leu Thr Ser Val Arg Pro Ala Gly Gln Pro Leu Val Asp Asn Trp
                405                 410                 415

Asp Cys Leu Lys Ser Tyr Val Arg Thr Phe Glu Thr His Cys Gly Ser
            420                 425                 430

Leu Ser Gln Tyr Gly Met Lys His Met Arg Ser Val Ala Asn Ile Cys
            435                 440                 445

Asn Ala Gly Ile Lys Met Glu Gln Met Val Glu Ala Ser Ala Gln Ala
450                 455                 460

Cys Pro Ser Val Pro Ser Tyr Thr Trp Ser Ser Leu His Arg Gly Phe
465                 470                 475                 480

Ser Ala

<210> SEQ ID NO 43
<211> LENGTH: 494
<212> TYPE: PRT
<213> ORGANISM: Citrus clementina

<400> SEQUENCE: 43

Met Thr Arg Leu Ala Ser Gly Val Leu Ile Thr Leu Val Ala Leu
1               5                   10                  15

Ala Gly Ile Ala Asp Gly Ser Arg Asp Ile Ala Gly Asp Ile Leu Lys
            20                  25                  30

Leu Pro Ser Glu Ala Tyr Arg Phe Phe His Asn Gly Gly Gly Ala
            35                  40                  45

Lys Val Asn Asp Asp Asp Ser Val Gly Thr Arg Trp Ala Val Leu
50                  55                  60

Leu Ala Gly Ser Asn Gly Phe Trp Asn Tyr Arg His Gln Ala Asp Ile
65                  70                  75                  80

Cys His Ala Tyr Gln Leu Leu Arg Lys Gly Gly Leu Lys Asp Glu Asn
                85                  90                  95

Ile Ile Val Phe Met Tyr Asp Asp Ile Ala Phe Asn Glu Glu Asn Pro
            100                 105                 110

Arg Pro Gly Val Ile Ile Asn His Pro His Gly Asp Val Tyr Lys
            115                 120                 125

Gly Val Pro Lys Asp Tyr Thr Gly Glu Asp Val Thr Val Glu Asn Phe
            130                 135                 140
```

```
Phe Ala Val Ile Leu Gly Asn Lys Thr Ala Leu Thr Gly Gly Ser Gly
145                 150                 155                 160

Lys Val Val Asp Ser Gly Pro Asn Asp His Ile Phe Ile Phe Tyr Ser
                165                 170                 175

Asp His Gly Gly Pro Gly Val Leu Gly Met Pro Thr Ser Arg Tyr Ile
            180                 185                 190

Tyr Ala Asp Glu Leu Ile Asp Val Leu Lys Lys His Ala Ser Gly
        195                 200                 205

Asn Tyr Lys Ser Leu Val Phe Tyr Leu Glu Ala Cys Glu Ser Gly Ser
    210                 215                 220

Ile Phe Glu Gly Leu Leu Pro Glu Gly Leu Asn Ile Tyr Ala Thr Thr
225                 230                 235                 240

Ala Ser Asn Ala Glu Glu Ser Ser Trp Gly Thr Tyr Cys Pro Gly Glu
                245                 250                 255

Ile Pro Gly Pro Pro Glu Tyr Ser Thr Cys Leu Gly Asp Leu Tyr
            260                 265                 270

Ser Ile Ala Trp Met Glu Asp Ser Asp Ile His Asn Leu Arg Thr Glu
        275                 280                 285

Thr Leu His Gln Gln Tyr Glu Leu Val Lys Thr Arg Thr Ala Ser Tyr
290                 295                 300

Asn Ser Tyr Gly Ser His Val Met Gln Tyr Gly Asp Ile Gly Leu Ser
305                 310                 315                 320

Lys Asn Asn Leu Phe Thr Tyr Leu Gly Thr Asn Pro Ala Asn Asp Asn
                325                 330                 335

Tyr Thr Phe Val Asp Glu Asn Ser Leu Arg Pro Ala Ser Lys Ala Val
            340                 345                 350

Asn Gln Arg Asp Ala Asp Leu Leu His Phe Trp Asp Lys Tyr Arg Lys
        355                 360                 365

Ala Pro Glu Gly Thr Pro Arg Lys Ala Glu Ala Gln Lys Gln Phe Phe
370                 375                 380

Glu Ala Met Ser His Arg Met His Val Asp His Ser Ile Lys Leu Ile
385                 390                 395                 400

Gly Lys Leu Leu Phe Gly Ile Glu Lys Gly Pro Glu Ile Leu Asn Thr
                405                 410                 415

Val Arg Pro Ala Gly Gln Pro Leu Val Asp Asp Trp Gly Cys Leu Lys
            420                 425                 430

Ser Leu Val Arg Thr Phe Glu Ser His Cys Gly Ala Leu Ser Gln Tyr
        435                 440                 445

Gly Met Lys His Met Arg Ser Leu Ala Asn Ile Cys Asn Thr Gly Ile
450                 455                 460

Gly Lys Glu Lys Met Ala Glu Ala Ser Ala Gln Ala Cys Glu Asn Ile
465                 470                 475                 480

Pro Ser Gly Pro Trp Ser Ser Leu Asp Lys Gly Phe Ser Ala
            485                 490

<210> SEQ ID NO 44
<211> LENGTH: 481
<212> TYPE: PRT
<213> ORGANISM: Nicotiana tabacum

<400> SEQUENCE: 44

Met Ile Ser Tyr Ala Ala Gly Ile Phe Phe Leu Val Gly Phe Ser Ile
1               5                   10                  15

Ala Ala Ala Ala Asp Gly Arg Asn Val Leu Lys Leu Pro Ser Glu Ala
                20                  25                  30
```

```
Ser Arg Phe Phe Asp Glu Ala Asp Asp Ser Val Gly Thr Arg Trp Ala
             35                  40                  45

Val Leu Leu Ala Gly Ser Asn Gly Tyr Trp Asn Tyr Arg His Gln Ala
 50                  55                  60

Asp Val Cys His Ala Tyr Gln Leu Leu Arg Lys Gly Gly Leu Lys Asp
 65                  70                  75                  80

Glu Asn Ile Ile Met Phe Met Tyr Asp Ile Ala Tyr Asn Glu Glu
                 85                  90                  95

Asn Pro Arg Gln Gly Val Ile Ile Asn Ser Pro Ala Gly Glu Asp Val
             100                 105                 110

Tyr Lys Gly Val Pro Lys Asp Tyr Thr Gly Asp Val Asn Val Asp
             115                 120                 125

Asn Phe Leu Ala Val Leu Leu Gly Asn Lys Thr Ala Leu Thr Gly Gly
130                 135                 140

Ser Gly Lys Val Val Asp Ser Gly Pro Asn Asp His Ile Phe Ile Phe
145                 150                 155                 160

Tyr Ser Asp His Gly Gly Pro Gly Val Leu Gly Met Pro Thr Asn Pro
                 165                 170                 175

Tyr Leu Tyr Ala Ser Asp Leu Ile Asp Val Leu Lys Lys Lys His Ala
             180                 185                 190

Ser Gly Thr Tyr Lys Ser Leu Val Leu Tyr Ile Glu Ala Cys Glu Ser
             195                 200                 205

Gly Ser Ile Phe Glu Gly Leu Leu Pro Lys Gly Leu Asn Ile Tyr Ala
210                 215                 220

Thr Thr Ala Ser Asn Ala Val Glu Ser Ser Trp Gly Thr Tyr Cys Pro
225                 230                 235                 240

Gly Asp Tyr Pro Ser Leu Pro Pro Gly Tyr Glu Thr Cys Leu Gly Asp
                 245                 250                 255

Leu Tyr Ala Val Ser Trp Met Glu Asp Ser Glu Met His Asn Leu Arg
             260                 265                 270

Thr Glu Asn Leu Arg Gln Gln Tyr His Leu Val Lys Glu Arg Thr Ala
             275                 280                 285

Asn Gly Asn Ser Ala Tyr Gly Ser His Val Leu Gln Phe Gly Asp Leu
             290                 295                 300

Gln Leu Gly Met Asp Ser Leu Phe Met Tyr Met Gly Thr Asn Pro Ala
305                 310                 315                 320

Asn Asp Asn Tyr Thr Tyr Val Asp Asp Asn Ser Leu Arg Ala Ser Ser
                 325                 330                 335

Lys Ala Val Asn Gln Arg Asp Ala Asp Leu Leu His Phe Trp Asp Lys
             340                 345                 350

Phe Arg Lys Ala Pro Glu Gly Ser Ala Arg Lys Val Glu Ala Gln Lys
             355                 360                 365

Gln Phe Thr Glu Ala Met Ser His Arg Met His Leu Asp Asn Ser Met
370                 375                 380

Ala Leu Val Gly Lys Leu Leu Phe Gly Ile Gln Lys Gly Pro Glu Val
385                 390                 395                 400

Leu Lys Arg Val Arg Pro Val Gly Gln Pro Leu Val Asp Asp Trp Thr
                 405                 410                 415

Cys Leu Lys Tyr Phe Val Arg Thr Phe Glu Thr His Cys Gly Ser Leu
             420                 425                 430

Ser Gln Tyr Gly Met Lys His Met Arg Ser Ile Ala Asn Ile Cys Asn
             435                 440                 445
```

```
Ala Gly Ile Lys Met Glu Gln Met Val Glu Ala Ser Thr Gln Ala Cys
    450                 455                 460

Pro Ser Val Pro Thr Asn Ile Trp Ser Ser Leu His Arg Gly Phe Ser
465                 470                 475                 480

Ala

<210> SEQ ID NO 45
<211> LENGTH: 481
<212> TYPE: PRT
<213> ORGANISM: Capsella rubella

<400> SEQUENCE: 45

Met Thr Arg Ile Val Ala Val Ile Val Val Leu Phe Leu Ser Leu
1               5                   10                  15

Val Ala Ala Ala Ser Asp Asn Phe Ile Arg Leu Pro Ser Glu Ala Ser
                20                  25                  30

Lys Phe Phe Arg Pro Asn Asn Glu Asn Asp Asp Ser Thr Arg Trp Ala
            35                  40                  45

Val Leu Val Ala Gly Ser Ser Gly Tyr Trp Asn Tyr Arg His Gln Ala
    50                  55                  60

Asp Val Cys His Ala Tyr Gln Leu Leu Lys Lys Gly Val Lys Glu
65                  70                  75                  80

Glu Asn Ile Val Val Phe Met Tyr Asp Asp Ile Ala Asn Asn Glu Glu
                85                  90                  95

Asn Pro Arg Pro Gly Val Ile Ile Asn Ser Pro Asn Gly Glu Asp Val
            100                 105                 110

Tyr Asn Gly Val Pro Lys Asp Tyr Thr Gly Asp Glu Val Asn Val Asn
    115                 120                 125

Asn Phe Phe Ala Val Leu Leu Gly Asn Lys Thr Ala Leu Lys Gly Gly
130                 135                 140

Ser Gly Lys Val Val Asn Ser Gly Pro Asn Asp His Ile Phe Ile Tyr
145                 150                 155                 160

Tyr Ser Asp His Gly Gly Pro Gly Val Leu Gly Met Pro Thr Ser Pro
                165                 170                 175

Tyr Leu Tyr Ala Lys Asp Leu Asn Asp Val Leu Lys Lys Lys His Ala
            180                 185                 190

Ser Gly Thr Tyr Lys Ser Leu Val Phe Tyr Leu Glu Ala Cys Glu Ser
        195                 200                 205

Gly Ser Ile Phe Glu Gly Leu Leu Pro Glu Gly Leu Asn Ile Tyr Ala
    210                 215                 220

Thr Thr Ala Ser Asn Ala Glu Glu Ser Ser Trp Gly Thr Tyr Cys Pro
225                 230                 235                 240

Gly Glu Asp Pro Ser Pro Ser Glu Tyr Glu Thr Cys Leu Gly Asp
                245                 250                 255

Leu Tyr Ser Val Ala Trp Met Glu Asp Ser Asp Lys His Asn Leu Gln
            260                 265                 270

Thr Glu Ser Leu His Gln Gln Tyr Glu Leu Val Lys Lys Arg Thr Ala
        275                 280                 285

Gly Thr Gly Ser Ser Tyr Gly Ser His Val Leu Glu Phe Gly Asp Ile
    290                 295                 300

Gly Leu Ser Lys Glu Lys Leu Val Leu Tyr Met Gly Thr Asn Pro Ala
305                 310                 315                 320

Asn Glu Asn Phe Thr Phe Val Asp Glu Asn Ser Ser Leu Arg Leu Pro
                325                 330                 335
```

```
Ser Arg Val Thr Asn Gln Arg Asp Ala Asp Leu Val His Phe Trp Asp
            340                 345                 350

Lys Tyr Arg Lys Ala Pro Glu Gly Ser Ala Arg Lys Val Glu Ala Gln
        355                 360                 365

Lys Gln Val Leu Glu Ala Met Ser His Arg Leu His Val Asp Asn Ser
    370                 375                 380

Val Leu Leu Ile Gly Lys Leu Leu Phe Gly Leu Glu Gly Pro Ala Val
385                 390                 395                 400

Leu Asn Lys Val Arg Pro Ser Gly Arg Pro Leu Val Asp Asp Trp Asp
                405                 410                 415

Cys Leu Lys Ser Met Val Arg Ala Phe Glu Arg His Cys Gly Ser Leu
            420                 425                 430

Ser Gln Tyr Gly Ile Lys His Met Arg Ser Ile Ala Asn Ile Cys Asn
        435                 440                 445

Ala Gly Ile Gln Met Gly Leu Met Glu Glu Ala Ala Lys Gln Ala Cys
    450                 455                 460

Pro Ser Ile Pro Ala Gly Pro Trp Ser Ser Leu His Arg Gly Phe Ser
465                 470                 475                 480

Ala

<210> SEQ ID NO 46
<211> LENGTH: 479
<212> TYPE: PRT
<213> ORGANISM: Arabidopsis lyrata subsp. lyrata

<400> SEQUENCE: 46

Met Thr Thr Val Ala Val Thr Phe Leu Ala Leu Phe Leu Tyr Leu Val
1               5                   10                  15

Ala Ala Val Ser Gly Asp Val Ile Lys Leu Pro Ser Gln Ala Ser Lys
            20                  25                  30

Phe Phe His Pro Thr Glu Asn Asp Asp Ser Thr Arg Trp Ala Val
        35                  40                  45

Leu Val Ala Gly Ser Ser Gly Tyr Trp Asn Tyr Arg His Gln Ala Asp
    50                  55                  60

Val Cys His Ala Tyr Gln Leu Leu Lys Lys Gly Gly Val Lys Glu Glu
65                  70                  75                  80

Asn Ile Val Val Phe Met Tyr Asp Asp Ile Ala Lys Asn Glu Glu Asn
                85                  90                  95

Pro Arg Pro Gly Val Ile Ile Asn Ser Pro Asn Gly Glu Asp Val Tyr
            100                 105                 110

Asn Gly Val Pro Lys Asp Tyr Thr Gly Asp Asp Val Asn Val Asp Asn
        115                 120                 125

Leu Leu Ala Val Ile Leu Gly Asn Lys Thr Ala Val Lys Gly Gly Ser
    130                 135                 140

Gly Lys Val Val Asp Ser Gly Pro Asn Asp His Ile Phe Ile Tyr Tyr
145                 150                 155                 160

Ser Asp His Gly Gly Pro Gly Val Leu Gly Met Pro Thr Ser Pro Tyr
                165                 170                 175

Leu Tyr Ala Asn Asp Leu Asn Asp Val Leu Lys Lys His Ala Ser
            180                 185                 190

Gly Thr Tyr Lys Ser Leu Val Phe Tyr Leu Glu Ala Cys Glu Ser Gly
        195                 200                 205

Ser Ile Phe Glu Gly Leu Leu Pro Glu Gly Leu Asn Ile Tyr Ala Thr
    210                 215                 220
```

Thr Ala Ser Asn Ala Val Glu Ser Ser Trp Gly Thr Tyr Cys Pro Gly
225                 230                 235                 240

Glu Asp Pro Ser Pro Ser Glu Tyr Glu Thr Cys Leu Gly Asp Leu
            245                 250                 255

Tyr Ser Val Ala Trp Met Glu Asp Ser Asp Ile His Asn Leu Gln Thr
            260                 265                 270

Glu Thr Leu His Gln Gln Tyr Glu Leu Val Lys Lys Arg Thr Ala Gly
            275                 280                 285

Ser Gly Lys Ser Phe Gly Ser His Val Met Glu Phe Gly Asp Ile Gly
290                 295                 300

Leu Ser Lys Glu Lys Leu Val Leu Tyr Met Gly Thr Asn Pro Ala Asn
305                 310                 315                 320

Glu Asn Phe Thr Phe Val Asn Glu Asn Ser Leu Arg Pro Pro Ser Arg
            325                 330                 335

Val Thr Asn Gln Arg Asp Ala Asp Leu Val His Phe Trp Asp Lys Tyr
            340                 345                 350

Arg Lys Ala Pro Glu Gly Ser Ala Arg Lys Val Glu Ala Gln Lys Gln
            355                 360                 365

Val Leu Glu Ala Met Ser His Arg Leu His Val Asp Asn Ser Ile Leu
370                 375                 380

Leu Ile Gly Lys Leu Leu Phe Gly Leu Asp Ser Pro Ala Val Leu Asn
385                 390                 395                 400

Asn Val Arg Pro Ser Gly Thr Pro Leu Val Asp Asp Trp Asp Cys Leu
            405                 410                 415

Lys Ser Leu Val Arg Val Phe Glu Met His Cys Gly Ser Leu Ser Gln
            420                 425                 430

Tyr Gly Ile Lys His Met Arg Ser Ile Ala Asn Ile Cys Asn Ala Gly
            435                 440                 445

Ile Gln Met Gly Gln Met Glu Glu Ala Ala Met Gln Ala Cys Pro Thr
450                 455                 460

Ile Pro Ala Ser Pro Trp Ser Leu Glu Arg Gly Phe Ser Ala
465                 470                 475

<210> SEQ ID NO 47
<211> LENGTH: 482
<212> TYPE: PRT
<213> ORGANISM: Capsella rubella

<400> SEQUENCE: 47

Met Thr Arg Leu Thr Val Gly Val Leu Phe Leu Ser Leu Ile Ala Leu
1               5                   10                  15

Ser Ala Ala Arg Asn Gly Pro Asp Asp Val Ile Lys Leu Pro Ser Gln
            20                  25                  30

Ala Ser Arg Phe Phe Arg Pro Pro Glu Asn Asp Ala Gly Thr Arg Trp
        35                  40                  45

Ala Val Leu Val Ala Gly Ser Ser Gly Tyr Gly Asn Tyr Arg His Gln
    50                  55                  60

Ala Asp Ile Cys His Ala Tyr Gln Leu Leu Arg Lys Gly Gly Leu Lys
65                  70                  75                  80

Glu Glu Asn Ile Val Val Phe Met Tyr Asp Asp Ile Ala Asn Asn Tyr
                85                  90                  95

Glu Asn Pro Arg Pro Gly Thr Ile Ile Asn Ser Pro His Gly Lys Asp
            100                 105                 110

Val Tyr Gln Gly Val Pro Lys Asp Tyr Thr Gly Asp Asp Val Thr Val
        115                 120                 125

Asp Asn Leu Phe Ala Val Ile Leu Gly Asp Lys Thr Ala Ile Lys Gly
            130                 135                 140

Gly Ser Gly Lys Val Val Asp Ser Gly Pro Asn Asp His Ile Phe Ile
145                 150                 155                 160

Phe Tyr Ser Asp His Gly Gly Pro Gly Val Leu Gly Met Pro Thr Phe
                165                 170                 175

Pro Tyr Ile Tyr Ala Asn Asp Leu Asn Asp Val Leu Lys Lys Lys His
                180                 185                 190

Ala Leu Gly Thr Tyr Lys Ser Leu Val Phe Tyr Leu Glu Ala Cys Glu
            195                 200                 205

Ser Gly Ser Ile Phe Glu Gly Leu Leu Pro Glu Gly Leu Asn Ile Tyr
210                 215                 220

Ala Thr Thr Ala Ser Asn Ala Glu Glu Ser Ser Trp Gly Thr Tyr Cys
225                 230                 235                 240

Pro Gly Glu Glu Pro Ser Pro Pro Glu Tyr Asp Thr Cys Leu Gly
                245                 250                 255

Asp Leu Tyr Ser Val Ala Trp Met Glu Asp Ser Gly Ile His Asn Leu
                260                 265                 270

Gln Thr Glu Thr Leu Gln Gln Tyr Glu Leu Val Lys Lys Arg Thr
            275                 280                 285

Ala Leu Asp Gly Tyr Tyr Tyr Gly Ser His Val Met Gln Tyr Gly Asp
290                 295                 300

Val Gly Leu Ser Lys Asp Lys Leu Glu Ile Tyr Met Gly Thr Asn Pro
305                 310                 315                 320

Ala Asn Glu Asn Ser Thr Phe Val Asp Ser Asn Ser Leu Lys Leu Pro
                325                 330                 335

Ser Arg Val Thr Asn Gln Arg Asp Ala Asp Leu Val His Phe Trp Glu
            340                 345                 350

Lys Tyr Arg Lys Ala Pro Glu Gly Ser Ser Arg Lys Ala Glu Ala Gln
            355                 360                 365

Lys Gln Val Leu Glu Val Met Ser His Arg Leu His Val Asp Asn Ser
370                 375                 380

Val Ile Leu Val Gly Lys Ile Leu Phe Gly Ile Ser Lys Gly Pro Gln
385                 390                 395                 400

Val Leu Asn Glu Val Arg Ser Ala Gly Gln Pro Leu Val Asp Asp Trp
                405                 410                 415

Asn Cys Leu Lys Asn Met Val Arg Ala Phe Glu Arg His Cys Gly Ser
            420                 425                 430

Leu Ser Gln Tyr Gly Ile Lys His Met Arg Ser Phe Ala Asn Phe Cys
            435                 440                 445

Asn Ser Gly Ile Gln Met Glu Gln Met Glu Glu Ala Ala Ser Gln Ala
450                 455                 460

Cys Thr Thr Ile Pro Pro Gly Pro Trp Ser Ser Leu His Arg Gly Phe
465                 470                 475                 480

Ser Ala

<210> SEQ ID NO 48
<211> LENGTH: 482
<212> TYPE: PRT
<213> ORGANISM: Vigna mungo
<400> SEQUENCE: 48

Met Ala Thr Thr Thr Ser Leu Ser Thr Leu Phe Leu Leu Phe Leu Ala
1               5                   10                  15

-continued

```
Thr Val Ala Leu Val Ala Ala Arg Arg Asp His Val Gly Asp Phe Leu
             20                  25                  30
Arg Leu Pro Ser Asp Ser Gly Asn Asp Asn Val Gln Gly Thr Arg
 35                  40                  45
Trp Ala Ile Leu Phe Ala Gly Ser Asn Gly Tyr Trp Asn Tyr Arg His
 50                  55                  60
Gln Ala Asp Ile Cys His Ala Tyr Gln Ile Leu Arg Lys Gly Leu
 65                  70                  75                  80
Lys Glu Glu Asn Ile Ile Val Phe Met Tyr Asp Asp Ile Ala Phe Asn
                 85                  90                  95
Trp Asp Asn Pro Arg Pro Gly Val Ile Ile Asn Lys Pro Asp Gly Asp
                100                 105                 110
Asp Val Tyr Glu Gly Val Pro Lys Asp Tyr Thr Gly Glu Asp Ala Thr
             115                 120                 125
Ala His Asn Phe Tyr Ser Ala Leu Leu Gly Asp Lys Ser Ala Leu Thr
 130                 135                 140
Gly Gly Ser Gly Lys Val Val Ser Ser Gly Pro Asp Asp Arg Ile Phe
145                 150                 155                 160
Ile Phe Tyr Ser Asp His Gly Gly Pro Gly Val Leu Gly Thr Pro Ala
                165                 170                 175
Gly Pro Tyr Ile Tyr Ala Ser Asp Leu Val Glu Val Leu Lys Lys Lys
             180                 185                 190
His Ala Ser Gly Thr Tyr Lys Asn Leu Val Phe Tyr Leu Glu Ala Cys
         195                 200                 205
Glu Ala Gly Ser Ile Phe Glu Gly Leu Leu Pro Glu Asp Ile Asn Ile
210                 215                 220
Tyr Ala Thr Thr Ala Ser Asn Ala Glu Glu Ser Ser Trp Gly Thr Tyr
225                 230                 235                 240
Cys Pro Gly Glu Tyr Pro Ser Pro Pro Glu Tyr Ser Thr Cys Leu
                245                 250                 255
Gly Asp Leu Tyr Ser Val Ala Trp Met Glu Asp Ser Asp Arg His Asn
             260                 265                 270
Leu Arg Thr Glu Ser Leu His Gln Gln Tyr Lys Val Val Lys Asp Arg
         275                 280                 285
Thr Leu Ser Gly Gly Trp Tyr Gly Ser His Val Met Gln Tyr Gly Asp
 290                 295                 300
Val Glu Phe Ser Lys Asp Ala Leu Phe Leu Tyr Leu Gly Thr Asp Pro
305                 310                 315                 320
Ala Asn Asp Asn Leu Thr Phe Val Asp Glu Asn Ser Leu Trp Ser Ser
                325                 330                 335
Ser Thr Ala Val Asn Gln Arg Asp Ala Asp Leu Val His Phe Trp His
             340                 345                 350
Lys Phe Arg Lys Ala Pro Glu Gly Ser Pro Lys Lys Asn Glu Ala Arg
         355                 360                 365
Lys Gln Val Leu Glu Val Met Ser His Arg Met His Ile Asp Asp Ser
 370                 375                 380
Val Lys Leu Val Gly Lys Leu Phe Gly Phe Glu Lys Ala Pro Glu
385                 390                 395                 400
Val Leu Asn Ala Val Arg Pro Ala Gly Ser Ala Leu Val Asp Asp Trp
                405                 410                 415
Ala Cys Leu Lys Thr Met Val Arg Thr Phe Glu Thr His Cys Gly Ser
             420                 425                 430
```

```
Leu Ser Gln Tyr Gly Met Lys His Met Ser Pro Phe Ala Asn Ile Cys
            435                 440                 445

Asn Val Gly Ile Lys Lys Glu Gln Met Ala Glu Ala Ser Ala Gln Ala
450                 455                 460

Cys Val Thr Val Pro Ala Ser Ser Trp Ser Ser Leu Gln Arg Gly Phe
465                 470                 475                 480

Ser Ala

<210> SEQ ID NO 49
<211> LENGTH: 488
<212> TYPE: PRT
<213> ORGANISM: Eutrema salsugineum

<400> SEQUENCE: 49

Met Thr Ser Val Ala Val Pro Leu Leu Val Leu Leu Ser Leu Ile
1               5                   10                  15

Ala Val Ser Ala Ala Arg Gln Gly Pro Asp Asp Ile Ile Lys Leu Pro
            20                  25                  30

Ser Gln Ala Ser Met Phe Phe Arg Pro Ala Asp Asp Asn Asp Ser
        35                  40                  45

Ser Ala Gly Thr Arg Trp Ala Val Leu Val Ala Gly Ser Asn Gly Tyr
    50                  55                  60

Trp Asn Tyr Arg His Gln Ala Asp Ile Cys His Ala Tyr Gln Leu Leu
65                  70                  75                  80

Arg Lys Gly Gly Val Lys Glu Asp Asn Ile Val Val Phe Met Tyr Asp
                85                  90                  95

Asp Ile Ala Asn Asn Glu Glu Asn Pro Arg Arg Gly Ile Ile Ile Asn
            100                 105                 110

Ser Pro His Gly Lys Asp Val Tyr Gln Gly Val Pro Lys Asp Tyr Thr
        115                 120                 125

Gly Asp Asp Val Thr Val Asp Asn Leu Phe Ala Val Ile Leu Gly Asn
    130                 135                 140

Lys Thr Ala Thr Lys Gly Gly Ser Gly Lys Val Val Asp Ser Gly Pro
145                 150                 155                 160

Asn Asp His Ile Phe Ile Phe Tyr Ser Asp His Gly Gly Pro Gly Val
                165                 170                 175

Leu Gly Met Pro Thr Ser Pro Tyr Leu Tyr Ala Asn Asp Leu Asn Asp
            180                 185                 190

Val Leu Lys Lys Lys His Ala Ser Gly Thr Tyr Lys Ser Leu Val Phe
        195                 200                 205

Tyr Leu Glu Ala Cys Glu Ser Gly Ser Ile Phe Glu Gly Leu Leu Glu
    210                 215                 220

Glu Gly Leu Asn Ile Tyr Ala Thr Thr Ala Ser Asn Ala Val Glu Ser
225                 230                 235                 240

Ser Trp Gly Thr Tyr Cys Pro Gly Glu Asp Pro Ser Leu Pro Pro Glu
                245                 250                 255

Tyr Glu Thr Cys Leu Gly Asp Leu Tyr Ser Val Ser Trp Met Glu Asp
            260                 265                 270

Ser Gly Met His Asn Leu Gln Thr Glu Thr Leu Arg Gln Gln Tyr Glu
        275                 280                 285

Leu Val Lys Arg Arg Thr Ala Gly Val Gly Ser Ala Tyr Gly Ser His
    290                 295                 300

Val Met Gln Tyr Gly Asp Val Gly Leu Ser Lys Asp Lys Leu Asp Leu
305                 310                 315                 320
```

```
Tyr Met Gly Thr Asn Pro Ala Asn Asp Asn Phe Thr Phe Val Asp Glu
                325                 330                 335

Asn Ser Leu Thr Pro Pro Ser Arg Val Thr Asn Gln Arg Asp Ala Asp
            340                 345                 350

Leu Val His Phe Trp Asp Lys Tyr Arg Lys Ala Pro Glu Gly Ser Thr
        355                 360                 365

Arg Lys Thr Glu Ala Gln Lys Gln Val Leu Glu Ala Met Ser His Arg
    370                 375                 380

Leu His Val Asp Asn Ser Val Lys Leu Val Lys Leu Leu Phe Gly
385                 390                 395                 400

Ile Ser Glu Gly Pro Glu Val Leu Asn Lys Val Arg Ser Ala Gly Gln
                405                 410                 415

Pro Leu Val Asp Asp Trp Asn Cys Leu Lys Asn Leu Val Arg Ala Phe
            420                 425                 430

Glu Arg His Cys Gly Ser Leu Ser Gln Tyr Gly Ile Lys His Met Arg
        435                 440                 445

Ser Phe Ala Asn Ile Cys Asn Ala Gly Ile Gln Met Glu Gln Met Glu
    450                 455                 460

Glu Ala Ser Ser Gln Ala Cys Thr Thr Ile Pro Pro Gly Pro Trp Ser
465                 470                 475                 480

Ser Leu His Arg Gly Phe Ser Ala
                485

<210> SEQ ID NO 50
<211> LENGTH: 494
<212> TYPE: PRT
<213> ORGANISM: Citrus sinensis

<400> SEQUENCE: 50

Met Thr Arg Leu Ala Ser Gly Val Leu Ile Thr Leu Leu Val Ala Leu
1               5                   10                  15

Ala Gly Ile Ala Asp Gly Ser Arg Asp Ile Ala Gly Asp Ile Leu Lys
            20                  25                  30

Leu Pro Ser Glu Ala Tyr Arg Phe Phe His Asn Gly Gly Gly Gly Ala
        35                  40                  45

Lys Val Asn Asp Asp Asp Ser Val Gly Thr Arg Trp Ala Val Leu
    50                  55                  60

Leu Ala Gly Ser Asn Gly Phe Trp Asn Tyr Arg His Gln Ala Asp Ile
65                  70                  75                  80

Cys His Ala Tyr Gln Leu Leu Arg Lys Gly Gly Leu Lys Asp Glu Asn
                85                  90                  95

Ile Ile Val Phe Met Tyr Asp Asp Ile Ala Phe Asn Glu Glu Asn Pro
            100                 105                 110

Arg Pro Gly Val Ile Ile Asn His Pro His Gly Asp Asp Val Tyr Lys
        115                 120                 125

Gly Val Pro Lys Asp Tyr Thr Gly Glu Asp Val Thr Val Glu Lys Phe
    130                 135                 140

Phe Ala Val Val Leu Gly Asn Lys Thr Ala Leu Thr Gly Gly Ser Gly
145                 150                 155                 160

Lys Val Val Asp Ser Gly Pro Asn Asp His Ile Phe Ile Phe Tyr Ser
                165                 170                 175

Asp His Gly Gly Pro Gly Val Leu Gly Met Pro Thr Ser Arg Tyr Ile
            180                 185                 190

Tyr Ala Asp Glu Leu Ile Asp Val Leu Lys Lys His Ala Ser Gly
        195                 200                 205
```

Asn Tyr Lys Ser Leu Val Phe Tyr Leu Glu Ala Cys Glu Ser Gly Ser
            210                 215                 220

Ile Phe Glu Gly Leu Leu Glu Gly Leu Asn Ile Tyr Ala Thr Thr
225                 230                 235                 240

Ala Ser Asn Ala Glu Glu Ser Ser Trp Gly Thr Tyr Cys Pro Gly Glu
                245                 250                 255

Ile Pro Gly Pro Pro Glu Tyr Ser Thr Cys Leu Gly Asp Leu Tyr
                260                 265                 270

Ser Ile Ala Trp Met Glu Asp Ser Asp Ile His Asn Leu Arg Thr Glu
            275                 280                 285

Thr Leu His Gln Gln Tyr Glu Leu Val Lys Thr Arg Thr Ala Ser Tyr
290                 295                 300

Asn Ser Tyr Gly Ser His Val Met Gln Tyr Gly Asp Ile Gly Leu Ser
305                 310                 315                 320

Lys Asn Asn Leu Phe Thr Tyr Leu Gly Thr Asn Pro Ala Asn Asp Asn
                325                 330                 335

Tyr Thr Phe Val Asp Glu Asn Ser Leu Arg Pro Ala Ser Lys Ala Val
                340                 345                 350

Asn Gln Arg Asp Ala Asp Leu Leu His Phe Trp Asp Lys Tyr Arg Lys
            355                 360                 365

Ala Pro Glu Gly Thr Pro Arg Lys Ala Glu Ala Gln Lys Gln Phe Phe
370                 375                 380

Glu Ala Met Ser His Arg Met His Val Asp His Ser Ile Lys Leu Ile
385                 390                 395                 400

Gly Lys Leu Leu Phe Gly Ile Glu Lys Gly Pro Glu Ile Leu Asn Thr
                405                 410                 415

Val Arg Pro Ala Gly Gln Pro Leu Val Asp Asp Trp Gly Cys Leu Lys
            420                 425                 430

Ser Leu Val Arg Thr Phe Glu Ser His Cys Gly Ala Leu Ser Gln Tyr
435                 440                 445

Gly Met Lys His Met Arg Ser Leu Ala Asn Ile Cys Asn Thr Gly Ile
            450                 455                 460

Gly Lys Glu Lys Met Ala Glu Ala Ser Ala Gln Ala Cys Glu Asn Ile
465                 470                 475                 480

Pro Ser Gly Pro Trp Ser Ser Leu Asp Lys Gly Phe Ser Ala
                485                 490

<210> SEQ ID NO 51
<211> LENGTH: 484
<212> TYPE: PRT
<213> ORGANISM: Capsicum annuum

<400> SEQUENCE: 51

Met Asn Tyr Gln Val Ala Gly Ile Leu Phe Ile Val Gly Leu Ser Val
1               5                   10                  15

Ala Ile Ala Val Thr Ala Val Asp Gly Arg Asn Val Leu Lys Leu Pro
                20                  25                  30

Thr Glu Ala Ser Arg Phe Phe Asp His Ala Asp Asp Ser Val Gly
            35                  40                  45

Thr Arg Trp Ala Val Leu Leu Ala Gly Ser Asn Gly Tyr Trp Asn Tyr
50                  55                  60

Arg His Gln Ala Asp Val Cys His Ala Tyr Gln Leu Leu Arg Lys Gly
65                  70                  75                  80

Gly Leu Lys Asp Glu Asn Ile Ile Val Phe Met Tyr Asp Asp Ile Ala

```
                    85                  90                  95
Tyr Asn Glu Glu Asn Pro Arg Pro Gly Val Ile Ile Asn Asn Pro Ala
                100                 105                 110

Ala Glu Asp Val Tyr Glu Gly Val Pro Lys Asp Tyr Thr Arg Asp Glu
                115                 120                 125

Val Asn Val His Asn Phe Leu Ala Val Leu Leu Gly Asn Lys Thr Ala
130                 135                 140

Leu Thr Gly Gly Ser Gly Lys Val Val Asn Ser Gly Pro Asn Asp His
145                 150                 155                 160

Ile Phe Ile Phe Tyr Ser Asp His Gly Gly Pro Gly Val Leu Gly Met
                165                 170                 175

Pro Thr Asn Pro Tyr Leu Tyr Ala Ser Asp Leu Ile Asn Ala Leu Lys
                180                 185                 190

Lys Lys His Ala Ala Gly Ala Tyr Lys Ser Leu Val Leu Tyr Ile Glu
                195                 200                 205

Ala Cys Glu Ser Gly Ser Ile Phe Glu Gly Leu Leu Pro Thr Gly Leu
                210                 215                 220

Asn Ile Tyr Ala Thr Thr Ala Ser Asn Ala Val Glu Ser Ser Trp Gly
225                 230                 235                 240

Thr Tyr Cys Pro Gly Glu Tyr Pro Ser Pro Pro Glu Tyr Glu Thr
                245                 250                 255

Cys Leu Gly Asp Leu Tyr Ala Val Ser Trp Met Glu Asp Ser Glu Met
                260                 265                 270

His Asn Leu Arg Thr Glu Asn Leu Arg Gln Gln Tyr His Leu Val Lys
                275                 280                 285

Arg Arg Thr Ala Asn Gly Asn Thr Cys Gly Ser His Val Met Gln Phe
                290                 295                 300

Gly Asp Leu Gln Leu Ser Met Glu Ser Leu Phe Ser Phe Met Gly Thr
305                 310                 315                 320

Asn Pro Ala Asn Asp Asn Tyr Thr Tyr Val Asp Asp Asn Ser Leu Trp
                325                 330                 335

Ala Ser Ser Arg Ala Val Asn Gln Arg Asp Ala Asp Leu Leu His Phe
                340                 345                 350

Trp Asp Lys Phe Arg Lys Ala Pro Glu Gly Ser Ala Arg Lys Val Glu
                355                 360                 365

Ala Gln Lys Gln Phe Thr Glu Ala Met Ser His Arg Met His Leu Asp
                370                 375                 380

Asn Ser Ile Ala Leu Val Gly Lys Leu Leu Phe Gly Ile Gln Lys Gly
385                 390                 395                 400

Pro Glu Val Leu Lys Arg Val Arg Ser Ala Gly Gln Pro Leu Val Asp
                405                 410                 415

Asp Trp Ala Cys Leu Lys Ser Phe Val Arg Thr Phe Glu Thr His Cys
                420                 425                 430

Gly Ser Leu Ser Gln Tyr Gly Met Lys His Met Arg Ser Ile Ala Asn
                435                 440                 445

Ile Cys Asn Ala Gly Ile His Thr Glu Gln Met Val Glu Ala Ser Ala
                450                 455                 460

Gln Ala Cys Pro Ser Ile Pro Ala Asn Thr Trp Ser Ser Leu His Arg
465                 470                 475                 480

Gly Phe Ser Ala

<210> SEQ ID NO 52
<211> LENGTH: 480
```

```
<212> TYPE: PRT
<213> ORGANISM: Solanum lycopersicum

<400> SEQUENCE: 52

Met Val His Val Ala Gly Val Phe Ile Leu Val Gly Ile Ala Val Leu
1               5                   10                  15

Ala Ala Val Glu Gly Arg Asn Val Leu Lys Leu Pro Ser Glu Ala Ser
            20                  25                  30

Arg Phe Phe Asp Asp Ala Asp Asp Ser Val Gly Thr Arg Trp Ala Val
        35                  40                  45

Leu Leu Ala Gly Ser Asn Gly Tyr Trp Asn Tyr Arg His Gln Ala Asp
    50                  55                  60

Val Cys His Ala Tyr Gln Leu Leu Arg Lys Gly Gly Leu Lys Asp Glu
65                  70                  75                  80

Asn Ile Ile Val Phe Met Tyr Asp Asp Ile Ala His Glu Glu Asn
                    85                  90                  95

Pro Arg Pro Gly Val Ile Ile Asn Ser Pro Ala Gly Glu Asp Val Tyr
                100                 105                 110

Glu Gly Val Pro Lys Asp Tyr Thr Gly Asp Val Asn Val His Asn
            115                 120                 125

Phe Leu Ala Val Leu Leu Gly Asn Lys Thr Ala Leu Thr Gly Gly Ser
    130                 135                 140

Gly Lys Val Val Asn Ser Gly Pro Asn Asp His Ile Phe Ile Phe Tyr
145                 150                 155                 160

Ser Asp His Gly Gly Pro Gly Val Leu Gly Met Pro Thr Asn Pro Tyr
                165                 170                 175

Leu Tyr Ala Asp Asp Leu Ile Ala Val Leu Lys Lys His Ala Ala
            180                 185                 190

Gly Thr Tyr Lys Ser Leu Val Leu Tyr Ile Glu Ala Cys Glu Ser Gly
        195                 200                 205

Ser Ile Phe Glu Gly Leu Leu Pro Asn Gly Leu Asn Ile Tyr Ala Thr
210                 215                 220

Thr Ala Ser Asn Ala Glu Glu Ser Ser Trp Gly Thr Tyr Cys Pro Gly
225                 230                 235                 240

Glu Tyr Pro Ser Pro Pro Glu Tyr Glu Thr Cys Leu Gly Asp Leu
                245                 250                 255

Tyr Ala Val Ser Trp Met Glu Asp Ser Glu Met His Asn Leu Arg Thr
            260                 265                 270

Glu Asn Leu Arg Gln Gln Tyr His Leu Val Lys Lys Arg Thr Ala Asn
        275                 280                 285

Gly Asn Thr Ala Tyr Gly Ser His Val Met Gln Phe Gly Asp Leu Gln
    290                 295                 300

Leu Ser Met Glu Ser Leu Phe Arg Phe Met Gly Thr Asn Pro Ala Asn
305                 310                 315                 320

Asp Asn Tyr Thr Tyr Val Asp Asp Asn Ser Leu Leu Ala Ser Ser Lys
                325                 330                 335

Ala Val Asn Gln Arg Asp Ala Asp Leu Leu His Phe Trp Asp Lys Phe
            340                 345                 350

Arg Lys Ala Pro Glu Gly Ser Arg Lys Val Glu Ala Gln Lys Gln
        355                 360                 365

Phe Thr Glu Ala Met Ser His Arg Met His Leu Asp Glu Arg Ile Ala
    370                 375                 380

Leu Val Gly Lys Leu Leu Phe Gly Ile Gln Lys Gly Pro Glu Val Leu
385                 390                 395                 400
```

Lys His Val Arg Ser Ala Gly Gln Pro Leu Val Asp Asp Trp Ala Cys
                405                 410                 415

Leu Lys Ser Phe Val Arg Thr Phe Glu Ser His Cys Gly Ser Leu Ser
            420                 425                 430

Gln Tyr Gly Met Lys His Met Arg Ser Ile Ala Asn Ile Cys Asn Ala
        435                 440                 445

Gly Ile Gln Met Glu Gln Met Val Glu Ala Ser Ala Gln Ala Cys Pro
    450                 455                 460

Ser Ile Pro Ser Asn Ile Trp Ser Ser Leu His Arg Gly Phe Ser Ala
465                 470                 475                 480

<210> SEQ ID NO 53
<211> LENGTH: 480
<212> TYPE: PRT
<213> ORGANISM: Solanum tuberosum

<400> SEQUENCE: 53

Met Ile His Val Ala Gly Val Phe Ile Leu Val Gly Val Ala Val Leu
1               5                   10                  15

Ala Ala Val Glu Gly Arg Asn Val Leu Lys Leu Pro Ser Glu Ala Ser
            20                  25                  30

Arg Phe Phe Asp Val Ala Asp Asp Ser Val Gly Thr Arg Trp Ala Val
        35                  40                  45

Leu Leu Ala Gly Ser Asn Gly Tyr Trp Asn Tyr Arg His Gln Ala Asp
    50                  55                  60

Val Cys His Ala Tyr Gln Leu Leu Arg Lys Gly Gly Leu Lys Asp Glu
65                  70                  75                  80

Asn Ile Ile Val Phe Met Tyr Asp Asp Ile Ala His His Glu Glu Asn
                85                  90                  95

Pro Arg Pro Gly Val Ile Ile Asn Ser Pro Ala Gly Glu Asp Val Tyr
            100                 105                 110

Glu Gly Val Pro Lys Asp Tyr Thr Gly Asp Asp Val Asn Val His Asn
        115                 120                 125

Phe Leu Thr Val Leu Leu Gly Asn Lys Thr Ala Leu Thr Gly Gly Ser
    130                 135                 140

Gly Lys Val Val Asn Ser Gly Pro Asn Asp His Ile Phe Ile Phe Tyr
145                 150                 155                 160

Ser Asp His Gly Gly Pro Gly Val Leu Gly Met Pro Thr Asn Pro Tyr
                165                 170                 175

Leu Tyr Ala Asn Asp Leu Ile Ala Val Leu Lys Lys Lys His Ala Ala
            180                 185                 190

Gly Thr Tyr Lys Ser Leu Val Leu Tyr Ile Glu Ala Cys Glu Ser Gly
        195                 200                 205

Ser Ile Phe Glu Gly Leu Leu Pro Lys Gly Leu Asn Ile Tyr Ala Thr
    210                 215                 220

Thr Ala Ser Asn Ala Glu Glu Ser Ser Trp Gly Thr Tyr Cys Pro Gly
225                 230                 235                 240

Glu Tyr Pro Ser Pro Pro Glu Tyr Glu Thr Cys Leu Gly Asp Leu
                245                 250                 255

Tyr Ala Val Ser Trp Met Glu Asp Ser Glu Met His Asn Leu Arg Thr
            260                 265                 270

Glu Asn Leu Arg Gln Gln Tyr His Leu Val Lys Lys Arg Thr Ala Asn
        275                 280                 285

Gly Asn Thr Ala Tyr Gly Ser His Val Met Gln Phe Gly Asp Leu Gln

```
            290                 295                 300

Leu Ser Met Glu Ser Leu Phe Arg Phe Met Gly Thr Asn Pro Ala Asn
305                 310                 315                 320

Asp Asn Tyr Thr Tyr Val Asp Asn Ser Leu Trp Ala Ser Ser Lys
                325                 330                 335

Ala Val Asn Gln Arg Asp Ala Asp Leu Leu His Phe Trp Asp Lys Phe
                340                 345                 350

Arg Lys Ala Pro Glu Gly Ser Ala Arg Lys Val Glu Ala Gln Lys Gln
                355                 360                 365

Phe Thr Glu Ala Met Ser His Arg Met His Leu Asp Glu Arg Ile Ala
370                 375                 380

Leu Val Gly Lys Leu Leu Phe Gly Ile Gln Lys Gly Pro Glu Val Leu
385                 390                 395                 400

Lys His Val Arg Ser Ala Gly Gln Pro Leu Val Asp Asp Trp Ala Cys
                405                 410                 415

Leu Lys Ser Phe Val Arg Thr Phe Glu Ser His Cys Gly Ser Leu Ser
                420                 425                 430

Gln Tyr Gly Met Lys His Met Arg Ser Ile Ala Asn Ile Cys Asn Ala
                435                 440                 445

Gly Val Gln Met Glu Gln Met Val Glu Ala Ser Val Gln Ala Cys Pro
450                 455                 460

Ser Ile Pro Ser Asn Thr Trp Ser Ser Leu His Arg Gly Phe Ser Ala
465                 470                 475                 480

<210> SEQ ID NO 54
<211> LENGTH: 480
<212> TYPE: PRT
<213> ORGANISM: Solanum lycopersicum

<400> SEQUENCE: 54

Met Val His Val Ala Gly Val Phe Ile Leu Val Gly Ile Ala Val Leu
1               5                   10                  15

Ala Ala Val Glu Gly Arg Asn Val Leu Lys Leu Pro Ser Glu Ala Ser
                20                  25                  30

Arg Phe Phe Asp Asp Ala Asp Asp Ser Val Gly Thr Arg Trp Ala Val
                35                  40                  45

Leu Leu Ala Gly Ser Asn Gly Tyr Trp Asn Tyr Arg His Gln Ala Asp
50                  55                  60

Val Cys His Ala Tyr Gln Leu Leu Arg Lys Gly Gly Leu Lys Asp Glu
65                  70                  75                  80

Asn Ile Ile Val Phe Met Tyr Asp Asp Ile Ala His His Glu Glu Asn
                85                  90                  95

Pro Arg Pro Gly Val Ile Ile Asn Ser Pro Ala Gly Glu Asp Val Tyr
                100                 105                 110

Glu Gly Val Pro Lys Asp Tyr Thr Gly Asp Asp Val Asn Val His Asn
                115                 120                 125

Phe Leu Ala Val Leu Leu Gly Asn Lys Thr Ala Leu Thr Gly Gly Ser
130                 135                 140

Gly Lys Val Val Asn Ser Gly Pro Asn Asp His Ile Phe Ile Phe Tyr
145                 150                 155                 160

Ser Asp His Gly Gly Pro Gly Val Leu Gly Met Pro Thr Asn Pro Tyr
                165                 170                 175

Leu Tyr Ala Asp Asp Leu Ile Ala Val Leu Lys Lys Lys His Ala Pro
                180                 185                 190
```

```
Gly Thr Tyr Lys Ser Leu Val Leu Tyr Ile Glu Ala Cys Glu Ser Gly
            195                 200                 205

Ser Ile Phe Glu Gly Leu Leu Pro Asn Gly Leu Asn Ile Tyr Ala Thr
210                 215                 220

Thr Ala Ser Asn Ala Glu Glu Ser Ser Trp Gly Thr Tyr Cys Pro Gly
225                 230                 235                 240

Glu Tyr Pro Ser Pro Pro Glu Tyr Glu Thr Cys Leu Gly Asp Leu
            245                 250                 255

Tyr Ala Val Ser Trp Met Glu Asp Ser Glu Met His Asn Leu Arg Thr
            260                 265                 270

Glu Asn Leu Arg Gln Gln Tyr His Leu Val Lys Lys Arg Thr Ala Asn
            275                 280                 285

Gly Asn Thr Ala Tyr Gly Ser His Val Met Gln Phe Gly Asp Leu Gln
290                 295                 300

Leu Ser Met Glu Ser Leu Phe Arg Phe Met Gly Thr Asn Pro Ala Asn
305                 310                 315                 320

Asp Asn Tyr Thr Tyr Val Asp Asp Asn Ser Leu Leu Ala Ser Ser Lys
                325                 330                 335

Ala Val Asn Gln Arg Asp Ala Asp Leu Leu His Phe Trp Asp Lys Phe
            340                 345                 350

Arg Lys Ala Pro Glu Gly Ser Ala Arg Lys Val Glu Ala Gln Lys Gln
            355                 360                 365

Phe Thr Glu Ala Met Ser His Arg Met His Leu Asp Glu Arg Ile Ala
370                 375                 380

Leu Val Gly Lys Leu Leu Phe Gly Ile Gln Lys Gly Pro Glu Val Leu
385                 390                 395                 400

Lys His Val Arg Ser Ala Gly Gln Pro Leu Val Asp Asp Trp Ala Cys
                405                 410                 415

Leu Lys Ser Phe Val Arg Thr Phe Glu Ser His Cys Gly Ser Leu Ser
            420                 425                 430

Gln Tyr Gly Met Lys His Met Arg Ser Ile Ala Asn Ile Cys Asn Ala
            435                 440                 445

Gly Ile Gln Met Glu Gln Met Val Glu Ala Ser Ala Gln Ala Cys Pro
450                 455                 460

Ser Ile Pro Ser Asn Ile Trp Ser Ser Leu His Arg Gly Phe Ser Ala
465                 470                 475                 480

<210> SEQ ID NO 55
<211> LENGTH: 490
<212> TYPE: PRT
<213> ORGANISM: Eutrema salsugineum

<400> SEQUENCE: 55

Met Ser Arg Val Ser Val Thr Val Thr Val Ala Val Ser Phe Leu Ala
1               5                   10                  15

Leu Phe Ile Ser Leu Val Thr Val Ser Cys Asp Val Ile Lys Leu Pro
            20                  25                  30

Ser Gln Ala Ser Lys Phe Phe Arg Thr Thr Lys His Asn Asp Asp Gly
        35                  40                  45

Asp Ser Ser Ala Gly Thr Lys Trp Ala Val Leu Val Ala Gly Ser Ser
    50                  55                  60

Gly Tyr Trp Asn Tyr Arg His Gln Ala Asp Val Cys His Ala Tyr Gln
65                  70                  75                  80

Leu Leu Arg Lys Gly Gly Leu Lys Glu Glu Asn Ile Ile Val Phe Met
                85                  90                  95
```

Tyr Asp Asp Ile Ala Lys Asn Lys Glu Asn Pro Arg Pro Gly Ile Ile
                100                 105                 110

Ile Asn Ser Pro Asn Gly Asn Asp Val Tyr Asn Gly Val Pro Lys Asp
            115                 120                 125

Tyr Thr Gly Asp Asp Val Asn Val Asp Asn Leu Phe Ala Val Ile Leu
        130                 135                 140

Ala Asn Lys Thr Ala Leu Lys Gly Gly Ser Gly Lys Val Val Asp Ser
145                 150                 155                 160

Gly Pro Asp Asp His Ile Phe Ile Tyr Tyr Ser Asp His Gly Gly Pro
                165                 170                 175

Gly Val Leu Gly Met Pro Thr Ser Pro His Leu Tyr Ala Asn Asp Leu
            180                 185                 190

Ile Asp Ile Leu Lys Lys Lys His Ala Ser Gly Thr Tyr Lys Ser Leu
        195                 200                 205

Val Phe Tyr Leu Glu Ala Cys Glu Ser Gly Ser Ile Phe Glu Gly Leu
    210                 215                 220

Leu Pro Glu Gly Leu Asn Ile Tyr Ala Thr Thr Ala Ser Asn Ala Glu
225                 230                 235                 240

Glu Ser Ser Trp Gly Thr Tyr Cys Pro Gly Asp Asp Ser Ser Pro Pro
                245                 250                 255

Lys Glu Tyr Glu Thr Cys Leu Gly Asp Leu Tyr Ser Val Ser Trp Met
            260                 265                 270

Glu Asp Ser Asp Gln His Asn Leu Gln Thr Glu Ser Leu His Gln Gln
        275                 280                 285

Tyr Glu Leu Val Lys Lys Arg Thr Ala Gly Ser Asn Thr Ser Tyr Gly
    290                 295                 300

Ser His Val Met Glu Phe Gly Asp Ile Gly Leu Ser Lys Glu Met Leu
305                 310                 315                 320

Val Leu Tyr Met Gly Thr Asn Pro Asp Asn Glu Asn Tyr Thr Phe Val
                325                 330                 335

Asp Lys Asn Ser Leu Arg Pro Pro Ser Arg Val Thr Asn Gln Arg Asp
            340                 345                 350

Ala Asp Leu Val His Phe Trp Asp Lys Tyr Gln Lys Ala Pro Glu Gly
        355                 360                 365

Ser Ala Arg Lys Ala Glu Ala Gln Lys Gln Val Leu Glu Ala Met Ser
    370                 375                 380

His Arg Leu His Ile Asp Asn Ser Phe Leu Met Ile Gly Lys Leu Leu
385                 390                 395                 400

Phe Gly Ile Ser Glu Gly Pro Leu Val Leu Asn Lys Val Arg Pro Ser
                405                 410                 415

Gly Lys Pro Leu Val Asp Asp Trp Asp Cys Leu Lys Thr Leu Val Arg
            420                 425                 430

Ala Tyr Glu Arg His Cys Gly Ser Leu Ser Gln Tyr Gly Ile Lys His
        435                 440                 445

Met Arg Ser Ile Ala Asn Ile Cys Asn Ala Gly Ile Gln Val Glu Gln
    450                 455                 460

Met Glu Glu Ala Ala Met Gln Ala Cys Pro Thr Ile Pro Ala Gly Pro
465                 470                 475                 480

Trp Ser Ser Leu His Arg Gly Phe Ser Ala
                485                 490

<210> SEQ ID NO 56
<211> LENGTH: 492

<212> TYPE: PRT
<213> ORGANISM: Ipomoea batatas

<400> SEQUENCE: 56

```
Met Ile Arg Ser Val Val Ala Ser Leu Leu Leu Thr Val Ser Ile
1               5                   10                  15

Val Ala Val Ala Asp Gly Arg Gly Phe Leu Lys Leu Pro Ser Glu Ala
                20                  25                  30

Arg Arg Phe Phe Arg Pro Ala Glu Glu Glu Asn Arg Glu Ala Asp Gly
            35                  40                  45

Asp Asp Ser Val Gly Thr Arg Trp Ala Val Leu Ile Ala Gly Ser Asn
        50                  55                  60

Gly Tyr Trp Asn Tyr Arg His Gln Ala Asp Ile Cys His Ala Tyr Gln
65                  70                  75                  80

Ile Leu Lys Ala Gly Gly Leu Lys Asp Glu Asn Ile Val Val Phe Met
                85                  90                  95

Tyr Asp Asp Ile Ala Tyr Asn Glu Glu Asn Pro Arg Lys Gly Ile Ile
                100                 105                 110

Ile Asn Ser Pro His Gly Glu Asp Val Tyr His Gly Val Pro Lys Asp
            115                 120                 125

Tyr Thr Gly Asp Asp Val Thr Ala Asn Asn Leu Leu Ala Val Ile Leu
        130                 135                 140

Gly Asp Lys Ser Ala Val Lys Gly Gly Ser Lys Val Val Asp Ser
145                 150                 155                 160

Gly Pro Asn Asp His Ile Phe Ile Tyr Tyr Ser Asp His Gly Gly Pro
                165                 170                 175

Gly Val Leu Gly Met Pro Thr Ser Pro Tyr Leu Tyr Ala Asp Glu Leu
                180                 185                 190

Asn Ala Ala Leu Lys Lys His Ala Ala Gly Ala Tyr Lys Ser Leu
                195                 200                 205

Val Phe Tyr Leu Glu Ala Cys Glu Ser Gly Ser Ile Phe Glu Gly Ile
            210                 215                 220

Leu Pro Lys Asp Ile Asn Ile Tyr Ala Thr Thr Ala Ser Asn Ala Ile
225                 230                 235                 240

Glu Ser Ser Trp Gly Thr Tyr Cys Pro Gly Glu Tyr Pro Ser Pro Pro
                245                 250                 255

Pro Glu Tyr Glu Thr Cys Leu Gly Asp Leu Tyr Ser Ile Ala Trp Met
                260                 265                 270

Glu Asp Ser Asp Ile His Asn Leu Arg Thr Glu Ser Leu Lys Gln Gln
                275                 280                 285

Tyr Asn Leu Val Lys Asp Arg Thr Leu Asn Gly Asn Thr Ala Tyr Gly
                290                 295                 300

Ser His Val Met Gln Tyr Gly Asp Leu Glu Leu Asn Ala Asp Ser Leu
305                 310                 315                 320

Phe Met Tyr Met Gly Thr Asn Pro Ala Asn Glu Asn Phe Thr Phe Val
                325                 330                 335

Asp Glu Lys Ser Leu Lys Leu Ser Ala Pro Arg Arg Ala Val Asn Gln
                340                 345                 350

Arg Asp Ala Asp Leu Leu His Phe Trp Asp Lys Phe Arg Asn Ala Pro
                355                 360                 365

Glu Gly Ser Ala Arg Lys Ser Glu Ala Gln Lys Gln Phe Thr Glu Ala
                370                 375                 380

Ile Thr His Arg Thr His Leu Asp Asn Ser Ile Ala Leu Val Gly Lys
385                 390                 395                 400
```

```
Leu Leu Phe Gly Met Glu Lys Gly Pro Glu Val Leu Ser Ser Val Arg
                405                 410                 415
Ala Thr Gly Leu Pro Leu Val Asp Asp Trp Ser Cys Leu Lys Ser Tyr
            420                 425                 430
Val Arg Ala Phe Glu Thr His Cys Gly Ser Leu Ser Gln Tyr Gly Met
        435                 440                 445
Lys His Met Arg Ser Ile Ala Asn Ile Cys Asn Ala Gly Ile Ser Glu
    450                 455                 460
Glu Arg Met Ala Glu Ala Ser Ala Gln Ala Cys Pro Thr Phe Pro Ser
465                 470                 475                 480
Tyr Ser Trp Ser Ser Leu Arg Gly Gly Phe Ser Ala
                485                 490

<210> SEQ ID NO 57
<211> LENGTH: 490
<212> TYPE: PRT
<213> ORGANISM: Nicotiana tabacum

<400> SEQUENCE: 57

Met Ile Arg His Ile Ala Gly Thr Leu Phe Ile Ile Gly Leu Ala Leu
1               5                   10                  15
Asn Val Ala Val Ser Glu Ser Arg Asn Val Leu Lys Leu Pro Ser Glu
            20                  25                  30
Val Ser Arg Phe Phe Gly Ala Asp Lys Ser Asn Val Gly Asp Asp His
        35                  40                  45
Asp Asp Asp Ser Val Gly Thr Arg Trp Ala Ile Leu Leu Ala Gly Ser
    50                  55                  60
Asn Gly Tyr Trp Asn Tyr Arg His Gln Ala Asp Ile Cys His Ala Tyr
65                  70                  75                  80
Gln Leu Leu Lys Lys Gly Gly Leu Lys Asp Glu Asn Ile Val Val Phe
                85                  90                  95
Met Tyr Asp Asp Ile Ala Asn Asn Glu Glu Asn Pro Arg Pro Gly Val
            100                 105                 110
Ile Ile Asn Ser Pro His Gly Glu Asp Val Tyr Lys Gly Val Pro Lys
        115                 120                 125
Asp Tyr Thr Gly Asp Asp Val Thr Val Asn Asn Phe Phe Ala Ala Leu
    130                 135                 140
Leu Gly Asn Lys Thr Ala Leu Ser Gly Gly Ser Gly Lys Val Val Asn
145                 150                 155                 160
Ser Gly Pro Asn Asp His Ile Leu Ile Phe Tyr Ser Asp His Gly Gly
                165                 170                 175
Pro Gly Val Leu Gly Met Pro Thr Asp Pro Tyr Leu Tyr Ala Asn Asp
            180                 185                 190
Leu Ile Asp Val Leu Lys Lys His Ala Ser Gly Thr Tyr Lys Ser
        195                 200                 205
Leu Val Phe Tyr Leu Glu Ala Cys Glu Ser Gly Ser Ile Phe Glu Gly
    210                 215                 220
Leu Leu Pro Glu Gly Leu Asn Ile Tyr Ala Thr Thr Ala Ser Asn Ala
225                 230                 235                 240
Glu Glu Ser Ser Trp Gly Thr Tyr Cys Pro Gly Glu Tyr Pro Ser Pro
                245                 250                 255
Pro Ile Glu Tyr Glu Thr Cys Leu Gly Asp Leu Tyr Ser Ile Ser Trp
            260                 265                 270
Met Glu Asp Ser Glu Leu His Asn Leu Arg Thr Glu Ser Leu Lys Gln
```

```
                275                 280                 285
Gln Tyr His Leu Val Arg Glu Arg Thr Ala Thr Gly Asn Pro Val Tyr
290                 295                 300

Gly Ser His Val Met Gln Tyr Gly Asp Leu His Leu Ser Lys Asp Ala
305                 310                 315                 320

Leu Tyr Leu Tyr Met Gly Thr Asn Pro Ala Asn Asp Asn Tyr Thr Phe
                325                 330                 335

Met Asp Asp Asn Ser Leu Arg Val Ser Lys Ala Val Asn Gln Arg Asp
                340                 345                 350

Ala Asp Leu Leu His Phe Trp Tyr Lys Phe Arg Lys Ala Pro Glu Gly
                355                 360                 365

Ser Val Arg Lys Ile Glu Ala Gln Lys Gln Leu Asn Glu Ala Ile Ser
370                 375                 380

His Arg Val His Leu Asp Asn Ser Ile Ala Leu Val Gly Lys Leu Leu
385                 390                 395                 400

Phe Gly Ile Lys Lys Gly Pro Glu Val Leu Ser Ser Val Arg Pro Ala
                405                 410                 415

Gly Gln Pro Leu Val Asp Asp Trp Asp Cys Leu Lys Ser Phe Val Arg
                420                 425                 430

Thr Phe Glu Thr His Cys Gly Ser Leu Ser Gln Tyr Gly Met Lys His
                435                 440                 445

Met Arg Ser Ile Ala Asn Ile Cys Asn Val Gly Ile Lys Met Ala Gln
450                 455                 460

Met Val Glu Ala Ser Ala Gln Ala Cys Pro Ser Phe Ala Ser Asn Thr
465                 470                 475                 480

Trp Ser Ser Leu Gln Arg Gly Phe Ser Ala
                485                 490

<210> SEQ ID NO 58
<211> LENGTH: 494
<212> TYPE: PRT
<213> ORGANISM: Arabidopsis lyrata subsp. lyrata

<400> SEQUENCE: 58

Met Ala Thr Thr Met Thr Arg Val Pro Val Gly Ala Phe Leu Leu Val
1               5                   10                  15

Leu Leu Val Ser Leu Val Ala Val Ser Thr Ala Arg Ser Gly Pro Asp
                20                  25                  30

Asp Val Ile Lys Leu Pro Ser Gln Ala Ser Arg Phe Phe Arg Pro Ala
                35                  40                  45

Gln Asp Asp Asp Ser Asn Ala Gly Thr Arg Trp Ala Val Leu Val
50                  55                  60

Ala Gly Ser Ser Gly Tyr Trp Asn Tyr Arg His Gln Ala Asp Ile Cys
65                  70                  75                  80

His Ala Tyr Gln Leu Leu Arg Lys Gly Gly Leu Lys Glu Glu Asn Ile
                85                  90                  95

Val Val Phe Met Tyr Asp Asp Ile Ala Asn Asn Tyr Glu Asn Pro Arg
                100                 105                 110

Pro Gly Thr Leu Ile Asn Ser Pro His Gly Lys Asp Val Tyr Gln Gly
                115                 120                 125

Val Pro Lys Asp Tyr Thr Gly Asp Asp Val Asn Val Asp Asn Leu Phe
130                 135                 140

Ala Val Ile Leu Gly Asp Lys Thr Ala Val Lys Gly Gly Ser Gly Lys
145                 150                 155                 160
```

Val Val Asp Ser Gly Pro Asn Asp His Ile Phe Ile Phe Tyr Ser Asp
                165                 170                 175

His Gly Gly Pro Gly Val Leu Gly Met Pro Thr Ser Pro Tyr Leu Tyr
            180                 185                 190

Ala Asn Asp Leu Asn Asp Val Leu Lys Lys Lys His Ala Ser Gly Thr
            195                 200                 205

Tyr Lys Ser Leu Val Phe Tyr Leu Glu Ala Cys Glu Ser Gly Ser Ile
            210                 215                 220

Phe Glu Gly Leu Leu Pro Glu Gly Leu Asn Ile Tyr Ala Thr Thr Ala
225                 230                 235                 240

Ser Asn Ala Glu Glu Ser Ser Trp Gly Thr Tyr Cys Pro Gly Glu Glu
                245                 250                 255

Pro Ser Pro Pro Glu Tyr Glu Thr Cys Leu Gly Asp Leu Tyr Ser
                260                 265                 270

Val Ala Trp Met Glu Asp Ser Gly Met His Asn Leu Gln Thr Glu Thr
            275                 280                 285

Leu His Gln Gln Tyr Glu Leu Val Lys Arg Arg Thr Ala Pro Val Gly
            290                 295                 300

Tyr Ser Tyr Gly Ser His Val Met Gln Tyr Gly Asp Val Gly Leu Ser
305                 310                 315                 320

Lys Asp Asn Leu Asp Leu Tyr Met Gly Thr Asn Pro Ala Asn Asp Asn
                325                 330                 335

Phe Thr Phe Ala Asp Ala Asn Ser Leu Lys Pro Pro Ser Arg Val Thr
                340                 345                 350

Asn Gln Arg Asp Ala Asp Leu Val His Phe Trp Glu Lys Tyr Arg Lys
            355                 360                 365

Ala Pro Glu Gly Ser Ala Arg Lys Thr Glu Ala Gln Lys Gln Val Leu
370                 375                 380

Glu Ala Met Ser His Arg Leu His Val Asp Asn Ser Val Ile Leu Val
385                 390                 395                 400

Gly Lys Ile Leu Phe Gly Ile Ser Glu Gly Pro Glu Val Leu Asn Lys
                405                 410                 415

Val Arg Ser Ala Gly Gln Pro Leu Val Asp Asp Trp Asn Cys Leu Lys
            420                 425                 430

Asn Leu Val Arg Ala Phe Glu Arg His Cys Gly Ser Leu Ser Gln Tyr
            435                 440                 445

Gly Ile Lys His Met Arg Ser Phe Ala Asn Ile Cys Asn Ala Gly Ile
            450                 455                 460

Arg Thr Glu Gln Met Glu Glu Ala Ala Ser Gln Ala Cys Thr Ser Ile
465                 470                 475                 480

Pro Pro Gly Pro Trp Ser Ser Leu His Arg Gly Phe Ser Ala
                485                 490

<210> SEQ ID NO 59
<211> LENGTH: 478
<212> TYPE: PRT
<213> ORGANISM: Thellungiella halophila

<400> SEQUENCE: 59

Met Thr Ser Val Ala Val Pro Leu Leu Val Leu Leu Leu Ser Leu Ile
1               5                   10                  15

Ala Val Ser Ala Ala Arg Gln Gly Pro Asp Asp Ile Ile Lys Leu Pro
            20                  25                  30

Ser Gln Ala Ser Met Phe Phe Arg Pro Ala Asp Asp Asn Asp Ser
            35                  40                  45

```
Ser Ala Gly Thr Arg Trp Ala Val Leu Val Ala Gly Ser Asn Gly Tyr
 50                  55                  60

Trp Asn Tyr Arg His Gln Ala Asp Ile Cys His Ala Tyr Gln Leu Leu
 65                  70                  75                  80

Arg Lys Gly Gly Val Lys Glu Asp Asn Ile Val Phe Met Tyr Asp
                 85                  90                  95

Asp Ile Ala Asn Asn Glu Glu Asn Pro Arg Arg Gly Ile Ile Ile Asn
                100                 105                 110

Ser Pro His Gly Lys Asp Val Tyr Gln Gly Val Pro Lys Asp Tyr Thr
        115                 120                 125

Gly Asp Asp Val Thr Val Asp Asn Leu Phe Ala Val Ile Leu Gly Asn
    130                 135                 140

Lys Thr Ala Thr Lys Gly Gly Ser Gly Lys Val Val Asp Ser Gly Pro
145                 150                 155                 160

Asn Asp His Ile Phe Ile Phe Tyr Ser Asp His Gly Gly Pro Gly Val
                165                 170                 175

Leu Gly Met Pro Thr Ser Pro Tyr Leu Tyr Ala Asn Asp Leu Asn Asp
            180                 185                 190

Val Leu Lys Lys Lys His Ala Ser Gly Thr Tyr Lys Ser Leu Val Phe
        195                 200                 205

Tyr Leu Glu Ala Cys Glu Ser Gly Ser Ile Phe Glu Gly Leu Leu Glu
    210                 215                 220

Glu Gly Leu Asn Ile Tyr Ala Thr Thr Ala Ser Asn Ala Val Glu Ser
225                 230                 235                 240

Ser Trp Gly Thr Tyr Cys Pro Gly Glu Asp Pro Ser Leu Pro Pro Glu
                245                 250                 255

Tyr Glu Thr Cys Leu Gly Asp Leu Tyr Ser Val Ser Trp Met Glu Asp
            260                 265                 270

Ser Gly Met His Asn Leu Gln Thr Glu Thr Leu Arg Gln Gln Tyr Glu
        275                 280                 285

Leu Val Lys Arg Arg Thr Ala Gly Val Gly Ser Ala Tyr Gly Ser His
    290                 295                 300

Val Met Gln Tyr Gly Asp Val Gly Leu Ser Lys Asp Lys Leu Asp Leu
305                 310                 315                 320

Tyr Met Gly Thr Asn Pro Ala Asn Asp Asn Phe Thr Phe Val Asp Glu
                325                 330                 335

Asn Ser Leu Thr Pro Pro Ser Arg Val Thr Asn Gln Arg Asp Ala Asp
            340                 345                 350

Leu Val His Phe Trp Asp Lys Tyr Arg Lys Ala Pro Glu Gly Ser Thr
        355                 360                 365

Arg Lys Thr Glu Ala Gln Lys Gln Val Leu Glu Ala Met Ser His Arg
    370                 375                 380

Leu His Val Asp Asn Ser Val Lys Leu Val Gly Lys Leu Leu Phe Gly
385                 390                 395                 400

Ile Ser Glu Gly Pro Glu Val Leu Asn Lys Val Arg Ser Ala Gly Gln
                405                 410                 415

Pro Leu Val Asp Asp Trp Asn Cys Leu Lys Asn Leu Val Arg Ala Phe
            420                 425                 430

Glu Arg His Cys Gly Ser Leu Ser Gln Tyr Gly Ile Lys His Met Arg
        435                 440                 445

Ser Phe Ala Asn Ile Cys Asn Ala Gly Ile Gln Met Glu Gln Met Glu
    450                 455                 460
```

```
Glu Ala Ser Ser Gln Ala Cys Thr Thr Ile Pro Pro Gly Pro
465                 470                 475
```

<210> SEQ ID NO 60
<211> LENGTH: 486
<212> TYPE: PRT
<213> ORGANISM: Beta vulgaris

<400> SEQUENCE: 60

```
Met Met Ile Arg Tyr Thr Ser Gly Val Leu Ile Val Leu Cys Val Leu
1               5                   10                  15

Met Ser Ser Val Val Asp Ser Arg Leu Met Val Asp Asn Leu Ile Arg
            20                  25                  30

Trp Pro Ser Asp His Pro Ser Ile Phe Glu Ser Asp Asp Ser Val
        35                  40                  45

Gly Thr Arg Trp Ala Val Leu Ile Ala Gly Ser Ser Gly Tyr Trp Asn
    50                  55                  60

Tyr Arg His Gln Ala Asp Val Cys His Ala Tyr Gln Val Leu Lys Lys
65                  70                  75                  80

Gly Gly Leu Lys Asp Glu Asn Ile Ile Val Phe Met Tyr Asp Asp Ile
                85                  90                  95

Ala Tyr Asp Glu Glu Asn Pro Arg Pro Gly Val Leu Ile Asn Ser Pro
            100                 105                 110

Tyr Gly His Asp Val Tyr Ala Gly Val Pro Lys Asp Tyr Thr Gly Glu
        115                 120                 125

Asp Val Thr Val Asn Asn Phe Phe Ala Ala Ile Leu Gly Asn Lys Asp
    130                 135                 140

Ala Ile Thr Gly Gly Ser Gly Lys Val Val Asn Ser Gly Pro Asn Asp
145                 150                 155                 160

His Ile Phe Ile Phe Tyr Ser Asp His Gly Gly Ala Gly Val Leu Gly
                165                 170                 175

Met Pro Thr Tyr Pro Tyr Leu Tyr Ala Asp Glu Leu Ile Glu Thr Leu
            180                 185                 190

Lys Glu Lys His Ala Ser Gly Thr Tyr Lys Ser Leu Val Val Tyr Ile
        195                 200                 205

Glu Ala Cys Glu Ser Gly Ser Ile Phe Glu Gly Ile Leu Pro Glu Gly
    210                 215                 220

Leu Asn Ile Tyr Ala Thr Thr Ala Ser Asn Ala Val Glu Ser Ser Trp
225                 230                 235                 240

Gly Thr Tyr Cys Pro Gly Gln Asp Pro Asn Val Pro Pro Glu Tyr Asp
                245                 250                 255

Thr Cys Leu Gly Asp Leu Tyr Ser Val Ser Trp Ile Glu Asp Ser Glu
            260                 265                 270

Arg His Asn Leu His Thr Glu Ser Leu Lys Gln Gln Tyr Glu Val Val
        275                 280                 285

Lys Thr Lys Thr Ala Glu Lys Pro Phe Tyr Gly Ser His Val Met Gln
    290                 295                 300

Tyr Gly Asp Lys Glu Leu Thr Gln Asp Met Leu Tyr Leu Tyr Met Gly
305                 310                 315                 320

Thr Asn Pro Asn Asn Glu Asn Tyr Thr Tyr Val Asp Asp Asn Ser Leu
                325                 330                 335

His Pro Thr Ser Ser Asn Ala Val Asn Gln Arg Asp Ala Asp Leu Ile
            340                 345                 350

His Phe Trp Asn Lys Phe Arg Lys Ala Ser Glu Gly Ser Gln Arg Lys
        355                 360                 365
```

```
Ile Asn Ala Gln Lys Gln Phe Met Glu Val Met Ser His Arg Val His
    370                 375                 380

Leu Asp Asp Ser Ile Lys Leu Ile Gly Lys Leu Phe Gly Ile Glu
385                 390                 395                 400

Lys Gly Leu Gly Val Leu Gln Thr Val Arg Pro Thr Gly Gln Pro Leu
                405                 410                 415

Val Asp Asp Trp Asn Cys Leu Lys Thr Leu Val Arg Thr Phe Glu Lys
                420                 425                 430

His Cys Gly Ser Leu Ser Gln Tyr Gly Met Lys His Met Arg Ser Ile
                435                 440                 445

Ala Asn Ile Cys Asn Ala Gly Ile Thr Thr Asn Gln Met Ala Glu Ala
                450                 455                 460

Ser Ala Gln Ala Cys Pro Ser Phe Pro Ser Gly Pro Trp Ser Ser Leu
465                 470                 475                 480

His Arg Gly Phe Ser Ala
                485

<210> SEQ ID NO 61
<211> LENGTH: 494
<212> TYPE: PRT
<213> ORGANISM: Arabidopsis thaliana

<400> SEQUENCE: 61

Met Ala Thr Thr Met Thr Arg Val Ser Val Gly Val Val Leu Phe Val
1               5                   10                  15

Leu Leu Val Ser Leu Val Ala Val Ser Ala Ala Arg Ser Gly Pro Asp
                20                  25                  30

Asp Val Ile Lys Leu Pro Ser Gln Ala Ser Arg Phe Phe Arg Pro Ala
                35                  40                  45

Glu Asn Asp Asp Asp Ser Asn Ser Gly Thr Arg Trp Ala Val Leu Val
            50                  55                  60

Ala Gly Ser Ser Gly Tyr Trp Asn Tyr Arg His Gln Ala Asp Ile Cys
65              70                  75                  80

His Ala Tyr Gln Leu Leu Arg Lys Gly Gly Leu Lys Glu Glu Asn Ile
                85                  90                  95

Val Val Phe Met Tyr Asp Asp Ile Ala Asn Asn Tyr Glu Asn Pro Arg
                100                 105                 110

Pro Gly Thr Ile Ile Asn Ser Pro His Gly Lys Asp Val Tyr Gln Gly
                115                 120                 125

Val Pro Lys Asp Tyr Thr Gly Asp Val Asn Val Asp Asn Leu Phe
                130                 135                 140

Ala Val Ile Leu Gly Asp Lys Thr Ala Val Lys Gly Ser Gly Lys
145                 150                 155                 160

Val Val Asp Ser Gly Pro Asn Asp His Ile Phe Ile Phe Tyr Ser Asp
                165                 170                 175

His Gly Gly Pro Gly Val Leu Gly Met Pro Thr Ser Pro Tyr Leu Tyr
                180                 185                 190

Ala Asn Asp Leu Asn Asp Val Leu Lys Lys His Ala Leu Gly Thr
                195                 200                 205

Tyr Lys Ser Leu Val Phe Tyr Leu Glu Ala Cys Glu Ser Gly Ser Ile
                210                 215                 220

Phe Glu Gly Leu Leu Pro Glu Gly Leu Asn Ile Tyr Ala Thr Thr Ala
225                 230                 235                 240

Ser Asn Ala Glu Glu Ser Ser Trp Gly Thr Tyr Cys Pro Gly Glu Glu
```

245                 250                 255
Pro Ser Pro Pro Glu Tyr Glu Thr Cys Leu Gly Asp Leu Tyr Ser
            260                 265                 270

Val Ala Trp Met Glu Asp Ser Gly Met His Asn Leu Gln Thr Glu Thr
            275                 280                 285

Leu His Gln Gln Tyr Glu Leu Val Lys Arg Thr Ala Pro Val Gly
        290                 295                 300

Tyr Ser Tyr Gly Ser His Val Met Gln Tyr Gly Asp Val Gly Ile Ser
305                 310                 315                 320

Lys Asp Asn Leu Asp Leu Tyr Met Gly Thr Asn Pro Ala Asn Asp Asn
                325                 330                 335

Phe Thr Phe Ala Asp Ala Asn Ser Leu Lys Pro Pro Ser Arg Val Thr
                340                 345                 350

Asn Gln Arg Asp Ala Asp Leu Val His Phe Trp Glu Lys Tyr Arg Lys
                355                 360                 365

Ala Pro Glu Gly Ser Ala Arg Lys Thr Glu Ala Gln Lys Gln Val Leu
            370                 375                 380

Glu Ala Met Ser His Arg Leu His Ile Asp Asn Ser Val Ile Leu Val
385                 390                 395                 400

Gly Lys Ile Leu Phe Gly Ile Ser Arg Gly Pro Glu Val Leu Asn Lys
                405                 410                 415

Val Arg Ser Ala Gly Gln Pro Leu Val Asp Asp Trp Asn Cys Leu Lys
            420                 425                 430

Asn Gln Val Arg Ala Phe Glu Arg His Cys Gly Ser Leu Ser Gln Tyr
                435                 440                 445

Gly Ile Lys His Met Arg Ser Phe Ala Asn Ile Cys Asn Ala Gly Ile
            450                 455                 460

Gln Met Glu Gln Met Glu Ala Ala Ser Gln Ala Cys Thr Thr Leu
465                 470                 475                 480

Pro Thr Gly Pro Trp Ser Ser Leu Asn Arg Gly Phe Ser Ala
            485                 490

<210> SEQ ID NO 62
<211> LENGTH: 490
<212> TYPE: PRT
<213> ORGANISM: Arabidopsis thaliana

<400> SEQUENCE: 62

Met Thr Arg Val Ser Val Gly Val Val Leu Phe Val Leu Val Ser
1               5                   10                  15

Leu Val Ala Val Ser Ala Ala Arg Ser Gly Pro Asp Asp Val Ile Lys
                20                  25                  30

Leu Pro Ser Gln Ala Ser Arg Phe Phe Arg Pro Ala Glu Asn Asp Asp
            35                  40                  45

Asp Ser Asn Ser Gly Thr Arg Trp Ala Val Leu Val Ala Gly Ser Ser
        50                  55                  60

Gly Tyr Trp Asn Tyr Arg His Gln Ala Asp Ile Cys His Ala Tyr Gln
65                  70                  75                  80

Leu Leu Arg Lys Gly Gly Leu Lys Glu Glu Asn Ile Val Val Phe Met
                85                  90                  95

Tyr Asp Asp Ile Ala Asn Asn Tyr Glu Asn Pro Arg Pro Gly Thr Ile
            100                 105                 110

Ile Asn Ser Pro His Gly Lys Asp Val Tyr Gln Gly Val Pro Lys Asp
        115                 120                 125

Tyr Thr Gly Asp Asp Val Asn Val Asp Asn Leu Phe Ala Val Ile Leu
            130                 135                 140

Gly Asp Lys Thr Ala Val Lys Gly Gly Ser Gly Lys Val Val Asp Ser
145                 150                 155                 160

Gly Pro Asn Asp His Ile Phe Ile Phe Tyr Ser Asp His Gly Gly Pro
                165                 170                 175

Gly Val Leu Gly Met Pro Thr Ser Pro Tyr Leu Tyr Ala Asn Asp Leu
            180                 185                 190

Asn Asp Val Leu Lys Lys His Ala Leu Gly Thr Tyr Lys Ser Leu
                195                 200                 205

Val Phe Tyr Leu Glu Ala Cys Glu Ser Gly Ser Ile Phe Glu Gly Leu
210                 215                 220

Leu Pro Glu Gly Leu Asn Ile Tyr Ala Thr Thr Ala Ser Asn Ala Glu
225                 230                 235                 240

Glu Ser Ser Trp Gly Thr Tyr Cys Pro Gly Glu Pro Ser Pro Pro
                245                 250                 255

Pro Glu Tyr Glu Thr Cys Leu Gly Asp Leu Tyr Ser Val Ala Trp Met
            260                 265                 270

Glu Asp Ser Gly Met His Asn Leu Gln Thr Glu Thr Leu His Gln Gln
            275                 280                 285

Tyr Glu Leu Val Lys Arg Arg Thr Ala Pro Val Gly Tyr Ser Tyr Gly
            290                 295                 300

Ser His Val Met Gln Tyr Gly Asp Val Gly Ile Ser Lys Asp Asn Leu
305                 310                 315                 320

Asp Leu Tyr Met Gly Thr Asn Pro Ala Asn Asp Asn Phe Thr Phe Ala
                325                 330                 335

Asp Ala Asn Ser Leu Lys Pro Pro Ser Arg Val Thr Asn Gln Arg Asp
            340                 345                 350

Ala Asp Leu Val His Phe Trp Glu Lys Tyr Arg Lys Ala Pro Glu Gly
            355                 360                 365

Ser Ala Arg Lys Thr Glu Ala Gln Lys Gln Val Leu Glu Ala Met Ser
370                 375                 380

His Arg Leu His Ile Asp Asn Ser Val Ile Leu Val Gly Lys Ile Leu
385                 390                 395                 400

Phe Gly Ile Ser Arg Gly Pro Glu Val Leu Asn Lys Val Arg Ser Ala
                405                 410                 415

Gly Gln Pro Leu Val Asp Asp Trp Asn Cys Leu Lys Asn Gln Val Arg
            420                 425                 430

Ala Phe Glu Arg His Cys Gly Ser Leu Ser Gln Tyr Gly Ile Lys His
            435                 440                 445

Met Arg Ser Phe Ala Asn Ile Cys Asn Ala Gly Ile Gln Met Glu Gln
450                 455                 460

Met Glu Glu Ala Ala Ser Gln Ala Cys Thr Thr Leu Pro Thr Gly Pro
465                 470                 475                 480

Trp Ser Ser Leu Asn Arg Gly Phe Ser Ala
                485                 490

<210> SEQ ID NO 63
<211> LENGTH: 484
<212> TYPE: PRT
<213> ORGANISM: Nicotiana tabacum

<400> SEQUENCE: 63

Met Ile Val Arg Tyr Val Val Ser Ala Ile Leu Ile Ile Gly Leu Ser
1               5                   10                  15

```
Val Val Ala Ala Val Asp Gly Arg Asp Val Leu Lys Leu Pro Ser Glu
            20              25              30

Ala Ser Thr Phe Phe Ser Gly Asn Tyr Asp Asp Ser Ile Gly Thr
        35              40              45

Lys Trp Ala Val Leu Val Ala Gly Ser Arg Gly Tyr Trp Asn Tyr Arg
 50              55              60

His Gln Ala Asp Val Cys His Ala Tyr Gln Leu Leu Lys Lys Gly Gly
 65              70              75              80

Leu Lys Asp Glu Asn Ile Ile Val Phe Met Tyr Asp Asp Ile Ala His
            85              90              95

Asn Phe Glu Asn Pro Arg Pro Gly Val Ile Ile Asn Ser Pro Asn Gly
            100             105             110

Asp Asp Val Tyr Lys Gly Val Pro Lys Asp Tyr Thr Gly His His Val
            115             120             125

Thr Ala Asn Asn Phe Leu Ala Val Ile Leu Gly Asn Lys Ala Ala Leu
 130             135             140

Ser Gly Gly Ser Gly Lys Val Val Glu Ser Gly Pro Asn Asp His Ile
 145             150             155             160

Phe Ile Phe Tyr Ser Asp His Gly Gly Pro Gly Val Leu Gly Met Pro
            165             170             175

Ser Gly Pro Tyr Leu Tyr Ala Asp Asp Leu Ile Asp Val Leu Lys Arg
            180             185             190

Lys His Ala Ser Gly Thr Tyr Lys Ser Leu Val Phe Tyr Ile Glu Ala
            195             200             205

Cys Glu Ser Gly Ser Ile Phe Glu Gly Leu Leu Pro Glu Gly Leu Asn
            210             215             220

Ile Tyr Ala Thr Thr Ala Ser Asn Ala Glu Glu Asp Ser Trp Gly Thr
225             230             235             240

Tyr Cys Pro Gly Asp Tyr Pro Gly Pro Pro Glu Tyr Gln Thr Cys
            245             250             255

Leu Gly Asp Leu Tyr Ala Val Ser Trp Met Glu Asp Ser Glu Lys His
            260             265             270

Asn Leu Arg Arg Glu Thr Leu Gly Met Gln Tyr Glu Leu Val Lys Arg
            275             280             285

Arg Thr Ala Asn Ser Phe Pro Tyr Ala Ser His Val Met Gln Tyr
            290             295             300

Gly Asp Leu Lys Leu Met Asp Asp Pro Leu Ser Leu Tyr Met Gly Thr
305             310             315             320

Asn Pro Ala Asn Asp Asn Tyr Thr Phe Leu Asp Glu Asn Ser Ser Leu
            325             330             335

Leu Ser Ala Lys Pro Val Asn Gln Arg Asp Ala Asp Leu Leu His Phe
            340             345             350

Trp Asp Lys Phe Leu Lys Ala Pro Gln Gly Ser Val Arg Lys Val Glu
            355             360             365

Ala Gln Lys Gln Leu Ser Glu Ala Met Ser His Arg Met His Ile Asp
            370             375             380

Asp Ser Ile Ala Leu Val Gly Arg Leu Leu Phe Gly Ile Glu Lys Gly
385             390             395             400

Pro Asp Val Leu Ile Arg Val Arg Pro Thr Gly Glu Pro Leu Val Asp
            405             410             415

Asp Trp Asn Cys Leu Lys Ser Phe Val Arg Thr Phe Glu Thr Arg Cys
            420             425             430
```

```
Gly Ser Leu Ser Gln Tyr Gly Met Lys His Met Arg Ala Val Ala Asn
            435                 440                 445

Ile Cys Asn Ser Cys Ile Thr Met Glu Gln Ile Ala Lys Ala Ser Ala
    450                 455                 460

Gln Ala Cys Val Ser Ile Pro Ser Asn Ser Trp Ser Ser Leu Asp Glu
465                 470                 475                 480

Gly Phe Ser Ala

<210> SEQ ID NO 64
<211> LENGTH: 478
<212> TYPE: PRT
<213> ORGANISM: Arabidopsis thaliana

<400> SEQUENCE: 64

Met Thr Thr Val Val Ser Phe Leu Ala Leu Phe Leu Phe Leu Val Ala
1               5                   10                  15

Ala Val Ser Gly Asp Val Ile Lys Leu Pro Ser Leu Ala Ser Lys Phe
                20                  25                  30

Phe Arg Pro Thr Glu Asn Asp Asp Ser Thr Lys Trp Ala Val Leu
        35                  40                  45

Val Ala Gly Ser Ser Gly Tyr Trp Asn Tyr Arg His Gln Ala Asp Val
    50                  55                  60

Cys His Ala Tyr Gln Leu Leu Lys Lys Gly Val Lys Glu Glu Asn
65                  70                  75                  80

Ile Val Val Phe Met Tyr Asp Asp Ile Ala Lys Asn Glu Glu Asn Pro
                85                  90                  95

Arg Pro Gly Val Ile Ile Asn Ser Pro Asn Gly Glu Asp Val Tyr Asn
            100                 105                 110

Gly Val Pro Lys Asp Tyr Thr Gly Asp Glu Val Asn Val Asp Asn Leu
        115                 120                 125

Leu Ala Val Ile Leu Gly Asn Lys Thr Ala Leu Lys Gly Gly Ser Gly
    130                 135                 140

Lys Val Val Asp Ser Gly Pro Asn Asp His Ile Phe Ile Tyr Tyr Ser
145                 150                 155                 160

Asp His Gly Gly Pro Gly Val Leu Gly Met Pro Thr Ser Pro Asn Leu
                165                 170                 175

Tyr Ala Asn Asp Leu Asn Asp Val Leu Lys Lys Lys Tyr Ala Ser Gly
            180                 185                 190

Thr Tyr Lys Ser Leu Val Phe Tyr Leu Glu Ala Cys Glu Ser Gly Ser
        195                 200                 205

Ile Phe Glu Gly Leu Leu Pro Glu Gly Leu Asn Ile Tyr Ala Thr Thr
    210                 215                 220

Ala Ser Asn Ala Glu Glu Ser Ser Trp Gly Thr Tyr Cys Pro Gly Glu
225                 230                 235                 240

Asp Pro Ser Pro Pro Ser Glu Tyr Glu Thr Cys Leu Gly Asp Leu Tyr
                245                 250                 255

Ser Val Ala Trp Ile Glu Asp Ser Glu Lys His Asn Leu Gln Thr Glu
            260                 265                 270

Thr Leu His Glu Gln Tyr Glu Leu Val Lys Arg Thr Ala Gly Ser
        275                 280                 285

Gly Lys Ser Tyr Gly Ser His Val Met Glu Phe Gly Asp Ile Gly Leu
    290                 295                 300

Ser Lys Glu Lys Leu Val Leu Phe Met Gly Thr Asn Pro Ala Asp Glu
305                 310                 315                 320
```

```
Asn Phe Thr Phe Val Asn Glu Asn Ser Ile Arg Pro Pro Ser Arg Val
                325                 330                 335

Thr Asn Gln Arg Asp Ala Asp Leu Val His Phe Trp His Lys Tyr Gln
            340                 345                 350

Lys Ala Pro Glu Gly Ser Ala Arg Lys Val Glu Ala Gln Lys Gln Val
        355                 360                 365

Leu Glu Ala Met Ser His Arg Leu His Val Asp Asn Ser Ile Leu Leu
    370                 375                 380

Ile Gly Ile Leu Leu Phe Gly Leu Glu Gly His Ala Val Leu Asn Lys
385                 390                 395                 400

Val Arg Pro Ser Gly Glu Pro Leu Val Asp Asp Trp Asp Cys Leu Lys
                405                 410                 415

Ser Leu Val Arg Ala Phe Glu Arg His Cys Gly Ser Leu Ser Gln Tyr
            420                 425                 430

Gly Ile Lys His Met Arg Ser Ile Ala Asn Met Cys Asn Ala Gly Ile
        435                 440                 445

Gln Met Arg Gln Met Glu Glu Ala Ala Met Gln Ala Cys Pro Thr Ile
    450                 455                 460

Pro Thr Ser Pro Trp Ser Ser Leu Asp Arg Gly Phe Ser Ala
465                 470                 475

<210> SEQ ID NO 65
<211> LENGTH: 478
<212> TYPE: PRT
<213> ORGANISM: Genlisea aurea

<400> SEQUENCE: 65

Ile Val Leu Leu Leu Ser Val Ser Ile Leu Thr Ser Asp Cys Arg
1               5                   10                  15

Asn Gln Phe Ile Lys Leu Pro Ser Glu Val Phe Ser Tyr Gly Gly Glu
                20                  25                  30

Ser Glu Asp Asp Ser Val Gly Thr Arg Trp Ala Val Leu Val Ala Gly
            35                  40                  45

Ser Ser Gly Tyr Trp Asn Tyr Arg His Gln Ala Asp Val Cys His Ala
        50                  55                  60

Tyr Gln Ile Leu Lys Arg Gly Gly Leu Lys Asp Glu Asn Ile Ile Val
65                  70                  75                  80

Phe Met Tyr Asp Asp Ile Ala Gln Asn Leu Glu Asn Pro Arg Pro Gly
                85                  90                  95

Ile Val Ile Asn Asn Pro His Gly Glu Asp Val Tyr His Gly Val Pro
            100                 105                 110

Lys Asp Tyr Val Gly Arg Gln Val Thr Ala His Asn Phe Tyr Ser Val
        115                 120                 125

Leu Leu Gly Asp Lys Ala Gly Leu Thr Gly Gly Ser Gly Lys Val Ile
    130                 135                 140

Glu Ser Gly Pro Asn Asp His Ile Phe Ile Tyr Tyr Thr Asp His Gly
145                 150                 155                 160

Gly Pro Gly Val Leu Gly Met Pro Ser Gly Pro Tyr Ile Tyr Ala Asp
                165                 170                 175

Asp Leu Asn Asp Val Leu Lys Lys Lys His Ala Ser Gly Thr Tyr Lys
            180                 185                 190

Ser Leu Val Phe Tyr Leu Glu Ala Cys Glu Ser Gly Ser Ile Phe Glu
        195                 200                 205

Gly Ile Leu Pro Asp Asn Leu Asn Ile Tyr Ala Thr Thr Ala Ser Asn
    210                 215                 220
```

Ala Glu Glu Ser Ser Trp Gly Thr Tyr Cys Pro Gly Asp Ile Ile Ala
225                 230                 235                 240

Pro Pro Leu Glu Tyr Asp Thr Cys Leu Gly Asp Leu Tyr Ser Ile Ala
            245                 250                 255

Trp Met Glu Asp Ser Asp Ile His Asn Leu Arg Thr Glu Ser Leu Glu
        260                 265                 270

Gln Gln Tyr Gln Val Val Lys Lys Arg Thr Ala Asn Gly Asp Ser Tyr
    275                 280                 285

Tyr Gly Ser His Val Met Gln Tyr Gly Glu Leu Lys Leu Asp Leu Glu
290                 295                 300

Asn Leu Phe Leu Tyr Leu Gly Thr Asp Pro Ala Asn Asp Asn Tyr Thr
305                 310                 315                 320

Phe Val Glu Gly Asn Ser Leu Ser Thr Ser Pro Ser Gly Arg Val Asn
                325                 330                 335

Gln Arg Asp Ala Asp Leu Leu His Phe Trp His Lys Phe Trp Lys Ala
            340                 345                 350

Pro Glu Arg Ser Ser Glu Lys Asp Glu Ala Gln Arg Leu Ala Glu
        355                 360                 365

Val Val Ser His Arg Ser His Ile Asp Asp Ser Ile Glu Leu Ile Gly
370                 375                 380

Asp Leu Leu Phe Gly Ser Thr Glu Gly Thr Arg Val Leu Lys His Val
385                 390                 395                 400

Arg Pro Ser Gly Arg Pro Val Val Asp Asp Trp Asp Cys Leu Arg Ser
                405                 410                 415

Leu Val Arg Thr Phe Glu Thr Tyr Cys Gly Ser Leu Ser Gln Tyr Gly
            420                 425                 430

Met Lys His Met Arg Ser Phe Ala Asn Ile Cys Asn Ser Gly Val Lys
        435                 440                 445

Ala Glu Lys Met Gly Glu Ala Thr Gln Gln Val Cys Thr Ala Phe Pro
    450                 455                 460

Ser His Asn Pro Trp Ser Ser Leu His Arg Gly Phe Ser Ala
465                 470                 475

<210> SEQ ID NO 66
<211> LENGTH: 486
<212> TYPE: PRT
<213> ORGANISM: Zea mays

<400> SEQUENCE: 66

Met Val Ala Ala Arg Leu Arg Leu Ala Leu Leu Leu Ser Val Cys Leu
1               5                   10                  15

Cys Ser Ala Trp Ala Arg Pro Arg Leu Glu Thr Ala Ile Arg Leu Pro
            20                  25                  30

Ser Gln Arg Ala Ala Ala Ala Asp Glu Thr Asp Asp Gly Ala Val Gly
        35                  40                  45

Thr Arg Trp Ala Val Leu Ile Ala Gly Ser Ser Gly Tyr Tyr Asn Tyr
    50                  55                  60

Arg His Gln Ala Asp Ile Cys His Ala Tyr Gln Ile Met Lys Lys Gly
65                  70                  75                  80

Gly Leu Lys Asp Glu Asn Ile Ile Val Phe Met Tyr Asp Asp Ile Ala
                85                  90                  95

His Ser Pro Glu Asn Pro Arg Pro Gly Val Ile Ile Asn His Pro Gln
            100                 105                 110

Gly Gly Asp Val Tyr Ala Gly Val Pro Lys Asp Tyr Thr Gly Arg Asp

```
            115                 120                 125
Val Asn Val Asp Asn Phe Phe Ala Val Leu Leu Gly Asn Lys Thr Ala
130                 135                 140

Leu Arg Gly Gly Ser Gly Lys Val Val Asp Ser Gly Pro Asp Asp His
145                 150                 155                 160

Ile Phe Val Phe Tyr Ser Asp His Gly Gly Pro Gly Val Leu Gly Met
                165                 170                 175

Pro Thr Tyr Pro Tyr Leu Tyr Gly Asp Asp Leu Val Asp Val Leu Lys
            180                 185                 190

Lys Lys His Ala Ala Gly Thr Tyr Lys Ser Leu Val Phe Tyr Leu Glu
        195                 200                 205

Ala Cys Glu Ser Gly Ser Ile Phe Glu Gly Leu Leu Pro Asn Asp Ile
    210                 215                 220

Asn Val Tyr Ala Thr Thr Ala Ser Asn Ala Glu Glu Ser Ser Trp Gly
225                 230                 235                 240

Thr Tyr Cys Pro Gly Glu Phe Pro Ser Pro Pro Glu Tyr Asp Thr
                245                 250                 255

Cys Leu Gly Asp Leu Tyr Ser Val Ala Trp Met Glu Asp Ser Asp Phe
                260                 265                 270

His Asn Leu Arg Thr Glu Ser Leu Lys Gln Gln Tyr Lys Leu Val Lys
            275                 280                 285

Asp Arg Thr Ala Val His Asp Thr Phe Ser Tyr Gly Ser His Val Met
290                 295                 300

Gln Tyr Gly Ala Leu Glu Leu Asn Val Gln Arg Leu Phe Ser Tyr Ile
305                 310                 315                 320

Gly Thr Asp Pro Ala Asn Asp Gly Asn Thr Phe Ile Glu Asp Asn Ser
                325                 330                 335

Leu Pro Ser Phe Ser Lys Ala Val Asn Gln Arg Asp Ala Asp Leu Val
                340                 345                 350

Tyr Phe Trp Gln Lys Tyr Arg Lys Leu Ala Asp Ser Ser Pro Pro Lys
            355                 360                 365

Ser Glu Ala Arg Lys Glu Leu Leu Glu Val Met Ala His Arg Ser His
        370                 375                 380

Val Asp Ser Ser Val Glu Leu Ile Gly Ser Leu Leu Phe Gly Ser Glu
385                 390                 395                 400

Asp Gly Pro Arg Val Leu Lys Ala Val Arg Ala Pro Gly Glu Pro Leu
                405                 410                 415

Val Asp Asp Trp Ser Cys Leu Lys Ser Ile Val Arg Thr Phe Glu Ala
                420                 425                 430

Arg Cys Gly Ser Leu Ala Gln Tyr Gly Met Lys His Met Arg Ser Phe
            435                 440                 445

Ala Asn Met Cys Asn Ala Gly Ile Leu Pro Glu Ala Val Ser Lys Val
        450                 455                 460

Thr Ala Gln Ala Cys Ser Ser Ile Pro Ser Asn Pro Trp Ser Ser Ile
465                 470                 475                 480

His Lys Gly Phe Ser Ala
                485

<210> SEQ ID NO 67
<211> LENGTH: 486
<212> TYPE: PRT
<213> ORGANISM: Zea mays

<400> SEQUENCE: 67
```

```
Met Val Ala Ala Arg Leu Arg Leu Ser Leu Leu Ser Val Cys Leu
 1               5                  10                  15

Ser Ser Ala Trp Ala Arg Pro Arg Leu Glu Pro Ala Ile Arg Leu Pro
             20                  25                  30

Ser Gln Arg Ala Ala Ala Asp Glu Thr Asp Asp Gly Asp Val Gly
             35                  40                  45

Thr Arg Trp Ala Val Leu Ile Ala Gly Ser Ser Gly Tyr Tyr Asn Tyr
 50                  55                  60

Arg His Gln Ala Asp Ile Cys His Ala Tyr Gln Ile Met Lys Lys Gly
 65                  70                  75                  80

Gly Leu Lys Asp Glu Asn Ile Ile Val Phe Met Tyr Asp Asp Ile Ala
                 85                  90                  95

His Ser Pro Glu Asn Pro Arg Pro Gly Val Ile Ile Asn His Pro Gln
             100                 105                 110

Gly Gly Asp Val Tyr Ala Gly Val Pro Lys Asp Tyr Thr Gly Arg Asp
             115                 120                 125

Val Asn Val Asp Asn Phe Phe Ala Val Leu Leu Gly Asn Lys Thr Ala
130                 135                 140

Leu Arg Gly Gly Ser Gly Lys Val Val Asp Ser Gly Pro Asn Asp His
145                 150                 155                 160

Ile Phe Val Phe Tyr Ser Asp His Gly Gly Pro Gly Val Leu Gly Met
                 165                 170                 175

Pro Thr Tyr Pro Tyr Leu Tyr Gly Asp Asp Leu Val Asp Val Leu Lys
             180                 185                 190

Lys Lys His Ala Ala Gly Thr Tyr Lys Ser Leu Val Phe Tyr Leu Glu
             195                 200                 205

Ala Cys Glu Ser Gly Ser Ile Phe Glu Gly Leu Leu Pro Asn Asp Ile
210                 215                 220

Asn Val Tyr Ala Thr Thr Ala Ser Asn Ala Asp Glu Ser Ser Trp Gly
225                 230                 235                 240

Thr Tyr Cys Pro Gly Glu Phe Pro Ser Pro Pro Glu Tyr Asp Thr
             245                 250                 255

Cys Leu Gly Asp Leu Tyr Ser Val Ala Trp Met Glu Asp Ser Asp Phe
             260                 265                 270

His Asn Leu Arg Thr Glu Ser Leu Lys Gln Gln Tyr Lys Leu Val Lys
             275                 280                 285

Asp Arg Thr Ala Val His Asp Thr Phe Ser Tyr Gly Ser His Val Met
             290                 295                 300

Gln Tyr Gly Ala Leu Glu Leu Asn Val Gln Arg Leu Phe Ser Tyr Ile
305                 310                 315                 320

Gly Thr Asp Pro Ala Asn Asp Gly Asn Thr Phe Ile Glu Asp Asn Ser
             325                 330                 335

Leu Pro Ser Phe Ser Lys Ala Val Asn Gln Arg Asp Ala Asp Leu Val
             340                 345                 350

Tyr Phe Trp Gln Lys Tyr Arg Lys Leu Ala Asp Ser Ser His Ala Lys
             355                 360                 365

Asn Glu Ala Arg Lys Glu Leu Leu Glu Val Met Ala His Arg Ser His
             370                 375                 380

Val Asp Ser Ser Val Glu Leu Ile Gly Ser Leu Leu Phe Gly Ser Glu
385                 390                 395                 400

Asp Gly Pro Arg Val Leu Lys Ala Val Arg Ala Pro Gly Glu Pro Leu
             405                 410                 415

Val Asp Asp Trp Ser Cys Leu Lys Ser Ile Val Arg Thr Phe Glu Ala
```

```
                420             425             430
Arg Cys Gly Ser Leu Ala Gln Tyr Gly Met Lys His Met Arg Ser Phe
            435                 440                 445

Ala Asn Met Cys Asn Ala Gly Ile Leu Pro Glu Ala Val Ser Lys Val
            450                 455                 460

Ala Ala Gln Ala Cys Ser Ser Ile Pro Ser Asn Pro Trp Ser Ser Ile
465                 470                 475                 480

His Lys Gly Phe Ser Ala
                485

<210> SEQ ID NO 68
<211> LENGTH: 488
<212> TYPE: PRT
<213> ORGANISM: Saccharum officinarum

<400> SEQUENCE: 68

Met Val Thr Ala Arg Leu Arg Leu Ala Leu Leu Leu Ser Val Phe
1               5                   10                  15

Leu Cys Ser Ala Trp Ala Arg Pro Arg Leu Glu Pro Thr Ile Arg Leu
                20                  25                  30

Pro Ser Glu Arg Ala Ala Ala Ala Gly Asp Glu Thr Asp Asp Ala
            35                  40                  45

Val Gly Thr Arg Trp Ala Val Leu Val Ala Gly Ser Ser Gly Tyr Tyr
    50                  55                  60

Asn Tyr Arg His Gln Ala Asp Ile Cys His Ala Tyr Gln Ile Met Lys
65                  70                  75                  80

Lys Gly Gly Leu Lys Asp Glu Asn Ile Ile Val Phe Met Tyr Asp Asp
                85                  90                  95

Ile Ala His Ser Ala Glu Asn Pro Arg Pro Gly Val Val Ile Asn His
                100                 105                 110

Pro Gln Gly Gly Asp Val Tyr Ala Gly Val Pro Lys Asp Tyr Thr Gly
            115                 120                 125

Arg Gln Val Ser Val Asn Asn Phe Phe Ala Val Leu Leu Gly Asn Lys
130                 135                 140

Thr Ala Leu Thr Gly Gly Ser Gly Lys Val Val Asp Ser Gly Pro Asn
145                 150                 155                 160

Asp His Ile Phe Val Phe Tyr Ser Asp His Gly Gly Pro Gly Val Leu
                165                 170                 175

Gly Met Pro Thr Tyr Pro Tyr Leu Tyr Gly Asp Asp Leu Val Asp Val
            180                 185                 190

Leu Lys Lys Lys His Ala Ala Gly Ser Tyr Lys Ser Leu Val Phe Tyr
        195                 200                 205

Leu Glu Ala Cys Glu Ser Gly Ser Ile Phe Glu Gly Leu Leu Pro Asp
    210                 215                 220

Asp Ile Asn Val Tyr Ala Thr Thr Ala Ser Asn Ala Glu Glu Ser Ser
225                 230                 235                 240

Trp Gly Thr Tyr Cys Pro Gly Glu Phe Pro Ser Pro Pro Glu Tyr
                245                 250                 255

Asp Thr Cys Leu Gly Asp Leu Tyr Ser Val Ser Trp Met Glu Asp Ser
            260                 265                 270

Asp Phe His Asn Leu Arg Thr Glu Ser Leu Lys Gln Gln Tyr Lys Leu
        275                 280                 285

Val Lys Asp Arg Thr Ala Ala Gln Asp Thr Phe Ser Tyr Gly Ser His
    290                 295                 300
```

```
Val Met Gln Tyr Gly Ser Leu Glu Leu Asn Val Gln Lys Leu Phe Ser
305                 310                 315                 320

Tyr Ile Gly Thr Asn Pro Ala Asn Asp Gly Asn Thr Phe Val Glu Asp
            325                 330                 335

Asn Ser Leu Pro Ser Phe Ser Lys Ala Val Asn Gln Arg Asp Ala Asp
        340                 345                 350

Leu Val Tyr Phe Trp Gln Lys Tyr Arg Lys Leu Ala Asp Gly Ser Ser
    355                 360                 365

Lys Lys Asn Glu Ala Arg Lys Glu Leu Leu Val Met Ser His Arg
370                 375                 380

Ser His Val Asp Asn Ser Val Glu Leu Ile Gly Ser Leu Leu Phe Gly
385                 390                 395                 400

Ser Glu Asp Gly Pro Arg Val Leu Lys Ala Val Arg Ala Ala Gly Glu
                405                 410                 415

Pro Leu Val Asp Asp Trp Ser Cys Leu Lys Ser Met Val Arg Thr Phe
            420                 425                 430

Glu Ala Gln Cys Gly Ser Leu Ala Gln Tyr Gly Met Lys His Met Arg
                435                 440                 445

Thr Phe Ala Asn Ile Cys Asn Ala Gly Ile Leu Pro Glu Ala Val Ser
    450                 455                 460

Lys Val Ala Ala Gln Ala Cys Thr Ser Ile Pro Ser Asn Pro Trp Ser
465                 470                 475                 480

Ser Ile Asp Lys Gly Phe Ser Ala
                485

<210> SEQ ID NO 69
<211> LENGTH: 486
<212> TYPE: PRT
<213> ORGANISM: Zea mays

<400> SEQUENCE: 69

Met Val Ala Ala Arg Leu Arg Leu Ala Leu Leu Leu Ser Val Cys Leu
1               5                   10                  15

Cys Ser Ala Trp Ala Arg Pro Arg Leu Glu Thr Ala Ile Arg Leu Pro
            20                  25                  30

Ser Gln Arg Ala Ala Ala Ala Asp Glu Thr Asp Asp Gly Ala Val Gly
        35                  40                  45

Thr Arg Trp Ala Val Leu Ile Ala Gly Ser Ser Gly Tyr Tyr Asn Tyr
    50                  55                  60

Arg His Gln Ala Asp Ile Cys His Ala Tyr Gln Ile Met Lys Lys Gly
65                  70                  75                  80

Gly Leu Lys Asp Glu Asn Ile Ile Val Phe Met Tyr Asp Asp Ile Ala
                85                  90                  95

His Ser Pro Glu Asn Pro Arg Pro Gly Val Ile Ile Asn His Pro Gln
            100                 105                 110

Gly Gly Asp Val Tyr Ala Gly Val Pro Lys Asp Tyr Thr Gly Arg Asp
        115                 120                 125

Val Asn Val Asp Asn Phe Phe Ala Val Leu Leu Gly Asn Lys Thr Ala
    130                 135                 140

Leu Arg Gly Gly Ser Gly Lys Val Val Asp Ser Gly Pro Asp His
145                 150                 155                 160

Ile Phe Val Phe Tyr Ser Asp His Gly Gly Pro Gly Val Leu Gly Met
                165                 170                 175

Pro Thr Tyr Pro Tyr Leu Tyr Gly Asp Asp Leu Val Asp Val Leu Lys
            180                 185                 190
```

```
Lys Lys His Ala Ala Gly Thr Tyr Lys Ser Leu Val Phe Tyr Leu Glu
            195                 200                 205

Ala Cys Glu Ser Gly Ser Ile Phe Glu Gly Leu Leu Pro Asn Asp Ile
210                 215                 220

Asn Val Tyr Ala Thr Thr Ala Ser Asn Ala Glu Glu Ser Ser Trp Gly
225                 230                 235                 240

Thr Tyr Cys Pro Gly Glu Phe Pro Ser Pro Pro Glu Tyr Asp Thr
                245                 250                 255

Cys Leu Gly Asp Leu Tyr Ser Val Ala Trp Met Glu Asp Ser Asp Phe
                260                 265                 270

His Asn Leu Arg Thr Glu Ser Leu Lys Gln Gln Tyr Lys Leu Val Lys
            275                 280                 285

Asp Arg Thr Ala Val His Asp Thr Phe Ser Tyr Gly Ser His Val Met
290                 295                 300

Gln Tyr Gly Ala Leu Glu Leu Asn Val Gln His Leu Phe Ser Tyr Ile
305                 310                 315                 320

Gly Thr Asp Pro Ala Asn Asp Gly Asn Thr Phe Ile Glu Asp Asn Ser
                325                 330                 335

Leu Pro Ser Phe Ser Lys Ala Val Asn Gln Arg Asp Ala Asp Leu Val
            340                 345                 350

Tyr Phe Trp Gln Lys Tyr Arg Lys Phe Ala Asp Ser Pro Pro Ala Lys
            355                 360                 365

Ser Glu Ala Arg Lys Glu Leu Leu Glu Val Met Ala His Arg Ser His
370                 375                 380

Val Asp Ser Ser Val Glu Leu Ile Gly Ser Leu Leu Phe Gly Ser Glu
385                 390                 395                 400

Asp Gly Pro Arg Val Leu Lys Ala Val Arg Ala Pro Gly Glu Pro Leu
                405                 410                 415

Val Asp Asp Trp Ser Cys Leu Lys Ser Ile Val Arg Thr Phe Glu Ala
                420                 425                 430

Arg Cys Gly Ser Leu Ala Gln Tyr Gly Met Lys His Met Arg Ser Phe
            435                 440                 445

Ala Asn Met Cys Asn Ala Gly Ile Leu Pro Glu Ala Val Ser Lys Val
            450                 455                 460

Ala Ala Gln Ala Cys Ser Ser Ile Pro Ser Asn Pro Trp Ser Ser Ile
465                 470                 475                 480

His Lys Gly Phe Ser Ala
                485

<210> SEQ ID NO 70
<211> LENGTH: 481
<212> TYPE: PRT
<213> ORGANISM: Sorghum bicolor

<400> SEQUENCE: 70

Met Val Ala Ala Arg Leu Arg Leu Ala Leu Leu Leu Leu Leu Pro Val
1               5                   10                  15

Phe Leu Cys Ser Ala Trp Ala Arg Pro Arg Leu Glu Pro Thr Ile Arg
            20                  25                  30

Leu Pro Ser Asp Arg Ala Asp Ala Val Gly Thr Arg Trp Ala Val
            35                  40                  45

Leu Val Ala Gly Ser Asn Gly Tyr Tyr Asn Tyr Arg His Gln Ala Asp
50                  55                  60

Ile Cys His Ala Tyr Gln Ile Met Lys Lys Gly Gly Leu Lys Asp Glu
```

```
                65                  70                  75                  80
            Asn Ile Ile Val Phe Met Tyr Asp Asp Ile Ala His Ser Pro Glu Asn
                            85                  90                  95
            Pro Arg Pro Gly Val Leu Ile Asn His Pro Gln Gly Gly Asp Val Tyr
                            100                 105                 110
            Ala Gly Val Pro Lys Asp Tyr Thr Gly Arg Glu Val Ser Val Asn Asn
                            115                 120                 125
            Phe Phe Ala Val Leu Leu Gly Asn Lys Thr Ala Leu Lys Gly Gly Ser
                            130                 135                 140
            Gly Lys Val Val Asp Ser Gly Pro Asn Asp His Ile Phe Val Phe Tyr
            145                 150                 155                 160
            Ser Asp His Gly Gly Pro Gly Val Leu Gly Met Pro Thr Tyr Pro Tyr
                            165                 170                 175
            Leu Tyr Gly Asp Asp Leu Val Asp Val Leu Lys Lys His Ala Ala
                            180                 185                 190
            Gly Thr Tyr Lys Ser Leu Val Phe Tyr Leu Glu Ala Cys Glu Ser Gly
                            195                 200                 205
            Ser Ile Phe Glu Gly Leu Leu Pro Asp Asp Ile Asn Val Tyr Ala Thr
                            210                 215                 220
            Thr Ala Ser Asn Ala Glu Glu Ser Ser Trp Gly Thr Tyr Cys Pro Gly
            225                 230                 235                 240
            Glu Phe Pro Ser Pro Pro Glu Tyr Asp Thr Cys Leu Gly Asp Leu
                            245                 250                 255
            Tyr Ser Val Ser Trp Met Glu Asp Ser Asp Phe His Asn Leu Arg Thr
                            260                 265                 270
            Glu Ser Leu Lys Gln Gln Tyr Lys Leu Val Lys Asp Arg Thr Ala Val
                            275                 280                 285
            Gln Asp Thr Phe Ser Tyr Gly Ser His Val Met Gln Tyr Gly Ser Leu
                            290                 295                 300
            Glu Leu Asn Val Gln Lys Leu Phe Ser Tyr Ile Gly Thr Asn Pro Ala
            305                 310                 315                 320
            Asn Asp Gly Asn Thr Phe Val Glu Asp Asn Ser Leu Pro Ser Phe Ser
                            325                 330                 335
            Lys Ala Val Asn Gln Arg Asp Ala Asp Leu Val Tyr Phe Trp Gln Lys
                            340                 345                 350
            Tyr Arg Lys Leu Ala Asp Asp Ser Ser Lys Asn Glu Ala Arg Lys
                            355                 360                 365
            Glu Leu Leu Glu Val Met Ala His Arg Ser His Val Asp Asn Ser Val
            370                 375                 380
            Glu Leu Ile Gly Ser Leu Leu Phe Gly Ser Glu Asp Gly Pro Arg Val
            385                 390                 395                 400
            Leu Lys Ala Val Arg Ala Ala Gly Glu Pro Leu Val Asp Asp Trp Ser
                            405                 410                 415
            Cys Leu Lys Ser Met Val Arg Thr Phe Glu Ala Gln Cys Gly Ser Leu
                            420                 425                 430
            Ala Gln Tyr Gly Met Lys His Met Arg Ser Phe Ala Asn Ile Cys Asn
                            435                 440                 445
            Ala Gly Ile Leu Pro Glu Ala Val Ser Lys Val Ala Ala Gln Ala Cys
                            450                 455                 460
            Thr Ser Ile Pro Ser Asn Pro Trp Ser Ser Ile Asp Lys Gly Phe Ser
            465                 470                 475                 480
            Ala
```

<210> SEQ ID NO 71
<211> LENGTH: 488
<212> TYPE: PRT
<213> ORGANISM: Saccharum hybrid cultivar SP80-3280

<400> SEQUENCE: 71

```
Met Val Ala Ala Arg Leu Arg Leu Ala Leu Leu Leu Leu Ser Val Cys
1               5                   10                  15

Leu Cys Ser Ala Trp Ala Arg Pro Arg Leu Glu Pro Thr Ile Arg Leu
            20                  25                  30

Pro Ser Glu Arg Ala Ala Ala Ala Gly Asp Glu Thr Asp Asp Ala
        35                  40                  45

Val Gly Thr Arg Trp Ala Val Leu Val Ala Gly Ser Ser Gly Tyr Tyr
    50                  55                  60

Asn Tyr Arg His Gln Ala Asp Ile Cys His Ala Tyr Gln Ile Met Lys
65                  70                  75                  80

Lys Gly Gly Leu Lys Asp Glu Asn Ile Ile Val Phe Met Tyr Asp Asp
                85                  90                  95

Ile Ala His Ser Ala Glu Asn Pro Arg Pro Gly Val Val Ile Asn His
            100                 105                 110

Pro Gln Gly Gly Asp Val Tyr Ala Gly Val Pro Lys Asp Tyr Thr Gly
        115                 120                 125

Arg Gln Val Ser Val Asn Asn Phe Phe Ala Val Leu Leu Gly Asn Lys
    130                 135                 140

Thr Ala Leu Thr Gly Gly Ser Gly Lys Val Val Asp Ser Gly Pro Asn
145                 150                 155                 160

Asp His Ile Phe Val Phe Tyr Ser Asp His Gly Gly Pro Gly Val Leu
                165                 170                 175

Gly Met Pro Thr Tyr Pro Tyr Leu Tyr Gly Asp Asp Leu Val Asp Val
            180                 185                 190

Leu Lys Lys Lys His Ala Ala Gly Thr Tyr Lys Ser Leu Val Phe Tyr
        195                 200                 205

Leu Glu Ala Cys Glu Ser Gly Ser Ile Phe Glu Gly Leu Leu Pro Asp
    210                 215                 220

Asp Ile Asn Val Tyr Ala Thr Thr Ala Ser Asn Ala Glu Glu Ser Ser
225                 230                 235                 240

Trp Gly Thr Tyr Cys Pro Gly Glu Phe Pro Ser Pro Pro Glu Tyr
                245                 250                 255

Asp Thr Cys Leu Gly Asp Leu Tyr Ser Val Ser Trp Met Glu Asp Ser
            260                 265                 270

Asp Phe His Asn Leu Arg Thr Glu Ser Leu Lys Gln Gln Tyr Lys Leu
        275                 280                 285

Val Lys Asp Arg Thr Ala Ala Gln Asp Thr Phe Ser Tyr Gly Ser His
    290                 295                 300

Val Met Gln Tyr Gly Ser Leu Glu Leu Asn Val Gln Lys Leu Phe Ser
305                 310                 315                 320

Tyr Ile Gly Thr Asn Pro Ala Asn Asp Gly Asn Thr Phe Val Glu Asp
                325                 330                 335

Asn Ser Leu Pro Ser Phe Phe Lys Ser Cys Gln Arg Asp Ala Asp
            340                 345                 350

Leu Val Tyr Phe Trp Gln Lys Tyr Arg Lys Leu Ala Asp Gly Ser Ser
        355                 360                 365

Lys Lys Asn Glu Ala Arg Lys Glu Leu Leu Glu Val Met Ser His Arg
370                 375                 380
```

```
Ser His Val Asp Asn Ser Val Glu Leu Ile Gly Ser Leu Leu Phe Gly
385                 390                 395                 400

Ser Glu Asp Gly Pro Arg Val Leu Lys Ala Val Arg Ala Ala Gly Glu
                405                 410                 415

Pro Leu Val Asp Asp Trp Ser Cys Leu Lys Ser Met Val Arg Thr Phe
                420                 425                 430

Glu Ala Gln Cys Gly Ser Leu Ala Gln Tyr Gly Met Lys His Met Arg
                435                 440                 445

Thr Phe Ala Asn Ile Cys Asn Ala Gly Ile Leu Pro Glu Ala Val Ser
                450                 455                 460

Lys Val Ala Ala Gln Ala Cys Thr Ser Ile Pro Ser Asn Pro Trp Ser
465                 470                 475                 480

Ser Ile Asp Lys Gly Phe Ser Ala
                485

<210> SEQ ID NO 72
<211> LENGTH: 503
<212> TYPE: PRT
<213> ORGANISM: Oryza sativa Japonica Group

<400> SEQUENCE: 72

Met Ala Ala Arg Ala Ser Ala Phe Arg Leu Val Leu Pro Pro Ala Arg
1               5                   10                  15

Gly Ala Ala Pro Ser Phe Ala His Leu Ala Ala Val Ala Val Ala Arg
                20                  25                  30

Pro Arg Trp Glu Glu Glu Gly Ser Asn Leu Arg Leu Pro Ser Glu Arg
                35                  40                  45

Ala Val Ala Ala Gly Ala Ala Asp Asp Ala Ala Glu Ala Ala Glu
        50                  55                  60

Gly Thr Arg Trp Ala Val Leu Ile Ala Gly Ser Asn Gly Tyr Tyr Asn
65                  70                  75                  80

Tyr Arg His Gln Ala Asp Val Cys His Ala Tyr Gln Ile Met Lys Arg
                85                  90                  95

Gly Gly Leu Lys Asp Glu Asn Ile Ile Val Phe Met Tyr Asp Asp Ile
                100                 105                 110

Ala His Asn Pro Glu Asn Pro Arg Pro Gly Val Ile Ile Asn His Pro
            115                 120                 125

Gln Gly Gly Asp Val Tyr Ala Gly Val Pro Lys Asp Tyr Thr Gly Lys
            130                 135                 140

Glu Val Asn Val Lys Asn Leu Phe Ala Val Leu Leu Gly Asn Lys Thr
145                 150                 155                 160

Ala Val Lys Gly Gly Ser Gly Lys Val Leu Asp Ser Gly Pro Asn Asp
                165                 170                 175

His Ile Phe Ile Phe Tyr Ser Asp His Gly Gly Pro Gly Val Leu Gly
                180                 185                 190

Met Pro Thr Tyr Pro Tyr Leu Tyr Gly Asp Leu Val Asp Val Leu
                195                 200                 205

Lys Lys Lys His Ala Ala Gly Thr Tyr Lys Ser Leu Val Phe Tyr Leu
210                 215                 220

Glu Ala Cys Glu Ser Gly Ser Ile Phe Glu Gly Leu Leu Pro Asn Gly
225                 230                 235                 240

Ile Asn Val Tyr Ala Thr Thr Ala Ser Asn Ala Asp Glu Ser Ser Trp
                245                 250                 255

Gly Thr Tyr Cys Pro Gly Glu Tyr Pro Ser Pro Pro Glu Tyr Asp
```

```
                260                 265                 270
Thr Cys Leu Gly Asp Leu Tyr Ser Val Ala Trp Met Glu Asp Ser Asp
            275                 280                 285

Val His Asn Leu Arg Thr Glu Ser Leu Lys Gln Gln Tyr Asn Leu Val
        290                 295                 300

Lys Glu Arg Thr Ser Val Gln His Thr Tyr Tyr Ser Gly Ser His Val
305                 310                 315                 320

Met Glu Tyr Gly Ser Leu Glu Leu Asn Ala His His Val Phe Met Tyr
            325                 330                 335

Met Gly Ser Asn Pro Ala Asn Asp Asn Ala Thr Phe Val Glu Asp Asn
        340                 345                 350

Ser Leu Pro Ser Phe Ser Arg Ala Val Asn Gln Arg Asp Ala Asp Leu
    355                 360                 365

Val Tyr Phe Trp Gln Lys Tyr Arg Lys Leu Pro Glu Ser Ser Pro Glu
        370                 375                 380

Lys Asn Glu Ala Arg Lys Gln Leu Leu Glu Met Met Ala His Arg Ser
385                 390                 395                 400

His Val Asp Asn Ser Val Glu Leu Ile Gly Asn Leu Leu Phe Gly Ser
            405                 410                 415

Glu Glu Gly Pro Arg Val Leu Lys Ala Val Arg Ala Thr Gly Glu Pro
        420                 425                 430

Leu Val Asp Asp Trp Ser Cys Leu Lys Ser Met Val Arg Thr Phe Glu
    435                 440                 445

Ala Gln Cys Gly Ser Leu Ala Gln Tyr Gly Met Lys His Met Arg Ser
        450                 455                 460

Phe Ala Asn Ile Cys Asn Ala Gly Ile Ser Ala Glu Ala Met Ala Lys
465                 470                 475                 480

Val Ala Ala Gln Ala Cys Thr Ser Ile Pro Ser Asn Pro Trp Ser Ser
            485                 490                 495

Thr His Arg Gly Phe Ser Ala
            500

<210> SEQ ID NO 73
<211> LENGTH: 481
<212> TYPE: PRT
<213> ORGANISM: Zea mays

<400> SEQUENCE: 73

Met Val Ala Asp Arg Leu Arg Leu Ala Leu Leu Ser Ala Cys Leu
1               5                   10                  15

Cys Ser Ala Trp Ala Arg Pro Arg Leu Glu Pro Thr Ile Arg Leu Pro
            20                  25                  30

Ser Glu Arg Ala Ala Ala Asp Asp Ala Val Gly Thr Arg Trp Ala Val
        35                  40                  45

Leu Ile Ala Gly Ser Asn Gly Tyr Tyr Asn Tyr Arg His Gln Ala Asp
    50                  55                  60

Ile Cys His Ala Tyr Gln Ile Met Lys Lys Gly Leu Lys Asp Glu
65              70                  75                  80

Asn Ile Val Val Phe Met Tyr Asp Asp Ile Ala His Ser Pro Glu Asn
            85                  90                  95

Pro Arg Pro Gly Val Ile Ile Asn His Pro Gln Gly Gly Asp Val Tyr
        100                 105                 110

Ala Gly Val Pro Lys Asp Tyr Thr Gly Arg Glu Val Asn Val Asp Asn
    115                 120                 125
```

```
Phe Phe Ala Val Leu Leu Gly Asn Lys Thr Ala Leu Arg Gly Gly Ser
    130                 135                 140

Gly Lys Val Val Asp Ser Gly Pro Asn Asp His Ile Phe Val Phe Tyr
145                 150                 155                 160

Ser Asp His Gly Gly Pro Gly Val Leu Gly Met Pro Thr Tyr Pro Tyr
                165                 170                 175

Leu Tyr Gly Asp Asp Leu Val Asp Val Leu Lys Lys His Ala Ala
            180                 185                 190

Gly Thr Tyr Lys Ser Leu Val Phe Tyr Leu Glu Ala Cys Glu Ser Gly
        195                 200                 205

Ser Ile Phe Glu Gly Leu Leu Pro Asn Asp Ile Asn Val Tyr Ala Thr
210                 215                 220

Thr Ala Ser Asn Ala Glu Glu Ser Ser Trp Gly Thr Tyr Cys Pro Gly
225                 230                 235                 240

Glu Phe Pro Ser Pro Pro Glu Tyr Asp Thr Cys Leu Gly Asp Leu
                245                 250                 255

Tyr Ser Val Ala Trp Met Glu Asp Ser Asp Phe His Asn Leu Arg Thr
                260                 265                 270

Glu Ser Leu Lys Gln Gln Tyr Asn Leu Val Lys Asp Arg Thr Ala Val
        275                 280                 285

Gln Asp Thr Phe Ser Tyr Gly Ser His Val Met Gln Tyr Gly Ser Leu
290                 295                 300

Glu Leu Asn Val Lys His Leu Phe Ser Tyr Ile Gly Thr Asn Pro Ala
305                 310                 315                 320

Asn Asp Asp Asn Thr Phe Ile Glu Asp Asn Ser Leu Pro Ser Phe Ser
                325                 330                 335

Lys Ala Val Asn Gln Arg Asp Ala Asp Leu Val Tyr Phe Trp Gln Lys
                340                 345                 350

Tyr Arg Lys Leu Ala Asp Ser Ser Pro Glu Lys Asn Glu Ala Arg Lys
        355                 360                 365

Glu Leu Leu Glu Val Met Ala His Arg Ser His Val Asp Ser Ser Val
370                 375                 380

Glu Leu Ile Gly Ser Leu Leu Phe Gly Ser Glu Asp Gly Pro Arg Val
385                 390                 395                 400

Leu Lys Ala Val Arg Ala Ala Gly Glu Pro Leu Val Asp Asp Trp Ser
                405                 410                 415

Cys Leu Lys Ser Thr Val Arg Thr Phe Glu Ala Gln Cys Gly Ser Leu
                420                 425                 430

Ala Gln Tyr Gly Met Lys His Met Arg Ser Phe Ala Asn Ile Cys Asn
        435                 440                 445

Ala Gly Ile Leu Pro Glu Ala Val Ser Lys Val Ala Ala Gln Ala Cys
    450                 455                 460

Thr Ser Ile Pro Ser Asn Pro Trp Ser Ser Ile His Lys Gly Phe Ser
465                 470                 475                 480

Ala
```

<210> SEQ ID NO 74
<211> LENGTH: 481
<212> TYPE: PRT
<213> ORGANISM: Zea mays

<400> SEQUENCE: 74

```
Met Val Ala Asp Arg Leu Arg Leu Ala Leu Leu Leu Ser Ala Cys Leu
1               5                   10                  15
```

```
Cys Ser Ala Trp Ala Arg Pro Arg Leu Glu Pro Thr Ile Arg Leu Pro
            20                  25                  30

Ser Asp Arg Ala Ala Ala Asp Asp Ala Val Gly Thr Arg Trp Ala Val
        35                  40                  45

Leu Ile Ala Gly Ser Asn Gly Tyr Tyr Asn Tyr Arg His Gln Ala Asp
    50                  55                  60

Ile Cys His Ala Tyr Gln Ile Met Lys Lys Gly Gly Leu Lys Asp Glu
 65                  70                  75                  80

Asn Ile Val Val Phe Met Tyr Asp Asp Ile Ala His Ser Pro Glu Asn
                85                  90                  95

Pro Arg Pro Gly Val Ile Ile Asn His Pro Gln Gly Gly Asp Val Tyr
            100                 105                 110

Ala Gly Val Pro Lys Asp Tyr Thr Gly Arg Asp Val Asn Val Asp Asn
        115                 120                 125

Phe Phe Ala Val Leu Leu Gly Asn Lys Thr Ala Leu Arg Gly Gly Ser
    130                 135                 140

Gly Lys Val Val Asp Ser Gly Pro Asn Asp His Ile Ser Val Phe Tyr
145                 150                 155                 160

Ser Asp His Gly Gly Pro Gly Val Leu Gly Met Pro Thr Tyr Pro Tyr
            165                 170                 175

Leu Tyr Gly Asp Asp Leu Val Asp Val Leu Lys Lys Lys His Ala Ala
        180                 185                 190

Gly Thr Tyr Lys Ser Leu Val Phe Tyr Leu Glu Ala Cys Glu Ser Gly
    195                 200                 205

Ser Ile Phe Glu Gly Leu Leu Pro Asn Asp Ile Asn Val Tyr Ala Thr
210                 215                 220

Thr Ala Ser Asn Ala Glu Glu Ser Ser Trp Gly Thr Tyr Cys Pro Gly
225                 230                 235                 240

Glu Phe Pro Ser Pro Pro Glu Tyr Asp Thr Cys Leu Gly Asp Leu
                245                 250                 255

Tyr Ser Val Ala Trp Met Glu Asp Ser Asp Phe His Asn Leu Arg Thr
            260                 265                 270

Glu Ser Leu Lys Gln Gln Tyr Asn Leu Val Lys Asp Arg Thr Ala Val
        275                 280                 285

Gln Asp Thr Phe Ser Tyr Gly Ser His Val Met Gln Tyr Gly Ser Leu
    290                 295                 300

Gly Leu Asn Val Lys His Leu Phe Ser Tyr Ile Gly Thr Asn Pro Ala
305                 310                 315                 320

Asn Asp Asp Asn Thr Phe Ile Glu Asp Asn Ser Leu Pro Ser Phe Ser
            325                 330                 335

Lys Ala Val Asn Gln Arg Asp Ala Asp Leu Val Tyr Phe Trp Gln Lys
        340                 345                 350

Tyr Arg Lys Leu Ala Asp Ser Ser Pro Glu Lys Asn Glu Ala Arg Arg
    355                 360                 365

Glu Leu Leu Glu Val Met Ala His Arg Ser His Val Asp Ser Ser Val
370                 375                 380

Glu Leu Ile Gly Ser Leu Leu Phe Gly Ser Glu Asp Gly Pro Arg Val
385                 390                 395                 400

Leu Lys Ala Val Arg Ala Ala Gly Glu Pro Leu Val Asp Asp Trp Ser
            405                 410                 415

Cys Leu Lys Ser Thr Val Arg Thr Phe Glu Ala Gln Cys Gly Ser Leu
        420                 425                 430

Ala Gln Tyr Gly Met Lys His Met Arg Ser Phe Ala Asn Ile Cys Asn
```

```
                    435                 440                 445
Ala Gly Ile Leu Pro Glu Ala Val Ser Lys Val Ala Ala Gln Ala Cys
                450                 455                 460

Thr Ser Ile Pro Ser Asn Pro Trp Ser Ser Ile His Lys Gly Phe Ser
465                 470                 475                 480

Ala

<210> SEQ ID NO 75
<211> LENGTH: 501
<212> TYPE: PRT
<213> ORGANISM: Oryza sativa Japonica Group

<400> SEQUENCE: 75

Met Ala Ala Arg Ala Arg Leu Arg Leu Val Leu Pro Pro Leu Ala Ala
1               5                   10                  15

Leu Leu Leu Phe Ala His Leu Ala Ala Val Ala Val Ala Arg Pro Arg
                20                  25                  30

Trp Glu Glu Gly Ser Asn Leu Arg Leu Pro Ser Glu Arg Ala Val
            35                  40                  45

Ala Ala Gly Ala Ala Ala Asp Asp Ala Ala Glu Ala Ala Glu Gly Thr
        50                  55                  60

Arg Trp Ala Val Leu Ile Ala Gly Ser Asn Gly Tyr Tyr Asn Tyr Arg
65                  70                  75                  80

His Gln Ala Asp Val Cys His Ala Tyr Gln Ile Met Lys Arg Gly Gly
                85                  90                  95

Leu Lys Asp Glu Asn Ile Ile Val Phe Met Tyr Asp Asp Ile Ala His
            100                 105                 110

Asn Pro Glu Asn Pro Arg Pro Gly Val Ile Ile Asn His Pro Gln Gly
        115                 120                 125

Gly Asp Val Tyr Ala Gly Val Pro Lys Asp Tyr Thr Gly Lys Glu Val
    130                 135                 140

Asn Val Lys Asn Leu Phe Ala Val Leu Leu Gly Asn Lys Thr Ala Val
145                 150                 155                 160

Lys Gly Gly Ser Gly Lys Val Leu Asp Ser Gly Pro Asn Asp His Ile
                165                 170                 175

Phe Ile Phe Tyr Ser Asp His Gly Gly Pro Gly Val Leu Gly Met Pro
            180                 185                 190

Thr Tyr Pro Tyr Leu Tyr Gly Asp Asp Leu Val Asp Val Leu Lys Lys
        195                 200                 205

Lys His Ala Ala Gly Thr Tyr Lys Ser Leu Val Phe Tyr Leu Glu Ala
    210                 215                 220

Cys Glu Ser Gly Ser Ile Phe Glu Gly Leu Leu Pro Asn Gly Ile Asn
225                 230                 235                 240

Val Tyr Ala Thr Thr Ala Ser Asn Ala Asp Glu Ser Ser Trp Gly Thr
                245                 250                 255

Tyr Cys Pro Gly Glu Tyr Pro Ser Pro Pro Glu Tyr Asp Thr Cys
            260                 265                 270

Leu Gly Asp Leu Tyr Ser Val Ala Trp Met Glu Asp Ser Asp Val His
        275                 280                 285

Asn Leu Arg Thr Glu Ser Leu Lys Gln Gln Tyr Asn Leu Val Lys Glu
    290                 295                 300

Arg Thr Ser Val Gln His Thr Tyr Tyr Ser Gly Ser His Val Met Glu
305                 310                 315                 320

Tyr Gly Ser Leu Glu Leu Asn Ala His His Val Phe Met Tyr Met Gly
```

```
                    325                 330                 335
Ser Asn Pro Ala Asn Asp Asn Ala Thr Phe Val Glu Asp Asn Ser Leu
                340                 345                 350

Pro Ser Phe Ser Arg Ala Val Asn Gln Arg Asp Ala Asp Leu Val Tyr
            355                 360                 365

Phe Trp Gln Lys Tyr Arg Lys Leu Pro Glu Ser Ser Pro Glu Lys Asn
        370                 375                 380

Glu Ala Arg Lys Gln Leu Leu Glu Met Met Ala His Arg Ser His Val
385                 390                 395                 400

Asp Asn Ser Val Glu Leu Ile Gly Asn Leu Leu Phe Gly Ser Glu Glu
                405                 410                 415

Gly Pro Arg Val Leu Lys Ala Val Arg Ala Thr Gly Glu Pro Leu Val
            420                 425                 430

Asp Asp Trp Ser Cys Leu Lys Ser Met Val Arg Thr Phe Glu Ala Gln
        435                 440                 445

Cys Gly Ser Leu Ala Gln Tyr Gly Met Lys His Met Arg Ser Phe Ala
450                 455                 460

Asn Ile Cys Asn Ala Gly Ile Ser Ala Glu Met Ala Lys Val Ala
465                 470                 475                 480

Ala Gln Ala Cys Thr Ser Ile Pro Ser Asn Pro Trp Ser Ser Thr His
                485                 490                 495

Arg Gly Phe Ser Ala
            500

<210> SEQ ID NO 76
<211> LENGTH: 485
<212> TYPE: PRT
<213> ORGANISM: Zea mays

<400> SEQUENCE: 76

Met Val Ala Asp Arg Leu Arg Leu Ala Leu Leu Ser Ala Cys Leu
1               5                   10                  15

Cys Ser Ala Trp Ala Arg Pro Arg Leu Glu Pro Thr Ile Arg Leu Pro
                20                  25                  30

Ser Glu Arg Ala Ala Ala Asp Glu Thr Asp Asp Ala Val Gly Thr
            35                  40                  45

Arg Trp Ala Val Leu Ile Ala Gly Ser Asn Gly Tyr Tyr Asn Tyr Arg
    50                  55                  60

His Gln Ala Asp Ile Cys His Ala Tyr Gln Ile Met Lys Lys Gly Gly
65                  70                  75                  80

Leu Lys Asp Glu Asn Ile Val Val Phe Met Tyr Asp Asp Ile Ala His
                85                  90                  95

Ser Pro Glu Asn Pro Arg Pro Gly Val Ile Ile Asn His Pro Gln Gly
            100                 105                 110

Gly Asp Val Tyr Ala Gly Val Pro Lys Asp Tyr Thr Gly Arg Asp Val
        115                 120                 125

Asn Val Asp Asn Phe Phe Ala Val Leu Leu Gly Asn Lys Thr Ala Leu
    130                 135                 140

Arg Gly Gly Ser Gly Lys Val Val Asp Ser Gly Pro Asn Asp His Ile
145                 150                 155                 160

Phe Val Phe Tyr Ser Asp His Gly Gly Pro Gly Val Leu Gly Met Pro
                165                 170                 175

Thr Tyr Pro Tyr Leu Tyr Gly Asp Asp Leu Val Asp Val Leu Lys Lys
            180                 185                 190
```

```
Lys His Ala Ala Gly Thr Tyr Lys Ser Leu Val Phe Tyr Leu Glu Ala
            195                 200                 205

Cys Glu Ser Gly Ser Ile Phe Glu Gly Leu Leu Pro Asn Asp Ile Asn
210                 215                 220

Val Tyr Ala Thr Thr Ala Ser Asn Ala Glu Glu Ser Ser Trp Gly Thr
225                 230                 235                 240

Tyr Cys Pro Gly Glu Phe Pro Ser Pro Pro Glu Tyr Asp Thr Cys
                245                 250                 255

Leu Gly Asp Leu Tyr Ser Val Ala Trp Met Glu Asp Ser Asp Phe His
            260                 265                 270

Asn Leu Arg Thr Glu Ser Leu Lys Gln Gln Tyr Asn Leu Val Lys Asp
            275                 280                 285

Arg Thr Ala Val Gln Asp Thr Phe Ser Tyr Gly Ser His Val Met Gln
290                 295                 300

Tyr Gly Ser Leu Glu Leu Asn Val Lys His Leu Phe Ser Tyr Ile Gly
305                 310                 315                 320

Thr Asn Pro Ala Asn Asp Asn Thr Phe Ile Glu Asp Asn Ser Leu
                325                 330                 335

Pro Ser Leu Ser Lys Ala Val Asn Gln Arg Asp Ala Asp Leu Val Tyr
            340                 345                 350

Phe Trp Gln Lys Tyr Arg Lys Leu Ala Asp Ser Ser Pro Glu Lys Asn
            355                 360                 365

Glu Ala Arg Arg Glu Leu Leu Glu Val Met Ala His Arg Ser His Val
            370                 375                 380

Asp Ser Ser Val Glu Leu Ile Gly Ser Leu Leu Phe Gly Ser Glu Asp
385                 390                 395                 400

Gly Pro Arg Val Leu Lys Ala Val Arg Ala Ala Gly Glu Pro Leu Val
                405                 410                 415

Asp Asp Trp Ser Cys Leu Lys Ser Thr Val Arg Thr Phe Glu Ala Gln
                420                 425                 430

Cys Gly Ser Leu Ala Gln Tyr Gly Met Lys His Met Arg Ser Phe Ala
            435                 440                 445

Asn Ile Cys Asn Ala Gly Ile Leu Pro Glu Ala Val Ser Lys Val Ala
450                 455                 460

Ala Gln Ala Cys Thr Ser Ile Pro Ser Asn Pro Trp Ser Ser Ile His
465                 470                 475                 480

Lys Gly Phe Ser Ala
                485

<210> SEQ ID NO 77
<211> LENGTH: 488
<212> TYPE: PRT
<213> ORGANISM: Brachypodium distachyon

<400> SEQUENCE: 77

Met Ala Ser Phe Arg Leu Leu Pro Leu Ala Leu Leu Leu Cys Ala Cys
1               5                   10                  15

Leu Ser Ala His Ala Arg Thr Ser Leu Leu Glu Gln Thr Ile Arg Leu
            20                  25                  30

Pro Ser Gln Arg Gly Ala Ala Gly Gln Gln Glu Val Asp Asp Asp Ser
        35                  40                  45

Val Gly Thr Arg Trp Ala Val Leu Ile Ala Gly Ser Asn Gly Tyr Tyr
    50                  55                  60

Asn Tyr Arg His Gln Ala Asp Ile Cys His Ala Tyr Gln Ile Met Lys
65                  70                  75                  80
```

```
Lys Gly Gly Leu Lys Asp Glu Asn Ile Ile Val Phe Met Tyr Asp Asp
                85                  90                  95

Ile Ala His Asn Pro Glu Asn Pro Arg Pro Gly Val Ile Ile Asn His
            100                 105                 110

Pro Gln Gly Gly Asp Val Tyr Ala Gly Val Pro Lys Asp Tyr Thr Gly
            115                 120                 125

Lys Glu Val Asn Val Lys Asn Phe Phe Ala Val Leu Leu Gly Asn Lys
        130                 135                 140

Ala Ala Val Ser Gly Gly Ser Gly Lys Val Val Asp Ser Gly Pro Asn
145                 150                 155                 160

Asp His Ile Phe Val Phe Tyr Ser Asp His Gly Gly Pro Gly Val Leu
                165                 170                 175

Gly Met Pro Thr Tyr Pro Tyr Leu Tyr Gly Asp Asp Leu Val Asp Val
                180                 185                 190

Leu Lys Lys Lys His Ala Ala Gly Thr Tyr Lys Ser Leu Val Phe Tyr
            195                 200                 205

Leu Glu Ala Cys Glu Ser Gly Ser Ile Phe Glu Gly Leu Leu Pro Asn
        210                 215                 220

Asp Ile Gly Ile Tyr Ala Thr Thr Ala Ser Asn Ala Glu Glu Ser Ser
225                 230                 235                 240

Trp Gly Thr Tyr Cys Pro Gly Glu Tyr Pro Ser Pro Pro Glu Tyr
                245                 250                 255

Asp Thr Cys Leu Gly Asp Leu Tyr Ser Ile Ala Trp Met Glu Asp Ser
                260                 265                 270

Asp Val His Asn Leu Arg Thr Glu Ser Leu Lys Gln Gln Tyr Asp Leu
                275                 280                 285

Val Lys Lys Arg Thr Ala Pro Glu Asn Ser Tyr Ser Tyr Gly Ser His
        290                 295                 300

Val Met Gln Tyr Gly Ser Leu Asp Leu Asn Ala Glu His Leu Phe Leu
305                 310                 315                 320

Tyr Ile Gly Ser Asn Pro Ala Asn Asp Asn Thr Thr Phe Val Glu Gly
                325                 330                 335

Asn Ser Leu Pro Ser Phe Ser Arg Ala Val Asn Gln Arg Asp Ala Asp
            340                 345                 350

Leu Val Tyr Phe Trp Gln Lys Tyr Arg Lys Leu Ala Glu Ser Ser Pro
            355                 360                 365

Ala Lys Asn Asp Ala Arg Lys Glu Leu Leu Glu Met Met Ala His Arg
        370                 375                 380

Ser His Val Asp Asn Ser Val Glu Leu Thr Gly Asn Leu Leu Phe Gly
385                 390                 395                 400

Ser Glu Asp Gly Pro Met Val Leu Lys Thr Val Arg Thr Ala Gly Glu
                405                 410                 415

Pro Leu Val Asp Asp Trp Gly Cys Leu Lys Ser Thr Val Arg Ala Phe
                420                 425                 430

Glu Ser Gln Cys Gly Ser Leu Ala Gln Tyr Gly Met Lys His Met Arg
        435                 440                 445

Ser Phe Ala Asn Ile Cys Asn Ala Gly Ile Leu Pro Glu Ala Thr Ala
    450                 455                 460

Lys Val Ala Ala Gln Ala Cys Pro Ser Ile Pro Ala Asn Pro Trp Ser
465                 470                 475                 480

Ala Thr His Lys Gly Phe Ser Ala
                485
```

<210> SEQ ID NO 78
<211> LENGTH: 484
<212> TYPE: PRT
<213> ORGANISM: Hordeum vulgare subsp. vulgare

<400> SEQUENCE: 78

```
Met Ala Met Ala Ser Phe Arg Leu Leu Pro Leu Ala Leu Leu Leu Ser
1               5                   10                  15

Val Ala His Ala Arg Thr Pro Arg Leu Glu Pro Thr Ile Arg Leu Pro
            20                  25                  30

Ser Gln Arg Ala Ala Gly Gln Glu Asp Asp Ser Val Gly Thr Arg
        35                  40                  45

Trp Ala Val Leu Ile Ala Gly Ser Asn Gly Tyr Tyr Asn Tyr Arg His
    50                  55                  60

Gln Ala Asp Ile Cys His Ala Tyr Gln Ile Met Lys Lys Gly Gly Leu
65                  70                  75                  80

Lys Asp Glu Asn Ile Ile Val Phe Met Tyr Asp Asp Ile Ala Arg Asn
                85                  90                  95

Pro Glu Asn Pro Arg Pro Gly Val Ile Ile Asn His Pro Gln Gly Gly
            100                 105                 110

Asp Val Tyr Ala Gly Val Pro Lys Asp Tyr Thr Gly Lys Glu Val Asn
        115                 120                 125

Val Lys Asn Phe Phe Ala Val Leu Leu Gly Asn Lys Thr Ala Val Asn
    130                 135                 140

Gly Gly Ser Gly Lys Val Val Asp Ser Gly Pro Asn Asp His Ile Phe
145                 150                 155                 160

Val Phe Tyr Ser Asp His Gly Gly Pro Gly Val Leu Gly Met Pro Thr
                165                 170                 175

Tyr Pro Tyr Leu Tyr Gly Asp Asp Leu Val Asp Val Leu Lys Lys Lys
            180                 185                 190

His Ala Ala Gly Thr Tyr Lys Ser Leu Val Phe Tyr Leu Glu Ala Cys
        195                 200                 205

Glu Ser Gly Ser Ile Phe Glu Gly Leu Leu Pro Asn Asp Ile Gly Val
    210                 215                 220

Tyr Ala Thr Thr Ala Ser Asn Ala Glu Glu Ser Ser Trp Gly Thr Tyr
225                 230                 235                 240

Cys Pro Gly Glu Tyr Pro Ser Pro Pro Glu Tyr Asp Thr Cys Leu
                245                 250                 255

Gly Asp Leu Tyr Ser Ile Ser Trp Met Glu Asp Ser Asp Val His Asn
            260                 265                 270

Leu Arg Thr Glu Ser Leu Lys Gln Gln Tyr Asn Leu Val Lys Lys Arg
        275                 280                 285

Thr Ala Ala Gln Asp Ser Tyr Ser Tyr Gly Ser His Val Met Gln Tyr
    290                 295                 300

Gly Ser Leu Asp Leu Asn Ala Glu His Leu Phe Ser Tyr Ile Gly Ser
305                 310                 315                 320

Asn Pro Ala Asn Glu Asn Thr Thr Phe Val Glu Asp Asn Ala Leu Pro
                325                 330                 335

Ser Leu Ser Arg Ala Val Asn Gln Arg Asp Ala Asp Leu Val Tyr Phe
            340                 345                 350

Trp Gln Lys Tyr Arg Lys Leu Ala Glu Ser Ser Pro Ala Lys Asn Asn
        355                 360                 365

Ala Arg Lys Gln Leu Leu Glu Met Met Gly His Arg Ser His Ile Asp
    370                 375                 380
```

```
Ser Ser Val Glu Leu Ile Gly Asn Leu Leu Phe Gly Ser Ala Gly Gly
385                 390                 395                 400

Pro Met Val Leu Lys Thr Val Arg Pro Ala Gly Glu Pro Leu Val Asp
                405                 410                 415

Asp Trp Ser Cys Leu Lys Ser Thr Val Arg Thr Phe Glu Ser Gln Cys
            420                 425                 430

Gly Ser Leu Ala Gln Tyr Gly Met Lys His Met Arg Ser Phe Ala Asn
        435                 440                 445

Met Cys Asn Ala Gly Ile Val Pro Glu Ala Met Ala Lys Val Ala Ala
    450                 455                 460

Gln Ala Cys Thr Ser Phe Pro Thr Asn Pro Trp Ser Ala Thr His Lys
465                 470                 475                 480

Gly Phe Ser Ala

<210> SEQ ID NO 79
<211> LENGTH: 493
<212> TYPE: PRT
<213> ORGANISM: Aegilops tauschii

<400> SEQUENCE: 79

Met Ala Met Ala Ser Phe Arg Pro Leu Pro Leu Ala Leu Leu Leu Ala
1               5                   10                  15

Ala Cys Leu Ser Ala Phe Val Leu Ala Val Ala His Ala Arg Thr Pro
            20                  25                  30

Arg Leu Glu Pro Thr Ile Arg Leu Pro Ser Gln Arg Ala Ala Gly Gln
        35                  40                  45

Glu Asp Asp Asp Ser Val Gly Thr Arg Trp Ala Val Leu Ile Ala Gly
50                  55                  60

Ser Asn Gly Tyr Tyr Asn Tyr Arg His Gln Ala Asp Ile Cys His Ala
65                  70                  75                  80

Tyr Gln Ile Met Lys Lys Gly Gly Leu Lys Asp Glu Asn Ile Ile Val
                85                  90                  95

Phe Met Tyr Asp Asp Ile Ala His Asn Pro Glu Asn Pro Arg Pro Gly
            100                 105                 110

Val Ile Ile Asn His Pro Gln Gly Gly Asp Val Tyr Ala Gly Val Pro
        115                 120                 125

Lys Asp Tyr Thr Gly Lys Glu Val Asn Val Lys Asn Phe Phe Ala Val
130                 135                 140

Leu Leu Gly Asn Lys Thr Ala Val Ser Gly Gly Ser Gly Lys Val Val
145                 150                 155                 160

Asp Ser Gly Pro Asn Asp His Ile Phe Val Phe Tyr Ser Asp His Gly
                165                 170                 175

Gly Pro Gly Val Leu Gly Met Pro Thr Tyr Pro Tyr Leu Tyr Gly Asp
            180                 185                 190

Asp Leu Val Asp Val Leu Lys Lys Lys His Ala Ala Gly Thr Tyr Lys
        195                 200                 205

Ser Leu Val Phe Tyr Leu Glu Ala Cys Glu Ser Gly Ser Ile Phe Glu
210                 215                 220

Gly Leu Leu Pro Asn Asp Ile Gly Val Tyr Ala Thr Thr Ala Ser Asn
225                 230                 235                 240

Ala Glu Glu Ser Ser Trp Gly Thr Tyr Cys Pro Gly Glu Tyr Pro Ser
                245                 250                 255

Pro Pro Pro Glu Tyr Asp Thr Cys Leu Gly Asp Leu Tyr Ser Ile Ser
            260                 265                 270
```

```
Trp Met Glu Asp Ser Asp Val His Asn Leu Arg Thr Glu Ser Leu Lys
        275                 280                 285

Gln Gln Tyr Asn Leu Val Lys Lys Arg Thr Ala Ala Gln Asp Ser Tyr
    290                 295                 300

Ser Tyr Gly Ser His Val Met Gln Tyr Gly Ser Leu Asp Leu Asn Ala
305                 310                 315                 320

Glu His Leu Phe Ser Tyr Ile Gly Ser Asn Pro Ala Asn Glu Asn Thr
                325                 330                 335

Thr Phe Val Glu Asp Asn Ala Leu Pro Ser Phe Ser Arg Ala Val Asn
            340                 345                 350

Gln Arg Asp Ala Asp Leu Val Tyr Phe Trp Gln Lys Tyr Arg Lys Leu
        355                 360                 365

Ala Glu Ser Ser Pro Glu Lys Asn Asp Ala Arg Lys Gln Leu Leu Glu
    370                 375                 380

Met Met Gly His Arg Ser His Ile Asp Asn Ser Val Glu Pro Ile Gly
385                 390                 395                 400

Asn Leu Leu Phe Gly Ser Ala Gly Gly Pro Met Val Leu Lys Ala Val
                405                 410                 415

Arg Pro Ala Gly Glu Pro Leu Val Asp Asp Trp Ser Cys Leu Lys Ser
            420                 425                 430

Thr Val Arg Thr Phe Glu Ser Gln Cys Gly Ser Leu Ala Gln Tyr Gly
        435                 440                 445

Met Lys His Met Arg Ser Phe Ala Asn Ile Cys Asn Ala Gly Ile Val
    450                 455                 460

Pro Glu Ala Met Ala Lys Val Ala Ala Gln Ala Arg Thr Ser Ile Pro
465                 470                 475                 480

Thr Asn Pro Trp Ser Ala Thr His Lys Gly Phe Ser Ala
                485                 490

<210> SEQ ID NO 80
<211> LENGTH: 493
<212> TYPE: PRT
<213> ORGANISM: Triticum monococcum

<400> SEQUENCE: 80

Met Ala Met Ala Ser Phe Arg Pro Leu Pro Leu Ala Leu Leu Leu Ala
1               5                   10                  15

Ala Cys Leu Ser Ala Leu Val Leu Ala Val Ala His Ala Arg Ser Pro
            20                  25                  30

Arg Leu Glu Pro Thr Ile Arg Leu Pro Ser Gln Arg Ala Ala Gly Gln
        35                  40                  45

Glu Asp Asp Asp Ser Val Gly Thr Arg Trp Ala Val Leu Ile Ala Gly
    50                  55                  60

Ser Asn Gly Tyr Tyr Asn Tyr Arg His Gln Ala Asp Ile Cys His Ala
65                  70                  75                  80

Tyr Gln Ile Met Lys Lys Gly Gly Leu Lys Asp Glu Asn Ile Ile Val
                85                  90                  95

Phe Met Tyr Asp Asp Ile Ala His Asn Leu Glu Asn Pro Gly Pro Gly
            100                 105                 110

Val Ile Ile Asn His Pro Gln Gly Gly Asp Val Tyr Ala Gly Val Pro
        115                 120                 125

Lys Asp Tyr Thr Gly Lys Glu Val Asn Val Lys Asn Leu Phe Ala Val
    130                 135                 140

Leu Leu Gly Asn Lys Thr Ala Val Ser Gly Gly Ser Gly Lys Val Val
```

```
           145                 150                 155                 160
Asp Ser Gly Pro Asn Asp His Ile Phe Val Phe Tyr Ser Asp His Gly
                165                 170                 175
Gly Pro Gly Val Leu Gly Met Pro Thr Tyr Pro Tyr Leu Tyr Gly Asp
                180                 185                 190
Asp Leu Val Asp Val Leu Lys Lys His Ala Ala Gly Thr Tyr Lys
                195                 200                 205
Ser Leu Val Phe Tyr Leu Glu Ala Cys Glu Ser Gly Ser Ile Phe Glu
        210                 215                 220
Gly Leu Leu Pro Asn Asp Ile Gly Val Tyr Ala Thr Thr Ala Ser Asn
225                 230                 235                 240
Ala Glu Glu Ser Ser Trp Gly Thr Tyr Cys Pro Gly Glu Tyr Pro Ser
                245                 250                 255
Pro Pro Pro Glu Tyr Asp Thr Cys Leu Gly Asp Leu Tyr Ser Ile Ser
                260                 265                 270
Trp Met Glu Asp Ser Asp Val His Asn Leu Arg Thr Glu Ser Leu Lys
                275                 280                 285
Gln Gln Tyr Asn Leu Val Lys Lys Arg Thr Ala Ala Gln Asp Ser Tyr
            290                 295                 300
Ser Tyr Gly Ser His Val Met Gln Tyr Gly Ser Leu Asp Leu Asn Ala
305                 310                 315                 320
Glu His Leu Phe Ser Tyr Ile Gly Ser Asn Pro Ala Asn Glu Asn Thr
                325                 330                 335
Thr Phe Val Glu Asp Asn Ala Leu Pro Ser Phe Ser Arg Ala Val Asn
                340                 345                 350
Gln Arg Asp Ala Asp Leu Val Tyr Phe Trp Gln Lys Tyr Arg Lys Leu
            355                 360                 365
Ala Glu Ser Ser Pro Glu Lys Asn Asp Ala Arg Lys Gln Leu Leu Glu
        370                 375                 380
Met Met Gly His Arg Ser His Ile Asp Asn Ser Val Glu Leu Ile Gly
385                 390                 395                 400
Asn Leu Leu Phe Gly Ser Ala Gly Gly Pro Met Val Leu Lys Ala Val
                405                 410                 415
Arg Pro Ala Gly Glu Pro Leu Val Asp Asp Trp Ser Cys Leu Lys Ser
                420                 425                 430
Thr Val Arg Thr Phe Glu Ser Gln Cys Gly Ser Leu Ala Gln Tyr Gly
                435                 440                 445
Met Lys His Met Arg Ser Phe Ala Asn Ile Cys Asn Ala Gly Ile Val
                450                 455                 460
Pro Glu Ala Thr Ala Lys Val Ala Ala Gln Ala Cys Thr Ser Ile Pro
465                 470                 475                 480
Thr Asn Pro Trp Ser Ala Thr His Lys Gly Phe Ser Ala
                485                 490

<210> SEQ ID NO 81
<211> LENGTH: 493
<212> TYPE: PRT
<213> ORGANISM: Aegilops speltoides

<400> SEQUENCE: 81

Met Ala Met Ala Ser Phe Arg Pro Leu Pro Leu Ala Leu Leu Leu Ala
1               5                   10                  15
Ala Cys Leu Ser Glu Leu Val Leu Ala Val Ala His Ala Arg Thr Pro
            20                  25                  30
```

-continued

Arg Leu Glu Pro Thr Ile Arg Leu Pro Ser Gln Arg Ala Gly Gln
         35                  40                  45

Glu Asp Asp Ser Val Gly Thr Arg Trp Ala Val Leu Ile Ala Gly
 50                  55                  60

Ser Asn Gly Tyr Tyr Asn Tyr Arg His Gln Ala Asp Ile Cys His Ala
65                  70                  75                  80

Tyr Gln Ile Met Lys Lys Gly Gly Leu Lys Asp Glu Asn Ile Ile Ile
                 85                  90                  95

Phe Met Tyr Asp Asp Ile Ala His Asn Pro Glu Asn Pro Arg Pro Gly
             100                 105                 110

Val Ile Ile Asn His Pro Gln Gly Gly Asp Val Tyr Ala Gly Val Pro
         115                 120                 125

Lys Asp Tyr Thr Gly Lys Glu Val Asn Val Lys Asn Phe Phe Ala Val
         130                 135                 140

Leu Leu Gly Asn Arg Thr Ala Val Ser Gly Ser Gly Lys Val Val
145                 150                 155                 160

Asp Ser Gly Pro Asn Asp His Ile Phe Val Phe Tyr Ser Asp His Gly
                 165                 170                 175

Gly Pro Gly Val Leu Gly Met Pro Thr Tyr Pro Tyr Leu Tyr Gly Asp
             180                 185                 190

Asp Leu Val Asp Val Leu Lys Lys His Ala Ala Gly Thr Tyr Lys
         195                 200                 205

Ser Leu Val Phe Tyr Leu Glu Ala Cys Glu Ser Gly Ser Ile Phe Glu
             210                 215                 220

Gly Leu Leu Pro Asn Asp Ile Gly Val Tyr Ala Thr Thr Ala Ser Asn
225                 230                 235                 240

Ala Glu Glu Ser Ser Trp Gly Thr Tyr Cys Pro Gly Glu Tyr Pro Ser
                 245                 250                 255

Pro Pro Pro Glu Tyr Asp Thr Cys Leu Gly Asp Leu Tyr Ser Ile Ser
             260                 265                 270

Trp Met Glu Asp Ser Asp Val His Asn Leu Arg Thr Glu Ser Leu Lys
             275                 280                 285

Gln Gln Tyr Asn Leu Val Lys Lys Arg Thr Ala Ala Gln Asp Ser Tyr
290                 295                 300

Ser Tyr Gly Ser His Val Met Gln Tyr Gly Ser Leu Asp Leu Asn Ala
305                 310                 315                 320

Glu His Leu Phe Ser Tyr Ile Gly Ser Asn Pro Ala Asn Glu Asn Thr
             325                 330                 335

Thr Phe Val Glu Asp Asn Ala Leu Pro Ser Phe Ser Gly Ala Val Asn
             340                 345                 350

Gln Arg Asp Ala Asp Leu Val Tyr Phe Trp Gln Lys Tyr Arg Lys Leu
             355                 360                 365

Ala Glu Ser Ser Pro Glu Lys Asn Asp Ala Arg Lys Gln Leu Leu Glu
370                 375                 380

Met Met Gly His Arg Ser His Ile Asp Asn Ser Val Glu Leu Ile Gly
385                 390                 395                 400

Asn Leu Leu Phe Gly Ser Ala Gly Gly Pro Met Val Leu Lys Ala Val
             405                 410                 415

Arg Pro Ala Gly Glu Pro Leu Val Asp Asp Trp Ser Cys Leu Lys Ser
             420                 425                 430

Thr Val Arg Thr Phe Glu Ser Gln Cys Gly Ser Leu Ala Gln Tyr Gly
             435                 440                 445

Met Lys His Met Arg Ser Phe Ala Asn Ile Cys Asn Val Gly Ile Val

```
                    450                 455                 460
Pro Glu Ala Met Ala Lys Val Ala Ala Gln Ala Cys Thr Asn Ile Pro
465                 470                 475                 480

Thr Asn Pro Trp Ser Ala Thr His Lys Gly Phe Ser Ala
                    485                 490

<210> SEQ ID NO 82
<211> LENGTH: 469
<212> TYPE: PRT
<213> ORGANISM: Amborella trichopoda

<400> SEQUENCE: 82

Met Ala Phe Ser Gly Lys Ser Val Leu Phe Leu Ala Val Phe Met Ala
1               5                   10                  15

Phe Ser Gly Val Tyr Gly Arg Tyr Ser Thr Trp Ser Asp Phe Leu Arg
                20                  25                  30

Met Pro Gln Thr Glu Asp Ser Val Gly Thr Arg Trp Ala Val Leu Val
            35                  40                  45

Ala Gly Ser Ser Gly Tyr Gly Asn Tyr Arg His Gln Ala Asp Ile Cys
        50                  55                  60

His Ala Tyr Gln Thr Met Ile Arg Gly Gly Leu Lys Glu Lys Asn Ile
65                  70                  75                  80

Val Val Phe Met Tyr Asp Asp Ile Ala Tyr Asn Glu Glu Asn Pro Arg
                85                  90                  95

Pro Gly Val Ile Ile Asn Arg Pro His Gly Glu Asp Val Tyr Ala Gly
                100                 105                 110

Val Pro Lys Asp Tyr Val Gly Asp Val Asn Val Asp Asn Leu Phe
            115                 120                 125

Ala Val Ile Leu Gly Asn Lys Ser Ala Leu Thr Gly Gly Ser Gly Lys
        130                 135                 140

Val Val Asp Ser Gly Pro Asp Asp His Ile Phe Ile Phe Tyr Ser Asp
145                 150                 155                 160

His Gly Gly Ala Gly Val Leu Gly Met Pro Thr Tyr Pro Tyr Leu Tyr
                165                 170                 175

Ala Asp Asp Leu Val Asn Val Leu Lys Lys His Val Ser Gly Thr
            180                 185                 190

Tyr Lys Ser Leu Val Phe Tyr Leu Glu Ala Cys Glu Ser Gly Ser Ile
        195                 200                 205

Phe Glu Gly Leu Leu Pro Glu Gly Leu Asn Ile Tyr Ala Thr Thr Ala
        210                 215                 220

Ser Asn Ala Val Glu Ser Ser Trp Gly Thr Tyr Cys Pro Asp Asp Ser
225                 230                 235                 240

Pro Asp Phe Pro Gln Glu Tyr Asp Thr Cys Leu Gly Asp Leu Tyr Ser
                245                 250                 255

Val Ser Trp Met Glu Asp Ser Asp Ile His Asn Leu Gln Phe Glu Thr
            260                 265                 270

Leu Lys Gln Gln Tyr Glu Leu Val Lys Met Arg Thr Ser Asn Phe Glu
        275                 280                 285

Thr Tyr Met Phe Gly Ser His Val Met Gln Tyr Gly Asp Ser Gly Leu
    290                 295                 300

Gly Lys Glu Gln Leu Val Leu Tyr Met Gly Ser Asn Pro Ala Asn Asp
305                 310                 315                 320

Asn Ser Thr Phe Ile Ser Arg Asn Glu Leu Pro Ser Phe Ser Lys Ala
                325                 330                 335
```

-continued

```
Val Asn Gln Arg Asp Ala Asp Leu Val Tyr Phe Trp Asn Lys Tyr Arg
            340                 345                 350

Lys Ser Pro Val Gly Ser Ile Lys Lys Arg Asn Ala Gln Lys Glu Leu
        355                 360                 365

Phe Asp Val Met Ala His Arg Leu His Leu Asp Asn Ser Ile Glu Leu
370                 375                 380

Ile Gly Lys Leu Leu Phe Gly Ser Glu Lys Gly Pro Glu Ile Leu Lys
385                 390                 395                 400

Thr Val Arg Thr Thr Gly Leu Pro Leu Val Asp Trp Asp Cys Leu
                405                 410                 415

Lys Ala Met Val Arg Thr Phe Glu Thr Lys Cys Gly Ser Ile Ser Gln
                420                 425                 430

Tyr Gly Met Lys His Met Arg Ser Met Ala Asn Ile Cys Asn Ala Gly
            435                 440                 445

Ile Ser Lys Glu Val Met Ala Glu Ala Ser Ala Glu Ala Cys Thr Arg
450                 455                 460

Ile Pro Thr Thr Ser
465

<210> SEQ ID NO 83
<211> LENGTH: 489
<212> TYPE: PRT
<213> ORGANISM: Hordeum vulgare subsp. vulgare

<400> SEQUENCE: 83

Met Ala Met Ala Ser Phe His Leu Leu Pro Leu Ser Leu Leu Leu Leu
1               5                   10                  15

Leu Leu Val Val Ala Asn Ala Gly Thr Pro Pro Leu Glu Pro Gly Leu
                20                  25                  30

Arg Leu Pro Ser Gln Arg Ala Ala Ala Gly Arg Gln Glu Asn Asp Gly
            35                  40                  45

Ser Val Gly Thr Lys Trp Ala Val Leu Val Ala Gly Ser Asn Gly Tyr
        50                  55                  60

Gln Asn Tyr Arg His Gln Ala Asp Val Cys His Ala Tyr Gln Ile Ile
65                  70                  75                  80

Lys Lys Gly Gly Leu Lys Asp Glu Asn Ile Ile Val Phe Met Tyr Asp
                85                  90                  95

Asp Ile Ala His Asn Pro Glu Asn Pro Arg Pro Gly Val Ile Ile Asn
            100                 105                 110

His Pro Gln Gly Gly Asp Val Tyr Ala Gly Val Pro Lys Asp Tyr Thr
        115                 120                 125

Gly Lys Glu Val Asn Ala Lys Asn Leu Phe Ala Val Leu Leu Gly Asn
130                 135                 140

Lys Thr Ala Val Ser Gly Gly Ser Gly Lys Val Val Asp Ser Gly Pro
145                 150                 155                 160

Asn Asp His Ile Phe Val Phe Tyr Ser Asp His Gly Gly Pro Gly Val
                165                 170                 175

Ile Gly Met Pro Thr Tyr Pro Tyr Ile Tyr Gly Asp Asp Leu Val Asp
            180                 185                 190

Val Leu Lys Lys His Ala Ala Gly Thr Tyr Lys Ser Leu Val Phe
        195                 200                 205

Tyr Leu Glu Ala Cys Glu Ala Gly Ser Val Phe Glu Gly Leu Leu Pro
        210                 215                 220

Asn Asp Ile Gly Val Tyr Ala Thr Thr Ala Ser Asn Ala Glu Glu Ser
225                 230                 235                 240
```

-continued

Ser Trp Gly Ala Tyr Cys Pro Gly Glu Tyr Pro Ser Pro Pro Glu
              245                 250                 255

Tyr Asp Thr Cys Leu Gly Asp Leu Tyr Ser Ile Ser Trp Met Glu Asp
              260                 265                 270

Ser Asp Val His Asn Leu Arg Thr Glu Ser Leu Lys Glu Gln Tyr Asn
              275                 280                 285

Leu Val Lys Lys Arg Thr Ala Ala Gln Asp Ser Tyr Ser Tyr Gly Ser
    290                 295                 300

His Val Met Gln Tyr Gly Ser Leu Asp Leu Asn Ala Gln His Leu Phe
305                 310                 315                 320

Leu Tyr Ile Gly Ser Asn Pro Ala Asn Asp Asn Ala Thr Phe Val Glu
                325                 330                 335

Glu Asn Ser Leu Pro Ser Phe Ser Arg Ala Val Asn Gln Arg Asp Ala
                340                 345                 350

Asp Leu Val Tyr Phe Trp His Lys Tyr Arg Lys Leu Ala Glu Ser Ser
                355                 360                 365

Pro Glu Lys Asn Asn Ala Arg Lys Gln Leu Leu Glu Met Met Gly His
                370                 375                 380

Arg Ser His Val Asp Asn Ser Val Glu Leu Ile Gly Asn Leu Leu Phe
385                 390                 395                 400

Gly Ser Ala Asp Gly Pro Met Val Leu Lys Ser Val Arg Pro Ala Gly
                405                 410                 415

Glu Pro Leu Val Asp Asp Trp Asn Cys Leu Lys Ser Thr Val His Thr
                420                 425                 430

Phe Glu Ser Gln Cys Gly Ser Leu Ala Gln Tyr Gly Met Lys His Met
                435                 440                 445

Arg Ser Phe Ala Asn Ile Cys Asn Ala Gly Ile Leu Pro Glu Thr Met
450                 455                 460

Val Lys Val Ala Ala Gln Ala Cys Thr Ser Ile Pro Thr Asn Pro Trp
465                 470                 475                 480

Ser Gly Thr His Lys Gly Phe Ser Ala
                485

<210> SEQ ID NO 84
<211> LENGTH: 485
<212> TYPE: PRT
<213> ORGANISM: Zea mays

<400> SEQUENCE: 84

Met Val Ala Asp Arg Leu Arg Leu Ala Leu Leu Leu Ser Ala Cys Leu
1               5                   10                  15

Cys Ser Ala Trp Ala Arg Pro Arg Leu Glu Pro Thr Ile Arg Leu Pro
                20                  25                  30

Ser Glu Arg Ala Ala Ala Asp Glu Thr Asp Asp Ala Val Gly Thr
            35                  40                  45

Arg Trp Ala Val Leu Ile Ala Gly Ser Asn Gly Tyr Tyr Asn Tyr Arg
    50                  55                  60

His Gln Ala Asp Ile Cys His Ala Tyr Gln Ile Met Lys Lys Gly Gly
65                  70                  75                  80

Leu Lys Asp Glu Asn Ile Val Val Phe Met Tyr Asp Asp Ile Ala His
                85                  90                  95

Ser Pro Glu Asn Pro Arg Pro Gly Val Ile Ile Asn His Pro Gln Gly
                100                 105                 110

Gly Asp Val Tyr Ala Gly Val Pro Lys Asp Tyr Thr Gly Arg Glu Val

```
            115                 120                 125
Asn Val Asp Asn Phe Phe Ala Val Leu Leu Gly Asn Lys Thr Ala Leu
        130                 135                 140

Arg Gly Gly Ser Gly Lys Val Val Asp Ser Gly Pro Asn Asp His Ile
145                 150                 155                 160

Phe Val Phe Tyr Ser Asp His Gly Gly Pro Gly Val Leu Gly Met Pro
                165                 170                 175

Thr Tyr Pro Tyr Leu Tyr Gly Asp Asp Leu Val Asp Val Leu Lys Lys
            180                 185                 190

Lys His Ala Ala Gly Thr Tyr Lys Ser Leu Val Phe Tyr Leu Glu Ala
        195                 200                 205

Cys Glu Ser Gly Ser Ile Phe Glu Gly Leu Leu Pro Asn Asp Ile Asn
    210                 215                 220

Val Tyr Ala Thr Thr Ala Ser Asn Ala Glu Ser Ser Trp Gly Thr
225                 230                 235                 240

Tyr Cys Pro Gly Glu Phe Pro Ser Pro Pro Glu Tyr Asp Thr Cys
                245                 250                 255

Leu Gly Asp Leu Tyr Ser Val Ala Trp Met Glu Asp Ser Asp Phe His
            260                 265                 270

Asn Leu Arg Thr Glu Ser Leu Lys Gln Gln Tyr Asn Leu Val Lys Asp
        275                 280                 285

Arg Thr Ala Val Gln Asp Thr Phe Ser Tyr Gly Ser His Val Met Gln
290                 295                 300

Tyr Gly Ser Leu Glu Leu Asn Val Lys His Leu Phe Ser Tyr Ile Gly
305                 310                 315                 320

Thr Asn Pro Ala Asn Asp Asp Asn Thr Ser Ile Glu Asp Asn Ser Leu
                325                 330                 335

Pro Ser Phe Ser Lys Ala Val Asn Gln Arg Asp Ala Asp Leu Val Tyr
            340                 345                 350

Phe Trp Gln Lys Tyr Arg Lys Leu Ala Asp Ser Ser His Glu Lys Asn
        355                 360                 365

Glu Ala Arg Arg Glu Leu Leu Glu Val Met Ala His Arg Ser His Val
    370                 375                 380

Asp Ser Ser Val Glu Leu Ile Gly Ser Leu Leu Phe Gly Ser Glu Asp
385                 390                 395                 400

Gly Pro Arg Val Leu Lys Ala Val Arg Ala Gly Glu Pro Leu Val
                405                 410                 415

Asp Asp Trp Ser Cys Leu Lys Ser Thr Val Arg Thr Phe Glu Ala Gln
            420                 425                 430

Cys Gly Ser Leu Ala His Tyr Gly Met Lys His Met Arg Ser Phe Pro
        435                 440                 445

Asn Ile Cys Asn Ala Gly Ile Leu Pro Glu Ala Val Ser Lys Val Ala
    450                 455                 460

Ala Gln Ala Cys Thr Ser Ile Pro Ser Asn Pro Trp Ser Ser Ile His
465                 470                 475                 480

Lys Gly Phe Ser Ala
                485

<210> SEQ ID NO 85
<211> LENGTH: 487
<212> TYPE: PRT
<213> ORGANISM: Setaria italica

<400> SEQUENCE: 85
```

-continued

```
Met Met Ala Ala Ala Arg Leu Arg Leu Ala Leu Leu Leu Tyr Val Phe
1               5                   10                  15

Met Cys Ala Ala Trp Ala Arg Pro Gly Leu Glu Pro Ala Ile Arg Leu
            20                  25                  30

Pro Ser Glu Arg Ala Ala Ala Gly Glu Gly Thr Asp Asp Ala Val
        35                  40                  45

Gly Thr Arg Trp Ala Val Leu Ile Ala Gly Ser Asn Gly Tyr Tyr Asn
    50                  55                  60

Tyr Arg His Gln Ala Asp Ile Cys His Ala Tyr Gln Ile Leu Lys Lys
65                  70                  75                  80

Gly Gly Leu Lys Asp Glu Asn Ile Ile Val Phe Met Tyr Asp Asp Ile
                85                  90                  95

Ala His Ser Pro Glu Asn Pro Arg Pro Gly Val Ile Ile Asn His Pro
            100                 105                 110

Gln Gly Gly Asp Val Tyr Ala Gly Val Pro Lys Asp Tyr Thr Gly Arg
        115                 120                 125

Glu Val Asn Val Asn Asn Phe Phe Ala Val Leu Leu Gly Asn Lys Thr
    130                 135                 140

Ala Val Ser Gly Gly Ser Gly Lys Val Val Asp Ser Gly Pro Asn Asp
145                 150                 155                 160

His Ile Phe Val Phe Tyr Ser Asp His Gly Gly Pro Gly Val Leu Gly
                165                 170                 175

Met Pro Thr Tyr Pro Tyr Leu Tyr Gly Asp Asp Leu Val Asn Val Leu
            180                 185                 190

Lys Lys Lys His Ala Ala Gly Thr Tyr Lys Ser Leu Val Phe Tyr Leu
        195                 200                 205

Glu Ala Cys Glu Ser Gly Ser Ile Phe Glu Gly Leu Leu Pro Asn Asp
    210                 215                 220

Ile Asn Val Tyr Ala Thr Thr Ala Ser Asn Ala Asp Glu Ser Ser Trp
225                 230                 235                 240

Gly Thr Tyr Cys Pro Gly Glu Ser Pro Ser Pro Pro Glu Tyr Asp
                245                 250                 255

Thr Cys Leu Gly Asp Leu Tyr Ser Val Ala Trp Met Glu Asp Ser Asp
            260                 265                 270

Phe His Asn Leu Arg Thr Glu Ser Leu Lys Gln Gln Tyr Asn Leu Val
        275                 280                 285

Lys Asp Arg Thr Ser Val His Asn Thr Phe Thr Tyr Gly Ser His Val
    290                 295                 300

Met Gln Tyr Gly Ser Leu Asn Leu Asn Val Gln His Leu Phe Ser Tyr
305                 310                 315                 320

Ile Gly Thr Asn Pro Ala Asn Asp Asp Asn Lys Phe Val Glu Gly Asn
                325                 330                 335

Ser Leu Pro Ser Phe Thr Arg Ala Val Asn Gln Arg Asp Ala Asp Leu
            340                 345                 350

Val Tyr Phe Trp Gln Lys Tyr Arg Lys Val Ala Glu Gly Ser Pro Gly
        355                 360                 365

Lys Asn Asp Ala Arg Lys Glu Leu Leu Glu Val Met Ala His Arg Ser
    370                 375                 380

His Val Asp Asn Ser Val Glu Leu Ile Gly Ser Leu Leu Phe Gly Ser
385                 390                 395                 400

Glu Asp Gly Pro Arg Val Leu Lys Ala Val Arg Ala Ala Gly Glu Pro
                405                 410                 415

Leu Val Asp Asp Trp Ser Cys Leu Lys Ser Met Val Arg Ala Phe Glu
```

```
                420            425            430
Ala Gln Cys Gly Ser Leu Ser Gln Tyr Gly Met Lys His Met Arg Ser
            435                440                445

Phe Ala Asn Ile Cys Asn Ala Gly Ile Leu Pro Asp Ala Val Ser Lys
        450                455                460

Val Ala Ala Gln Ala Cys Thr Ser Ile Pro Ser Asn Pro Trp Ser Ser
465                470                475                480

Ile His Met Gly Phe Ser Ala
                485

<210> SEQ ID NO 86
<211> LENGTH: 460
<212> TYPE: PRT
<213> ORGANISM: Medicago truncatula

<400> SEQUENCE: 86

Met Asp Phe Ser Gln Phe Ser Thr Ile Leu Phe Leu Thr Val Ile Leu
1               5                   10                  15

Thr Ile Phe Ala Ala Val Ser Gly Ser Arg Asp Leu Pro Gly Asp Tyr
                20                  25                  30

Ile Arg Leu Pro Ser Gln Ser Gln Ala Ser Arg Phe Phe His Glu Pro
            35                  40                  45

Glu Asn Asp Asp Asn Asp Gln Gly Thr Arg Trp Ala Ile Leu Leu Ala
    50                  55                  60

Gly Ser Asn Gly Tyr Trp Asn Tyr Arg His Gln Ala Asp Val Cys His
65                  70                  75                  80

Ala Tyr Gln Leu Leu Arg Lys Gly Gly Leu Lys Glu Glu Asn Ile Ile
                85                  90                  95

Val Phe Met Tyr Asp Asp Ile Ala Ser Asn Val Glu Asn Pro Arg Pro
                100                 105                 110

Gly Val Ile Ile Asn Lys Pro Asp Gly Asp Val Tyr Glu Gly Val
            115                 120                 125

Pro Lys Asp Tyr Thr Gly Ala Glu Val His Ala Asp Asn Phe Tyr Ala
    130                 135                 140

Ala Leu Leu Gly Asn Lys Ser Ala Leu Thr Gly Gly Ser Gly Lys Val
145                 150                 155                 160

Val Asp Ser Gly Pro Asn Asp His Ile Phe Val Tyr Tyr Thr Asp His
                165                 170                 175

Gly Gly Pro Gly Val Leu Gly Met Pro Val Gly Pro Tyr Leu Tyr Ala
            180                 185                 190

Ser Asp Leu Asn Glu Val Leu Lys Lys His Ala Ser Gly Ser Tyr
    195                 200                 205

Lys Ser Leu Val Phe Tyr Leu Glu Lys Ile Ser Ile Ser Met Arg Gln
210                 215                 220

Thr Ala Ser Asn Ala Val Glu Ser Ser Trp Gly Thr Tyr Cys Pro Gly
225                 230                 235                 240

Glu Tyr Pro Pro Pro Pro Glu Tyr Ser Thr Cys Leu Gly Asp Leu
                245                 250                 255

Tyr Ser Ile Ala Trp Met Glu Asp Ser Asp Ile His Asn Leu Arg Thr
                260                 265                 270

Glu Ser Leu His Gln Gln Tyr Lys Leu Val Lys Asp Arg Thr Ile Asn
            275                 280                 285

Gly Tyr Tyr Gly Ser His Val Met Glu Tyr Gly Asp Val Gly Leu Ser
    290                 295                 300
```

```
Asn Asn His Leu Phe Leu Tyr Leu Gly Thr Asn Pro Ala Asn Asp Asn
305                 310                 315                 320

Ile Ser Phe Val Asp Glu Ser Ser Leu Lys Leu Arg Ser Pro Ser Thr
            325                 330                 335

Ala Val Asn Gln Arg Asp Ala Asp Leu Ile His Phe Trp Asp Lys Phe
            340                 345                 350

Arg Lys Ala Pro Glu Gly Ser Leu Arg Lys Asn Glu Ala Gln Lys Glu
            355                 360                 365

Val Leu Glu Ala Met Ser His Arg Met His Val Asp Asn Ser Val Lys
            370                 375                 380

Leu Ile Gly Lys Leu Leu Phe Gly Ile Glu Lys Gly Thr Glu Leu Leu
385                 390                 395                 400

Asp Asn Val Arg Pro Ala Gly Ser Pro Leu Val Asp Asn Trp Asp Cys
            405                 410                 415

Leu Lys Thr Met Val Lys Thr Phe Glu Thr His Cys Gly Ser Leu Ser
            420                 425                 430

Gln Tyr Gly Met Lys His Met Arg Ser Phe Ala Asn Ile Cys Asn Ala
            435                 440                 445

Gly Ile Gln Thr Glu Gln Met Ala Glu Ala Ser Ala
450                 455                 460

<210> SEQ ID NO 87
<211> LENGTH: 478
<212> TYPE: PRT
<213> ORGANISM: Populus trichocarpa

<400> SEQUENCE: 87

Met Thr Gly Leu Ala Thr Gly Ala Ile Phe Leu Leu Ile Ser Leu Cys
1               5                   10                  15

Gly Ile Ala Ala Ala Gly Arg Asp Thr Val Gly Asp Val Leu Arg Leu
            20                  25                  30

Pro Ser Glu Ala Ser Arg Phe Phe His Asn Asp Asp Asn Ser Asp Asp
            35                  40                  45

Asp Ser Thr Gly Thr Arg Trp Ala Ile Leu Leu Ala Gly Ser Asn Gly
    50                  55                  60

Tyr Trp Asn Tyr Arg His Gln Ala Asp Val Cys His Ala Tyr Gln Leu
65                  70                  75                  80

Leu Arg Lys Gly Gly Leu Lys Glu Glu Asn Ile Ile Val Phe Met Tyr
            85                  90                  95

Asp Asp Ile Ala Tyr Asn Ser Glu Asn Pro Arg Arg Gly Val Ile Ile
            100                 105                 110

Asn Ser Pro Gln Gly Glu Asp Val Tyr Lys Gly Val Pro Lys Asp Tyr
            115                 120                 125

Thr Gly Glu Asp Val Thr Val Gly Asn Phe Phe Ala Ile Leu Gly
            130                 135                 140

Asn Lys Thr Ala Leu Thr Gly Gly Ser Gly Lys Val Val Asp Ser Gly
145                 150                 155                 160

Pro Asn Asp His Ile Phe Ile Tyr Tyr Thr Asp His Gly Gly Pro Gly
            165                 170                 175

Val Leu Gly Met Pro Thr Asn Pro Tyr Leu Tyr Ala Asp Leu Ile
            180                 185                 190

Asp Val Leu Lys Lys Lys His Ala Ser Gly Thr Tyr Lys Ser Leu Val
            195                 200                 205

Phe Tyr Leu Glu Ala Cys Glu Ser Gly Ser Ile Phe Glu Gly Leu Leu
            210                 215                 220
```

```
Pro Gln Gly Leu Asn Ile Tyr Ala Thr Thr Ala Ser Asn Ala Glu Glu
225                 230                 235                 240

Ser Ser Trp Gly Thr Tyr Cys Pro Gly Glu Asn Pro Ser Pro Pro Pro
            245                 250                 255

Glu Tyr Glu Thr Cys Leu Gly Asp Leu Tyr Ser Val Ala Trp Met Glu
        260                 265                 270

Asp Ser Asp Ile His Asn Leu Gln Thr Glu Thr Leu His Gln Gln Tyr
        275                 280                 285

Glu Leu Val Lys Arg Arg Thr Ser Asn Asp Asn Ser Pro Tyr Gly Ser
        290                 295                 300

His Val Met Gln Tyr Gly Asp Val Gly Leu Ser Lys Asp Asn Ile Phe
305                 310                 315                 320

Leu Tyr Met Gly Thr Asn Pro Ala Asn Asp Asn Phe Thr Phe Met Asp
                325                 330                 335

Glu Asn Leu Leu Arg Pro Arg Ser Lys Ala Val Asn Gln Arg Asp Ala
                340                 345                 350

Asp Leu Val His Phe Trp Asp Lys Tyr Arg Lys Ala Pro Glu Gly Ser
                355                 360                 365

Ser Arg Lys Val Glu Ala Gln Lys Gln Phe Val Glu Ala Met Ser His
        370                 375                 380

Arg Met His Ile Asp His Ser Ile Lys Leu Ile Gly Lys Leu Leu Phe
385                 390                 395                 400

Gly Ile Glu Lys Ala Ser Glu Val Leu Asn Ala Ile Arg Pro Ala Gly
                405                 410                 415

Gln Pro Leu Val Asp Asp Trp Asp Cys Leu Lys Thr Leu Val Lys Phe
                420                 425                 430

Tyr Gly Ser Gln Pro Leu Leu Tyr His Arg Leu Thr Cys Leu Phe Ser
                435                 440                 445

Leu Ile Ala Ser Pro Ala Gly Asp Thr Ser Lys Asp Ser Phe Pro Phe
                450                 455                 460

Leu Arg Lys Cys Leu Leu Phe Phe Tyr Ala Gly Glu Asp Phe
465                 470                 475

<210> SEQ ID NO 88
<211> LENGTH: 431
<212> TYPE: PRT
<213> ORGANISM: Genlisea aurea

<400> SEQUENCE: 88

Asp Asp Asp Ile Val Gly Thr Arg Trp Ala Val Leu Val Ala Gly Ser
1               5                   10                  15

Asn Gly Tyr Trp Asn Tyr Arg His Gln Ala Asp Val Cys His Ala Tyr
            20                  25                  30

Gln Thr Leu Lys Lys Gly Gly Leu Lys Asp Glu Asn Ile Ile Val Phe
        35                  40                  45

Met Tyr Asp Asp Ile Ala Tyr Asn Asp Glu Asn Pro Arg Pro Gly Val
    50                  55                  60

Ile Ile Asn His Pro His Gly Glu Asn Val Tyr Asp Gly Val Pro Lys
65                  70                  75                  80

Asp Tyr Val Gly Asp Asp Val Thr Val Asp Asn Phe Phe Ala Val Leu
                85                  90                  95

Leu Gly Asn Lys Thr Ala Leu Ser Gly Gly Ser Gly Lys Val Val Asp
            100                 105                 110

Ser Gly Pro Asn Asp His Ile Phe Val Tyr Tyr Ser Asp His Gly Gly
```

```
            115                 120                 125
Pro Gly Val Leu Gly Met Pro Thr Asp Pro Tyr Leu Tyr Ala Asn Asp
    130                 135                 140

Leu Ile Asp Val Leu Lys Arg Lys His Ala Ser Gly Thr Tyr Lys Ser
145                 150                 155                 160

Leu Val Phe Tyr Val Glu Ala Cys Glu Ser Gly Ser Ile Phe Glu Gly
                165                 170                 175

Leu Leu Pro Glu Gly Leu Asn Ile Phe Ala Thr Thr Ala Ser Asn Ala
            180                 185                 190

Glu Glu Asn Ser Trp Gly Thr Tyr Cys Pro Gly Asp Asp Ile Gly Pro
        195                 200                 205

Pro Pro Glu Tyr Glu Thr Cys Leu Gly Asp Met Tyr Ser Val Ser Trp
    210                 215                 220

Met Glu Asp Ser Asp Gln His Asn Leu Arg Thr Glu Thr Leu Arg Gln
225                 230                 235                 240

Gln Tyr His Val Val Arg Glu Arg Thr Ala Arg Asp Asn Ser His Arg
                245                 250                 255

Tyr Gly Ser His Val Met Gln Tyr Gly Asp Leu Lys Leu Ser Val Asp
            260                 265                 270

Lys Leu Phe Leu Tyr Met Gly Ser Asn Pro Ser Asn Asp Asn Ser Thr
        275                 280                 285

Phe Gly Gly Ser Val His Leu Ser Gly Asn Ser Ser Trp Pro Ser Ser
    290                 295                 300

Met Ala Val Ser Gln Arg Asp Ala Asp Val Leu His Phe Trp Asp Lys
305                 310                 315                 320

Phe Arg Lys Ala Pro Glu Gly Ser Ser Arg Lys Ala Glu Ala Gln Lys
                325                 330                 335

Gln Leu Ala Glu Val Met Val Arg Arg Ser Arg Val Asp Ile Ser Val
            340                 345                 350

Val Ser Ile Gly Lys Leu Leu Phe Gly Ser Ser Glu Ile Met Asn Ala
        355                 360                 365

Ile Arg Pro Ser Gly Lys Ser Leu Val Asp Asp Trp Asp Cys Leu Lys
    370                 375                 380

Ser Leu Val Arg Ile Phe Glu Thr Tyr Cys Ser Ser Leu Ser Gly Tyr
385                 390                 395                 400

Gly Met Lys His Met Arg Ser Ile Ala Asn Met Cys Asn Ala Gly Val
                405                 410                 415

Ser Glu Glu Gln Met Ser Glu Ala Ser Ser Gln Val Cys Ser Ser
            420                 425                 430

<210> SEQ ID NO 89
<211> LENGTH: 422
<212> TYPE: PRT
<213> ORGANISM: Triticum urartu

<400> SEQUENCE: 89

Met Ser Arg Ala Asp Ile Cys His Ala Tyr Gln Ile Leu Lys Lys Gly
1               5                   10                  15

Gly Leu Lys Asp Glu Asn Ile Ile Val Phe Met Tyr Asp Asp Ile Ala
                20                  25                  30

His Asn Leu Glu Asn Pro Arg Pro Gly Val Ile Ile Asn His Pro Gln
            35                  40                  45

Gly Gly Asp Val Tyr Ala Gly Val Pro Lys Asp Tyr Thr Gly Lys Glu
        50                  55                  60
```

Val Asn Val Lys Asn Leu Phe Ala Val Leu Leu Gly Asn Lys Thr Ala
 65                  70                  75                  80

Val Asn Gly Gly Ser Gly Lys Val Leu Asp Ser Gly Pro Asn Asp His
             85                  90                  95

Ile Phe Val Phe Tyr Ser Asp His Gly Gly Pro Gly Val Ile Gly Met
            100                 105                 110

Pro Thr Asn Pro Tyr Val Tyr Gly Asp Asp Leu Val Asp Val Leu Lys
            115                 120                 125

Lys Lys His Ala Ala Gly Ser Tyr Lys Ser Leu Val Phe Tyr Leu Glu
130                 135                 140

Ala Cys Glu Ala Gly Ser Val Phe Glu Gly Leu Leu Pro Asn Asp Ile
145                 150                 155                 160

Gly Val Tyr Ala Thr Thr Ala Ser Asp Ala Glu Glu Ser Ser Trp Gly
                165                 170                 175

Thr Tyr Cys Pro Gly Glu Tyr Pro Ser Pro Pro Glu Tyr Asp Thr
                180                 185                 190

Cys Leu Gly Asp Leu Tyr Ser Ile Ser Trp Met Glu Asp Ser Asp Val
                195                 200                 205

His Asn Leu Arg Thr Glu Ser Leu Lys Gln Gln Tyr Asp Leu Val Lys
            210                 215                 220

Lys Arg Thr Ala Ala Gln Asp Ser Tyr Ser Tyr Gly Ser His Val Met
225                 230                 235                 240

Gln Tyr Gly Ser Leu Asp Leu Asn Ala Gln Gln Leu Phe Leu Tyr Ile
                245                 250                 255

Gly Ser Asn Pro Ala Asn Asn Asn Thr Thr Phe Val Glu Asp Asn Ser
            260                 265                 270

Leu Pro Ser Phe Ser Arg Ala Val Asn Gln Arg Asp Ala Asp Leu Val
            275                 280                 285

Tyr Phe Trp His Lys Tyr Arg Lys Leu Ala Glu Ser Ser Pro Glu Lys
            290                 295                 300

Asn Asp Ala Arg Lys Gln Leu Leu Glu Met Thr Ser His Arg Ser His
305                 310                 315                 320

Ile Asp Asn Ser Val Glu Leu Ile Gly Asn Leu Leu Phe Gly Phe Ala
                325                 330                 335

Asp Gly Pro Met Val Leu Lys Thr Val Arg Pro Ala Gly Glu Pro Leu
            340                 345                 350

Val Asp Asp Trp Ser Cys Leu Lys Ser Thr Val Arg Ala Phe Glu Ser
            355                 360                 365

Gln Cys Gly Ser Leu Ala Gln Tyr Gly Met Lys His Met Arg Ser Phe
370                 375                 380

Ala Asn Ile Cys Asn Ala Gly Val Leu Pro Glu Ala Met Val Lys Val
385                 390                 395                 400

Ala Ala Gln Ala Cys Lys Ser Ile Pro Thr Asn Pro Trp Ser Ala Thr
                405                 410                 415

His Lys Gly Phe Ser Ala
            420

<210> SEQ ID NO 90
<211> LENGTH: 474
<212> TYPE: PRT
<213> ORGANISM: Hordeum vulgare subsp. vulgare

<400> SEQUENCE: 90

Met Ala Arg Leu Pro Cys Ser Pro Leu Leu Leu Leu Val Leu Ser
1               5                   10                  15

-continued

```
Ser Gln Leu Ala Leu Leu Val Ala Gly Glu Phe Leu Arg Leu Pro Ser
             20                  25                  30
Glu Lys Asp Val Val Gly Thr Arg Trp Ala Val Leu Ile Ala Gly Ser
         35                  40                  45
Asn Gly Tyr Tyr Asn Tyr Arg His Gln Ala Asp Val Cys His Ala Tyr
     50                  55                  60
Gln Ile Met Lys Lys Gly Gly Leu Lys Asp Glu Asn Ile Ile Val Phe
 65                  70                  75                  80
Met Tyr Asp Asp Ile Ala Asn Asn Arg Asp Asn Pro Arg Pro Gly Val
                 85                  90                  95
Ile Ile Asn His Pro Lys Gly Gly Asp Val Tyr Ala Gly Val Pro Lys
            100                 105                 110
Asp Tyr Thr Gly Ala Asp Val Asn Thr Asn Asn Phe Leu Ala Ala Leu
        115                 120                 125
Leu Gly Asp Lys Ser Lys Leu Thr Gly Ser Gly Ser Gly Lys Val Val
130                 135                 140
Ser Ser Gly Pro Asp Asp His Ile Phe Val Tyr Tyr Ala Asp His Gly
145                 150                 155                 160
Gly Pro Gly Ile Leu Gly Met Pro Glu Asp Glu Glu Tyr Leu Tyr Ala
                165                 170                 175
Asn Asp Leu Val Arg Thr Leu Glu Lys Lys His Ala Gly Gly Ala Gly
            180                 185                 190
Tyr Lys Ser Leu Val Phe Tyr Leu Glu Ala Cys Glu Ser Gly Ser Ile
        195                 200                 205
Phe Glu Gly Leu Leu Pro Gly Asn Ile Ser Val Tyr Ala Thr Thr Ala
    210                 215                 220
Ala Asn Ala Glu Glu Ser Ser Trp Gly Thr Tyr Cys Pro Gly Asp Asp
225                 230                 235                 240
Glu Gly Ala Pro Pro Pro Glu Tyr Asp Thr Cys Leu Gly Asp Leu Tyr
                245                 250                 255
Ser Val Ala Trp Met Glu Asp Ser Asp Ala His Asn Leu Asn Ala Glu
            260                 265                 270
Ser Leu Lys Gln Gln Tyr Glu Arg Val Arg Asn Arg Thr Ser Ala Asp
        275                 280                 285
Gly Thr Tyr Ser Leu Gly Ser His Val Met Gln Tyr Gly Asp Leu Gly
    290                 295                 300
Leu Asn Asp Gln Ser Leu Phe Gln Tyr Ile Gly Thr Asn Pro Ala Asn
305                 310                 315                 320
Asp Asn Ala Thr Phe Val Gln Ser Ser Ser Ser Arg Gln Leu Pro
                325                 330                 335
Gly Ala Arg Val Asn Gln Arg Asp Ala Asp Leu Val His Phe Trp His
            340                 345                 350
Lys Tyr Arg Arg Ser Ala Glu Gly Ser Ala Glu Lys Val Glu Ala Arg
        355                 360                 365
Arg Arg Leu Val Glu Thr Met Ala Arg Ser Arg Val Asp Ser Ser
    370                 375                 380
Val Glu Leu Ile Gly Gly Leu Leu Phe Gly Ser Glu Glu Gly Ala Lys
385                 390                 395                 400
Val Leu Gly Thr Val Arg Pro Ala Gly Gln Pro Val Val Asp Trp
                405                 410                 415
Gly Cys Leu Lys Ser Val Val Arg Phe Glu Glu Arg Cys Gly Pro
            420                 425                 430
```

```
Leu Thr Gln Tyr Gly Met Lys His Met Arg Ser Leu Ala Asn Ile Cys
            435                 440                 445

Asn Ala Gly Val Arg Glu Glu Val Met Asp Lys Ala Ala Ser Gln Ala
        450                 455                 460

Cys Ala Ala Ser Pro Ser Ser Leu Ile Ile
465                 470

<210> SEQ ID NO 91
<211> LENGTH: 424
<212> TYPE: PRT
<213> ORGANISM: Aegilops tauschii

<400> SEQUENCE: 91

Met Ser Gln Val Arg Ala Asp Ile Cys His Ala Tyr Gln Ile Leu Lys
1               5                   10                  15

Thr Gly Gly Leu Lys Asp Glu Asn Ile Ile Val Phe Met Tyr Asp Asp
            20                  25                  30

Ile Ala His Asn Leu Glu Asn Pro Arg Pro Gly Val Ile Ile Asn His
        35                  40                  45

Pro Gln Gly Gly Asp Val Tyr Ala Gly Val Pro Lys Asp Tyr Thr Gly
    50                  55                  60

Lys Glu Val Asn Val Lys Asn Leu Phe Ala Val Leu Leu Gly Asn Lys
65                  70                  75                  80

Thr Ala Val Ser Gly Gly Ser Gly Lys Val Val Asp Ser Gly Pro Asn
                85                  90                  95

Asp His Ile Phe Val Phe Tyr Ser Asp His Gly Gly Pro Gly Val Ile
            100                 105                 110

Gly Met Pro Thr Tyr Pro Tyr Val Tyr Gly Asp Asp Leu Val Asp Val
        115                 120                 125

Leu Lys Lys Lys His Ala Ala Gly Thr Tyr Lys Ser Leu Val Phe Tyr
    130                 135                 140

Leu Glu Ala Cys Glu Ala Gly Ser Val Phe Glu Gly Leu Leu Pro Asn
145                 150                 155                 160

Asp Ile Gly Val Tyr Ala Thr Thr Ala Ser Asn Ala Glu Glu Ser Ser
                165                 170                 175

Trp Gly Thr Tyr Cys Pro Gly Glu Tyr Pro Ser Pro Ser Glu Tyr
            180                 185                 190

Asp Thr Cys Leu Gly Asp Leu Tyr Ser Ile Ser Trp Met Glu Asp Ser
        195                 200                 205

Asp Val His Asn Leu Arg Thr Glu Ser Leu Lys Gln Gln Tyr Asp Leu
    210                 215                 220

Val Lys Lys Arg Thr Ala Ala Gln Asp Ser Tyr Ser Tyr Gly Ser His
225                 230                 235                 240

Val Met Gln Tyr Gly Ser Leu Asp Leu Asn Asp Gln His Leu Phe Leu
                245                 250                 255

Tyr Ile Gly Ser Asn Pro Ala Asn Asp Asn Thr Thr Phe Val Glu Asp
            260                 265                 270

Asn Ser Leu Pro Ser Phe Ser Arg Ala Val Asn Gln Arg Asp Ala Asp
        275                 280                 285

Leu Val Tyr Phe Trp Arg Lys Tyr Gln Lys Leu Ala Glu Ser Ser Thr
    290                 295                 300

Glu Lys Asn Asp Ala Arg Lys Gln Leu Leu Glu Met Met Gly His Arg
305                 310                 315                 320

Ser His Ile Asp Asn Ser Val Glu Leu Ile Gly Asn Leu Leu Phe Gly
                325                 330                 335
```

```
Phe Ala Asp Gly Pro Met Val Leu Lys Thr Val Arg Pro Ala Gly Glu
            340                 345                 350

Pro Leu Ala Asp Asp Trp Ser Cys Leu Lys Ser Met Val Arg Ala Phe
            355                 360                 365

Glu Ser Gln Cys Gly Ser Leu Ala Gln Tyr Gly Met Lys His Met Arg
370                 375                 380

Ser Phe Ala Asn Ile Cys Asn Ala Gly Ile Leu Pro Glu Ala Met Val
385                 390                 395                 400

Lys Met Ala Ala Gln Ala Cys Thr Ser Ile Pro Thr Asn Pro Trp Ser
                405                 410                 415

Ala Thr His Asn Gly Phe Ser Ala
            420

<210> SEQ ID NO 92
<211> LENGTH: 461
<212> TYPE: PRT
<213> ORGANISM: Solanum tuberosum

<400> SEQUENCE: 92

Met Asn Arg Ser Ile Ala Gly Val Leu Phe Leu Ile Ala Leu Ser Leu
1               5                   10                  15

Asn Val Ser Val Ser Glu Ser Arg Asn Phe Leu Lys Leu Pro Ser Glu
            20                  25                  30

Gly Ser Arg Phe Phe Asp Ala Asp Glu Ser Asp Ser Val Gly Thr Arg
        35                  40                  45

Trp Ala Ile Leu Leu Ala Gly Ser Asn Gly Tyr Trp Asn Tyr Arg His
    50                  55                  60

Gln Ala Asp Ile Cys His Ala Tyr Gln Leu Leu Lys Lys Gly Leu
65                  70                  75                  80

Lys Asp Glu Asn Ile Val Val Phe Met Tyr Asp Asp Ile Ala Asn Asn
                85                  90                  95

Glu Glu Asn Pro Arg Gln Gly Val Ile Ile Asn Ser Pro His Gly Glu
            100                 105                 110

Asp Val Tyr Lys Gly Val Pro Lys Asp Tyr Thr Gly Asp Asp Val Thr
        115                 120                 125

Val Asn Asn Phe Leu Ala Ala Leu Leu Gly Asn Lys Thr Ala Leu Thr
    130                 135                 140

Gly Gly Ser Gly Lys Val Val Asp Ser Gly Pro Asn Asp His Ile Phe
145                 150                 155                 160

Ile Phe Cys Ser Asp His Gly Gly Ala Gly Val Ile Gly Met Pro Thr
                165                 170                 175

Asp Pro Tyr Leu Tyr Ala Asn Asp Leu Ile Asp Ala Leu Lys Lys Lys
            180                 185                 190

His Ala Ser Gly Thr Tyr Lys Ser Leu Val Phe Tyr Leu Glu Ala Cys
        195                 200                 205

Glu Ser Gly Ser Met Ser Glu Gly Leu Leu Pro Glu Gly Leu Asn Val
    210                 215                 220

Tyr Ala Thr Thr Ala Ser Asn Ala Asp Glu Ser Ser Trp Gly Thr Tyr
225                 230                 235                 240

Cys Pro Gly Glu Tyr Pro Ser Pro Ile Glu Tyr Gly Thr Cys Leu
                245                 250                 255

Gly Asp Leu Tyr Ser Ile Ser Trp Met Glu Asp Ser Asp Arg His Asn
            260                 265                 270

Leu Arg Thr Glu Thr Leu Lys Gln Gln Tyr His Leu Val Lys Glu Arg
```

```
                275                 280                 285
Thr Ala Ser Gly Asn Pro Ala Tyr Gly Ser His Val Met Gln Tyr Gly
290                 295                 300
Asp Val His Leu Ser Lys Asp Ala Leu Phe Leu Tyr Met Gly Thr Asp
305                 310                 315                 320
Pro Ala Asn Asp Asn Tyr Thr Phe Val Asp Asp Asn Ser Leu Arg Val
                325                 330                 335
Ser Lys Ala Val Asn Gln Arg Asp Ala Asp Leu Val His Phe Trp Tyr
            340                 345                 350
Lys Phe His Lys Ala Pro Glu Gly Ser Val Arg Lys Thr Glu Ala Gln
        355                 360                 365
Lys Gln Leu Asn Glu Ala Ile Ser His Arg Met His Leu Asp Asn Ser
    370                 375                 380
Ile Ala Leu Val Gly Lys Leu Leu Phe Gly Ile Lys Lys Gly Pro Glu
385                 390                 395                 400
Val Leu Thr Ser Val Arg Pro Ala Gly Gln Pro Leu Val Asp Asp Trp
                405                 410                 415
Asp Cys Leu Lys Ser Tyr Val Ser Thr Pro Thr Pro Phe Ser Ser Ile
            420                 425                 430
Ser Phe Glu Phe Ser Gln Ile Tyr Ser Cys Ile Ser Leu Tyr Gly Gly
        435                 440                 445
Met Arg Leu Arg Ser Leu Val Leu Asp Ile Leu Leu Val
    450                 455                 460

<210> SEQ ID NO 93
<211> LENGTH: 441
<212> TYPE: PRT
<213> ORGANISM: Triticum urartu

<400> SEQUENCE: 93

Met Ala Met Ala Ser Phe Arg Pro Pro Leu Ala Leu Leu Leu Ala
1               5                   10                  15
Ala Cys Leu Ser Ala Leu Ala Asp Ile Cys His Ala Tyr Gln Ile Met
                20                  25                  30
Lys Lys Gly Gly Leu Lys Asp Glu Asn Ile Ile Val Phe Met Tyr Asp
            35                  40                  45
Asp Ile Ala His Asn Pro Glu Asn Pro Arg Pro Gly Val Ile Ile Asn
        50                  55                  60
His Pro Gln Gly Gly Asp Val Tyr Ala Gly Val Pro Lys Asp Tyr Thr
65                  70                  75                  80
Gly Lys Glu Val Asn Val Lys Asn Phe Phe Ala Val Leu Leu Gly Asn
                85                  90                  95
Lys Thr Ala Val Ser Gly Gly Asn Gly Lys Val Val Asp Ser Gly Pro
            100                 105                 110
Asn Asp His Ile Phe Val Phe Tyr Ser Asp His Gly Pro Gly Val
        115                 120                 125
Leu Gly Met Pro Thr Tyr Pro Tyr Leu Tyr Gly Asp Asp Leu Val Asp
    130                 135                 140
Val Leu Lys Lys Lys His Ala Ala Gly Thr Tyr Lys Ser Leu Val Phe
145                 150                 155                 160
Tyr Leu Glu Ala Cys Glu Ser Gly Ser Ile Phe Glu Gly Leu Leu Pro
                165                 170                 175
Asn Asp Ile Gly Val Tyr Ala Thr Thr Ala Ser Asn Ala Glu Glu Ser
            180                 185                 190
```

```
Ser Trp Gly Thr Tyr Cys Pro Gly Glu Tyr Pro Ser Pro Pro Glu
        195                 200                 205

Tyr Asp Thr Cys Leu Gly Asp Leu Tyr Ser Ile Ser Trp Met Glu Asp
    210                 215                 220

Ser Asp Val His Asn Leu Arg Thr Glu Ser Leu Lys Gln Gln Tyr Asn
225                 230                 235                 240

Leu Val Lys Lys Arg Thr Ala Ala Gln Asp Ser Tyr Ser Tyr Gly Ser
                245                 250                 255

His Val Met Gln Tyr Gly Ser Leu Asp Leu Asn Ala Glu His Leu Phe
            260                 265                 270

Ser Tyr Ile Gly Ser Asn Pro Ala Asn Glu Asn Thr Thr Phe Val Glu
        275                 280                 285

Asp Asn Ala Leu Pro Ser Phe Ser Arg Ala Val Asn Gln Arg Asp Ala
    290                 295                 300

Asp Leu Val Tyr Phe Trp Gln Lys Tyr Arg Lys Leu Ala Glu Ser Ser
305                 310                 315                 320

Pro Glu Lys Asn Asp Ala Arg Lys Gln Leu Leu Glu Met Met Gly His
                325                 330                 335

Arg Ser His Ile Asp Asn Ser Ile Glu Leu Ile Gly Asn Leu Leu Phe
            340                 345                 350

Gly Ser Ala Gly Gly Pro Met Val Leu Lys Ala Val Arg Pro Ala Gly
        355                 360                 365

Glu Pro Leu Val Asp Asp Trp Ser Cys Leu Lys Ser Thr Val Arg Thr
    370                 375                 380

Phe Glu Ser Gln Cys Gly Ser Leu Ala Gln Tyr Gly Met Lys His Met
385                 390                 395                 400

Arg Ser Phe Ala Asn Ile Cys Asn Ala Gly Ile Val Pro Glu Ala Thr
                405                 410                 415

Ala Lys Val Ala Ala Gln Ala Cys Thr Ser Ile Pro Thr Asn Pro Trp
            420                 425                 430

Ser Ala Thr His Lys Gly Phe Ser Ala
        435                 440

<210> SEQ ID NO 94
<211> LENGTH: 394
<212> TYPE: PRT
<213> ORGANISM: Citrus clementina

<400> SEQUENCE: 94

Met Tyr Asp Asp Ile Ala Phe Asn Glu Asn Pro Arg Pro Gly Val
1               5                   10                  15

Ile Ile Asn His Pro His Gly Asp Asp Val Tyr Lys Gly Val Pro Lys
                20                  25                  30

Asp Tyr Thr Gly Glu Asp Val Thr Val Glu Asn Phe Ala Val Ile
        35                  40                  45

Leu Gly Asn Lys Thr Ala Leu Thr Gly Gly Ser Gly Lys Val Val Asp
    50                  55                  60

Ser Gly Pro Asn Asp His Ile Phe Ile Phe Tyr Ser Asp His Gly Gly
65                  70                  75                  80

Pro Gly Val Leu Gly Met Pro Thr Ser Arg Tyr Ile Tyr Ala Asp Glu
                85                  90                  95

Leu Ile Asp Val Leu Lys Lys Lys His Ala Ser Gly Asn Tyr Lys Ser
            100                 105                 110

Leu Val Phe Tyr Leu Glu Ala Cys Glu Ser Gly Ser Ile Phe Glu Gly
        115                 120                 125
```

Leu Leu Pro Glu Gly Leu Asn Ile Tyr Ala Thr Thr Ala Ser Asn Ala
            130                 135                 140

Glu Glu Ser Ser Trp Gly Thr Tyr Cys Pro Gly Ile Pro Gly Pro
145                 150                 155                 160

Pro Pro Glu Tyr Ser Thr Cys Leu Gly Asp Leu Tyr Ser Ile Ala Trp
                165                 170                 175

Met Glu Asp Ser Asp Ile His Asn Leu Arg Thr Glu Thr Leu His Gln
            180                 185                 190

Gln Tyr Glu Leu Val Lys Thr Arg Thr Ala Ser Tyr Asn Ser Tyr Gly
        195                 200                 205

Ser His Val Met Gln Tyr Gly Asp Ile Gly Leu Ser Lys Asn Asn Leu
    210                 215                 220

Phe Thr Tyr Leu Gly Thr Asn Pro Ala Asn Asp Asn Tyr Thr Phe Val
225                 230                 235                 240

Asp Glu Asn Ser Leu Arg Pro Ala Ser Lys Ala Val Asn Gln Arg Asp
                245                 250                 255

Ala Asp Leu Leu His Phe Trp Asp Lys Tyr Arg Lys Ala Pro Glu Gly
            260                 265                 270

Thr Pro Arg Lys Ala Glu Ala Gln Lys Gln Phe Phe Glu Ala Met Ser
        275                 280                 285

His Arg Met His Val Asp His Ser Ile Lys Leu Ile Gly Lys Leu Leu
    290                 295                 300

Phe Gly Ile Glu Lys Gly Pro Glu Ile Leu Asn Thr Val Arg Pro Ala
305                 310                 315                 320

Gly Gln Pro Leu Val Asp Asp Trp Gly Cys Leu Lys Ser Leu Val Arg
                325                 330                 335

Thr Phe Glu Ser His Cys Gly Ala Leu Ser Gln Tyr Gly Met Lys His
            340                 345                 350

Met Arg Ser Leu Ala Asn Ile Cys Asn Thr Gly Ile Gly Lys Glu Lys
        355                 360                 365

Met Ala Glu Ala Ser Ala Gln Ala Cys Glu Asn Ile Pro Ser Gly Pro
    370                 375                 380

Trp Ser Ser Leu Asp Lys Gly Phe Ser Ala
385                 390

<210> SEQ ID NO 95
<211> LENGTH: 473
<212> TYPE: PRT
<213> ORGANISM: Setaria italica

<400> SEQUENCE: 95

Met Ala Thr Ala Thr Thr Arg Leu Arg Cys Leu Leu Leu Leu Phe Leu
1               5                   10                  15

Val Gln Leu Leu Leu Leu Ser Ala Ala Gly Ala Arg Trp Gln
            20                  25                  30

Asp Phe Leu Arg Leu Pro Ser Glu Gly Asp Ala Ala Ala Gly Thr
            35                  40                  45

Arg Trp Ala Val Leu Ile Ala Gly Ser Asn Gly Tyr Tyr Asn Tyr Arg
50                  55                  60

His Gln Ala Asp Val Cys His Ala Tyr Gln Ile Met Lys Lys Gly Gly
65                  70                  75                  80

Leu Lys Asp Glu Asn Ile Ile Val Phe Met Tyr Asp Asp Ile Ala Ser
                85                  90                  95

Ser Pro Asp Asn Pro Arg Pro Gly Val Ile Ile Asn His Pro Ser Gly

```
            100                 105                 110
Gly Asp Val Tyr Ala Gly Val Pro Lys Asp Tyr Thr Gly Glu Asp Val
            115                 120                 125
Thr Val Asn Asn Phe Leu Ala Val Leu Leu Gly Asn Arg Ser Ala Val
            130                 135                 140
Ser Gly Gly Ser Gly Lys Val Val Ala Ser Gly Pro Gly Asp His Val
145                 150                 155                 160
Phe Val Tyr Tyr Ser Asp His Gly Gly Pro Gly Val Leu Gly Met Pro
                165                 170                 175
Ser Gly Asp Tyr Leu Tyr Ala Lys Asp Leu Val Gly Ala Leu Glu Arg
                180                 185                 190
Lys His Asp Ala Gly Gly Tyr Arg Ser Leu Val Phe Tyr Leu Glu Ala
                195                 200                 205
Cys Glu Ser Gly Ser Ile Phe Glu Gly Leu Leu Pro Glu Gly Ile Asn
                210                 215                 220
Val Tyr Ala Thr Thr Ala Ala Asn Ala Glu Glu Ser Ser Trp Gly Thr
225                 230                 235                 240
Tyr Cys Pro Gly Asp Asp Gln Gly Pro Pro Glu Phe Asp Thr Cys
                245                 250                 255
Leu Gly Asp Leu Tyr Ser Val Ala Trp Met Glu Asp Ser Asp Val His
                260                 265                 270
Asn Leu Arg Thr Glu Ser Leu Lys Gln Gln Tyr Glu Val Val Lys Asp
                275                 280                 285
Arg Thr Ser Ala His Gly Thr Tyr Ser Leu Gly Ser His Val Met Gln
                290                 295                 300
Tyr Gly Asp Gln Ser Leu Asn Gly Gln Ser Leu Tyr Gln Phe Ile Gly
305                 310                 315                 320
Thr Asp Pro Ala Asn Asp Asn Ala Thr Phe Gly Arg Asp Asn Ser Leu
                325                 330                 335
Arg Arg Arg Ser Ser Gly Thr Val Asn Gln Arg Asp Ala Asp Leu Val
                340                 345                 350
Tyr Phe Trp Gln Lys Tyr Lys Lys Ser Ala Glu Gly Thr Pro Glu Lys
                355                 360                 365
Ala Glu Ala Arg Lys Arg Leu Leu Gln Val Met Ser Arg Arg Ser Arg
                370                 375                 380
Val Asp Ser Ser Met Glu Leu Ile Gly Ser Leu Leu Phe Gly Ser Asp
385                 390                 395                 400
Glu Gly Pro Lys Val Leu Gly Ala Val Arg Pro Ala Gly Gln Pro Leu
                405                 410                 415
Ala Asp Asp Trp Asp Cys Leu Lys Ala Met Val His Ala Tyr Glu Ala
                420                 425                 430
Gln Cys Gly Pro Leu Lys Gln Tyr Gly Met Lys His Met Arg Ser Phe
                435                 440                 445
Ala Asn Ile Cys Asn Ala Gly Val Gly Glu Asp Ala Met Ala Lys Val
                450                 455                 460
Ala Ser Gln Ala Cys Ala Ala Arg
465                 470
```

<210> SEQ ID NO 96
<211> LENGTH: 543
<212> TYPE: PRT
<213> ORGANISM: Aegilops tauschii

<400> SEQUENCE: 96

```
Met Ala Ser Asn Arg Leu Leu Pro Leu Ala Leu Leu Leu Leu Leu
1               5                   10                  15

Ala Met Ala His Ala Asp Thr Pro Arg Leu Glu Pro Thr Val Arg Leu
            20                  25                  30

Pro Ser Gln Arg Met Ala Ala Gly Gln Gly Asp Asp Gly Ser Val Gly
            35                  40                  45

Thr Arg Trp Ala Ala Leu Val Ala Gly Ser Asn Gly Tyr Gln Asn Tyr
        50                  55                  60

Arg His Gln Gly Arg Thr Leu Tyr His Gly Phe Tyr Ser Leu Leu Val
65                  70                  75                  80

Gly Val Ser Ser Arg Asp Pro Pro Thr Phe Phe Phe Leu Ser Val Lys
                85                  90                  95

Ser Ile Pro Ser Trp Glu Ile Arg Trp Val Asp Asp Asn Glu Val Leu
            100                 105                 110

Cys Leu Ile Cys Gly Ala Lys Leu Cys Thr Val Gln Ala Asp Ile Cys
            115                 120                 125

His Ala Tyr Gln Ile Leu Lys Lys Gly Leu Lys Asp Glu Asn Ile
        130                 135                 140

Ile Val Phe Met Tyr Asp Asp Ile Ala His Asn Leu Glu Asn Pro Arg
145                 150                 155                 160

Pro Gly Val Ile Ile Asn His Pro Gln Gly Gly Asp Val Tyr Ser Gly
                165                 170                 175

Val Pro Met Asp Tyr Thr Gly Lys Glu Val Asn Val Lys Asn Leu Phe
            180                 185                 190

Ala Val Leu Leu Gly Asn Lys Thr Ala Val Ser Gly Gly Ser Gly Lys
            195                 200                 205

Val Leu Asp Ser Gly Pro Asn Asp His Ile Phe Val Phe Tyr Ser Asp
        210                 215                 220

His Gly Gly Pro Gly Val Ile Gly Met Pro Thr Asn Pro Tyr Val Tyr
225                 230                 235                 240

Gly Asp Asp Leu Val Asp Val Leu Lys Lys Lys His Ala Ala Gly Thr
                245                 250                 255

Tyr Arg Ser Leu Val Phe Tyr Leu Glu Ala Cys Glu Ala Gly Ser Val
            260                 265                 270

Phe Glu Gly Leu Leu Pro Asn Asp Ile Ser Val Tyr Thr Thr Thr Ala
            275                 280                 285

Ser Asn Ala Glu Glu Ser Ser Trp Gly Thr Tyr Cys Pro Gly Glu Tyr
        290                 295                 300

Pro Ser Pro Pro Glu Tyr Asp Thr Cys Leu Gly Asp Leu Tyr Ser
305                 310                 315                 320

Ile Ser Trp Met Glu Asp Ser Asp Val His Asn Leu Arg Thr Glu Ser
                325                 330                 335

Leu Lys Gln Gln Tyr Asp Leu Val Lys Lys Arg Thr Ala Ala Gln Asp
            340                 345                 350

Ser Tyr Asn Tyr Gly Ser His Val Met Gln Tyr Gly Ser Leu Asp Leu
        355                 360                 365

Asn Ala Gln Gln Leu Phe Leu Tyr Ile Gly Ser Asn Pro Ala Asn Asn
        370                 375                 380

Lys Thr Thr Phe Val Glu Asp Asn Ser Leu Pro Ser Phe Ser Arg Val
385                 390                 395                 400

Val Asn Gln Arg Asp Ala Asp Leu Val Tyr Phe Trp His Lys Tyr Arg
                405                 410                 415

Lys Leu Ala Glu Ser Ser Pro Glu Lys Asn Asp Ala Arg Lys Gln Leu
```

```
                420             425             430
Leu Glu Met Met Ser His Arg Ser His Ile Asp Asn Ser Val Glu Leu
            435                 440                 445

Ile Gly Asn Leu Leu Phe Gly Ser Ala Asp Gly Pro Met Val Leu Lys
            450                 455                 460

Thr Val Arg Pro Ala Gly Glu Pro Leu Val Asp Asp Trp Ser Cys Leu
465                 470                 475                 480

Lys Ser Thr Val Arg Ala Phe Glu Ser Gln Cys Gly Ser Leu Ala Gln
                485                 490                 495

Tyr Gly Met Lys His Met Arg Ser Phe Ala Asn Ile Cys Asn Ala Gly
            500                 505                 510

Val Leu Pro Glu Ala Thr Val Lys Val Ala Ala Gln Ala Cys Lys Ser
            515                 520                 525

Ile Pro Thr Asn Pro Trp Ser Ala Thr His Lys Gly Phe Ser Ala
            530                 535                 540

<210> SEQ ID NO 97
<211> LENGTH: 493
<212> TYPE: PRT
<213> ORGANISM: Picea sitchensis

<400> SEQUENCE: 97

Met Gly Ser Ser Lys Gly Phe Gln Leu Gly Leu Leu Cys Tyr Phe Leu
1               5                   10                  15

Leu Leu Ser Leu Asp Ser Ser Lys Val Ala Asp Gly Ala Arg Arg Asp
                20                  25                  30

Trp Asn Ser Leu Leu Lys Leu Pro Thr Asn His Val Asp Ala Asp Ser
            35                  40                  45

Asp Arg Ile Gly Thr Glu Trp Ala Val Leu Leu Ala Gly Ser Ser Gly
        50                  55                  60

Tyr Trp Asn Tyr Arg His Gln Ala Asp Val Cys His Ala Tyr Gln Ile
65                  70                  75                  80

Leu Arg Arg Gly Gly Leu Lys Glu Glu Asn Ile Val Val Phe Met Tyr
                85                  90                  95

Asp Asp Ile Ala Tyr Asp Glu Glu Asn Pro His Pro Gly Thr Ile Ile
            100                 105                 110

Asn His Pro Gln Gly Ser Asp Val Tyr Ala Gly Val Pro Lys Asp Tyr
        115                 120                 125

Thr Gly Glu Asp Val Thr Val Asn Asn Phe Phe Ala Ala Ile Leu Gly
130                 135                 140

Asn Lys Ser Leu Val Thr Gly Gly Ser Gly Lys Val Val Glu Ser Gly
145                 150                 155                 160

Pro Asn Asp Arg Ile Phe Ile Tyr Tyr Ser Asp His Gly Gly Pro Gly
                165                 170                 175

Val Leu Gly Met Pro Leu Pro Pro Tyr Leu Tyr Ala Asn Asp Phe Val
            180                 185                 190

Gln Val Leu Lys Lys Lys His Asp Ala Gly Ser Tyr Arg Glu Met Val
        195                 200                 205

Ile Tyr Val Glu Ala Cys Glu Ser Gly Ser Ile Phe Glu Gly Leu Leu
    210                 215                 220

Pro Thr Asp Leu Asn Ile Tyr Val Thr Thr Ala Ser Asn Ala Glu Glu
225                 230                 235                 240

Asn Ser Trp Gly Thr Tyr Cys Pro Gly Met Asp Pro Pro Pro Pro
                245                 250                 255
```

```
Glu Tyr Asp Thr Cys Leu Gly Asp Leu Tyr Ser Val Ala Trp Met Glu
            260                 265                 270

Asp Ser Glu Ile Asn Asn Leu Lys Glu Thr Leu Leu Gln Gln Tyr
        275                 280                 285

Asp Leu Val Lys Leu Arg Thr Ser Asn His Asn Thr Tyr Met Ser Gly
        290                 295                 300

Ser His Val Met Gln Tyr Gly Asn Ile Thr Ile Ser Gln Glu Glu Leu
305                 310                 315                 320

Tyr Leu Tyr Met Gly Phe Asp Ser Ala Asn Ser Asn Ala Ser Leu Val
                325                 330                 335

Leu Glu Asn Ser Pro Leu Leu Glu Lys Thr Glu Ala Lys Ala Ile Asn
            340                 345                 350

Gln Arg Asp Ala Asp Leu Leu Tyr Met Trp Gln Lys Tyr Lys Lys Ser
        355                 360                 365

Lys Glu Asp Ser Pro Glu Arg Leu Thr Ala Gln Thr Gln Leu Leu Glu
        370                 375                 380

Phe Met Ala His Arg Met His Val Asp Lys Ser Val Lys Leu Val Gly
385                 390                 395                 400

Asn Leu Leu Phe Gly Pro Glu Lys Gly Pro Ala Val Phe Asn Ala Val
                405                 410                 415

Arg Pro Gln Gly Glu Pro Leu Val Asp Asp Trp Asp Cys Leu Lys Lys
            420                 425                 430

Met Val Arg Thr Phe Glu Gly His Cys Gly Ser Leu Ala Gln Tyr Gly
        435                 440                 445

Met Lys His Met Arg Ala Leu Ala Asn Ile Cys Asn Glu Gly Ile Ser
        450                 455                 460

Met Asp Thr Met Ala Thr Val Ser Ala Glu Ala Cys Thr Gln Phe Pro
465                 470                 475                 480

Ala Gly Ser Trp Ser Ser Leu Gln Arg Gly Phe Ser Ala
                485                 490

<210> SEQ ID NO 98
<211> LENGTH: 380
<212> TYPE: PRT
<213> ORGANISM: Vicia narbonensis

<400> SEQUENCE: 98

Asp Val Cys His Ala Tyr Gln Leu Leu Arg Lys Gly Gly Leu Lys Glu
1               5                   10                  15

Glu Asn Ile Ile Val Phe Met Tyr Asp Asp Ile Ala Tyr Ser Glu Glu
                20                  25                  30

Asn Pro Arg Pro Gly Val Ile Ile Asn Ser Pro His Gly Glu Asn Val
            35                  40                  45

Tyr Glu Gly Val Pro Lys Asp Tyr Thr Gly Glu Asp Val Thr Val Gly
        50                  55                  60

Asn Phe Phe Ala Ala Leu Leu Gly Asn Lys Ser Ala Leu Ser Gly Gly
65                  70                  75                  80

Ser Gly Lys Val Val Asp Ser Gly Pro Asn Asp Arg Ile Phe Val Phe
                85                  90                  95

Tyr Ser Asp His Gly Gly Pro Gly Val Leu Gly Met Pro Thr Ser Pro
            100                 105                 110

Tyr Met Tyr Ala Ser Asp Leu Val Glu Val Leu Lys Ile Lys His Ala
        115                 120                 125

Ala Gly Thr Tyr Lys Ser Leu Val Phe Tyr Leu Glu Ala Cys Glu Ser
        130                 135                 140
```

```
Gly Ser Ile Phe Glu Gly Leu Leu Pro Glu Gly Leu Asn Ile Tyr Ala
145                 150                 155                 160

Thr Thr Ala Ala Asn Ala Glu Glu Ser Ser Trp Gly Thr Tyr Cys Pro
                165                 170                 175

Gly Glu Asn Pro Ser Pro Pro Glu Tyr Glu Thr Cys Leu Ala Asp
            180                 185                 190

Leu Tyr Ser Val Ala Trp Met Glu Asp Ser Asp Ile His Asn Leu Gln
        195                 200                 205

Thr Glu Thr Leu His Gln Gln Tyr Glu Leu Val Lys Glu Arg Thr Ser
210                 215                 220

Asn Gly Asn Ser Asn Tyr Gly Ser His Val Met Gln Tyr Gly Asp Ile
225                 230                 235                 240

Glu Leu Ser Lys Asp Ser Leu Phe Leu Tyr Leu Gly Ser Asn Pro Ser
            245                 250                 255

Asn Glu Asn Phe Thr Phe Val Gly Arg Asn Ser Leu Val Pro Pro Ser
            260                 265                 270

Lys Ala Ile Asn Gln Arg Asp Ala Asp Leu Ile His Phe Trp Asp Lys
        275                 280                 285

Phe Arg Lys Ala Pro Gln Gly Ser Pro Arg Lys Ala Ala Gln Lys
290                 295                 300

Glu Val Leu Glu Ala Met Ser His Arg Met His Ile Asp Asp Ser Ile
305                 310                 315                 320

Lys Leu Val Gly Lys Leu Leu Phe Gly Met Lys Lys Gly Pro Glu Val
            325                 330                 335

Leu Thr Ser Val Arg Pro Ala Gly Gln Pro Leu Val Asp Asp Trp Asp
            340                 345                 350

Cys Leu Lys Thr Leu Val Arg Thr Phe Glu Thr Tyr Cys Gly Ser Leu
        355                 360                 365

Ser Gln Tyr Gly Met Lys His Met Arg Ser Phe Ala
        370                 375                 380

<210> SEQ ID NO 99
<211> LENGTH: 455
<212> TYPE: PRT
<213> ORGANISM: Nicotiana tabacum

<400> SEQUENCE: 99

Met Ile Arg Lys Asn Gly Val Val Pro Phe Leu Val Ala Leu Phe Val
1               5                   10                  15

Leu Val Cys Thr Ala Glu Gly Arg Asn Leu Leu Glu Ser Ile Val Glu
            20                  25                  30

Asp Asp Asn Pro Thr Gly Thr Lys Trp Ala Val Leu Val Ala Gly Ser
        35                  40                  45

Asn Glu Trp Asp Asn Tyr Arg His Gln Ala Asp Val Cys His Ala Tyr
50                  55                  60

Gln Leu Leu Lys Lys Gly Gly Leu Lys Asp Glu Asn Ile Ile Val Phe
65                  70                  75                  80

Met Tyr Asp Asp Ile Ala Tyr Asn Lys Asn Asn Pro Arg Pro Gly Ile
                85                  90                  95

Ile Ile Asn Ser Pro His Gly His Asp Val Tyr Lys Gly Val Pro Lys
            100                 105                 110

Asp Tyr Thr Gly Lys Asp Cys Asn Ala Asp Asn Phe Phe Ala Val Ile
        115                 120                 125

Leu Gly Asn Lys Ser Ala Leu Thr Gly Gly Ser Gly Lys Val Val Glu
```

```
            130                 135                 140
Asn Gly Pro Asn Asp Tyr Ile Phe Ile Tyr Tyr Ala Asp His Gly Ala
145                 150                 155                 160
Pro Gly Leu Ile Gly Met Pro Ser Gly Asp Val Val Tyr Ala Asp Asp
                165                 170                 175
Leu Asn Arg Val Leu Ile Lys Lys His Thr Phe Gly Thr Tyr Ser Lys
            180                 185                 190
Leu Val Phe Tyr Met Glu Ala Cys Glu Ser Gly Ser Met Phe Asp Gly
        195                 200                 205
Leu Leu Pro Lys Gly Leu Asn Ile Tyr Val Thr Ala Ala Ser Lys Pro
    210                 215                 220
Asp Glu Ser Ser Trp Ala Thr Tyr Cys Ile Arg Leu Gly Asp Glu Asp
225                 230                 235                 240
Gln Cys Leu Gly Asp Leu Tyr Ser Val Ser Trp Leu Glu Asp Ser Asp
                245                 250                 255
Leu His Asp Arg Gln Val Glu Thr Leu Glu Lys Gln Tyr Gln Leu Val
            260                 265                 270
Arg Lys Arg Thr Leu Asn Asn Gly Thr Glu Glu Gly Ser His Val Met
        275                 280                 285
Gln Tyr Gly Asp Leu His Ile Ser Glu Asp Pro Leu Phe Arg Tyr Met
    290                 295                 300
Gly Ser Asn Ser Ala Lys Asn Ser Tyr Asn Thr Ser Asn Asn Asp Glu
305                 310                 315                 320
Ser Trp Leu Pro Ser Arg Thr Val Asn Gln Arg Asp Val His Leu Met
                325                 330                 335
His Leu Trp Ser Lys Phe Arg Ser Ala Pro Glu Gly Ser Ala Arg Lys
            340                 345                 350
Ala Glu Ala His Arg Gln Leu Ser Glu Ala Leu Ser Gln Arg Glu Asp
        355                 360                 365
Val Asp Asn Ser Val Arg His Ile Gly Glu Val Leu Phe Gly Val Glu
    370                 375                 380
Lys Ser His Lys Leu Leu Asn Thr Val Arg Pro Ala Gly Gln Pro Leu
385                 390                 395                 400
Val Asp Asp Trp Asp Cys Leu Lys Ser Phe Val Lys Ile Phe Glu Ser
                405                 410                 415
Gln Cys Gly Thr Leu Thr Pro Tyr Gly Arg Lys His Val Arg Gly Phe
            420                 425                 430
Ala Asn Leu Cys Asn Ala Gly Ile Arg Arg Glu Gln Met Ala Ala Ala
        435                 440                 445
Ala Lys Gln Ala Cys Pro Pro
450                 455

<210> SEQ ID NO 100
<211> LENGTH: 492
<212> TYPE: PRT
<213> ORGANISM: Aegilops tauschii

<400> SEQUENCE: 100

Met Ala Arg Leu Ser Cys Ser Pro Leu Leu Leu Leu Phe Leu Ser
1               5                   10                  15

Ser Gln Leu Ala Leu Leu Val Ala Gly Glu Phe Leu Arg Leu Pro Ser
            20                  25                  30

Glu Lys Asp Val Val Gly Thr Arg Trp Ala Val Leu Ile Ala Gly Ser
        35                  40                  45
```

```
Asn Gly Tyr Tyr Asn Tyr Arg His Gln Ala Gly Thr Lys Phe Pro Ile
    50                  55                  60
Lys Tyr Ser Ser Leu Ile Thr Leu Met Glu Asn Ala Asp Val Cys His
 65                  70                  75                  80
Ala Tyr Gln Ile Met Lys Lys Gly Gly Leu Lys Asp Glu Asn Ile Ile
                     85                  90                  95
Val Phe Met Tyr Asp Asp Ile Ala Gly Asn Arg Asp Asn Pro Arg Pro
                100                 105                 110
Gly Val Ile Ile Asn His Pro Lys Gly Asp Val Tyr Ala Gly Val
                115                 120                 125
Pro Lys Asp Tyr Thr Gly Ala Asp Val Asn Ala Asn Phe Leu Ala
    130                 135                 140
Ala Leu Leu Gly Asp Lys Ser Lys Leu Thr Gly Ser Gly Ser Gly Lys
145                 150                 155                 160
Val Val Ser Ser Gly Ser Asp Asp His Ile Phe Val Tyr Ala Asp
                165                 170                 175
His Gly Gly Pro Gly Ile Leu Gly Met Pro Gly Asp Glu Glu Tyr Leu
                180                 185                 190
Tyr Ala Asn Asp Leu Val Arg Thr Leu Glu Lys Lys His Ala Gly Gly
                195                 200                 205
Ala Gly Tyr Lys Ser Leu Val Phe Tyr Leu Glu Ala Cys Glu Ser Gly
    210                 215                 220
Ser Ile Phe Glu Gly Leu Leu Pro Gly Asn Ile Gly Val Tyr Ala Thr
225                 230                 235                 240
Thr Ala Ala Asn Ala Glu Glu Ser Ser Trp Gly Thr Tyr Cys Pro Gly
                    245                 250                 255
Asp Asp Glu Gly Ala Pro Pro Glu Tyr Asp Thr Cys Leu Gly Asp
                260                 265                 270
Leu Tyr Ser Val Ala Trp Met Glu Asp Ser Asp Ala His Asn Leu Asn
    275                 280                 285
Ala Glu Ser Leu Lys Gln Gln Tyr Glu Arg Val Arg Asp Arg Thr Ser
    290                 295                 300
Ala Ala Gly Thr Tyr Ser Leu Gly Ser His Val Met Gln Tyr Gly Asp
305                 310                 315                 320
Leu Asp Leu Asn Asp Gln Ser Leu Phe Leu Tyr Ile Gly Thr Asn Pro
                325                 330                 335
Ala Asn Asp Asn Ala Ser Phe Val Gln Gly Ser Ser Thr Ser Arg
                340                 345                 350
Gln Leu Pro Gly Gly Arg Val Asn Gln Arg Asp Ala Asp Leu Val His
    355                 360                 365
Phe Trp His Lys Tyr Arg Arg Ser Ala Glu Gly Ser Ala Lys Lys Gly
    370                 375                 380
Glu Ala Arg Arg Arg Leu Val Glu Thr Met Ala Arg Arg Ser Arg Val
385                 390                 395                 400
Asp Ser Ser Val Glu Leu Ile Gly Gly Leu Leu Phe Gly Ser Glu Gln
                405                 410                 415
Gly Ala Lys Val Leu Gly Ala Val Arg Pro Ala Gly Gln Pro Val Val
                420                 425                 430
Ala Asp Trp Asp Cys Leu Lys Ser Val Val Arg Arg Phe Gln Glu Arg
                435                 440                 445
Cys Gly Pro Leu Thr Gln Tyr Gly Met Lys His Met Arg Ser Leu Ala
    450                 455                 460
Asn Leu Cys Asn Ala Gly Val Arg Glu Glu Ala Met Asp Lys Ala Ala
```

```
                465                 470                 475                 480
Ala Gln Ala Cys Ala Ala Asn Pro Ser Ser Leu Phe
                    485                 490

<210> SEQ ID NO 101
<211> LENGTH: 467
<212> TYPE: PRT
<213> ORGANISM: Brachypodium distachyon

<400> SEQUENCE: 101

Met Ala Arg Leu Ser Cys Phe Leu Leu Leu Gln Ala Gln Leu Phe
1               5                   10                  15

Leu Leu Val Ala Gly Glu Phe Leu Arg Leu Pro Ser Glu Gln Asp Val
                20                  25                  30

Ala Gly Thr Arg Trp Ala Val Leu Ile Ala Gly Ser Asn Asp Tyr Tyr
            35                  40                  45

Asn Tyr Arg His Gln Ala Asp Val Cys His Ala Tyr Gln Ile Met Lys
        50                  55                  60

Lys Gly Gly Leu Lys Asp Glu Asn Ile Ile Val Phe Met Tyr Asp Asp
65                  70                  75                  80

Ile Ala Asn Asn Pro Asp Asn Pro Arg Pro Gly Val Ile Ile Asn His
                85                  90                  95

Pro Thr Gly Gly Asp Val Tyr Ala Gly Val Pro Lys Asp Tyr Thr Gly
            100                 105                 110

Lys Asp Val Asn Ala Asn Asn Phe Leu Ala Ala Leu Leu Gly Asp Lys
        115                 120                 125

Ser Lys Leu Thr Gly Ser Gly Ser Gly Lys Val Val Ser Ser Gly Pro
    130                 135                 140

Asn Asp His Ile Phe Val Tyr Tyr Ala Asp His Gly Gly Pro Gly Val
145                 150                 155                 160

Leu Gly Met Pro Glu Asp Glu Ser Tyr Leu Tyr Ala Asn Asp Leu Val
                165                 170                 175

Arg Ala Leu Glu Lys Lys His Ala Gly Gly Ala Gly Tyr Lys Ser Leu
            180                 185                 190

Val Phe Tyr Leu Glu Ala Cys Glu Ser Gly Ser Ile Phe Glu Gly Leu
        195                 200                 205

Leu Pro Gly Asn Ile Ser Val Tyr Ala Thr Thr Ala Ser Asn Ala Glu
    210                 215                 220

Glu Ser Ser Trp Gly Thr Tyr Cys Pro Gly Asp Val Asp Gly Ala Pro
225                 230                 235                 240

Pro Ala Glu Phe Asp Thr Cys Leu Gly Asp Leu Tyr Ser Val Ala Trp
                245                 250                 255

Met Glu Asp Ser Asp Ala His Asn Leu Lys Ala Glu Ser Leu Lys Gln
            260                 265                 270

Gln Tyr Asp Arg Val Arg Asp Arg Thr Ser Ala His Glu Thr Tyr Asn
        275                 280                 285

Leu Gly Ser His Val Met Gln Tyr Gly Asp Leu Gly Ile Asn Ala Gln
    290                 295                 300

Ser Leu Asp Ile Phe Ile Gly Ser Asn Pro Ala Asn Asp Lys Ser Asn
305                 310                 315                 320

Ser Ser Val Ser Ser Leu Leu Arg Asn Ala Arg Ala Gly Val Val His
                325                 330                 335

Gln Arg Asp Ala Asp Leu Leu His Phe Trp His Lys Tyr Lys Arg Ser
            340                 345                 350
```

Ala Glu Gly Ser Ala Arg Lys His Glu Ala Arg Arg Leu Val Glu
            355                 360                 365

Met Met Ala Arg Arg Ala Arg Val Asp Gly Ser Val Glu Leu Leu Gly
    370                 375                 380

Gly Leu Leu Phe Gly Ser Glu Glu Gly Ala Lys Val Met Asn Ala Val
385                 390                 395                 400

Arg Pro Ala Gly Gln Ala Leu Val Asp Asp Trp Asp Cys Leu Lys Asp
                405                 410                 415

Val Val Arg Arg Phe Glu Ala Arg Cys Gly Pro Leu Thr Gln Tyr Gly
            420                 425                 430

Met Lys His Met Arg Ala Leu Ala Asn Val Cys Asn Ala Gly Val Gly
        435                 440                 445

Val Glu Ala Val Asp Arg Ala Ala Ser Gln Ala Cys Ala Val His Pro
    450                 455                 460

Ser Val Phe
465

<210> SEQ ID NO 102
<211> LENGTH: 493
<212> TYPE: PRT
<213> ORGANISM: Sorghum bicolor

<400> SEQUENCE: 102

Met Ala Ala Ala Ala Trp Leu Cys Gly Leu Leu Trp Leu Leu Ala His
1               5                   10                  15

Ala Ala Ala Val Ala Ser Ala Ala Asp Gly Ala Asp Gly Gly Trp Glu
            20                  25                  30

Pro Leu Ile Arg Met Pro Thr Gly Lys Gly Gly Asp Ala Ala Ala Arg
        35                  40                  45

Ala Val Glu Glu Asp Asp Glu Val Gly Thr Arg Trp Ala Val Leu Val
    50                  55                  60

Ala Gly Ser Ser Gly Tyr Gly Asn Tyr Arg His Gln Ala Asp Val Cys
65                  70                  75                  80

His Ala Tyr Gln Ile Leu Arg Lys Gly Gly Val Lys Glu Glu Asn Ile
                85                  90                  95

Val Val Phe Met Tyr Asp Asp Ile Ala His Asn Ile Leu Asn Pro Arg
            100                 105                 110

Pro Gly Val Ile Ile Asn His Pro Lys Gly Glu Asn Val Tyr Asn Gly
        115                 120                 125

Val Pro Lys Asp Tyr Thr Gly Asp Gln Val Thr Thr Glu Asn Phe Phe
    130                 135                 140

Ala Val Leu Leu Gly Asn Lys Ser Ala Ile Thr Gly Gly Ser Lys Lys
145                 150                 155                 160

Val Ile Asp Ser Lys Pro Asn Asp His Ile Phe Ile Tyr Tyr Ser Asp
                165                 170                 175

His Gly Gly Pro Gly Val Leu Gly Met Pro Asn Leu Pro Tyr Leu Tyr
            180                 185                 190

Ala Gly Asp Phe Ile Lys Val Leu Lys Lys His Ala Cys Asn Ser
        195                 200                 205

Tyr Ser Lys Met Val Ile Tyr Val Glu Ala Cys Glu Ser Gly Ser Ile
    210                 215                 220

Phe Glu Gly Leu Met Pro Glu Asp Leu Asn Ile Tyr Val Thr Thr Ala
225                 230                 235                 240

Ser Asn Pro Val Glu Asn Ser Trp Gly Thr Tyr Cys Pro Gly Met Glu
                245                 250                 255

Pro Ser Pro Pro Glu Tyr Ile Thr Cys Leu Gly Asp Leu Tyr Ser
            260                 265                 270

Val Ser Trp Met Glu Asp Ser Gln Thr His Asn Leu Lys Glu Thr
        275                 280                 285

Ile Lys Asp Gln Tyr Glu Val Val Lys Thr Arg Thr Ser Asn Ser Asn
290                 295                 300

Lys Tyr Lys Glu Gly Ser His Val Met Glu Tyr Gly Asp Lys Thr Phe
305                 310                 315                 320

Lys Asp Glu Lys Leu Phe Leu Tyr Gln Gly Phe Asp Pro Ala Asn Ala
            325                 330                 335

Asn Ile Ala Asn Met Leu Leu Trp Pro Gly Pro Lys Gly Ala Val Asn
            340                 345                 350

Gln Arg Asp Ala Asp Leu Leu Phe Met Trp Lys Arg Tyr Glu Gln Leu
            355                 360                 365

Asn Gly Glu Ser Val Glu Lys Leu Arg Ala Leu Ile Glu Ile Lys Glu
            370                 375                 380

Thr Val Gln His Arg Lys His Leu Asp Ser Ser Ile Asp Phe Ile Gly
385                 390                 395                 400

Arg Leu Leu Phe Gly Phe Glu Lys Gly Pro Ser Met Leu Glu Ala Val
            405                 410                 415

Arg Ala Ser Gly Leu Pro Leu Val Asp Asp Trp Asp Cys Leu Lys Arg
            420                 425                 430

Met Val Arg Ile Phe Glu Ser Gln Cys Gly Ser Leu Thr Gln Tyr Gly
            435                 440                 445

Met Lys Tyr Met Arg Ala Phe Ala Asn Ile Cys Asn Ser Gly Ile Ser
            450                 455                 460

Glu Met Lys Met Arg Glu Ser Ser Ile Ser Ala Cys Ser Ser Tyr Asn
465                 470                 475                 480

Ser Ala Arg Trp Ser Pro Met Ala Gln Gly His Ser Ala
                485                 490

<210> SEQ ID NO 103
<211> LENGTH: 491
<212> TYPE: PRT
<213> ORGANISM: Triticum monococcum

<400> SEQUENCE: 103

Met Ala Pro Arg Trp Cys Phe Ala Leu Leu Leu Leu Cys Ala Ala
1               5                   10                  15

Ala Arg Pro Gly Ala Asp Ala Ser Lys Gly Lys Trp Asp Pro Val Ile
            20                  25                  30

Arg Met Pro Gly Glu Glu Pro Ala Thr Gly Asp Glu Ser Ser Glu
            35                  40                  45

Glu Gly Glu Asp Gly Val Gly Thr Arg Trp Ala Val Leu Val Ala Gly
            50                  55                  60

Ser Ser Gly Tyr Gly Asn Tyr Arg His Gln Ala Asp Ile Cys His Ala
65                  70                  75                  80

Tyr Gln Ile Leu Arg Lys Gly Gly Val Lys Glu Glu Asn Ile Val Val
                85                  90                  95

Phe Met Tyr Asp Asp Ile Ala Asn Asn Pro Leu Asn Pro Arg Pro Gly
                100                 105                 110

Val Ile Ile Asn His Pro Glu Gly Glu Asp Val Tyr Ala Gly Val Pro
            115                 120                 125

Lys Asp Tyr Thr Gly Glu Glu Val Thr Ala Lys Asn Phe Tyr Ala Val

```
                130                 135                 140
Leu Leu Gly Asn Lys Thr Ala Val Thr Gly Ser Lys Lys Val Ile
145                 150                 155                 160

Asp Ser Lys Pro Asn Asp His Ile Phe Ile Tyr Tyr Ser Asp His Gly
                165                 170                 175

Gly Pro Gly Val Leu Gly Met Pro Asn Leu Pro Tyr Leu Tyr Ala Ala
            180                 185                 190

Asp Phe Ile Lys Val Leu Gln Glu Lys His Ala Ser Asn Thr Tyr Ala
            195                 200                 205

Lys Met Val Ile Tyr Val Glu Ala Cys Glu Ser Gly Ser Ile Phe Glu
            210                 215                 220

Gly Leu Met Pro Ala Asp Leu Asn Ile Tyr Val Thr Thr Ala Ser Asn
225                 230                 235                 240

Ala Glu Glu Ser Ser Trp Gly Thr Tyr Cys Pro Gly Met Glu Pro Ser
                245                 250                 255

Pro Pro Ser Glu Tyr Ile Thr Cys Leu Gly Asp Leu Tyr Ser Ile Ser
            260                 265                 270

Trp Met Glu Asp Ser Glu Thr Asn Asn Leu Lys Glu Thr Ile Lys
            275                 280                 285

Lys Gln Tyr Glu Val Val Lys Lys Arg Thr Ser Asp Met Asn Ser Tyr
            290                 295                 300

Ser Ala Gly Ser His Val Met Glu Tyr Gly Asp Lys Thr Phe Lys Asp
305                 310                 315                 320

Glu Lys Leu Tyr Leu Tyr Gln Gly Phe Asn Pro Ala Asn Thr Asn Ile
                325                 330                 335

Thr Asn Met Leu Leu Leu Gln Ala Pro Lys Ala Ala Ile Asn Gln Arg
            340                 345                 350

Asp Ala Asp Leu Leu Phe Leu Trp Arg Arg Tyr Glu Leu Leu His Glu
            355                 360                 365

Lys Ser Lys Glu Lys Gly Asn Val Leu Arg Glu Ile Ser Glu Thr Val
            370                 375                 380

Thr His Arg Lys His Leu Asp Ser Ser Ile Asp Phe Ile Gly Lys Leu
385                 390                 395                 400

Leu Phe Gly Phe Glu Asn Gly Pro Ser Val Leu Gln Ala Val Arg Pro
                405                 410                 415

Ser Gly Lys Pro Leu Val Asp Asp Trp Asp Cys Leu Lys Arg Met Val
            420                 425                 430

Arg Ile Phe Glu Ser His Cys Gly Ser Leu Thr Gln Tyr Gly Met Lys
            435                 440                 445

His Met Arg Ala Phe Ala Asn Ile Cys Asn Asn Gly Ile Ser Gly Thr
450                 455                 460

Thr Met Lys Glu Ala Ser Ile Gly Ala Cys Gly Val Gln Asn Ser Ala
465                 470                 475                 480

Arg Trp Ser Ser Leu Ile Gln Gly Tyr Ser Ala
                485                 490

<210> SEQ ID NO 104
<211> LENGTH: 491
<212> TYPE: PRT
<213> ORGANISM: Aegilops speltoides

<400> SEQUENCE: 104

Met Ala Pro Arg Trp Cys Phe Ala Leu Leu Leu Leu Cys Ala Ala
1               5                   10                  15
```

Ala Gly Ala Gly Ala Asp Ala Ser Lys Gly Lys Trp Asp Pro Val Ile
            20                  25                  30

Arg Met Pro Gly Glu Glu Pro Ala Thr Gly Asp Glu Ser Ser Glu
        35                  40                  45

Glu Gly Glu Asp Gly Val Gly Thr Arg Trp Ala Val Leu Val Ala Gly
    50                  55                  60

Ser Ser Gly Tyr Gly Asn Tyr Arg His Gln Ala Asp Ile Cys His Ala
65                  70                  75                  80

Tyr Gln Ile Leu Arg Lys Gly Val Lys Glu Asn Ile Val Val
                85                  90                  95

Phe Met Tyr Asp Asp Ile Ala Asn Asn Pro Leu Asn Pro Arg Pro Gly
            100                 105                 110

Val Ile Ile Asn His Pro Glu Gly Glu Asp Val Tyr Ala Gly Val Pro
        115                 120                 125

Lys Asp Tyr Thr Gly Glu Ala Val Thr Ala Lys Asn Phe Tyr Ala Val
    130                 135                 140

Leu Leu Gly Asn Asn Thr Ala Val Thr Gly Gly Ser Lys Lys Val Ile
145                 150                 155                 160

Asp Ser Lys Pro Asn Asp His Ile Phe Ile Tyr Tyr Ser Asp His Gly
                165                 170                 175

Gly Pro Gly Val Leu Gly Met Pro Asn Leu Pro Tyr Leu Tyr Ala Ala
            180                 185                 190

Asp Phe Ile Lys Val Leu Gln Glu Lys His Ala Ser Asn Thr Tyr Ala
        195                 200                 205

Lys Met Val Ile Tyr Val Glu Ala Cys Glu Ser Gly Ser Ile Phe Glu
    210                 215                 220

Gly Leu Met Pro Ala Asp Leu Asn Ile Tyr Val Thr Thr Ala Ser Asn
225                 230                 235                 240

Ala Glu Glu Ser Ser Trp Gly Thr Tyr Cys Pro Gly Met Glu Pro Ser
                245                 250                 255

Pro Pro Ser Glu Tyr Ile Thr Cys Leu Gly Asp Leu Tyr Ser Ile Ser
            260                 265                 270

Trp Met Glu Asp Ser Glu Thr Asn Asn Leu Lys Glu Glu Thr Ile Lys
        275                 280                 285

Lys Gln Tyr Glu Val Val Lys Lys Arg Thr Ser Asp Met Asn Ser Tyr
    290                 295                 300

Ser Ala Gly Ser His Val Met Glu Tyr Gly Asp Lys Thr Phe Lys Asp
305                 310                 315                 320

Glu Lys Leu Tyr Leu Tyr Gln Gly Phe Asn Pro Ala Asn Thr Asn Ile
                325                 330                 335

Thr Asn Lys Leu Phe Leu Gln Ala Pro Lys Ala Ala Ile Asn Gln Arg
            340                 345                 350

Asp Ala Asp Leu Leu Phe Leu Trp Arg Arg Tyr Glu Leu Leu His Glu
        355                 360                 365

Lys Ser Lys Glu Lys Ala Asn Val Leu Arg Glu Ile Ser Glu Thr Val
    370                 375                 380

Ala His Arg Lys His Leu Asp Ser Ser Ile Asp Phe Ile Gly Lys Leu
385                 390                 395                 400

Leu Phe Gly Phe Glu Asn Gly Pro Trp Glu Leu Gln Ala Val Arg Pro
                405                 410                 415

Ser Gly Lys Pro Leu Val Asp Asp Trp Asp Cys Leu Lys Arg Met Val
            420                 425                 430

Arg Ile Phe Glu Ser His Cys Gly Ser Leu Thr Gln Tyr Gly Met Lys

```
                435                 440                 445
His Met Arg Ala Phe Ala Asn Ile Cys Asn Asn Gly Val Ser Gly Thr
    450                 455                 460

Thr Met Asn Glu Ala Ser Ile Gly Ala Cys Gly Val Gln Asn Ser Ala
465                 470                 475                 480

Arg Trp Ser Thr Leu Ile Gln Gly Tyr Ser Ala
                485                 490

<210> SEQ ID NO 105
<211> LENGTH: 489
<212> TYPE: PRT
<213> ORGANISM: Aegilops tauschii

<400> SEQUENCE: 105

Met Ala Pro Arg Trp Cys Phe Ala Leu Leu Leu Leu Cys Ala Ala
1               5                   10                  15

Ala Gly Ala Asp Ala Ser Lys Gly Lys Trp Asp Pro Val Ile Arg Met
            20                  25                  30

Pro Gly Glu Glu Glu Pro Ala Thr Gly Asp Asp Ser Ser Glu Glu Gly
        35                  40                  45

Glu Asp Gly Val Gly Thr Arg Trp Ala Val Leu Val Ala Gly Ser Ser
50                  55                  60

Gly Tyr Gly Asn Tyr Arg His Gln Ala Asp Ile Cys His Ala Tyr Gln
65                  70                  75                  80

Ile Leu Arg Lys Gly Gly Val Lys Glu Glu Asn Ile Val Val Phe Met
                85                  90                  95

Tyr Asp Asp Ile Ala Asn Asn Pro Leu Asn Pro Arg Pro Gly Val Ile
            100                 105                 110

Ile Asn His Pro Glu Gly Glu Asp Val Tyr Ala Gly Val Pro Lys Asp
        115                 120                 125

Tyr Thr Gly Glu Ala Val Thr Ala Lys Asn Phe Tyr Ala Val Leu Leu
130                 135                 140

Gly Asn Lys Thr Ala Val Thr Gly Gly Ser Lys Lys Val Ile Asp Ser
145                 150                 155                 160

Lys Pro Asn Asp His Ile Phe Ile Tyr Tyr Ser Asp His Gly Gly Pro
                165                 170                 175

Gly Val Leu Gly Met Pro Asn Leu Pro Tyr Leu Tyr Ala Ala Asp Phe
            180                 185                 190

Ile Lys Val Leu Gln Glu Lys His Ala Ser Asn Thr Tyr Ala Lys Met
        195                 200                 205

Val Ile Tyr Val Glu Ala Cys Glu Ser Gly Ser Ile Phe Glu Gly Leu
210                 215                 220

Met Pro Ala Asp Leu Asn Ile Tyr Val Thr Thr Ala Ser Asn Ala Glu
225                 230                 235                 240

Glu Ser Ser Trp Gly Thr Tyr Cys Pro Gly Met Glu Pro Ser Pro Pro
                245                 250                 255

Ser Glu Tyr Ile Thr Cys Leu Gly Asp Leu Tyr Ser Ile Ser Trp Met
            260                 265                 270

Glu Asp Ser Glu Thr Asn Asn Leu Lys Glu Glu Thr Ile Lys Lys Gln
        275                 280                 285

Tyr Glu Val Val Lys Lys Arg Thr Ser Asp Met Asn Ser Tyr Ser Ala
290                 295                 300

Gly Ser His Val Met Glu Tyr Gly Asp Met Thr Phe Lys Asp Glu Lys
305                 310                 315                 320
```

-continued

```
Leu Tyr Leu Tyr Gln Gly Phe Asn Pro Ala Asn Thr Asn Ile Thr Asn
                325                 330                 335

Lys Leu Phe Leu Gln Ala Pro Lys Ala Ala Ile Asn Gln Arg Asp Ala
            340                 345                 350

Asp Leu Leu Phe Leu Trp Arg Arg Tyr Glu Leu Leu His Gly Lys Ser
        355                 360                 365

Lys Glu Lys Ala Asn Val Leu Thr Glu Ile Gly Glu Thr Val Ala His
    370                 375                 380

Arg Lys His Leu Asp Asn Ser Ile Asp Phe Ile Gly Lys Leu Leu Phe
385                 390                 395                 400

Gly Phe Glu Asn Gly Pro Ser Glu Leu Gln Ala Val Arg Pro Ser Gly
                405                 410                 415

Lys Pro Leu Val Asp Asp Trp Asp Cys Leu Lys Arg Met Val Arg Ile
            420                 425                 430

Phe Glu Ser His Cys Gly Ser Leu Thr Gln Tyr Gly Met Lys His Met
        435                 440                 445

Arg Ala Phe Ala Asn Ile Cys Asn Asn Gly Val Ser Gly Thr Thr Met
    450                 455                 460

Lys Glu Ala Ser Ile Asn Thr Cys Gly Gly His Asn Ser Ala Arg Leu
465                 470                 475                 480

Ser Thr Leu Ile Gln Gly Tyr Ser Ala
                485

<210> SEQ ID NO 106
<211> LENGTH: 460
<212> TYPE: PRT
<213> ORGANISM: Solanum tuberosum

<400> SEQUENCE: 106

Met Ile Phe Lys Tyr Asn Val Phe Val Ala Leu Val Val Val Leu Ser
1               5                   10                  15

Ile Trp Asp Asn Ile Glu Gly Arg Ser Val Ser Lys Phe Leu Thr Glu
            20                  25                  30

Glu Thr Val Gly Thr Lys Trp Ala Val Leu Val Ala Gly Ser Asn Gly
        35                  40                  45

Trp Phe Asn Tyr Arg His Gln Ala Asp Val Cys His Ala Tyr Gln Ile
    50                  55                  60

Leu Lys Lys Gly Gly Leu Lys Asp Glu Asn Ile Ile Val Phe Met Tyr
65                  70                  75                  80

Asp Asp Ile Ala Asn Asn Thr Met Asn Pro Arg Pro Gly Val Ile Ile
                85                  90                  95

Asn Asn Pro His Gly Gln Asp Val Tyr Lys Gly Val Pro Lys Asp Tyr
            100                 105                 110

Val Gly Glu Asp Val Asn Ala Glu Asn Phe Phe Asn Val Ile Leu Ala
        115                 120                 125

Asn Lys Ser Gly Ile Thr Gly Gly Ser Gly Lys Val Leu Asn Ser Gly
    130                 135                 140

Pro Asn Asp His Ile Phe Ile Tyr Tyr Thr Asp His Gly Gly Pro Gly
145                 150                 155                 160

Ile Ile Ser Met Pro Thr Gly Leu Val Tyr Ala Asn Asp Leu Ile Asn
                165                 170                 175

Val Leu Lys Lys Lys His Ala Ser Gly Thr Tyr Ser Lys Leu Val Phe
            180                 185                 190

Tyr Leu Glu Ala Cys Glu Ser Gly Ser Met Phe Asp Gly Leu Leu Pro
        195                 200                 205
```

```
Glu Gly Leu Asn Ile Tyr Val Thr Thr Ala Ser Asn Pro Asn Glu Ser
    210                 215                 220

Ser Trp Gly Thr Tyr Cys Gln Met Gly Ala Gly Pro Cys Leu Val
225                 230                 235                 240

Glu Cys Pro Pro Glu Phe Gln Gly Val Cys Leu Gly Asp Leu Tyr
                245                 250                 255

Ser Val Ala Trp Met Glu Asp Ser Glu Ala Glu Asp Arg Gln Thr Glu
                260                 265                 270

Thr Leu Asn Asp Gln Tyr Asn Thr Val Ala Asn Arg Thr Ala Ala Asn
            275                 280                 285

Leu Thr Tyr Gly Ser His Val Met Gln Tyr Gly Asp Thr Val Leu Ser
    290                 295                 300

Val Asp Val Leu Phe Gln Tyr Met Gly Ala Ala Ser Val Asn His Ser
305                 310                 315                 320

His Val Ser Met Asn Ser Glu Ser Ser Ser Gln Asn Val Asp Gln Arg
                325                 330                 335

Asp Val Glu Leu Phe Tyr Leu Thr Ser Lys Tyr Gln Asp Ala Pro Glu
                340                 345                 350

Gly Ser Asp Glu His Phe Glu Thr Arg Val Lys Leu Ile Lys Thr Ile
                355                 360                 365

Ala Glu Arg Ser Gln Val Asp Asn Ser Val Lys His Ile Gly Asp Leu
            370                 375                 380

Leu Phe Gly Val Glu Lys Gly Ser Glu Val Leu Gln His Val Arg Pro
385                 390                 395                 400

Ala Gly Gln Pro Leu Val Asp Asn Trp Asp Cys Leu Lys Ser Tyr Ile
                405                 410                 415

Glu Thr Phe Glu Val His Cys Gly Lys Leu Ser Ser Tyr Gly Lys Lys
                420                 425                 430

His Ile Arg Gly Ile Ala Asn Ile Cys Asn Ala Gly Ile Lys Ser Glu
            435                 440                 445

Gln Met Ala Ser Ala Thr Ala Gln Ala Cys Ser Ser
    450                 455                 460

<210> SEQ ID NO 107
<211> LENGTH: 490
<212> TYPE: PRT
<213> ORGANISM: Brachypodium distachyon

<400> SEQUENCE: 107

Met Ala Ala Trp Trp Cys Phe Ala Leu Leu Leu Val Leu Cys Ala Pro
1               5                   10                  15

Ala Gly Ala Asp Val Ser Lys Gly Lys Trp Glu Pro Leu Ile Arg Met
                20                  25                  30

Pro Gly Glu Lys Glu Pro Ala Thr Ala Arg Gly Phe Glu Gly Pro Glu
            35                  40                  45

Glu Glu Asp Gly Val Gly Thr Arg Trp Ala Val Leu Ile Ala Gly Ser
    50                  55                  60

Ser Gly Tyr Gly Asn Tyr Arg His Gln Ala Asp Ile Cys His Ala Tyr
65                  70                  75                  80

Gln Val Leu Arg Lys Gly Leu Lys Glu Glu Asn Ile Val Val Phe
                85                  90                  95

Met Tyr Asp Asp Ile Ala Asn Ser Ala Leu Asn Pro Arg Pro Gly Val
                100                 105                 110

Ile Ile Asn His Pro Gln Gly Glu Asp Val Tyr Ala Gly Val Pro Lys
```

```
            115                 120                 125
Asp Tyr Thr Gly Glu Gln Val Thr Ala Lys Asn Leu Tyr Ala Val Leu
    130                 135                 140
Leu Gly Asn Lys Thr Ala Val Thr Gly Gly Ser Lys Lys Val Ile Asp
145                 150                 155                 160
Ser Gln Pro Lys Asp His Ile Phe Ile Tyr Tyr Ser Asp His Gly Gly
                165                 170                 175
Pro Gly Val Leu Gly Met Pro Asn Leu Pro Tyr Leu Tyr Ala Gly Asp
            180                 185                 190
Phe Ile Lys Ile Leu Gln Gln Lys His Ala Ser Asn Thr Tyr Ala Lys
        195                 200                 205
Met Val Ile Tyr Val Glu Ala Cys Glu Ser Gly Ser Ile Phe Glu Gly
    210                 215                 220
Leu Met Pro Ala Asp Leu Asn Ile Tyr Val Thr Thr Ala Ser Asn Ala
225                 230                 235                 240
Glu Glu Ser Ser Trp Gly Thr Tyr Cys Pro Gly Met Glu Pro Ser Pro
                245                 250                 255
Pro Ser Glu Tyr Ile Thr Cys Leu Gly Asp Leu Tyr Ser Val Ser Trp
            260                 265                 270
Met Glu Asp Ser Glu Asn His Asn Leu Lys Glu Thr Ile Lys Lys
        275                 280                 285
Gln Tyr Glu Val Val Lys Arg Arg Thr Ser Asp Leu Asn Ser Tyr Ser
    290                 295                 300
Ala Gly Ser His Val Met Glu Tyr Gly Asp Lys Thr Phe Lys Asp Glu
305                 310                 315                 320
Lys Leu Tyr Leu Tyr Gln Gly Phe Asn Pro Ala Asn Ala Asn Ile Thr
                325                 330                 335
Asn Lys Leu Phe Trp Gln Ala Pro Arg Ala Ala Ile Asn Gln Arg Asp
            340                 345                 350
Ala Asp Leu Leu Phe Leu Trp Arg Arg Tyr Glu Met Leu His Glu Lys
        355                 360                 365
Ser Lys Glu Lys Val Lys Val Leu Arg Glu Ile Ser Glu Thr Val Met
    370                 375                 380
His Arg Lys His Leu Asp Asn Ser Val Asp Leu Ile Gly Gln Leu Leu
385                 390                 395                 400
Phe Gly Phe Glu Asn Gly Pro Ser Val Leu Gln Ala Val Arg Pro Ser
                405                 410                 415
Gly Lys Pro Leu Val Asp Asp Trp Asp Cys Leu Lys Arg Met Val Arg
            420                 425                 430
Ile Phe Glu Ser His Cys Gly Pro Leu Thr Gln Tyr Gly Met Lys His
        435                 440                 445
Met Arg Ala Phe Ala Asn Ile Cys Asn Asn Gly Ile Pro Gly Ser Thr
    450                 455                 460
Met Lys Glu Gly Ser Ile Ser Ala Cys Gly Ser Arg Asn Ile Ala Arg
465                 470                 475                 480
Trp Ser Pro Leu Ile Gln Gly Tyr Ser Ala
                485                 490
```

<210> SEQ ID NO 108
<211> LENGTH: 493
<212> TYPE: PRT
<213> ORGANISM: Zea mays

<400> SEQUENCE: 108

-continued

```
Met Met Ala Ala Ala Trp Leu Cys Gly Leu Leu Ser Leu Leu Ala
1               5                   10                  15

Leu Ala Gly Ala Ala Ser Ala Ala Asp Gly Ala Glu Gly Glu Trp Glu
        20                  25                  30

Pro Leu Ile Arg Met Pro Thr Ala Lys Gly Ser Asp Ala Ala Ser Ala
            35                  40                  45

Pro Ala Ala Glu Asp Asp Glu Val Gly Thr Arg Trp Ala Val Leu Val
50                  55                  60

Ala Gly Ser Phe Gly Tyr Gly Asn Tyr Arg His Gln Ala Asp Val Cys
65                  70                  75                  80

His Ala Tyr Gln Ile Leu Gln Lys Gly Gly Val Lys Lys Glu Asn Ile
                85                  90                  95

Val Val Phe Met Tyr Asp Asp Ile Ala His Asn Ile Leu Asn Pro Arg
            100                 105                 110

Pro Gly Val Ile Ile Asn His Pro Lys Gly Ala Asn Val Tyr Asp Gly
        115                 120                 125

Val Pro Lys Asp Tyr Thr Gly Asp Gln Val Thr Thr Glu Asn Phe Phe
    130                 135                 140

Ala Val Leu Leu Gly Asn Arg Ser Ala Thr Thr Gly Gly Ser Lys Lys
145                 150                 155                 160

Val Ile Asp Ser Lys Pro Asn Asp His Ile Phe Ile Tyr Tyr Ser Asp
                165                 170                 175

His Gly Gly Pro Gly Val Leu Gly Met Pro Asn Leu Pro Tyr Leu Tyr
                180                 185                 190

Ala Gly Asp Phe Ile Lys Val Leu Lys Lys His Ala Ser Asn Ser
            195                 200                 205

Tyr Ser Lys Met Val Ile Tyr Val Glu Ala Cys Glu Ser Gly Ser Ile
    210                 215                 220

Phe Glu Gly Leu Met Pro Glu Asp Leu Asn Ile Tyr Val Thr Thr Ala
225                 230                 235                 240

Ser Asn Pro Val Glu Asn Ser Trp Gly Thr Tyr Cys Pro Gly Met Glu
                245                 250                 255

Pro Ser Pro Pro Glu Tyr Ile Thr Cys Leu Gly Asp Leu Tyr Ser
            260                 265                 270

Val Ser Trp Met Glu Asp Ser Glu Thr His Asn Leu Lys Lys Glu Thr
    275                 280                 285

Ile Lys Asp Gln Tyr Glu Val Val Lys Thr Arg Thr Ser Asn Ser Asn
        290                 295                 300

Lys Tyr Lys Glu Gly Ser His Val Met Glu Tyr Gly Asp Lys Thr Phe
305                 310                 315                 320

Lys Asp Glu Lys Leu Ser Phe Tyr Gln Gly Phe Asp Pro Ala Asn Ala
                325                 330                 335

Asn Ile Ala Asn Met Leu Leu Trp Pro Gly Lys Gly Ala Val Asn
            340                 345                 350

Gln Arg Asp Ala Asp Leu Leu Phe Met Trp Lys Arg Tyr Glu Gln Leu
        355                 360                 365

Asn Gly Gly Thr Glu Glu Lys Leu Arg Ala Leu Ile Glu Ile Lys Glu
    370                 375                 380

Thr Val Gln His Arg Lys His Leu Asp Ser Ser Ile Asp Phe Val Gly
385                 390                 395                 400

Arg Leu Val Phe Gly Phe Glu Lys Gly Pro Ser Met Leu Glu Ala Val
                405                 410                 415

Arg Thr Ser Gly Gln Pro Leu Val Asp Asp Trp Asp Cys Leu Lys Arg
```

```
                420                 425                 430
Met Val Arg Ile Phe Glu Ser Gln Cys Gly Ser Leu Thr Gln Tyr Gly
            435                 440                 445

Met Lys Tyr Met Arg Ala Phe Ala Asn Ile Cys Asn Ser Gly Ile Ser
450                 455                 460

Glu Met Lys Met Arg Glu Ser Ser Ile Ser Ala Cys Ser Ser Tyr Asn
465                 470                 475                 480

Ser Ala Arg Trp Ser Pro Met Ala Arg Gly His Ser Ala
            485                 490

<210> SEQ ID NO 109
<211> LENGTH: 492
<212> TYPE: PRT
<213> ORGANISM: Setaria italica

<400> SEQUENCE: 109

Met Ala Ala Ala Ala Trp Leu Cys Gly Leu Leu Ser Leu Leu Ala Val
1               5                   10                  15

Ala Ala Ala Ala Ser Val Asp Gly Ala Glu Glu Glu Trp Glu Pro Leu
                20                  25                  30

Ile Arg Met Pro Thr Glu Lys Gly Gly Asn Ala Ala Ala Ala Ala Pro
            35                  40                  45

Ala Ala Glu Glu Asp Glu Val Gly Thr Arg Trp Ala Val Leu Val Ala
        50                  55                  60

Gly Ser Ser Gly Tyr Gly Asn Tyr Arg His Gln Ala Asp Val Cys His
65                  70                  75                  80

Ala Tyr Gln Ile Leu Leu Lys Gly Gly Val Lys Glu Glu Asn Ile Val
                85                  90                  95

Val Phe Met Tyr Asp Asp Ile Ala His Asn Ile Leu Asn Pro Arg Pro
            100                 105                 110

Gly Val Ile Ile Asn His Pro Lys Gly Glu Asn Val Tyr Pro Gly Val
        115                 120                 125

Pro Lys Asp Tyr Thr Gly Asp Gln Val Thr Thr Glu Asn Phe Phe Ala
130                 135                 140

Val Leu Leu Gly Asn Arg Ser Ala Ile Thr Gly Gly Ser Lys Lys Val
145                 150                 155                 160

Ile Asp Ser Lys Pro Asn Asp His Ile Phe Ile Tyr Tyr Ser Asp His
                165                 170                 175

Gly Gly Pro Gly Val Leu Gly Met Pro Asn Leu Pro Tyr Leu Tyr Ala
            180                 185                 190

Gly Asp Phe Ile Lys Val Leu Lys Lys His Ala Ser Asn Ser Tyr
        195                 200                 205

Ser Lys Met Val Ile Tyr Val Glu Ala Cys Glu Ser Gly Ser Ile Phe
        210                 215                 220

Glu Gly Leu Met Pro Gln Asp Leu Asn Ile Tyr Val Thr Thr Ala Ser
225                 230                 235                 240

Asn Pro Val Glu Asn Ser Trp Gly Thr Tyr Cys Pro Gly Met Asp Pro
                245                 250                 255

Ser Pro Pro Pro Glu Tyr Ile Thr Cys Leu Gly Asp Leu Tyr Ser Val
            260                 265                 270

Ser Trp Met Glu Asp Ser Gln Thr His Asn Leu Met Lys Glu Thr Ile
        275                 280                 285

Lys Asp Gln Tyr Glu Val Val Lys Thr Arg Thr Ser Asn Leu Lys Lys
    290                 295                 300
```

Tyr Lys Glu Gly Ser His Val Met Glu Tyr Gly Asp Lys Thr Phe Thr
305                 310                 315                 320

Asn Glu Lys Leu Phe Leu Tyr Gln Gly Phe Asp Pro Ala Asn Ala Asn
            325                 330                 335

Ala Ala Asn Thr Leu Leu Trp Pro Gly Pro Lys Gly Ala Val Asn Gln
            340                 345                 350

Arg Asp Ala Asp Leu Leu Phe Met Trp Lys Arg Tyr Glu Gln Leu Asp
            355                 360                 365

Gly Gly Ser Glu Glu Lys Leu Arg Ala Leu Arg Glu Ile Lys Glu Thr
            370                 375                 380

Val Gln His Arg Lys His Leu Asp Ser Ser Ile Asp Phe Ile Gly Arg
385                 390                 395                 400

Leu Val Phe Gly Phe Glu Asn Gly Pro Lys Met Leu Glu Ala Val Arg
                405                 410                 415

Ala Ser Gly Gln Pro Leu Val Asp Asp Trp Asp Cys Leu Lys Arg Met
                420                 425                 430

Val Arg Ile Phe Glu Ala Gln Cys Gly Ser Leu Thr Tyr Gly Met
                435                 440                 445

Lys Tyr Met Arg Ala Phe Ala Asn Ile Cys Asn Ser Gly Ile Ser Glu
450                 455                 460

Ala Lys Met Arg Glu Ser Ser Ile Ser Ala Cys Gly Gly Tyr Asn Ser
465                 470                 475                 480

Ala Arg Trp Ser Pro Met Ala Gln Gly His Ser Ala
                485                 490

<210> SEQ ID NO 110
<211> LENGTH: 31
<212> TYPE: PRT
<213> ORGANISM: Oldenlandia affinis

<400> SEQUENCE: 110

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn His Val
                20                  25                  30

<210> SEQ ID NO 111
<211> LENGTH: 17
<212> TYPE: PRT
<213> ORGANISM: Conus sp.

<400> SEQUENCE: 111

Gly Val Cys Cys Gly Tyr Lys Leu Cys His Pro Cys Ala Gly Asn His
1               5                   10                  15

Val

<210> SEQ ID NO 112
<211> LENGTH: 25
<212> TYPE: PRT
<213> ORGANISM: Artificial
<220> FEATURE:
<223> OTHER INFORMATION: Thanatin analog

<400> SEQUENCE: 112

Gly Ile Ser Lys Lys Pro Val Pro Ile Ile Tyr Cys Asn Arg Arg Thr
1               5                   10                  15

Gly Lys Cys Gln Arg Met Asn His Val
                20                  25

<210> SEQ ID NO 113
<211> LENGTH: 42
<212> TYPE: PRT
<213> ORGANISM: Homo sapiens

<400> SEQUENCE: 113

Ser Ala Asp Ser His Glu Lys Arg His His Gly Tyr Arg Arg Lys Phe
1               5                   10                  15

His Glu Lys His His Ser His Arg Glu Phe Pro Phe Tyr Gly Asp Tyr
            20                  25                  30

Gly Ser Asn Tyr Leu Tyr Asp Asn His Val
        35                  40

<210> SEQ ID NO 114
<211> LENGTH: 43
<212> TYPE: PRT
<213> ORGANISM: Homo sapiens

<400> SEQUENCE: 114

Gly Leu Pro Asp Ser His Glu Lys Arg His His Gly Tyr Arg Arg Lys
1               5                   10                  15

Phe His Glu Lys His His Ser His Arg Glu Phe Pro Phe Tyr Gly Asp
            20                  25                  30

Tyr Gly Ser Asn Tyr Leu Tyr Asp Asn His Val
        35                  40

<210> SEQ ID NO 115
<211> LENGTH: 36
<212> TYPE: PRT
<213> ORGANISM: Homo sapiens

<400> SEQUENCE: 115

Gly Ala Asp Ser His Ala Lys Arg His His Gly Tyr Lys Arg Lys Phe
1               5                   10                  15

His Glu Lys His His Ser His Arg Gly Tyr Arg Ser Asn Tyr Leu Tyr
            20                  25                  30

Asp Asn His Val
        35

<210> SEQ ID NO 116
<211> LENGTH: 36
<212> TYPE: PRT
<213> ORGANISM: Homo sapiens

<400> SEQUENCE: 116

Gly Leu Asp Ser His Ala Lys Arg His His Gly Tyr Lys Arg Lys Phe
1               5                   10                  15

His Glu Lys His His Ser His Arg Gly Tyr Arg Ser Asn Tyr Leu Tyr
            20                  25                  30

Asp Asn His Val
        35

<210> SEQ ID NO 117
<211> LENGTH: 10
<212> TYPE: PRT
<213> ORGANISM: Artificial
<220> FEATURE:
<223> OTHER INFORMATION: Artificial peptide

<400> SEQUENCE: 117

Gly Leu Pro Pro Pro Ile Phe Asn His Val

```
1               5                   10

<210> SEQ ID NO 118
<211> LENGTH: 10
<212> TYPE: PRT
<213> ORGANISM: Artificial
<220> FEATURE:
<223> OTHER INFORMATION: Artificial peptide

<400> SEQUENCE: 118

Ser Leu Pro Pro Pro Ile Phe Asn His Val
1               5                   10

<210> SEQ ID NO 119
<211> LENGTH: 10
<212> TYPE: PRT
<213> ORGANISM: Artificial
<220> FEATURE:
<223> OTHER INFORMATION: Artificial peptide

<400> SEQUENCE: 119

His Leu Pro Pro Pro Ile Phe Asn His Val
1               5                   10

<210> SEQ ID NO 120
<211> LENGTH: 10
<212> TYPE: PRT
<213> ORGANISM: Artificial
<220> FEATURE:
<223> OTHER INFORMATION: Artificial peptide

<400> SEQUENCE: 120

Glu Ile Asn Ser Thr Glu Ile Asn His Val
1               5                   10

<210> SEQ ID NO 121
<211> LENGTH: 9
<212> TYPE: PRT
<213> ORGANISM: Artificial
<220> FEATURE:
<223> OTHER INFORMATION: Artificial peptide

<400> SEQUENCE: 121

Arg Val Thr Arg Pro Val Asn His Val
1               5

<210> SEQ ID NO 122
<211> LENGTH: 8
<212> TYPE: PRT
<213> ORGANISM: Artificial
<220> FEATURE:
<223> OTHER INFORMATION: Artificial peptide

<400> SEQUENCE: 122

Lys Ala Leu Val Ile Asn His Val
1               5

<210> SEQ ID NO 123
<211> LENGTH: 6
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (1)..(1)
<223> OTHER INFORMATION: Xaa can be any naturally occurring amino acid
```

```
<400> SEQUENCE: 123

Xaa Ile Gly Gly Ile Arg
1               5

<210> SEQ ID NO 124
<211> LENGTH: 6
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 124

Leu Xaa Gly Gly Ile Arg
1               5

<210> SEQ ID NO 125
<211> LENGTH: 5
<212> TYPE: PRT
<213> ORGANISM: Artificial
<220> FEATURE:
<223> OTHER INFORMATION: Artificial peptide

<400> SEQUENCE: 125

Tyr Arg Asn His Val
1               5

<210> SEQ ID NO 126
<211> LENGTH: 5
<212> TYPE: PRT
<213> ORGANISM: Artificial
<220> FEATURE:
<223> OTHER INFORMATION: Artificial peptide

<400> SEQUENCE: 126

Gly Leu Pro Val Arg
1               5

<210> SEQ ID NO 127
<211> LENGTH: 5
<212> TYPE: PRT
<213> ORGANISM: Artificial
<220> FEATURE:
<223> OTHER INFORMATION: Artificial peptide

<400> SEQUENCE: 127

Thr Arg Asn His Val
1               5

<210> SEQ ID NO 128
<211> LENGTH: 26
<212> TYPE: PRT
<213> ORGANISM: Artificial
<220> FEATURE:
<223> OTHER INFORMATION: modified human neuromedin U

<400> SEQUENCE: 128

Arg Val Asp Glu Glu Phe Gln Ser Pro Phe Ala Ser Gln Ser Arg Gly
1               5                   10                  15

Tyr Phe Leu Phe Arg Pro Arg Asn His Val
            20                  25

<210> SEQ ID NO 129
```

```
<211> LENGTH: 33
<212> TYPE: PRT
<213> ORGANISM: Artificial
<220> FEATURE:
<223> OTHER INFORMATION: modified human salusin alpha

<400> SEQUENCE: 129

Gly Ile Ser Gly Ala Leu Pro Pro Ala Pro Ala Ala Pro Arg Pro Ala
1               5                   10                  15

Leu Arg Ala Gln Arg Ala Gly Pro Ala Gly Pro Gly Ala Lys Asn His
            20                  25                  30

Val

<210> SEQ ID NO 130
<211> LENGTH: 28
<212> TYPE: PRT
<213> ORGANISM: Artificial
<220> FEATURE:
<223> OTHER INFORMATION: modified rat neuromedin U

<400> SEQUENCE: 130

Gly Ile Lys Tyr Lys Val Asn Glu Tyr Gln Gly Pro Val Ala Pro Ser
1               5                   10                  15

Gly Gly Phe Phe Leu Phe Arg Pro Arg Asn His Val
            20                  25

<210> SEQ ID NO 131
<211> LENGTH: 40
<212> TYPE: PRT
<213> ORGANISM: Artificial
<220> FEATURE:
<223> OTHER INFORMATION: modified human apelin

<400> SEQUENCE: 131

Gly Leu Val Gln Pro Arg Gly Ser Arg Asn Gly Pro Gly Pro Trp Gln
1               5                   10                  15

Gly Gly Arg Arg Lys Phe Arg Arg Gln Arg Pro Arg Leu Ser His Lys
            20                  25                  30

Gly Pro Met Pro Phe Asn His Val
            35                  40

<210> SEQ ID NO 132
<211> LENGTH: 32
<212> TYPE: PRT
<213> ORGANISM: Artificial
<220> FEATURE:
<223> OTHER INFORMATION: modified human galanin

<400> SEQUENCE: 132

Gly Leu Thr Ser Gly Trp Thr Leu Asn Ser Ala Gly Tyr Leu Leu Gly
1               5                   10                  15

Pro His Ala Val Gly Asn His Arg Ser Phe Ser Asp Lys Asn His Val
            20                  25                  30

<210> SEQ ID NO 133
<211> LENGTH: 263
<212> TYPE: PRT
<213> ORGANISM: Artificial
<220> FEATURE:
<223> OTHER INFORMATION: GFP + NHV tag

<400> SEQUENCE: 133

Met His His His His His His Ser Ser Gly Val Asp Leu Gly Thr Glu
1               5                   10                  15
```

```
Asn Leu Tyr Phe Gln Ser Met Ser Lys Gly Glu Glu Leu Phe Thr Gly
            20                  25                  30
Val Val Pro Ile Leu Val Glu Leu Asp Gly Asp Val Asn Gly His Lys
        35                  40                  45
Phe Ser Val Ser Gly Glu Gly Glu Gly Asp Ala Thr Tyr Gly Lys Leu
    50                  55                  60
Thr Leu Lys Phe Ile Cys Thr Thr Gly Lys Leu Pro Val Pro Trp Pro
65                  70                  75                  80
Thr Leu Val Thr Thr Leu Thr Tyr Gly Val Gln Cys Phe Ser Arg Tyr
                85                  90                  95
Pro Asp His Met Lys Gln His Asp Phe Phe Lys Ser Ala Met Pro Glu
            100                 105                 110
Gly Tyr Val Gln Glu Arg Thr Ile Phe Phe Lys Asp Asp Gly Asn Tyr
        115                 120                 125
Lys Thr Arg Ala Glu Val Lys Phe Glu Gly Asp Thr Leu Val Asn Arg
    130                 135                 140
Ile Glu Leu Lys Gly Ile Asp Phe Lys Glu Asp Gly Asn Ile Leu Gly
145                 150                 155                 160
His Lys Leu Glu Tyr Asn Tyr Asn Ser His Asn Val Tyr Ile Met Ala
                165                 170                 175
Asp Lys Gln Lys Asn Gly Ile Lys Val Asn Phe Lys Ile Arg His Asn
            180                 185                 190
Ile Glu Asp Gly Ser Val Gln Leu Ala Asp His Tyr Gln Gln Asn Thr
        195                 200                 205
Pro Ile Gly Asp Gly Pro Val Leu Leu Pro Asp Asn His Tyr Leu Ser
    210                 215                 220
Thr Gln Ser Ala Leu Ser Lys Asp Pro Asn Glu Lys Arg Asp His Met
225                 230                 235                 240
Val Leu Leu Glu Phe Val Thr Ala Ala Gly Ile Thr Leu Gly Met Asp
                245                 250                 255
Glu Leu Tyr Lys Asn His Val
            260

<210> SEQ ID NO 134
<211> LENGTH: 5
<212> TYPE: PRT
<213> ORGANISM: Artificial
<220> FEATURE:
<223> OTHER INFORMATION: K at position 4 is biotinylated

<400> SEQUENCE: 134

Gly Ile Gly Lys Arg
1               5

<210> SEQ ID NO 135
<211> LENGTH: 16
<212> TYPE: PRT
<213> ORGANISM: Artificial
<220> FEATURE:
<223> OTHER INFORMATION: Artificial peptide

<400> SEQUENCE: 135

Gly Arg Cys Thr Lys Ser Ile Pro Pro Ile Cys Phe Pro Asn His Val
1               5                   10                  15

<210> SEQ ID NO 136
<211> LENGTH: 32
<212> TYPE: PRT
```

```
<213> ORGANISM: Artificial
<220> FEATURE:
<223> OTHER INFORMATION: Artificial peptide

<400> SEQUENCE: 136

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn His Val Ile
            20                  25                  30

<210> SEQ ID NO 137
<211> LENGTH: 33
<212> TYPE: PRT
<213> ORGANISM: Artificial
<220> FEATURE:
<223> OTHER INFORMATION: Artificial peptide

<400> SEQUENCE: 137

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn His Val Ile
            20                  25                  30

Ala

<210> SEQ ID NO 138
<211> LENGTH: 30
<212> TYPE: PRT
<213> ORGANISM: Artificial
<220> FEATURE:
<223> OTHER INFORMATION: Artificial peptide

<400> SEQUENCE: 138

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn His
            20                  25                  30

<210> SEQ ID NO 139
<211> LENGTH: 29
<212> TYPE: PRT
<213> ORGANISM: Artificial
<220> FEATURE:
<223> OTHER INFORMATION: Artificial peptide

<400> SEQUENCE: 139

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn
            20                  25

<210> SEQ ID NO 140
<211> LENGTH: 32
<212> TYPE: PRT
<213> ORGANISM: Artificial
<220> FEATURE:
<223> OTHER INFORMATION: Artificial peptide

<400> SEQUENCE: 140

Gly Gly Leu Pro Val Cys Gly Glu Thr Cys Val Gly Gly Thr Cys Asn
1               5                   10                  15

Thr Pro Gly Cys Thr Cys Ser Trp Pro Val Cys Thr Arg Asp His Val
            20                  25                  30
```

```
<210> SEQ ID NO 141
<211> LENGTH: 32
<212> TYPE: PRT
<213> ORGANISM: Artificial
<220> FEATURE:
<223> OTHER INFORMATION: Artificial peptide

<400> SEQUENCE: 141

Gly Gly Leu Pro Val Cys Gly Glu Thr Cys Val Gly Thr Cys Asn
1               5                   10                  15

Thr Pro Gly Cys Thr Cys Ser Trp Pro Val Cys Thr Arg Ala His Val
        20                  25                  30

<210> SEQ ID NO 142
<211> LENGTH: 32
<212> TYPE: PRT
<213> ORGANISM: Artificial
<220> FEATURE:
<223> OTHER INFORMATION: Artificial peptide

<400> SEQUENCE: 142

Gly Gly Leu Pro Val Cys Gly Glu Thr Cys Val Gly Thr Cys Asn
1               5                   10                  15

Thr Pro Gly Cys Thr Cys Ser Trp Pro Val Cys Thr Arg Gln His Val
        20                  25                  30

<210> SEQ ID NO 143
<211> LENGTH: 32
<212> TYPE: PRT
<213> ORGANISM: Artificial
<220> FEATURE:
<223> OTHER INFORMATION: Artificial peptide

<400> SEQUENCE: 143

Gly Gly Leu Pro Val Cys Gly Glu Thr Cys Val Gly Thr Cys Asn
1               5                   10                  15

Thr Pro Gly Cys Thr Cys Ser Trp Pro Val Cys Thr Arg Glu His Val
        20                  25                  30

<210> SEQ ID NO 144
<211> LENGTH: 16
<212> TYPE: PRT
<213> ORGANISM: Artificial
<220> FEATURE:
<223> OTHER INFORMATION: Artificial peptide

<400> SEQUENCE: 144

Gly Arg Cys Thr Lys Ser Ile Pro Pro Ile Cys Phe Pro Asp His Val
1               5                   10                  15

<210> SEQ ID NO 145
<211> LENGTH: 244
<212> TYPE: PRT
<213> ORGANISM: Artificial
<220> FEATURE:
<223> OTHER INFORMATION: modified GFP

<400> SEQUENCE: 145

Gly Ile Ser Met Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45
```

```
Phe Ile Cys Thr Thr Gly Lys Leu Pro Val Pro Trp Pro Thr Leu Val
    50                  55                  60

Thr Thr Leu Thr Tyr Gly Val Gln Cys Phe Ser Arg Tyr Pro Asp His
65                  70                  75                  80

Met Lys Gln His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
            115                 120                 125

Lys Gly Ile Asp Phe Lys Glu Asp Gly Asn Ile Leu Gly His Lys Leu
130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
            195                 200                 205

Ala Leu Ser Lys Asp Pro Asn Glu Lys Arg Asp His Met Val Leu Leu
210                 215                 220

Glu Phe Val Thr Ala Ala Gly Ile Thr Leu Gly Met Asp Glu Leu Tyr
225                 230                 235                 240

Lys Asn His Val

<210> SEQ ID NO 146
<211> LENGTH: 129
<212> TYPE: PRT
<213> ORGANISM: Artificial
<220> FEATURE:
<223> OTHER INFORMATION: human anti-ABL scFv fragment

<400> SEQUENCE: 146

Met His His His His His Ser Ser Gly Val Asp Leu Gly Thr Glu
1               5                   10                  15

Asn Leu Tyr Phe Gln Ser Met Gly Gly Ser Gly Ser Ser Val Ser Ser
                20                  25                  30

Val Pro Thr Lys Leu Glu Val Val Asp Ala Thr Pro Thr Ser Leu Lys
            35                  40                  45

Ile Ser Trp Asp Ala Tyr Tyr Ser Ser Trp Gln Asn Val Lys Tyr Tyr
    50                  55                  60

Arg Ile Thr Tyr Gly Thr Gly Gly Asp Ser Pro Val Gln Glu Phe
65                  70                  75                  80

Thr Val Pro Gly Tyr Tyr Ser Thr Ala Thr Ile Ser Gly Leu Lys Pro
                85                  90                  95

Gly Val Asp Tyr Thr Ile Thr Val Tyr Ala Tyr Asp Thr Phe Phe Pro
            100                 105                 110

Gly Tyr Glu Pro Asn Ser Pro Ile Ser Ile Asn Tyr Arg Thr Asn His
            115                 120                 125

Val

<210> SEQ ID NO 147
<211> LENGTH: 184
<212> TYPE: PRT
<213> ORGANISM: Artificial
```

```
<220> FEATURE:
<223> OTHER INFORMATION: darpin specific for ERK

<400> SEQUENCE: 147

Met His His His His His Ser Ser Gly Val Asp Leu Gly Thr Glu
1               5                   10                  15

Asn Leu Tyr Phe Gln Ser Met Gly Ser Asp Leu Gly Lys Lys Leu Leu
            20                  25                  30

Glu Ala Ala Arg Ala Gly Gln Asp Asp Glu Val Arg Ile Leu Met Ala
        35                  40                  45

Asn Gly Ala Asp Val Asn Ala His Asp Gln Gly Ser Thr Pro Leu
50                  55                  60

His Leu Ala Ala Trp Ile Gly His Pro Glu Ile Val Glu Val Leu Leu
65                  70                  75                  80

Lys His Gly Ala Asp Val Asn Ala Arg Asp Thr Asp Gly Trp Thr Pro
                85                  90                  95

Leu His Leu Ala Ala Asp Asn Gly His Leu Glu Ile Val Glu Val Leu
            100                 105                 110

Leu Lys Tyr Gly Ala Asp Val Asn Ala Gln Asp Ala Tyr Gly Leu Thr
        115                 120                 125

Pro Leu His Leu Ala Ala Asp Arg Gly His Leu Glu Ile Val Glu Val
    130                 135                 140

Leu Leu Lys His Gly Ala Asp Val Asn Ala Gln Asp Lys Phe Gly Lys
145                 150                 155                 160

Thr Ala Phe Asp Ile Ser Ile Asp Asn Gly Asn Glu Asp Leu Ala Glu
                165                 170                 175

Ile Leu Gln Lys Leu Asn His Val
            180

<210> SEQ ID NO 148
<211> LENGTH: 85
<212> TYPE: PRT
<213> ORGANISM: Artificial Sequence
<220> FEATURE:
<223> OTHER INFORMATION: ubiquitin

<400> SEQUENCE: 148

Met Gly Ile Met Gln Ile Phe Val Lys Thr Leu Thr Gly Lys Thr Ile
1               5                   10                  15

Thr Leu Glu Val Glu Pro Ser Asp Thr Ile Glu Asn Val Lys Ala Lys
            20                  25                  30

Ile Gln Asp Lys Glu Gly Ile Pro Pro Asp Gln Gln Arg Leu Ile Phe
        35                  40                  45

Ala Gly Lys Gln Leu Glu Asp Gly Arg Thr Leu Ser Asp Tyr Asn Ile
    50                  55                  60

Gln Lys Glu Ser Thr Leu His Leu Val Leu Arg Leu Arg Gly Gly His
65                  70                  75                  80

His His His His
        85

<210> SEQ ID NO 149
<211> LENGTH: 5
<212> TYPE: PRT
<213> ORGANISM: Artificial
<220> FEATURE:
<223> OTHER INFORMATION: Artificial peptide

<400> SEQUENCE: 149
```

Tyr Lys Asn His Val
1               5

<210> SEQ ID NO 150
<211> LENGTH: 5
<212> TYPE: PRT
<213> ORGANISM: Artificial
<220> FEATURE:
<223> OTHER INFORMATION: Artificial peptide

<400> SEQUENCE: 150

Gly Lys Asn His Val
1               5

<210> SEQ ID NO 151
<211> LENGTH: 29
<212> TYPE: PRT
<213> ORGANISM: Artificial
<220> FEATURE:
<223> OTHER INFORMATION: cyclized kB1 fragment

<400> SEQUENCE: 151

Asn Gly Leu Pro Val Cys Gly Glu Thr Cys Val Gly Gly Thr Cys Asn
1               5                   10                  15

Thr Pro Gly Cys Thr Cys Ser Trp Pro Val Cys Thr Arg
            20                  25

<210> SEQ ID NO 152
<211> LENGTH: 22
<212> TYPE: PRT
<213> ORGANISM: Artificial
<220> FEATURE:
<223> OTHER INFORMATION: fragment peptide

<400> SEQUENCE: 152

Thr Ile Val Ala Leu Ile Glu Asp Gly Thr His Val Val Gln Tyr Gly
1               5                   10                  15

Asp Val Gly Leu Ser Lys
            20

<210> SEQ ID NO 153
<211> LENGTH: 13
<212> TYPE: PRT
<213> ORGANISM: Artificial
<220> FEATURE:
<223> OTHER INFORMATION: peptide fragment

<400> SEQUENCE: 153

His Gln Ala Asp Val Cys His Ala Tyr Gln Leu Ile Lys
1               5                   10

<210> SEQ ID NO 154
<211> LENGTH: 9
<212> TYPE: PRT
<213> ORGANISM: Artificial
<220> FEATURE:
<223> OTHER INFORMATION: peptide fragment

<400> SEQUENCE: 154

Trp Ala Val Leu Val Ala Gly Ser Lys
1               5

<210> SEQ ID NO 155
<211> LENGTH: 6
<212> TYPE: PRT
<213> ORGANISM: Artificial

```
<220> FEATURE:
<223> OTHER INFORMATION: peptide fragment

<400> SEQUENCE: 155

Gly Tyr Val Asn Tyr Arg
1               5

<210> SEQ ID NO 156
<211> LENGTH: 7
<212> TYPE: PRT
<213> ORGANISM: Artificial
<220> FEATURE:
<223> OTHER INFORMATION: peptide fragment

<400> SEQUENCE: 156

His Ala Ser Gly Thr Tyr Lys
1               5

<210> SEQ ID NO 157
<211> LENGTH: 14
<212> TYPE: PRT
<213> ORGANISM: Artificial
<220> FEATURE:
<223> OTHER INFORMATION: Peptide library 1
<220> FEATURE:
<221> NAME/KEY: misc_feature
<222> LOCATION: (1)..(1)
<223> OTHER INFORMATION: Xaa can be any naturally occurring amino acid

<400> SEQUENCE: 157

Xaa Leu Tyr Arg Arg Gly Arg Tyr Leu Arg Arg Asn His Val
1               5                   10

<210> SEQ ID NO 158
<211> LENGTH: 14
<212> TYPE: PRT
<213> ORGANISM: Artificial
<220> FEATURE:
<223> OTHER INFORMATION: Peptide library 2
<220> FEATURE:
<221> NAME/KEY: misc_feature
<222> LOCATION: (1)..(1)
<223> OTHER INFORMATION: Xaa can be any naturally occurring amino acid

<400> SEQUENCE: 158

Xaa Arg Leu Tyr Arg Gly Arg Tyr Leu Arg Arg Asn His Val
1               5                   10

<210> SEQ ID NO 159
<211> LENGTH: 14
<212> TYPE: PRT
<213> ORGANISM: Artificial
<220> FEATURE:
<223> OTHER INFORMATION: Peptide library 3
<220> FEATURE:
<221> NAME/KEY: misc_feature
<222> LOCATION: (2)..(2)
<223> OTHER INFORMATION: Xaa can be any naturally occurring amino acid

<400> SEQUENCE: 159

Gly Xaa Leu Tyr Arg Gly Arg Tyr Leu Arg Arg Asn His Val
1               5                   10

<210> SEQ ID NO 160
<211> LENGTH: 5
<212> TYPE: PRT
<213> ORGANISM: Artificial Sequence
<220> FEATURE:
<223> OTHER INFORMATION: Pentapeptide recognition sequence from sorase A
```

```
<220> FEATURE:
<221> NAME/KEY: VARIANT
<222> LOCATION: 3
<223> OTHER INFORMATION: Xaa = any amino acid

<400> SEQUENCE: 160

Leu Pro Xaa Thr Gly
1               5

<210> SEQ ID NO 161
<211> LENGTH: 57
<212> TYPE: PRT
<213> ORGANISM: Artificial Sequence
<220> FEATURE:
<223> OTHER INFORMATION: Synthetic peptide to be cyclized
<220> FEATURE:
<221> NAME/KEY: VARIANT
<222> LOCATION: (1)...(57)
<223> OTHER INFORMATION: Xaa = any amino acid
<220> FEATURE:
<221> NAME/KEY: VARIANT
<222> LOCATION: (2)...(6)
<223> OTHER INFORMATION: any one or all of amino acids 2-6 can either be
      present or absent.
<220> FEATURE:
<221> NAME/KEY: VARIANT
<222> LOCATION: (9)...(13)
<223> OTHER INFORMATION: any one or all of amino acids 9-13 can either
      be present or absent.
<220> FEATURE:
<221> NAME/KEY: VARIANT
<222> LOCATION: (16)...(20)
<223> OTHER INFORMATION: any one or all of amino acids 17-20 can either
      be present or absent.
<220> FEATURE:
<221> NAME/KEY: VARIANT
<222> LOCATION: (23)...(27)
<223> OTHER INFORMATION: any one or all of amino acids 23-27 can either
      be present or absent.
<220> FEATURE:
<221> NAME/KEY: VARIANT
<222> LOCATION: (30)...(34)
<223> OTHER INFORMATION: any one or all of amino acids 30-34 can either
      be present or absent.
<220> FEATURE:
<221> NAME/KEY: VARIANT
<222> LOCATION: (37)...(41)
<223> OTHER INFORMATION: any one or all of amino acids 37-41 can either
      be present or absent.
<220> FEATURE:
<221> NAME/KEY: VARIANT
<222> LOCATION: (44)...(48)
<223> OTHER INFORMATION: any one or all of amino acids 44-48 can either
      be present or absent.
<220> FEATURE:
<221> NAME/KEY: VARIANT
<222> LOCATION: (53)...(57)
<223> OTHER INFORMATION: any one or all of amino acids 53-57 can either
      be present or absent.

<400> SEQUENCE: 161

Xaa Xaa Xaa Xaa Xaa Xaa Cys Xaa Xaa Xaa Xaa Xaa Xaa Cys Xaa Xaa
1               5                   10                  15

Xaa Xaa Xaa Xaa Cys Xaa Xaa Xaa Xaa Xaa Xaa Cys Xaa Xaa Xaa Xaa
                20                  25                  30

Xaa Xaa Cys Xaa Xaa Xaa Xaa Xaa Xaa Cys Xaa Xaa Xaa Xaa Xaa Xaa
            35                  40                  45

Asn His Val Xaa Xaa Xaa Xaa Xaa Xaa
        50                  55

<210> SEQ ID NO 162
<211> LENGTH: 10
```

```
<212> TYPE: PRT
<213> ORGANISM: Artificial Sequence
<220> FEATURE:
<223> OTHER INFORMATION: Synthetic sequence

<400> SEQUENCE: 162

Gly Ile Gly Lys Gly Ile Gly Asn Arg Tyr
1               5                   10

<210> SEQ ID NO 163
<211> LENGTH: 13
<212> TYPE: PRT
<213> ORGANISM: Artificial Sequence
<220> FEATURE:
<223> OTHER INFORMATION: Synthetic sequence

<400> SEQUENCE: 163

Tyr Arg Asn Gly Ile Gly Lys Gly Ile Gly Asn Arg Tyr
1               5                   10
```